United States Patent
Dukhan et al.

(10) Patent No.: US 10,202,411 B2
(45) Date of Patent: Feb. 12, 2019

(54) 3'-SUBSTITUTED METHYL OR ALKYNYL NUCLEOSIDES NUCLEOTIDES FOR THE TREATMENT OF HCV

(71) Applicant: IDENIX PHARMACEUTICALS LLC, Cambridge, MA (US)

(72) Inventors: David Dukhan, Saint Gely du Fesc (FR); Cyril B. Dousson, Canet (FR); Gilles Gosselin, Montpellier (FR); Jean-Laurent Paparin, Vendemian (FR); Guillaume Brandt, Montpellier (FR); Rachid Rahali, Saint Laurent des Arbres (FR); Aurelien Salanson, Montpellier (FR); François-René Alexandre, Montpellier (FR)

(73) Assignee: IDENIX PHARMACEUTICALS LLC, Cambridge, MA (US)

( * ) Notice: Subject to any disclaimer, the term of this patent is extended or adjusted under 35 U.S.C. 154(b) by 43 days.

(21) Appl. No.: 15/304,506

(22) PCT Filed: Apr. 16, 2015

(86) PCT No.: PCT/US2015/026264
§ 371 (c)(1),
(2) Date: Oct. 14, 2016

(87) PCT Pub. No.: WO2015/161137
PCT Pub. Date: Oct. 22, 2015

(65) Prior Publication Data
US 2017/0044205 A1 Feb. 16, 2017

Related U.S. Application Data

(60) Provisional application No. 61/980,326, filed on Apr. 16, 2014.

(51) Int. Cl.

| | |
|---|---|
| *A01N 43/04* | (2006.01) |
| *A61K 31/70* | (2006.01) |
| *C07H 19/20* | (2006.01) |
| *C07H 19/10* | (2006.01) |
| *C07H 19/11* | (2006.01) |
| *A61K 31/7068* | (2006.01) |
| *A61K 31/7072* | (2006.01) |
| *A61K 31/7076* | (2006.01) |
| *A61K 45/06* | (2006.01) |
| *A61K 31/7064* | (2006.01) |
| *A61K 31/708* | (2006.01) |
| *A61K 31/7052* | (2006.01) |
| *A61K 31/706* | (2006.01) |

(52) U.S. Cl.
CPC ......... *C07H 19/20* (2013.01); *A61K 31/7068* (2013.01); *A61K 31/7072* (2013.01); *A61K 31/7076* (2013.01); *A61K 45/06* (2013.01); *C07H 19/10* (2013.01); *C07H 19/11* (2013.01); *A61K 31/706* (2013.01); *A61K 31/708* (2013.01); *A61K 31/7052* (2013.01); *A61K 31/7064* (2013.01)

(58) Field of Classification Search
None
See application file for complete search history.

(56) References Cited

U.S. PATENT DOCUMENTS 3,480,613 A 11/1969 Walton et al.
6,174,868 B1 1/2001 Anderson et al.
(Continued)

FOREIGN PATENT DOCUMENTS

CN 1133642 C 1/2004
CN 103848876 A 6/2014
(Continued)

OTHER PUBLICATIONS

Tong Expert Opin. Ther. Patents (2009), vol. 19, pp. 415-431. (Year: 2009).*
Hammer et al. The New England Journal of Medicine (1996), vol. 335, pp. 1081-1090. (Year: 1996).*
Gould et al. Chem. Commun. (1997), pp. 243-244. (Year: 1997).*
Newman et al. "Solid-state analysis of the active pharmaceutical ingredient in drug products", DDT (2003), vol. 8, pp. 898-905. (Year: 2003).*
Aparna et al., 3D-QSAR studies on antitubercular thymidine monophosphate kinase inhibitors based on different alignment methods (2006) *Bioorganic & Medicinal Chemistry Letters* 16:1014-1020.

(Continued)

*Primary Examiner* — Patrick T Lewis
(74) *Attorney, Agent, or Firm* — Squire Patton Boggs (US) LLP

(57) ABSTRACT

Provided herein are compounds, compositions and methods for the treatment of Flaviviridae infections, including HCV infections. In certain embodiments, compounds and compositions of nucleoside derivatives are disclosed, which can be administered either alone or in combination with other anti-viral agents. In certain embodiments, the compounds are 3'-substituted methyl or alkynyl nucleosides of Formula I: (I); or a pharmaceutically acceptable salt, solvate, stereoisomeric form, tautomeric form or polymorphic form thereof, wherein Base, PD, $R^A$, $R^{B1}$, $R^{B2}$, $R^C$ and Z are as defined herein.

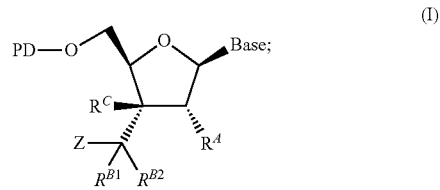

29 Claims, No Drawings

(56) References Cited

U.S. PATENT DOCUMENTS

| | | |
|---|---|---|
| 6,284,458 B1 | 9/2001 | Anderson et al. |
| 6,348,587 B1 | 2/2002 | Schinazi et al. |
| 6,391,542 B1 | 5/2002 | Anderson et al. |
| 6,423,489 B1 | 7/2002 | Anderson et al. |
| 6,433,159 B1 | 8/2002 | Anderson |
| 6,455,513 B1 | 9/2002 | McGuigan et al. |
| 6,566,365 B1 | 5/2003 | Storer |
| 6,573,247 B1 | 6/2003 | McGuigan et al. |
| 6,608,191 B1 | 8/2003 | Anderson et al. |
| 6,638,919 B2 | 10/2003 | McGuigan et al. |
| 6,660,721 B2 | 12/2003 | Devos et al. |
| 6,777,395 B2 | 8/2004 | Bhat et al. |
| 6,784,161 B2 | 8/2004 | Ismaili et al. |
| 6,784,166 B2 | 8/2004 | Devos et al. |
| 6,833,361 B2 | 12/2004 | Hong et al. |
| 6,846,810 B2 | 1/2005 | Martin |
| 6,911,424 B2 | 6/2005 | Schinazi et al. |
| 6,914,054 B2 | 7/2005 | Sommadossi et al. |
| 6,927,291 B2 | 8/2005 | Jin et al. |
| 6,995,146 B2 | 2/2006 | Anderson et al. |
| 7,018,989 B2 | 3/2006 | McGuigan et al. |
| 7,019,135 B2 | 3/2006 | McGuigan et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,115,590 B1 | 10/2006 | Daluge et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,285,658 B2 | 10/2007 | Cook et al. |
| 7,300,924 B2 | 11/2007 | Boojamra et al. |
| 7,307,065 B2 | 12/2007 | Schinazi et al. |
| 7,323,449 B2 | 1/2008 | Olsen et al. |
| 7,323,453 B2 | 1/2008 | Olsen et al. |
| 7,339,054 B2 | 3/2008 | Xu et al. |
| 7,365,057 B2 | 4/2008 | LaColla et al. |
| 7,378,402 B2 | 5/2008 | Martin et al. |
| 7,384,924 B2 | 6/2008 | LaColla et al. |
| 7,405,204 B2 | 7/2008 | Roberts et al. |
| 7,429,572 B2 | 9/2008 | Clark |
| 7,452,901 B2 | 11/2008 | Boojamra et al. |
| 7,456,155 B2 | 11/2008 | Sommadossi et al. |
| 7,524,825 B2 | 4/2009 | Keicher et al. |
| 7,534,767 B2 | 5/2009 | Butora et al. |
| 7,547,704 B2 | 6/2009 | LaColla et al. |
| 7,582,618 B2 | 9/2009 | Sommadossi et al. |
| 7,598,230 B2 | 10/2009 | Cook et al. |
| 7,598,373 B2 | 10/2009 | Storer et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,632,940 B2 | 12/2009 | Harrington et al. |
| 7,635,689 B2 | 12/2009 | LaColla et al. |
| 7,645,745 B2 | 1/2010 | Sarma |
| 7,645,747 B2 | 1/2010 | Boojamra et al. |
| 7,662,798 B2 | 2/2010 | LaColla et al. |
| 7,666,856 B2 | 2/2010 | Johansson et al. |
| 7,754,699 B2 | 7/2010 | Chun et al. |
| 7,772,208 B2 | 8/2010 | Schinazi et al. |
| 7,781,576 B2 | 8/2010 | Mayes et al. |
| 7,807,653 B2 | 10/2010 | Cook et al. |
| 7,820,631 B2 | 10/2010 | McGuigan et al. |
| 7,824,851 B2 | 11/2010 | Sommadossi et al. |
| 7,842,672 B2 | 11/2010 | Boojamra et al. |
| 7,871,991 B2 | 1/2011 | Boojamra et al. |
| 7,879,815 B2 | 2/2011 | MacCoss et al. |
| 7,902,202 B2 | 3/2011 | Sommadossi et al. |
| 7,915,232 B2 | 3/2011 | Martin et al. |
| 7,951,787 B2 | 5/2011 | McGuigan |
| 7,951,788 B2 | 5/2011 | Cheng |
| 7,951,789 B2 | 5/2011 | Sommadossi et al. |
| 7,964,580 B2 | 6/2011 | Sofia et al. |
| 7,973,013 B2 | 7/2011 | Cho et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,022,083 B2 | 9/2011 | Boojamra et al. |
| 8,071,567 B2 | 12/2011 | Devos et al. |
| 8,076,310 B2 | 12/2011 | Herdewijn et al. |
| 8,119,607 B2 | 2/2012 | Francom et al. |
| 8,119,779 B2 | 2/2012 | McGuigan et al. |
| 8,148,349 B2 | 4/2012 | Meppen et al. |
| 8,168,583 B2 | 5/2012 | Schinazi et al. |
| 8,173,621 B2 | 5/2012 | Du et al. |
| 8,183,216 B2 | 5/2012 | Di Francesco et al. |
| 8,236,779 B2 | 8/2012 | Ma et al. |
| 8,299,038 B2 | 10/2012 | Sommadossi et al. |
| 8,304,529 B2 * | 11/2012 | Kore .............. C07H 21/02 536/23.1 |
| 8,318,682 B2 | 11/2012 | Butler et al. |
| 8,318,701 B2 | 11/2012 | Boojamra et al. |
| 8,324,179 B2 | 12/2012 | Chen et al. |
| 8,329,926 B2 | 12/2012 | Boojamra et al. |
| 8,334,270 B2 | 12/2012 | Sofia et al. |
| 8,399,428 B2 | 3/2013 | Wagner |
| 8,404,651 B2 | 3/2013 | Iyer et al. |
| 8,415,308 B2 | 4/2013 | Cho et al. |
| 8,415,322 B2 | 4/2013 | Clark |
| 8,455,451 B2 | 6/2013 | Cho et al. |
| 8,481,712 B2 | 7/2013 | Bhat et al. |
| 8,481,713 B2 | 7/2013 | Wang et al. |
| 8,507,460 B2 | 8/2013 | Surleraux et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,569,478 B2 | 10/2013 | Du et al. |
| 8,575,119 B2 | 11/2013 | Wang et al. |
| 8,580,268 B2 | 11/2013 | Debelak et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,637,475 B1 | 1/2014 | Storer et al. |
| 8,642,756 B2 | 2/2014 | Ross et al. |
| 8,658,616 B2 | 2/2014 | McGuigan et al. |
| 8,680,071 B2 | 3/2014 | Surleraux et al. |
| 8,691,788 B2 | 4/2014 | Sommadossi et al. |
| 8,716,262 B2 | 5/2014 | Sofia et al. |
| 8,716,263 B2 | 5/2014 | Chun et al. |
| 8,728,725 B2 | 5/2014 | Paul et al. |
| 8,735,372 B2 | 5/2014 | Du et al. |
| 8,759,318 B2 | 6/2014 | Chamberlain et al. |
| 8,759,510 B2 | 6/2014 | Du et al. |
| 8,765,710 B2 | 7/2014 | Sofia et al. |
| 8,765,935 B2 | 7/2014 | Wagner |
| 8,772,474 B2 | 7/2014 | Beigelman et al. |
| 8,802,840 B2 | 8/2014 | Francom et al. |
| 8,816,074 B2 | 8/2014 | Chu et al. |
| 8,841,275 B2 | 9/2014 | Du et al. |
| 8,859,756 B2 | 10/2014 | Ross et al. |
| 8,871,737 B2 | 10/2014 | Smith et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,906,880 B2 | 12/2014 | Du et al. |
| 8,946,244 B2 | 2/2015 | Chu et al. |
| 8,951,985 B2 | 2/2015 | Surleraux et al. |
| 8,957,046 B2 | 2/2015 | Du et al. |
| 8,962,580 B2 | 2/2015 | Manoharan et al. |
| 9,006,209 B2 | 4/2015 | Jonckers et al. |
| 9,012,428 B2 | 4/2015 | Jonckers et al. |
| 9,060,971 B2 | 6/2015 | Or et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,095,599 B2 | 8/2015 | Chang et al. |

(56) References Cited

U.S. PATENT DOCUMENTS

| | | |
|---|---|---|
| 9,108,999 B2 | 8/2015 | Zhang et al. |
| 9,109,001 B2 | 8/2015 | Parsy et al. |
| 9,150,603 B2 | 10/2015 | Girijavallabhan et al. |
| 9,156,872 B2 | 10/2015 | Girijavallabhan et al. |
| 9,156,874 B2 | 10/2015 | Chang et al. |
| 9,187,515 B2 | 11/2015 | Mayes et al. |
| 9,192,621 B2 | 11/2015 | Mayes et al. |
| 9,211,300 B2 | 12/2015 | Mayes et al. |
| 9,242,988 B2 | 1/2016 | Girijavallabhan et al. |
| 9,243,025 B2 | 1/2016 | Surleraux |
| 9,296,778 B2 | 3/2016 | Parsy et al. |
| 9,309,275 B2 | 4/2016 | Stewart et al. |
| 9,339,541 B2 | 5/2016 | Dousson et al. |
| 2003/0008841 A1 | 1/2003 | Devos et al. |
| 2003/0087873 A1 | 5/2003 | Stuyver et al. |
| 2004/0006002 A1 | 1/2004 | Sommadossi et al. |
| 2004/0014108 A1 | 1/2004 | Eldrup et al. |
| 2004/0110718 A1 | 6/2004 | Devos et al. |
| 2004/0229840 A1 | 11/2004 | Bhat et al. |
| 2004/0266723 A1 | 12/2004 | Otto et al. |
| 2005/0009775 A1 | 1/2005 | Howes et al. |
| 2005/0038240 A1 | 2/2005 | Connolly et al. |
| 2005/0124532 A1 | 6/2005 | Sommadossi et al. |
| 2006/0040944 A1 | 2/2006 | Gosselin et al. |
| 2006/0234962 A1 | 10/2006 | Olsen et al. |
| 2006/0264389 A1 | 11/2006 | Bhat et al. |
| 2007/0004669 A1 | 1/2007 | Carroll et al. |
| 2007/0027065 A1 | 2/2007 | LaColla et al. |
| 2007/0027104 A1 | 2/2007 | LaColla et al. |
| 2007/0032449 A1 | 2/2007 | LaColla et al. |
| 2007/0037735 A1 | 2/2007 | Gosselin et al. |
| 2007/0042990 A1 | 2/2007 | Gosselin et al. |
| 2007/0060503 A1 | 3/2007 | Gosselin et al. |
| 2007/0060504 A1 | 3/2007 | Gosselin et al. |
| 2007/0060505 A1 | 3/2007 | Gosselin et al. |
| 2007/0060541 A1 | 3/2007 | Gosselin et al. |
| 2007/0265222 A1 | 11/2007 | MacCoss et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0280842 A1 | 11/2008 | MacCoss et al. |
| 2009/0004135 A1 | 1/2009 | Clark |
| 2009/0036666 A1 | 2/2009 | Clark |
| 2009/0048189 A1 | 2/2009 | Keicher et al. |
| 2009/0118223 A1 | 5/2009 | Erion et al. |
| 2009/0176732 A1 | 7/2009 | Beigelman et al. |
| 2009/0318380 A1 | 12/2009 | Sofia et al. |
| 2010/0003217 A1 | 1/2010 | Cretton-Scott et al. |
| 2010/0056468 A1 | 3/2010 | Kotra et al. |
| 2010/0077085 A1 | 3/2010 | Cohen |
| 2010/0240604 A1 | 9/2010 | Beigelman et al. |
| 2010/0249068 A1 | 9/2010 | Beigelman et al. |
| 2010/0279969 A1 | 11/2010 | Schinazi et al. |
| 2010/0279974 A1 | 11/2010 | Pierra et al. |
| 2010/0297079 A1 | 11/2010 | Almond et al. |
| 2010/0316594 A1 | 12/2010 | Sommadossi et al. |
| 2011/0269707 A1 | 11/2011 | Stuyver et al. |
| 2011/0306541 A1 | 12/2011 | Delaney, IV et al. |
| 2011/0306573 A1 | 12/2011 | Avolio et al. |
| 2012/0009147 A1 | 1/2012 | Cho et al. |
| 2012/0010164 A1 | 1/2012 | Surnma et al. |
| 2012/0034184 A1 | 2/2012 | Devos et al. |
| 2012/0070411 A1 | 3/2012 | Beigelman et al. |
| 2012/0107274 A1 | 5/2012 | Clarke et al. |
| 2012/0245335 A1 | 9/2012 | Clark |
| 2013/0017171 A1 | 1/2013 | Sommadossi et al. |
| 2013/0064794 A1 | 3/2013 | Surleraux et al. |
| 2013/0149283 A1 | 6/2013 | Sommadossi et al. |
| 2013/0273005 A1 | 10/2013 | Delaney et al. |
| 2013/0315862 A1 | 11/2013 | Sommadossi et al. |
| 2013/0315868 A1 | 11/2013 | Mayes et al. |
| 2013/0330297 A1 | 12/2013 | Storer et al. |
| 2014/0099283 A1 | 4/2014 | Gosselin et al. |
| 2014/0112886 A1 | 4/2014 | Moussa et al. |
| 2014/0112887 A1 | 4/2014 | Mayes et al. |
| 2014/0113880 A1 | 4/2014 | Storer et al. |
| 2014/0128339 A1 | 5/2014 | Girijavallabhan et al. |
| 2014/0140951 A1 | 5/2014 | Moussa et al. |
| 2014/0140952 A1 | 5/2014 | Moussa et al. |
| 2014/0140955 A1 | 5/2014 | McGuigan et al. |
| 2014/0205566 A1 | 7/2014 | Liao et al. |
| 2014/0212382 A1 | 7/2014 | Schinazi et al. |
| 2014/0221304 A1 | 8/2014 | Verma et al. |
| 2014/0235567 A1 | 8/2014 | Verma et al. |
| 2014/0271547 A1 | 9/2014 | Dukhan et al. |
| 2014/0315850 A1 | 10/2014 | Huang et al. |
| 2014/0356325 A1 | 12/2014 | Zhi et al. |
| 2014/0364446 A1 | 12/2014 | Dukhan et al. |
| 2014/0369959 A1 | 12/2014 | Smith et al. |
| 2015/0037282 A1 | 2/2015 | Mayes et al. |
| 2015/0231166 A1 | 8/2015 | Du et al. |
| 2016/0002281 A1 | 1/2016 | Mayes et al. |
| 2016/0031927 A1 | 2/2016 | Ivachtchenko |
| 2016/0045526 A1 | 2/2016 | Girijavallabhan et al. |
| 2016/0082030 A1 | 3/2016 | Mayes et al. |
| 2016/0083413 A1 | 3/2016 | Gosselin et al. |
| 2016/0113956 A1 | 4/2016 | Dukhan et al. |

FOREIGN PATENT DOCUMENTS

| | | | |
|---|---|---|---|
| CN | 103848877 A | 6/2014 | |
| WO | WO 1993/017651 A3 | 9/1993 | |
| WO | WO 2002/057287 A2 | 7/2002 | |
| WO | WO 2003/105770 A2 | 12/2003 | |
| WO | WO 2005/020884 A2 | 3/2005 | |
| WO | WO 2005/020885 A2 * | 3/2005 | |
| WO | WO-2005020885 A2 * | 3/2005 | ........... A61K 9/0014 |
| WO | WO 2007/027248 A2 | 3/2007 | |
| WO | WO 2012/048013 A2 | 4/2012 | |
| WO | WO 2013/084165 A1 | 6/2013 | |
| WO | WO 2014/124430 A1 | 8/2014 | |
| WO | WO 2014/204831 A1 | 12/2014 | |
| WO | WO 2015/061683 A1 | 4/2015 | |
| WO | WO 2015/066370 A1 | 5/2015 | |
| WO | WO 2015/077360 A2 | 5/2015 | |
| WO | WO 2015/081133 A2 | 6/2015 | |
| WO | WO 2015/081297 A1 | 6/2015 | |
| WO | WO 2015/095305 A1 | 6/2015 | |
| WO | WO 2015/095419 A1 | 6/2015 | |
| WO | WO 2015/134780 A1 | 9/2015 | |
| WO | WO 2015/161137 A1 | 10/2015 | |

OTHER PUBLICATIONS

Benzaria et al., 2'-C-Methyl branched pyrimidine ribonucleoside analogues: potent inhibitors of RNA virus replication (2007) *Antiviral Chemistry & Chemotherapy* 18:225-242.

Boyer et al., Pathogenesis, Diagnosis and Management of Hepatitis C, *J. Hepatology*, 2000, vol. 32 (suppl. 1), pp. 98-112.

Bueno et al., Structural and chemical basis for enhanced affinity to a series of mycobacterial thymidine monophosphate kinase inhibitors: fragment-based QSAR and QM/MM docking studies (2013) *J Mol Model* 19:179-192.

Cahard et al., Aryloxy Phosphoramidate Triesters as Pro-Tides (2004) *Mini-Reviews in Medicinal Chemistry* 4:371-381.

Congiatu et al., Novel Potential Anticancer Naphthyl Phosphoramidates of BVdU: Separation of Diastereoisomers and Assignment of the Absolute Configuration of the Phosphorus Center (2006) *Journal of Medicinal Chemistry* 49:452-455.

Devogelaere et al., TMC647055, a Potent Nonnucleoside Hepatitis C Virus NS5B Polymerase Inhibitor with Cross-Genotypic Coverage (2012) *Antimicrobial Agents and Chemotherapy* 56:4676-4684.

Di Besceglie et al., "The Unmet Challenges of Hepatitis C", *Scientific American*, Oct. 1, 1999, pp. 80-85.

Eldrup et al., Structure-Activity Relationship of Purine Ribonucleosides for Inhibition of Hepatitis C Virus RNA-Dependent RNA Polymerase (2004) *Journal of Medicinal Chemistry* 47:2283-2295.

Gardelli et al., Phosphoramidate Prodrugs of 2'-C-Methylcytidine for Therapy of Hepatitis C Virus Infection (2009) *Journal of Medicinal Chemistry* 52:5394-5407.

(56) References Cited

OTHER PUBLICATIONS

Gopalakrishnan et al., A Virtual Screening Approach for Thymidine Monophosphate Kinase Inhibitors as Antitubercular Agents Based on Docking and Pharmacophore Models (2005) *J. Chem. Inf. Model.* 45:1101-1108.

Hollecker et al., Synthesis of β-enantiomers of $N^4$-hydroxy-3'-deoxypyrimidine nucleosides and their evaluation against bovine viral diarrhoea virus and hepatitis C virus in cell culture (2004) *Antiviral Chemistry & Chemotherapy* 14:43-55.

Ivanov et al., Synthesis and biological properties of pyrimidine 4'-fluoronucleosides and 4'-fluorouridine 5'-O-triphosphate (2010) *Russian Journal of Bioorganic Chemistry* 36:488-496.

Kakefuda et al., Nucleosides and nucleotides. 120. Stereoselective Radical Deoxygenation of *tert*-Alcohols in the Sugar Moiety of Nucleosides: Synthesis of 2',3'-Dideoxy-2'-*C*-methyl- and -2'-*C*-ethynyl-β-d-*threo*-pentofuranosyl Pyrimidines and Adenine as Potential Antiviral and Antitumor Agents (1993) *Tetrahedron* 49:8513-8528.

Kawana et al., The deoxygenations of tosylated adenosine derivatives with Grignard reagents (1986) *Nucleic Acids Symp Ser.* 17:37-40.

Kawana et al., The Synthesis of *C*-Methyl Branched-Chain Deoxy Sugar Nucleosides by the Deoxygenative Methylation of *O*-Tosylated Adenosines with Grignard Reagents (1988) *Bull. Chem. Soc. Jpn.* 61:2437-2442.

King et al., Inhibition of the replication of a hepatitis C virus-like RNA template by interferon and 3'-deoxycytidine (2002) *Antiviral Chemistry & Chemotherapy* 13:363-370.

Kusano-Kitazume et al., Identification of Novel *N*-(Morpholine-4-Carbonyloxy) Amidine Compounds as Potent Inhibitors against Hepatitis C Virus Replication (2011) *Antimicrobial Agents and Chemotherapy* 56:1315-1323.

Leisvuori et al., Synthesis of 3',5'-Cyclic Phosphate and Thiophosphate Esters of 2'-*C*-Methyl Ribonucleosides (2012) *Helvetica Chimica Acta* 95:1512-1520.

Madela et al., Progress in the development of anti-hepatitis C virus nucleoside and nucleotide prodrugs (2012) *Future Med. Chem.* 4:625-650.

McGuigan et al., Phosphoramidate ProTides of 2'-*C*-Methylguanosine as Highly Potent Inhibitors of Hepatitis C Virus. Study of Their in Vitro and in Vivo Properties (2010) *Journal of Medicinal Chemistry* 53:4949-4957.

McGuigan et al., Phosphorodiamidates as a Promising New Phosphate Prodrug Motif for Antiviral Drug Discovery: Application to Anti-HCV Agents (2011) *Journal of Medicinal Chemistry* 54:8632-8645.

McGuigan et al., The application of phosphoramidate ProTide technology to the potent anti-HCV compound 4'-azidocytidine (R1479) (2009) *Bioorganic & Medicinal Chemistry Letters* 19:4250-4254.

Mehellou et al., Phosphoramidates of 2'-β-D-arabinouridine (AraU) as phosphate prodrugs; design, synthesis, in vitro activity and metabolism (2010) *Bioorganic & Medicinal Chemistry* 18:2439-2446.

Mehellou et al., The design, synthesis and antiviral evaluation of a series of 5-trimethylsilyl-1-β-D-(arabinofurano syl)uracil phosphoramidate ProTides (2010) *Antiviral Chemistry & Chemotherapy* 20:153-160.

Meneghesso et al., Synthesis and biological evaluation of pyrimidine nucleoside monophosphate prodrugs targeted against influenza virus (2012) *Antiviral Research* 94:35-43.

Müller et al., Novel Nucleotide Analogues as Potential Substrates for TMPK, a Key Enzyme in the Metabolism of AZT (2003) *Nucleosides, Nucleotides and Nucleic Acids* 22:821-823.

Murakami et al., Mechanism of Activation of PSI-7851 and Its Diastereoisomer PSI-7977 (2010) *Journal of Biological Chemistry* 285:34337-34347.

Murakami et al., Mechanism of Activation of β-D-2'-Fluoro-2'-*C*-Methylcytidine and Inhibition of Hepatitis C Virus NS5B RNA polymerase (2007) *Antimicrobial Agents and Chemotherapy* 51:503-509.

Olsen et al., A 7-Deaza-Adenosine Analog Is a Potent and Selective Inhibitor of Hepatitis C Virus Replication with Excellent Pharmacokinetic Properties (2004) *Antimicrobial Agents and Chemotherapy* 28:3944-3953.

Perrone et al., Application of the Phosphoramidate ProTide Approach to 4'-Azidouridine Confers Sub-micromolar Potency versus Hepatitis C Virus on an Inactive Nucleoside (2007) *Journal of Medicinal Chemistry* 50:1840-1849.

Pierra et al., Synthesis of 2'-*C*-Methylcytidine and 2'-*C*-Methyluridine Derivatives Modified in the 3'-Position as Potential Antiviral Agents (2006) *Collection of Czechoslovak Chemical Communications* 71:991-1010.

Prakash et al., Synthesis and Evaluation of *S*-Acyl-2-thioethyl Esters of Modified Nucleoside 5'-Monophosphates as Inhibitors of Hepatitis C Virus RNA Replication (2005) *J. Med. Chem.* 48:1199-1210.

Saboulard et al., Characterization of the Activation Pathway of Phosphoramidate Triester Prodrugs of Stavudine and Zidovudine (2009) *Molecular Pharmacology* 56:693-704.

Shen et al., Design and synthesis of vidarabine prodrugs as antiviral agents (2009) *Bioorganic & Medicinal Chemistry Letters* 19:792-796.

Sofia et al., Discovery of a β-D-2'-Deoxy-2'-α-fluoro-2'-β-*C*-methyluridine Nucleotide Prodrug (PSI-7977) for the Treatment of Hepatitis *C* Virus (2010) *Journal of Medicinal Chemistry* 53:7202-7218.

Sofia, M., Nucleotide prodrugs for HCV therapy (2011) *Antiviral Chemistry Et Chemotherapy* 22:23-49.

Stein et al., Phosphorylation of Nucleoside Analog Antiretrovirals: A Review for Clinicians (2001) *Pharmacotherapy* 21:11-34.

Tomassini et al., Inhibitory Effect of 2'-Substituted Nucleosides on Hepatitis C Virus Replication Correlates with Metabolic Properties in Replicon Cells (2005) *Antimicrobial Agents and Chemotherapy* 49:2050-2058.

Tong et al., Nucleosides of thioguanine and other 2-amino-6-substituted purines from 2-acetamido-5-chloropurine (1967) *J Org Chem.* 32:859-62.

Vernachio et al., INX-08189, a Phosphoramidate Prodrug of 6-*O*-Methyl-2'-*C*-Methyl Guanosine, Is a Potent Inhibitor of Hepatitis C Virus Replication with Excellent Pharmacokinetic and Pharmacodynamic Properties (2011) *Antimicrobial Agents and Chemotherapy* 55:1843-1851.

Bueno et al., "Structural and chemical basis for enhanced affinity to a series of mycobacterial thymidine monophosphate kinase inhibitors: fragment-based QSAR and QM/MM docking studies", *Journal of Molecular Modeling*, Springer, DE, Jul. 31, 2012, vol. 19, No. 1, pp. 179-192.

International Preliminary Report on Patentability dated Oct. 27, 2016 for application No. PCT/US2015/026264; 13 pages.

\* cited by examiner

3'-SUBSTITUTED METHYL OR ALKYNYL NUCLEOSIDES NUCLEOTIDES FOR THE TREATMENT OF HCV

PRIOR RELATED APPLICATION

This application is the National Stage of International Application No. PCT/US2015/026264, filed Apr. 16, 2015, which claims the benefit of, and priority to, U.S. Provisional Application No. 61/980,326, entitled "3'-SUBSTITUTED METHYL OR ALKYNYL NUCLEOSIDES FOR THE TREATMENT OF HCV," filed Apr. 16, 2014, the contents of each of which are incorporated by reference herein in their entireties.

FIELD

Provided herein are compounds, methods and pharmaceutical compositions for use in treatment of viral infections, including hepatitis C virus infections in hosts in need thereof. In certain embodiments, 3'-substituted methyl or alkynyl nucleosides are provided which display remarkable efficacy and bioavailability for the treatment of, for example, HCV infection in a human.

BACKGROUND

The hepatitis C virus (HCV) is the leading cause of chronic liver disease worldwide. (Boyer, N. et al., *J. Hepatol.* 32:98-112, 2000). HCV causes a slow growing viral infection and is the major cause of cirrhosis and hepatocellular carcinoma (Di Besceglie, A. M. and Bacon, B. R., Scientific American, October: 80-85, 1999; Boyer, N. et al., *J. Hepatol.* 32:98-112, 2000). It is estimated there are about 130-150 million people with chronic hepatitis C virus infection. Hepatitis C-related liver diseases cause approximately 350,000 to 500,000 deaths each year.

HCV infection becomes chronic in about 55-85% of cases, with many patients initially being asymptomatic. About 15 to 30% of patients with chronic hepatitis due to HCV develop cirrhosis within about 20 years. (Hepatitis C Fact Sheet, *World Health Organization Fact Sheet No.*, 164, April 2014). Development of cirrhosis due to HCV also increases the risk of hepatocellular cancer (The Merck Manual Online, *Chronic Hepatitis*, available at www.merckmanuals.com/professional/hepatic_and_biliary_disorders/hepatitis/chronic_hepatitis.html, last revision February 2014).

In light of the fact that HCV infection has reached epidemic levels worldwide, and has tragic effects on the infected patient, there remains a strong need to provide new effective pharmaceutical agents to treat hepatitis C that have low toxicity to the host. Further, given the rising threat of other flaviviridae infections, there remains a strong need to provide new effective pharmaceutical agents that have low toxicity to the host. Therefore, there is a continuing need for effective treatments of flavivirus infections and HCV infections.

SUMMARY

Provided herein are compounds useful, for example, for the treatment of flavivirus infections such as HCV infections. The compounds are 3'-substituted methyl or alkynyl nucleosides. In certain embodiments the 3'-substituted methyl or alkynyl nucleosides display remarkable efficacy or bioavailability, or both, for the treatment of, for example, HCV infection in a human.

In certain embodiments, the compounds provided herein are useful in the prevention and treatment of Flaviviridae infections and other related conditions such as anti-Flaviviridae antibody positive and Flaviviridae-positive conditions, chronic liver inflammation caused by HCV, cirrhosis, fibrosis, acute hepatitis, fulminant hepatitis, chronic persistent hepatitis and fatigue. These compounds or formulations can also be used prophylactically to prevent or retard the progression of clinical illness in individuals who are anti-Flaviviridae antibody or Flaviviridae-antigen positive or who have been exposed to a Flaviviridae. In particular embodiments, the Flaviviridae is hepatitis C. In certain embodiments, the compounds are used to treat any virus that replicates through an RNA-dependent RNA polymerase.

A method for the treatment of a Flaviviridae infection in a host, including a human, is also provided that includes administering an effective amount of a compound provided herein, administered either alone or in combination or alternation with another anti-Flaviviridae agent, optionally in a pharmaceutically acceptable carrier.

In certain embodiments, provided herein are compounds according to Formula I:

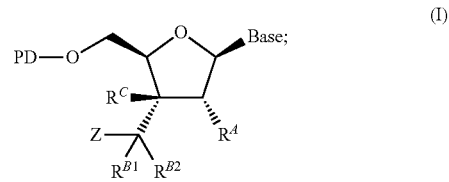

or a pharmaceutically acceptable salt thereof, wherein: $R^A$ hydroxyl, halo, hydrogen, or alkylcarbonyloxy; $R^{B1}$ is hydrogen, alkenyl, alkynyl, hydroxyl, fluoro, azido, —$NH_2$, CN, benzyloxycarbonyloxy, or alkylcarbonyloxy; $R^{B2}$ is hydrogen, methyl, or fluoro; $R^C$ is hydrogen, azido or methyl; Base is a nucleobase; PD is

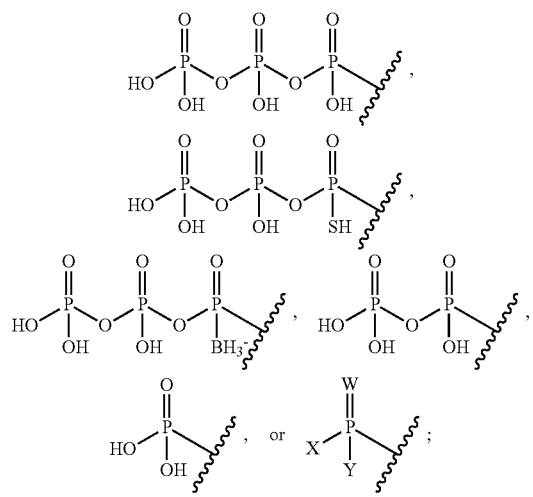

W is S or O; each of X and Y is independently hydrogen, —$OR^1$, —$SR^1$, —$NR^1R^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene; each R$^1$ is independently hydrogen, alkyl, aryl, arylalkyl, cycloalkyl, heterocycloalkyl, alkoxylcarbonylalkyl, alkoxycarbonyloxyalkyl or alkylcarbonylthioalkyl; and each R$^2$ is independently hydrogen, alkyl, cycloalkyl, aryl, or arylalkyl;

with the proviso that when: PD is

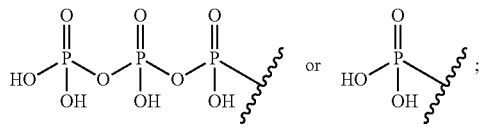 [SMILES: *P(=O)(O)OP(=O)(O)OP(=O)(O)O ; *P(=O)(O)O]

R$^A$ is hydroxyl; R$^{B1}$ is fluoro; R$^{B2}$ is hydrogen; R$^C$ is hydrogen; and Z is hydrogen; then Base is other than guanine; and with the proviso that when: PD is

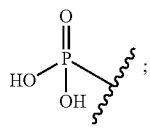

R$^A$ is hydrogen or hydroxyl; R$^{B1}$ is hydrogen; R$^{B2}$ is hydrogen; R$^C$ is hydrogen; and Z is azido or —NH$_2$; then Base is other than thymine.

In one aspect, the compounds provided herein are provided or administered in combination with a second therapeutic agent, such as one useful for the treatment or prevention of HCV infections. Exemplary second therapeutic agents are provided in detail elsewhere herein.

In another aspect, provided herein are pharmaceutical compositions, single unit dosage forms, and kits suitable for use in treating or preventing disorders such as HCV infections which comprise a therapeutically or prophylactically effective amount of a compound provided herein, e.g., of Formula 1001, I-XLVI, 101-122bii, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt thereof, and optionally with a therapeutically or prophylactically effective amount of a second therapeutic agent such as one useful for the treatment or prevention of HCV infections.

In certain embodiments, a method of treatment of a liver disorder is provided comprising administering to an individual in need thereof a treatment effective amount of a 3'-substituted methyl or alkynyl nucleoside compound.

Flaviviridae which can be treated are, e.g., discussed generally in *Fields Virology*, Fifth Ed., Editors: Knipe, D. M., and Howley, P. M., Lippincott Williams & Wilkins Publishers, Philadelphia, Pa., Chapters 33-35, 2006. In a particular embodiment of the invention, the Flaviviridae is HCV. In an alternate embodiment, the Flaviviridae is a flavivirus or pestivirus. In certain embodiments, the Flaviviridae can be from any class of Flaviviridae. In certain embodiments, the Flaviviridae is a mammalian tick-borne virus. In certain embodiments, the Flaviviridae is a seabird tick-borne virus. In certain embodiments, the Flaviviridae is a mosquito-borne virus. In certain embodiments, the Flaviviridae is an Aroa virus. In certain embodiments, the Flaviviridae is a Dengue virus. In certain embodiments, the Flaviviridae is a Japanese encephalitis virus. In certain embodiments, the Flaviviridae is a Kokobera virus. In certain embodiments, the Flaviviridae is a Ntaya virus. In certain embodiments, the Flaviviridae is a Spondweni virus. In certain embodiments, the Flaviviridae is a Yellow fever virus. In certain embodiments, the Flaviviridae is a Entebbe virus. In certain embodiments, the Flaviviridae is a Modoc virus. In certain embodiments, the Flaviviridae is a Rio Bravo virus.

Specific flaviviruses which can be treated include, without limitation: Absettarov, Aedes, Alfuy, Alkhurma, Apoi, Aroa, Bagaza, Banzi, Bukalasa bat, Bouboui, Bussuquara, Cacipacore, Calbertado, Carey Island, Cell fusing agent, Cowbone Ridge, Culex, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Kamiti River, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Nakiwogo, Naranjal, Negishi, Ntaya, Omsk hemorrhagic fever, Phnom-Penh bat, Powassan, Quang Binh, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tick-borne encephalitis, Turkish sheep encephalitis, Tyuleniy, Uganda S, Usutu, Wesselsbron, West Nile, Yaounde, Yellow fever, Yokose, and Zika.

Pestiviruses which can be treated are discussed generally in *Fields Virology*, Fifth Ed., Editors: Knipe, D. M., and Howley, P. M., Lippincott Williams & Wilkins Publishers, Philadelphia, Pa., Chapters 33-35, 2006. Specific pestiviruses which can be treated include, without limitation: bovine viral diarrhea virus ("BVDV"), classical swine fever virus ("CSFV," also called hog cholera virus), and border disease virus ("BDV").

DESCRIPTION OF EXEMPLARY EMBODIMENTS

Provided herein are compounds, compositions and methods useful for treating liver disorders such as HCV infection in a subject. Further provided are dosage forms useful for such methods.

Definitions

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., C$_1$ to C$_{10}$ alkyl. In certain embodiments, the alkyl group is methyl, CF$_3$, CCl$_3$, CFCl$_2$, CF$_2$Cl, ethyl, CH$_2$CF$_3$, CF$_2$CF$_3$, propyl, isopropyl, butyl, isobutyl, secbutyl, t-butyl, pentyl, isopentyl, neopentyl, hexyl, isohexyl, 3-methylpentyl, 2,2-dimethylbutyl, or 2,3-dimethylbutyl. The term includes both substituted and unsubstituted alkyl groups, preferably unsubstituted or halogenated alkyl groups. In certain embodiments, the alkyl group is a fluorinated alkyl group. In some embodiments, the alkyl group can be substituted with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), alkoxycarbonyl, alkoxycarbonyloxy, alkylcarbonylthio, aryloxy, nitro, cyano, sulfonic acid, sulfate, phosphonic acid, phosphate, and phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties, preferably unsubstituted.

The term "upper alkyl," as used herein, and unless otherwise specified, refers to a saturated straight or branched hydrocarbon having seven to thirty carbon atoms, i.e., $C_7$ to $C_{30}$ alkyl. In certain embodiments, the upper alkyl group is a primary, secondary, or tertiary hydrocarbon. The term includes both substituted and unsubstituted moieties, preferably unsubstituted.

The term "alkylcarbonyl," as used herein, unless otherwise specified, refers to a —C(O)R group where R is alkyl as defined herein. In some embodiments, the alkyl is unsubstituted.

The term "alkylsulfanyl," as used herein, unless otherwise specified, refers to a —SR group where R is alkyl as defined herein. In some embodiments, the alkyl is unsubstituted.

The term "cycloalkyl," as used herein, unless otherwise specified, refers to a saturated cyclic hydrocarbon. In certain embodiments, the cycloalkyl group is a bridged, non-bridged, spirocyclic and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl. The term includes both substituted and unsubstituted cycloalkyl groups, including halogenated cycloalkyl groups. In certain embodiments, the cycloalkyl group is a fluorinated cycloalkyl group. Preferably the cycloalkyl is unsubstituted or fluorinated. In some embodiments, the cycloalkyl group can be substituted with 1, 2, or 3 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

The term "cycloalkyloxy" refers to an —OR group where R is cycloalkyl as defined herein. In some embodiments, the cycloalkyl is unsubstituted.

The term "cycloalkylalkyl" refers to an alkyl group substituted with a cycloalkyl as defined herein. In some embodiments, the cycloalkyl is unsubstituted.

The term "cycloalkylalkyloxy" refers to an —OR group where R is cycloalkylalkyl as defined herein. In some embodiments, the cycloalkyl is unsubstituted.

"Alkylene" refers to divalent saturated aliphatic hydrocarbon groups particularly having from one to eleven carbon atoms which can be straight-chained or branched. In certain embodiments, the alkylene group contains 1 to 10 carbon atoms. The term includes both substituted and unsubstituted moieties, preferable unsubstituted. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like. The term includes halogenated alkylene groups. In certain embodiments, the alkylene group is a fluorinated alkylene group. In some embodiments, the alkylene group can be substituted with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), alkylaryl, arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

"Alkenyl" refers to monovalent olefinically unsaturated hydrocarbon groups, in certain embodiment, having 2 to 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties, preferable unsubstituted. Exemplary alkenyl groups include ethenyl (i.e., vinyl or —CH═CH$_2$), n-propenyl (—CH$_2$CH═CH$_2$), isopropenyl (—C(CH$_3$)═CH$_2$), and the like. The term includes halogenated alkenyl groups. In certain embodiments, the alkenyl group is a fluorinated alkenyl group. In some embodiments, the alkenyl group can be substituted with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

"Alkenylene" refers to divalent olefinically unsaturated hydrocarbon groups, in certain embodiment, having 2 to 11 carbon atoms, from 2 to 8 carbon atoms, or from 2 to 6 carbon atoms, which can be straight-chained or branched and having at least 1 or from 1 to 2 sites of olefinic unsaturation. The term includes both substituted and unsubstituted moieties, preferable unsubstituted. Exemplary alkenylene groups include ethenyl (i.e., —CH═CH—), (—CH$_2$CH═CH—), (—C(CH$_3$)═CH—), and the like. The term includes halogenated alkenylene groups. In certain embodiments, the alkenylene group is a fluorinated alkenyl group. In some embodiments, the alkenylene group can be substituted with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl (—CH$_2$C≡CH), and the like. The term includes both substituted and unsubstituted alkynyl groups, including halogenated alkynyl groups. In certain embodiments, the alkynyl group is a fluorinated alkynyl group or unsubstituted. In some embodiments, the alkynyl group can be with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

The term "alkynylene" refers to a divalent hydrocarbon radical which contains at least one (in some embodiments, 1 or 2 triple bonds), having 2 to 11 carbon atoms in certain embodiments, 2-11 or from 2 to 6 carbon atoms which can be straight-chained or branched. The term includes both substituted and unsubstituted alkynylene groups, including halogenated alkynylene groups. In certain embodiments, the alkynylene group is a fluorinated alkenylene group. In certain embodiments, the alkynylene group is substituted with 1, 2, 3, 4, or 5 groups independently selected from halogen (fluoro, chloro, bromo, or iodo), hydroxyl, alkylcarbonyl, alkylsulfanyl, amino (in some embodiments, —NH$_2$, NH(alkyl), —N(alkyl)$_2$), arylamino, alkoxy (in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary.

The term "aryl," as used herein, and unless otherwise specified, refers to a substituent derived from an aromatic ring. In an embodiment, an aryl group is a $C_6$-$C_{12}$ aryl group. In an embodiment, an aryl group is phenyl, biphenyl, or naphthyl. The term includes both substituted and unsubstituted moieties. An aryl group can be substituted with any described moiety, including, but not limited to, one or more moieties (in some embodiments, 1, 2, 3, or 4) independently selected from halogen (fluoro, chloro, bromo, or iodo), alkyl, haloalkyl, hydroxyl, amino (in some embodiments, —NH$_2$, NH(alkyl), —N(alkyl)$_2$), arylamino, alkoxy(in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991.

The term "aryloxy" refers to the group —OR where R is aryl, as defined herein. In some embodiments, the aryl is unsubstituted.

The term "aralkyloxy" refers to the group —OR where R is aralkyl, as defined herein. In some embodiments, the aryl and alkyl in aralkyl are unsubstituted.

"Alkoxy" and "alkoxyl" refer to the group —OR' where R' is alkyl or cycloalkyl as defined herein. In certain embodiments, the alkoxyl or alkoxy group is —OR', wherein R' is alkyl or cycloalkyl, and wherein alkyl is $C_1$ to $C_{10}$ alkyl and cycloalkyl is $C_3$ to $C_{15}$ cycloalkyl. Alkoxy and alkoxyl groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like. In some embodiments, R' is unsubstituted.

The term "alkoxycarbonyl" as defined herein refers to a —C(O)OR group where R is alkyl as defined herein. In some embodiments, the alkyl is unsubstituted.

The term "alkoxycarbonyloxy" as used herein refers to an —OR there R is alkoxycarbonyl as defined herein. In some embodiment the alkyl in alkoxycarbonyl is unsubstituted.

The term "alkoxycarbonyloxyalkyl" as used herein refers to an alkyl group substituted with —OR there R is alkoxycarbonyloxy as defined herein. In some embodiment the alkyl in alkoxycarbonyloxy is unsubstituted.

"Alkylcarbonyloxy" refers to a radical —O—C(O)-alkyl, wherein alkyl is as defined herein. In some embodiments, the alkyl is unsubstituted.

"Alkylcarbonylamino" refers to a radical -amino-C(O)-alkyl, wherein alkyl and amino are as defined herein. In some embodiments, the alkyl is unsubstituted. In some embodiments, the amino is —NH—.

"Alkylcarbonylthio" refers to an —SC(O)R where R is unsubstituted or substituted alkyl, as defined herein. In some embodiments R is unsubstituted alkyl. In some embodiments, R is hydroxyalkyl or unsubstituted alkyl.

"Alkylcarbonylthioalkyl" refers to an alkyl group, as defined herein, substituted with —SC(O)R where R is unsubstituted or substituted alkyl, as defined herein. In some embodiments each alkyl in "alkylcarbonylthioalkyl" is not further substituted. In some embodiments, R is hydroxyalkyl or unsubstituted alkyl.

"Alkoxylcarbonylalkyl" refers to a radical -alkyl-C(O)-alkoxyl where alkoxyl and alkyl are as defined herein. In some embodiments, each alkyl is unsubstituted.

The term "amido," as defined herein, and unless specified otherwise, is —C(O)NH$_2$.

"Amino" refers to the group —NR$^{1'}$R$^{2'}$ or —NR$^{1'}$—, wherein R$^{1'}$ and R$^{2'}$ are independently selected from hydrogen, alkyl, and cycloalkyl. In some embodiments, the alkyl and cycloalkyl are unsubstituted.

"Amino alcohol" refers to the radical —NHLOH, wherein L is alkylene. In some embodiments, the alkylene is unsubstituted.

"Carboxyl" or "carboxy" refers to the radical —C(O)OH.

The term "alkylamino" or "arylamino" refers to an amino group that has one or two alkyl or aryl substituents, respectively. In certain embodiments, the alkyl substituent is upper alkyl. In certain embodiments, the alkyl substituent is lower alkyl. In another embodiment, the alkyl, upper alkyl, or lower alkyl is unsubstituted.

"Halogen" or "halo" refers to chloro, bromo, fluoro, or iodo.

The term "haloalkyl," as used herein, unless specified otherwise, is an alkyl group substituted with 1, 2, 3, 4, or 5 halo groups. In some embodiments, the alkyl group is substituted with only 1, 2, 3, 4, or 5 halo groups.

The term "heterocyclyl," "heterocyclo," or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. In certain embodiments, the heterocyclyl is optionally substituted with 1, 2, 3, or 4 groups independently selected from halogen (fluoro, chloro, bromo, or iodo), alkyl, haloalkyl, hydroxyl, amino (in some embodiments, —NH$_2$, NH(alkyl), —N(alkyl)$_2$), arylamino, alkoxy(in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991.

The term "heteroaryl" refers to a monovalent monocyclic aromatic group and/or multicyclic aromatic group that contain at least one aromatic ring, wherein at least one aromatic ring contains one or more heteroatoms which are independently O, S, or N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. In certain embodiments, the heteroaryl is optionally substituted with 1, 2, 3, or 4 groups independently selected from halogen (fluoro, chloro, bromo, or iodo), alkyl, haloalkyl, hydroxyl, amino (in some embodiments, —NH$_2$, NH(alkyl), —N(alkyl)$_2$), arylamino, alkoxy(in some embodiments, —O-(unsubstituted alkyl), or —O-(unsubstituted cycloalkyl), aryloxy, nitro, cyano, sulfonic acid, sulfate, phosphonic acid, phosphate, and phosphonate, either unprotected, or protected as necessary, as known to those skilled in the art, for example, as taught in Greene, et al., *Protective Groups in Organic Synthesis*, John Wiley and Sons, Second Edition, 1991.

The term "alkylaryl" refers to an aryl group with an alkyl substituent, wherein aryl and alkyl are as defined herein. The term "aralkyl" or "arylalkyl" refers to an alkyl group with an aryl substituent, wherein aryl and alkyl are as defined herein.

The term "phosphonic acid" refers to —P(O)(OH)$_2$.

The term "phosphate" refers to the group —OP(O)(OR)$_2$ where each R is independently alkyl or arylalkyl.

The term "phosphonate" refers to the group —P(O)(OR)$_2$ where each R is independently alkyl or arylalkyl.

The term "sulfonic acid" refers to the group —S(O)$_2$OH.

The term "sulfonate ester" refers to the group —OS(O)$_2$R where R is, alkyl or arylalkyl.

The term "sulfate" refers to the group —OS(O)$_2$OR where R is hydrogen, alkyl or arylalkyl.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) base addition salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

As used herein, the term "nucleobase" refers to the base portion of a nucleoside or nucleotide. In certain embodiments, a nucleobase is a purine (which is used interchangeably with purinyl) or pyrimidine (which is used interchangeably with pyrimidinyl) base, as defined herein. In certain embodiments, the nucleobase is adeninyl, purinyl, thyminyl, cytosinyl, pyrimidinyl, uracilyl, triazolopyridinyl, imidazolopyridinyl, pyrrolopyrimidinyl, triazolopyrimidinyl, pyrazolopyrimidinyl, guaninyl, adeninyl, hypoxanthinyl, 7-deazaguaninyl, 7-deazaadeninyl, or pyrrolotriazinyl; each of which is optionally substituted with 1, 2, or 3 groups independently selected from acyl (where is acyl is —C(O)R and R is alkyl, aryl, alkylaryl, or arylalkyl), azido, hydroxy, amino, alkoxy, halo, alkyl, aminoalkyl, alkenyl, aralkyl, alkynyl, hydroxyalkyl, alkylthio, mercapto, thio, amido, cyano, benzyloxymethyl, and nitro.

In some embodiments, the term "purine" or "pyrimidine" base refers to, but is not limited to, adenine, $N^6$-alkylpurines, $N^6$-acylpurines, $N^6$-benzylpurine, $N^6$-halopurine, $N^6$-vinylpurine, $N^6$-acetylenic purine, $N^6$-acyl purine, $N^6$-hydroxyalkyl purine, $N^6$-alkylaminopurine, $N^6$-alkylthio purine, $N^2$-alkylpurines, $N^2$-alkyl-6-thiopurines, thymine, cytosine, 5-fluorocytosine, 5-methylcytosinyle, 6-azapyrimidineyl (including 6-azacytosine), 2- and/or 4-mercaptopyrmidine, uracil, benzyloxymethyluracil, 5-halouracil (including 5-fluorouracil), $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-iodo-pyrimidine, $C^5$—Br-vinyl pyrimidine, $C^6$—Br-vinyl pyrimidine, $C^5$-nitropyrimidine, $C^5$-aminopyrimidine, $N^2$-alkylpurines, $N^2$-alkyl-6-thiopurines, 5-azacytosine, 5-azauracil, triazolopyridine, imidazolopyridine, pyrrolopyrimidine, triazolopyrimidine, and pyrazolopyrimidine. Purine bases include, but are not limited to, guanine, adenine, hypoxanthine, 7-deazaguanine, 7-deazaadenine, 2-aminopurine, 6-aminopurine, 2,6-diaminopurine, 6-chloropurine, 7-fluoro-7-deazaguanine, 7-fluoro-7-deazaadenine, 2-amino-6-chloropurine, 6-methoxypurine, 6-ethoxypurine, 2-amino-6-hydroxypurine, 2-amino-6-methoxypurine, 2-amino-6-ethoxypurine, 2-amino-6-(n-propoxy)-purine, 2-amino-6-isopropoxypurine, 6-alkylthio-2-aminopurine, 4-azido-2-hydroxy-pyrimidine, and pyrrolotriazine. In some embodiments the purine or pyrimidine is optionally substituted with 1, 2, or 3 groups independently selected from acyl (where is acyl is —C(O)R and R is alkyl, aryl, alkylaryl, or arylalkyl), azido, hydroxy, amino, alkoxy, halo, alkyl, aminoalkyl, alkenyl, aralkyl, alkynyl, hydroxyalkyl, alkylthio, mercapto, thio, amido, cyano, benzyloxymethyl, and nitro. The acyl substituent as defined for nucleobase (e.g. purinyl and pyrimidinyl) is —C(O)R where R is alkyl, aryl, alkylaryl, or arylalkyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" refers to a group of the formula —C(O)R', wherein R' is alkyl (including unsubstituted and substituted alkyl and lower alkyl), cycloalkyl, aryl (including phenyl), alkaryl, arylalkyl (including benzyl), alkoxyalkyl (including methoxymethyl), aryloxyalkyl (such as phenoxymethyl); where each aryl and phenyl is optionally substituted with 1, 2, 3 or 4 groups selected from chloro, bromo, fluoro, iodo, $C_1$ to $C_4$ alkyl, $C_1$ to $C_4$ alkoxy, sulfonate ester, alkylsulphonyl (including methanesulfonyl), alkaryl, arylalkyl (including benzyl), alkoxyalkyl (including methoxymethyl), and aryloxyalkyl (such as phenoxymethyl). Aryl groups in acyl optimally comprise a phenyl group. In particular, acyl groups include acetyl, trifluoroacetyl, methylacetyl, cyclopropylacetyl, propionyl, butyryl, hexanoyl, heptanoyl, octanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "amino acid" refers to naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue including alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl, and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —$NR^X$-G1($S_{C1}$)—C(O)-$Q^1$, wherein $Q^1$ is —$SR^Y$, —$NR^YR^Y$, alkoxyl, cycloalkyloxy, cycloalkylalkyloxy, aryloxy, or aralkyloxy, $R^Y$ is hydrogen or alkyl, $S_C$ is a side chain of a naturally occurring or non-naturally occurring amino acid, G1 is $C_1$-$C_2$ alkylene, and $R^X$ is hydrogen or $R^X$ and $S_{C1}$, together with the atoms to which they are attached, combine to form a five-membered heterocyclic ring. In an embodiment, an amino acid derivative is provided as a substituent of a compound described herein, wherein the substituent is —$NR^X$-G1($S_{C1}$)—C(O)-$Q^1$, wherein $Q^1$ is —$SR^Y$, —$NR^YR^Y$, alkoxyl, $R^Y$ is hydrogen or alkyl, $S_C$ is a side chain of a naturally occurring or non-naturally occurring amino acid, G1 is $C_1$-$C_2$ alkylene, and $R^X$ is hydrogen or $R^X$ and $S_{C1}$, together with the atoms to which they are attached, combine to form a five-membered heterocyclic ring. In an embodiment, an amino acid derivative is provided as a substituent of a compound described herein, wherein the substituent is —O—C(O)-G2($S_{C2}$)—NH-$Q^2$, wherein $Q^2$ is hydrogen, alkoxyl, alkyl, aryl, or aralkyl, $S_{C2}$ is a side chain of a naturally occurring or non-naturally occurring amino acid and G2 is $C_1$-$C_2$ alkylene. In an embodiment, an amino acid derivative is provided as a substituent of a compound described herein, wherein the substituent is —O—C(O)-G2($S_{C2}$)—NH-$Q^2$, wherein $Q^2$ is hydrogen or alkoxyl, $S_{C2}$ is a side chain of a naturally occurring or non-naturally occurring amino acid and G2 is $C_1$-$C_2$ alkyl. In certain embodiments, $Q^2$ and $S_{C2}$, together with the atoms to which they are attached, combine to form a five-membered heterocyclic ring. In certain embodiments, each of G1 and G2 is independently $C_1$ alkylene and each of $S_{C1}$ and $S_{C2}$ is independently hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration. In another embodiment, the amino derivative is —$NR^X$-G1($S_{c1}$)—C(O)-$Q^1$, where $R^X$ is H, G1($S_{c1}$) is CH(CH$_3$) and $Q^1$ is O—$C_3$-$C_6$ unsubstituted alkyl, where CH(CH$_3$) is a D-configuration and in further embodiment a L-configuration.

As used herein, the term "hydroxylalkyl" refers an alkyl group substituted with 1, 2, or 3 hydroxy groups. In some embodiments, "hydroxyalkyl" refers to the group -alkyl-OH, where alkyl is as described herein.

As used herein, the term "aminoalkyl" refers to an alkyl group with an amino substituent, where alkyl and amino are as described herein.

The term "alkylaryl" refers to an aryl group with an alkyl substituent, wherein aryl and alkyl are as defined herein. The term "aralkyl" or "arylalkyl" refers to an alkyl group with an aryl substituent, wherein aryl and alkyl are as defined herein.

The term "alkylheterocyclyl" or "alkylheterocyclo" refers to a heterocyclyl or heterocyclo group with an alkyl substituent. The term "heterocycloalkyl" refers to an alkyl group with a heterocyclo substituent.

The term "alkylheteroaryl" refers to a heteroaryl group with an alkyl substituent. The term "heteroarylalkyl" refers to an alkyl group with a heteroaryl substituent.

"Alkylthio," as used herein refers to an —SR group where R is alkyl, as defined herein, In some embodiments, R is hydroxyalkyl, In some embodiments, the alkyl is unsubstituted.

As used herein, the term "carboxylalkyl" refers to the group -alkyl-C(O)OH, where alkyl is as described herein.

As used herein, the term "aminoiminoaminoalkyl" refers to the group -alkyl-amino-C(=NH)-amino, where alkyl and amino are as described herein.

As used herein, the term "aminocarbonylalkyl" refers to the group -alkyl-C(O)-amino, where alkyl and amino are as described herein.

As used herein, the term "sulfanylalkyl" refers to the group -alkyl-SH, where alkyl is as described herein.

As used herein, the term "carbamoylalkyl" refers to the group -alkyl-C(O)-amino, where alkyl and amino are as described herein.

As used herein, the term "alkylsulfanylalkyl" refers to the group -alkyl-S-alkyl, where alkyl is as described herein.

The term "alkylsulfonyl" as used herein refers to the group —S(O)$_2$R where R is unsubstituted or substituted alkyl.

As used herein, the term "hydroxylarylalkyl" refers to the group -alkyl-aryl-OH, where alkyl and aryl are as described herein.

As used herein when referring to a substituent on a sugar ring of a nucleoside, the term "beta" refers to a substituent on the same side of the plane of the sugar ring as the 5' carbon and the term "alpha" refers to a substituent on the opposite side of the plane of the sugar ring from the 5' carbon. As shown below, substituent "A" is in the "alpha" position, and substituent "B" is in the "beta" position with respect to the 5' carbon:

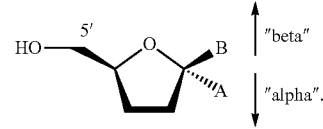

The term "substantially free of" or "substantially in the absence of," when used in connection with an article (including, but not limited to, a compound, a salt thereof, a solvate thereof, a solid form thereof, and the like), refers to the article that includes at least 85% or 90% by weight, in certain embodiments, 95%, 98%, 99%, or 100% by weight, of the designated article. For example, the term "substantially free of" or "substantially in the absence of" with respect to a nucleoside composition refers to a nucleoside composition that includes at least 85% or 90% by weight, in certain embodiments, 95%, 98%, 99%, or 100% by weight, of the designated diastereomer of that nucleoside. In certain embodiments, in the methods and compounds provided herein, the compounds are substantially free of undesignated diastereomers. For another example, the term "substantially free of" or "substantially in the absence of" with respect to a solid form can refer to a solid form that includes at least 85% or 90% by weight, in certain embodiments, 95%, 98%, 99%, or 100% by weight, of the designated solid form. In certain embodiments, in the methods and compounds provided herein, the solid form is substantially free of other solid forms.

Similarly, the term "isolated" with respect to a nucleoside composition refers to a nucleoside composition that includes at least 85%, 90%, 95%, 98%, or 99% to 100% by weight, of the nucleoside, the remainder comprising other chemical species or diastereomers. Similarly, the term "isolated" with respect to a solid form of a compound refers to a solid that includes at least 85%, 90%, 95%, 98%, or 99% to 100% by weight, of such solid form of the compound, the remainder comprising other solid forms of the compound, other compounds, solvents, and/or other impurities The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "cycloalkyl," "alkenyl," "alkynyl," "aryl," "alkoxy," "alkoxycarbonyl," "amino," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl," and "amino acid" groups optionally comprise deuterium at one or more positions where hydrogen atoms are present, and wherein the deuterium composition of the atom or atoms is other than the natural isotopic composition.

Also as used herein, "alkyl," "cycloalkyl," "alkenyl," "alkynyl," "aryl," "alkoxy," "alkoxycarbonyl," "alkoxycarbonylalkyl," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl" and "amino acid" groups optionally comprise carbon-13 at an amount other than the natural isotopic composition.

Also as used herein, "alkyl," "cycloalkyl," "alkenyl," "alkynyl," "aryl," "alkoxy," "alkoxycarbonyl," "alkoxycarbonylalkyl," "carboxyl," "alkylamino," "arylamino," "thioalkyoxy," "heterocyclo," "heteroaryl," "alkylheterocyclo," "alkylheteroaryl," "acyl," "aralkyl," "alkaryl," "purine," "pyrimidine," "carboxyl" for the different formulae described herein (including different referred-to embodiments) are each unsubstituted.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, the $IC_{50}$ refers to an amount, concentration or dosage of a particular test compound that achieves a 50% inhibition of a maximal response in an assay that measures such response.

The term "host," as used herein, refers to any unicellular or multicellular organism in which the virus can replicate, including cell lines and animals, and in certain embodiments, a human. Alternatively, the host can be carrying a part of the Flaviviridae viral genome, whose replication or function can be altered by the compounds of the present invention. The term host specifically includes infected cells, cells transfected with all or part of the Flaviviridae genome and animals, in particular, primates (including chimpanzees) and humans. In most animal applications of the present invention, the host is a human patient. Veterinary applications, in certain indications, however, are clearly anticipated by the present invention (such as chimpanzees).

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In certain embodiments, a therapeutic agent is an agent which is known to be useful for, or has been or is currently being used for the treatment or prevention of a disorder or one or more symptoms thereof.

"Therapeutically effective amount" refers to an amount of a compound or composition that, when administered to a subject for treating a disease, is sufficient to effect such treatment for the disease. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder, or to enhance or improve the prophylactic effect(s) of another therapy (e.g., another prophylactic agent).

Compounds

Provided herein are 3'-substituted methyl or alkynyl nucleoside compounds useful for the treatment of Flaviviridae infections such as HCV infection. The 3'-substituted methyl or alkynyl nucleoside compounds can be formed as described herein and used for the treatment of Flaviviridae infections such as HCV infection.

The compounds described herein may optionally be used in the form of a pharmaceutically acceptable salt. It is understood that references to compounds or pharmaceutically salts thereof would include compounds in present form as well as in different forms, such as polymorphs and solvates (including hydrates), as applicable.

In certain embodiments, provided herein are compounds according to Formula I:

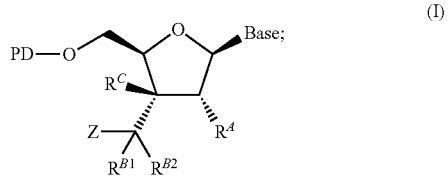

(I)

or a pharmaceutically acceptable salt, solvate, stereoisomeric form, tautomeric form or polymorphic form thereof, wherein: $R^A$ hydroxyl, halo, hydrogen or alkylcarbonyloxy; $R^{B1}$ is hydroxyl, fluoro or alkylcarbonyloxy; $R^{B2}$ is hydrogen, methyl or fluoro; $R^C$ is hydrogen, azido or methyl; Base is a nucleobase; PD

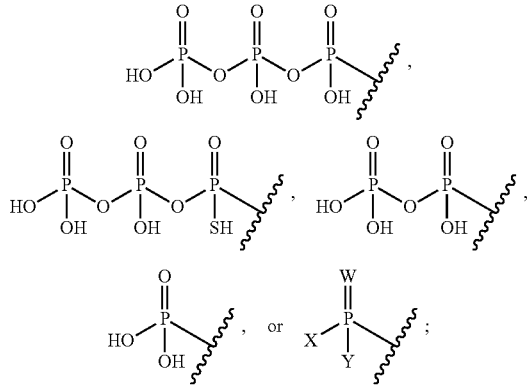

W is S or O; each of X and Y is independently hydrogen, $-OR^1$, $-SR^1$, $-NR^1R^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is $-OR^1$, $-SR^1$, $-NR^1R^2$, or an N-linked or O-linked amino acid residue, or derivative thereof; or Z, $R^{B1}$ and $R^{B2}$ combine to form $C_{2-6}$ alkynylene; each $R^1$ is independently hydrogen, alkyl, aryl, arylalkyl, cycloalkyl, heterocycloalkyl, alkoxylcarbonylalkyl or alkylcarbonylthioalkyl; and each $R^2$ is independently hydrogen, alkyl, cycloalkyl, aryl, or arylalkyl;

with the proviso that when: PD is

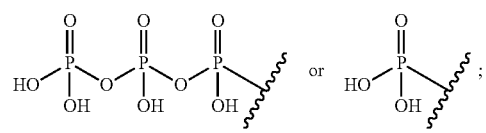 [SMILES: *P(=O)(O)OP(=O)(O)OP(=O)(O)O ; *P(=O)(O)O]

$R^A$ is hydroxyl; $R^{B1}$ is fluoro; $R^{B2}$ is hydrogen; $R^C$ is hydrogen; and Z is hydrogen; then Base is other than guanine; and with the proviso that when: PD is

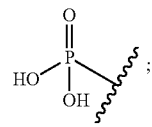

$R^A$ is hydrogen or hydroxyl; $R^{B1}$ is hydrogen; $R^{B2}$ is hydrogen; $R^C$ is hydrogen; and Z is azido or —NH$_2$; then Base is other than thymine.

In certain embodiments, provided herein are compounds according to Formula I:

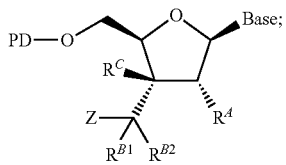

(I)

or a pharmaceutically acceptable salt thereof, wherein:

$R^A$ is hydrogen, hydroxyl, amino, halo, azido, alkylcarbonyloxy, or alkylcarbonylamino;

$R^C$ is hydrogen, alkyl, alkenyl, alkynyl, or azido;

Base is a nucleobase;

PD is alkylcarbonyl,

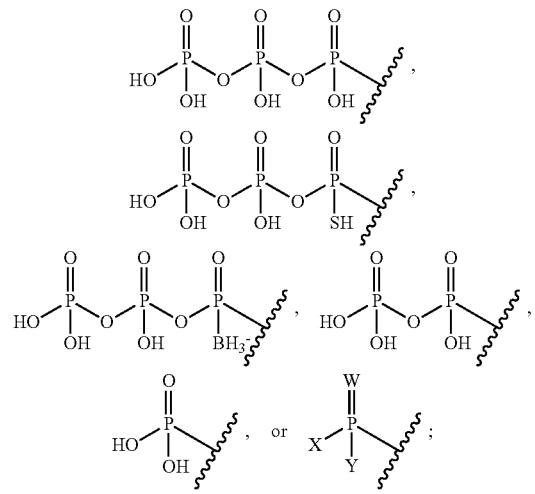

W is S or O;

each of X and Y is independently hydrogen, —$OR^1$, —$SR^1$, —$NR^1R^2$, or an N-linked or O-linked amino acid residue, or derivative thereof;

$R^{B1}$, $R^{B2}$, and Z each independently is hydrogen, alkyl, alkenyl, alkynyl, halo, azido, amino, cyano, nitro, hydroxyl, alkoxyl, alkylcarbonyloxy, or alkylcarbonylamino; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkenylene or $C_{2-6}$ alkynylene;

each $R^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each $R^2$ is independently hydrogen, alkyl, cycloalkyl, aryl, or arylalkyl.

In some embodiments, PD is

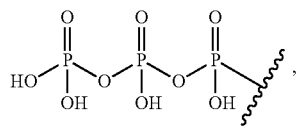

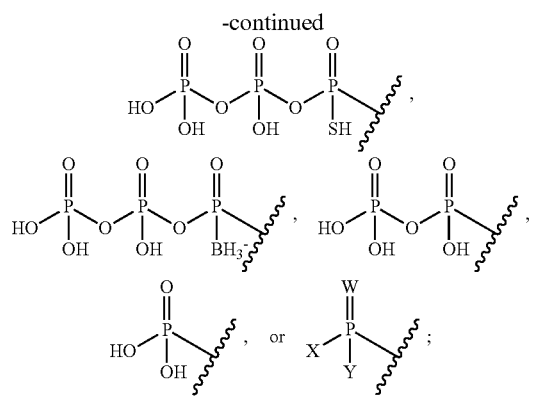

and $R^{B1}$, $R^{B2}$ and Z each independently is hydrogen, alkyl, alkenyl, alkynyl, halo, azido, amino, cyano, nitro, hydroxyl, alkoxyl, alkylcarbonyloxy, or alkylcarbonylamino; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkynylene; and each $R^1$ is independently hydrogen, alkyl, aryl, arylalkyl, cycloalkyl, heterocycloalkyl, alkoxylcarbonylalkyl, or alkylcarbonylthioalkyl.

In certain embodiments, provided are compounds of Formula I, wherein: PD is

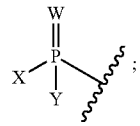

W is S or O; X is OH, Y is —$OR^1$ and $R^1$ is phenyl optionally substituted with 1, 2, or 3 groups independently selected from halo, unsubstituted $C_1$-$C_3$ alkyl, and $NH_2$.

In certain embodiments, provided are compounds of Formula I, wherein:

$R^A$ is hydroxyl, halo, hydrogen, or alkylcarbonyloxy;

$R^{B1}$ is hydroxyl, fluoro, or alkylcarbonyloxy;

$R^{B2}$ is hydrogen, methyl, or fluoro;

$R^C$ is hydrogen, azido, or methyl;

Base is a nucleobase;

PD is

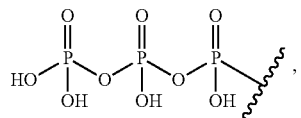

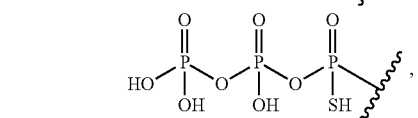

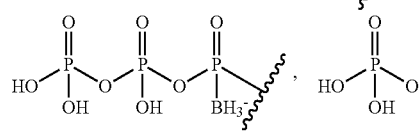

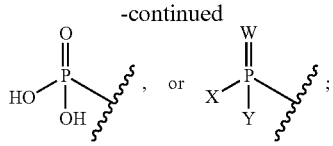, or

W is S or O;
each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene;

each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each R$^2$ is independently hydrogen, alkyl, cycloalkyl, aryl, or arylalkyl.

In some embodiments, PD is

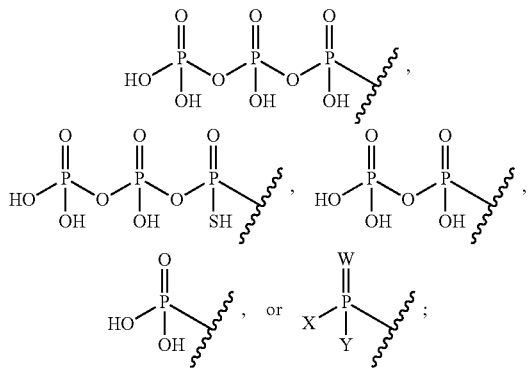

each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene; and each R$^1$ is independently hydrogen, alkyl, aryl, arylalkyl, cycloalkyl, heterocycloalkyl, alkoxylcarbonylalkyl or alkylcarbonylthioalkyl.

In particular embodiments, provided are compounds of Formula I, wherein when PD is

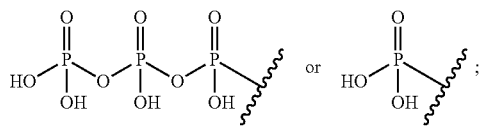 [SMILES: *P(=O)(O)OP(=O)(O)OP(=O)(O)O ; *P(=O)(O)O]

R$^A$ is hydroxyl; R$^{B1}$ is fluoro; R$^{B2}$ is hydrogen; R$^C$ is hydrogen; and Z is hydrogen; then Base is other than guanine.

In particular embodiments, provided are compounds of Formula I, wherein when PD is

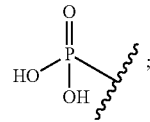

R$^A$ is hydrogen or hydroxyl; R$^{B1}$ is hydrogen; R$^{B2}$ is hydrogen; R$^C$ is hydrogen; and Z is azido or —NH$_2$; then Base is other than thymine.

In certain embodiments according to Formula I, the nucleobase is purine, pyrimidine, adenine, N$^6$-alkylpurines, N$^6$-acylpurines, N$^6$-benzylpurine, N$^6$-halopurine, N$^6$-vinylpurine, N$^6$-acetylenic purine, N$^6$-acyl purine, N$^6$-hydroxyalkyl purine, N$^6$-alkylaminopurine, N$^6$-alkylthio purine, N$^2$-alkylpurines, N$^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, benzyloxymethyluracil, 5-halouracil, 5-fluorouracil, C$^5$-alkylpyrimidines, C$^5$-benzylpyrimidines, C$^5$-halopyrimidines, C$^5$-vinylpyrimidine, C$^5$-acetylenic pyrimidine, C$^5$-acyl pyrimidine, C$^5$-hydroxyalkyl purine, C$^5$-amidopyrimidine, C$^5$-cyanopyrimidine, C$^5$-iodopyrimidine, C$^6$-iodopyrimidine, C$^5$—Br-vinyl pyrimidine, C$^6$—Br-vinyl pyrimidine, C$^5$-nitropyrimidine, C$^5$-amino-pyrimidine, N$^2$-alkylpurines, N$^2$-alkyl-6-thiopurines, 5-azacytosine, 5-azauracil, triazolopyridine, imidazolopyridine, pyrrolopyrimidine, triazolopyrimidine, 8-azaguanine, pyrazolopyrimidine, guanine, hypoxanthine, 7-deazaguanine, 7-deazaadenine, 2-aminopurine, 6-aminopurine, 2,6-diaminopurine, 6-chloropurine, 7-fluoro-7-deazaguanine, 7-fluoro-7-deazaadenine, 2-amino-6-chloropurine, 6-methoxypurine, 6-ethoxypurine, 2-amino-6-hydroxypurine, 2-amino-6-methoxypurine, 2-amino-6-ethoxypurine, 2-amino-6-(n-propoxy)-purine, 2-amino-6-isopropoxypurine, 6-alkylthio-2-aminopurine, 4-azido-2-hydroxy-pyrimidine, or pyrrolotriazine; where is acyl is —C(O)R and R is alkyl, aryl, alkylaryl, or arylalkyl;

R$^A$ is hydrogen, hydroxyl, amino, halo, azido, alkyl-carbonyl-oxy, or alkyl-carbonyl-amino;

R$^C$ is hydrogen, alkyl, alkenyl, alkynyl, or azido;

PD is alkylcarbonyl,

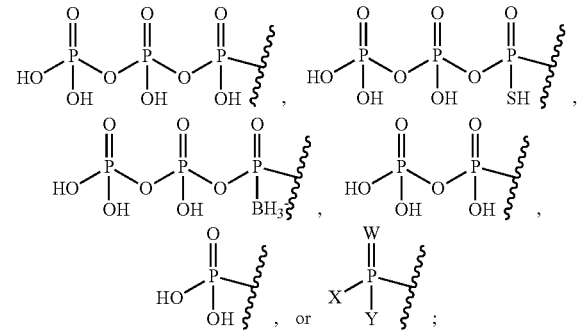

W is S or O;
each of X and Y is independently hydrogen, —OR$^1$, —SR$^1$, —NR$^1$R$^2$, or an N-linked or O-linked amino acid residue, or derivative thereof;

R$^{B1}$, R$^{B2}$, and Z are independently hydrogen, alkyl, alkenyl, alkynyl, halo, azido, amino, cyano, nitro, hydroxyl, alkoxyl, alkyl-carbonyl-oxy, or alkyl-carbonyl-amino; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene;

each R$^1$ is independently hydrogen, alkyl, aryl, aryl-alkyl, cycloalkyl, heterocyclo-alkyl, alkoxy-carbonyl-alkyl, alkoxycarbonyloxyalkyl, or alkyl-carbonyl-thio-alkyl; and each R$^2$ is independently hydrogen, alkyl, cycloalkyl, aryl, or aryl-alkyl;

each alkyl is independently straight or branched C$_{1-10}$ alkyl, unsubstituted or substituted with one or more (in some embodiments, 1, 2, or 3) groups independently selected from halogen, fluoro, chloro, bromo, iodo, hydroxyl, carbonyl, C$_{3-15}$ cycloalkyl, phenyl C$_{1-10}$ alkyl, biphenyl C$_{1-10}$ alkyl, naphthyl C$_{1-10}$ alkyl, sulfanyl, amino, C$_{1-10}$ alkyl-amino, phenyl-amino, biphenyl-amino, naphthyl-amino, C$_{1-10}$ alkoxy, alkoxycarbonyl, alkoxycarbonyloxy, alkylcarbonyl-thio, phenyloxy, biphenyloxy, naphthyloxy, nitro, cyano, sulfonic acid, sulfate, phosphonic acid, phosphate, or phosphonate;

each cycloalkyl is independently a C$_{3-15}$ cycloalkyl, unsubstituted or substituted with one or more (in some embodiments, 1, 2, or 3) groups independently selected from halogen, fluoro, chloro, bromo, iodo, hydroxyl, carbonyl, sulfanyl, amino, C$_{1-10}$ alkylamino, phenyl-amino, biphenyl-amino, naphthylamino, C$_{1-10}$ alkoxy, phenyloxy, biphenyloxy, naphthyloxy, nitro, cyano, sulfonic acid, sulfate, phosphonic acid, phosphate, and phosphonate;

each aryl is independently phenyl, biphenyl, or naphthyl, unsubstituted or substituted by one or more (in some embodiments, 1, 2, or 3) groups independently selected from halogen, fluoro, chloro, bromo, iodo, C$_{1-10}$ alkyl, halo C$_{1-10}$ alkyl, hydroxyl, amino, C$_{1-10}$ alkyl-amino, phenyl-amino, biphenyl-amino, naphthyl-amino, C$_{1-10}$ alkoxy, phenyloxy, biphenyloxy, naphthyloxy, nitro, cyano, sulfonic acid, sulfate, phosphonic acid, phosphate, or phosphonate;

each arylalkyl is independently aryl C$_{1-10}$ alkyl; wherein aryl is defined above;

each heteroaryl is independently each heteroaryl is independently furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, thienopyridyl, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, or xanthenyl; and is unsubstituted or substituted by one or more (in some embodiments, 1, 2, or 3) groups independently selected from halogen, fluoro, chloro, bromo, iodo, C$_{1-10}$ alkyl, halo C$_{1-10}$ alkyl, hydroxyl, amino, C$_{1-10}$ alkyl-amino, phenyl-amino, biphenyl-amino, naphthyl-amino, C$_{1-10}$ alkoxy, phenyloxy, biphenyloxy, naphthyloxy, nitro, cyano, sulfonic acid, sulfate, phosphonic acid, phosphate, or phosphonate;

each alkenyl and alkenylene is independently straight or branched alkenyl and alkenylene, respectively, each having 2 to 11 carbon atoms (unless specified otherwise), and is unsubstituted or substituted by one or more (in some embodiments, 1, 2, or 3) groups independently selected from halogen, fluoro, chloro, bromo, iodo, hydroxyl, carbonyl, sulfanyl, amino, alkylamino, arylamino, alkoxy, aryloxy, nitro, cyano, sulfonic acid, sulfate, phosphonic acid, phosphate, or phosphonate;

each alkynyl and alkynylene is independently straight or branched alkynyl and alkynylene, respectively, each having 2 to 11 carbon atoms (unless specified otherwise), and is unsubstituted or substituted by one or more (in some embodiments, 1, 2, or 3) groups independently selected from halogen, fluoro, chloro, bromo, iodo, hydroxyl, carbonyl, sulfanyl, amino, C$_{1-10}$ alkyl-amino, phenyl-amino, biphenyl-amino, naphthyl-amino, C$_{1-10}$ alkoxy, phenyloxy, biphenyloxy, naphthyloxy, nitro, cyano, sulfonic acid, sulfate, phosphonic acid, phosphate, or phosphonate;

each heteroaryl-alkyl is independently heteroaryl C$_{1-10}$ alkyl; wherein heteroaryl is defined above;

each alkoxy is independently —OR' wherein R' is alkyl or cycloalkyl, and wherein alkyl is C$_{1-10}$ alkyl and cycloalkyl is C$_{3-15}$ cycloalkyl;

each amino is independently —NR$^{1'}$R$^{2'}$ or —NR$^{1'}$—, wherein R$^{1'}$ and R$^{2'}$ are independently hydrogen, alkyl, or cycloalkyl.

In certain embodiments according to Formula I, the nucleobase is adeninyl, purinyl, thyminyl, cytosinyl, pyrimidinyl, uracilyl, triazolopyridinyl, imidazolopyridinyl, pyrrolopyrimidinyl, triazolopyrimidinyl, pyrazolopyrimidinyl, guaninyl, adeninyl, hypoxanthinyl, 7-deazaguaninyl, 7-deazaadeninyl, or pyrrolotriazinyl; each of which is optionally substituted with 1, 2, or 3 groups independently selected from acyl (where is acyl is —C(O)R and R is alkyl, aryl, alkylaryl, or arylalkyl), azido, hydroxy, amino, alkoxy, halo, alkyl, aminoalkyl, alkenyl, aralkyl, alkynyl, hydroxyalkyl, alkylthio, mercapto, thio, amido, cyano, and nitro.

R$^A$ is hydrogen, hydroxyl, amino, halo, azido, alkyl-carbonyl-oxy, or alkyl-carbonyl-amino;

R$^C$ is hydrogen, alkyl, alkenyl, alkynyl, or azido;

PD is alkylcarbonyl

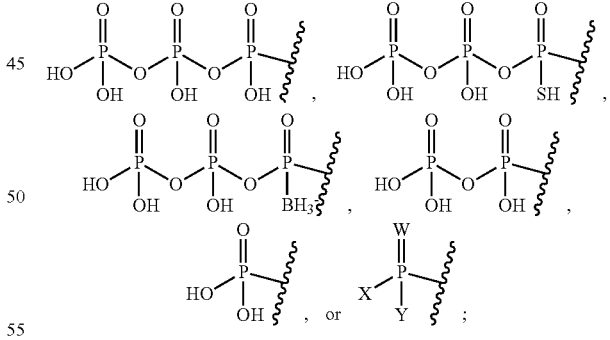

W is S or O;

each of X and Y is independently hydrogen, —OR$^1$, —SR$^1$, —NR$^1$R$^2$, or an N-linked or O-linked amino acid residue, or derivative thereof;

R$^{B1}$, R$^{B2}$, and Z are independently hydrogen, alkyl, alkenyl, alkynyl, halo, azido, amino, cyano, nitro, hydroxyl, alkoxyl, alkyl-carbonyl-oxy, or alkyl-carbonyl-amino; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, $R^{B1}$ and $R^{B2}$ combine to form $C_{2-6}$ alkenylene or $C_{2-6}$ alkynylene;

each $R^1$ is independently hydrogen, alkyl, aryl, aryl-alkyl, cycloalkyl, heterocyclo-alkyl, alkoxy-carbonyl-alkyl, alkoxycarbonyloxyalkyl, or alkyl-carbonyl-thio-alkyl; and each $R^2$ is independently hydrogen, alkyl, cycloalkyl, aryl, or aryl-alkyl;

each alkyl is independently straight or branched $C_{1-10}$ alkyl, unsubstituted or substituted with one or more (in some embodiments, 1, 2, or 3) groups independently selected from halogen, fluoro, chloro, bromo, iodo, hydroxyl, carbonyl, $C_{3-15}$ cycloalkyl, phenyl $C_{1-10}$ alkyl, biphenyl $C_{1-10}$ alkyl, naphthyl $C_{1-10}$ alkyl, sulfanyl, amino, $C_{1-10}$ alkyl-amino, phenyl-amino, biphenyl-amino, naphthyl-amino, $C_{1-10}$ alkoxy, alkoxycarbonyl, alkoxycarbonyloxy, alkylcarbonylthio, phenyloxy, biphenyloxy, naphthyloxy, nitro, cyano, sulfonic acid, sulfate, phosphonic acid, phosphate, or phosphonate;

each cycloalkyl is independently a $C_{3-15}$ cycloalkyl, unsubstituted or substituted with one or more (in some embodiments, 1, 2, or 3) groups independently selected from halogen, fluoro, chloro, bromo, iodo, hydroxyl, carbonyl, sulfanyl, amino, $C_{1-10}$ alkylamino, phenyl-amino, biphenyl-amino, naphthylamino, $C_{1-10}$ alkoxy, phenyloxy, biphenyloxy, naphthyloxy, nitro, cyano, sulfonic acid, sulfate, phosphonic acid, phosphate, and phosphonate;

each aryl is independently phenyl, biphenyl, or naphthyl, unsubstituted or substituted by one or more (in some embodiments, 1, 2, or 3) groups independently selected from halogen, fluoro, chloro, bromo, iodo, $C_{1-10}$ alkyl, halo $C_{1-10}$ alkyl, hydroxyl, amino, $C_{1-10}$ alkyl-amino, phenyl-amino, biphenyl-amino, naphthyl-amino, $C_{1-10}$ alkoxy, phenyloxy, biphenyloxy, naphthyloxy, nitro, cyano, sulfonic acid, sulfate, phosphonic acid, phosphate, or phosphonate;

each arylalkyl is independently aryl $C_{1-10}$ alkyl; wherein aryl is defined above;

each heteroaryl is independently each heteroaryl is independently furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, thienopyridyl, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, or xanthenyl; and is unsubstituted or substituted by one or more (in some embodiments, 1, 2, or 3) groups independently selected from halogen, fluoro, chloro, bromo, iodo, $C_{1-10}$ alkyl, halo $C_{1-10}$ alkyl, hydroxyl, amino, $C_{1-10}$ alkyl-amino, phenyl-amino, biphenyl-amino, naphthyl-amino, $C_{1-10}$ alkoxy, phenyloxy, biphenyloxy, naphthyloxy, nitro, cyano, sulfonic acid, sulfate, phosphonic acid, phosphate, or phosphonate;

each alkenyl and alkenylene is independently straight or branched alkenyl and alkenylene, respectively, each having 2 to 11 carbon atoms (unless specified otherwise), unsubstituted or substituted by one or more (in some embodiments, 1, 2, or 3) groups independently selected from halogen, fluoro, chloro, bromo, iodo, hydroxyl, carbonyl, sulfanyl, amino, alkylamino, arylamino, alkoxy, aryloxy, nitro, cyano, sulfonic acid, sulfate, phosphonic acid, phosphate, or phosphonate;

each alkynyl and alkynylene is independently straight or branched alkynyl and alkynylene, respectively, each having 2 to 11 carbon atoms (unless specified otherwise), and is unsubstituted or substituted by one or more (in some embodiments, 1, 2, or 3) groups independently selected from halogen, fluoro, chloro, bromo, iodo, hydroxyl, carbonyl, sulfanyl, amino, $C_{1-10}$ alkyl-amino, phenyl-amino, biphenyl-amino, naphthyl-amino, $C_{1-10}$ alkoxy, phenyloxy, biphenyloxy, naphthyloxy, nitro, cyano, sulfonic acid, sulfate, phosphonic acid, phosphate, or phosphonate;

each heteroaryl-alkyl is independently heteroaryl $C_{1-10}$ alkyl; wherein heteroaryl is defined above;

each alkoxy is independently —OR' wherein R' is alkyl or cycloalkyl, and wherein alkyl is $C_{1-10}$ alkyl and cycloalkyl is $C_{3-15}$ cycloalkyl;

each amino is independently —$NR^{1'}R^{2'}$ or —$NR^{1'}$—, wherein $R^{1'}$ and $R^{2'}$ are independently hydrogen, alkyl, or cycloalkyl.

In an embodiment, a compound of Formula I is provided wherein $R^C$ is hydrogen.

In certain embodiments, provided herein are compounds according to Formula II:

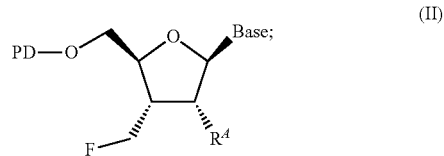

(II)

or a pharmaceutically acceptable salt thereof, wherein PD, Base, and $R^A$ are as described in the context of Formula I.

In certain embodiments, provided herein are compounds according to Formula III:

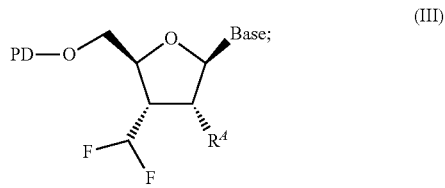

(III)

or a pharmaceutically acceptable salt thereof, wherein PD, Base, and $R^A$ are as described in the context of Formula I.

In certain embodiments, provided herein are compounds according to Formula IV:

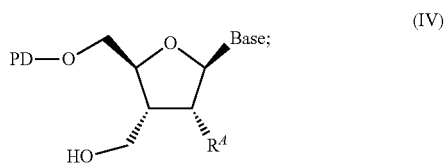

(IV)

or a pharmaceutically acceptable salt thereof, wherein PD, Base, and $R^A$ are as described in the context of Formula I.

In certain embodiments, provided herein are compounds according to Formula XXXVI:

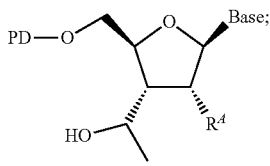

(XXXVI)

or a pharmaceutically acceptable salt thereof, wherein PD, Base, and $R^A$ are as described in the context of Formula I.

In certain embodiments, provided herein are compounds according to Formula XXXVII:

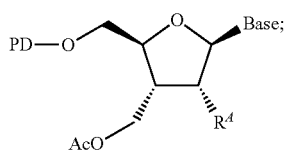

(XXXVII)

or a pharmaceutically acceptable salt thereof, wherein PD, Base, and $R^A$ are as described in the context of Formula I.

In certain embodiments, provided herein are compounds according to Formula XXXVIII:

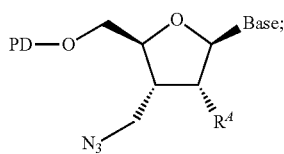

(XXXVIII)

or a pharmaceutically acceptable salt thereof, wherein PD, Base, and $R^A$ are as described in the context of Formula I.

In certain embodiments, provided herein are compounds according to Formula XXXIX:

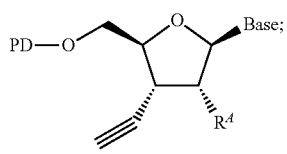

(XXXIX)

or a pharmaceutically acceptable salt thereof, wherein PD, Base, and $R^A$ are as described in the context of Formula I.

In certain embodiments, provided herein are compounds according to Formula XL:

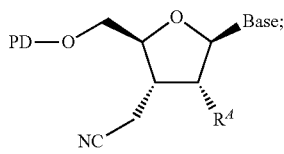

(XL)

or a pharmaceutically acceptable salt thereof, wherein PD, Base, and $R^A$ are as described in the context of Formula I.

In certain embodiments, provided herein are compounds according to Formula XLI:

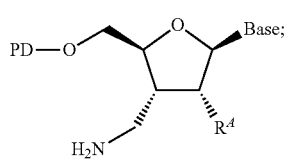

(XLI)

or a pharmaceutically acceptable salt thereof, wherein PD, Base, and $R^A$ are as described in the context of Formula I.

In certain embodiments, provided herein are compounds according to any of Formulas V-Vb:

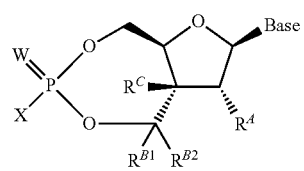

(V)

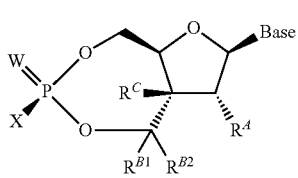

(Va)

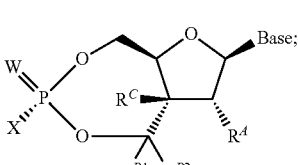

(Vb)

or a pharmaceutically acceptable salt thereof, wherein: X is $-OR^1$, $-SR^1$, $-NR^1R^2$, or an N-linked or O-linked amino acid residue, or derivative thereof; and Base, W, $R^1$, $R^2$, $R^A$, $R^{B1}$, $R^{B2}$ and $R^C$ are as described in the context of Formula I.

In certain embodiments, provided herein are compounds according to any of Formulas VI-VIb:

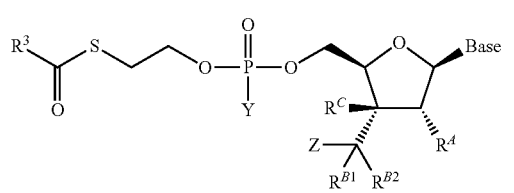

(VI)

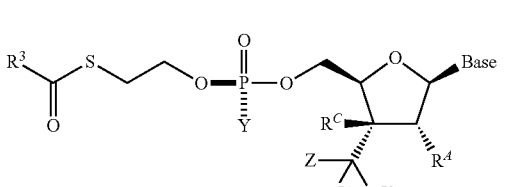

(VIa)

(VIb)

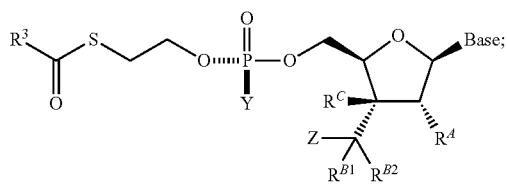

or a pharmaceutically acceptable salt thereof, wherein: $R^3$ is alkyl, alkoxyl, or hydroxylalkyl; and Base, Y, Z, $R^A$, $R^{B1}$, $R^{B2}$ and $R^C$ are as described in the context of Formula I.

In certain embodiments, provided herein are compounds according to any of Formulas VII-VIIbii:

(VII)

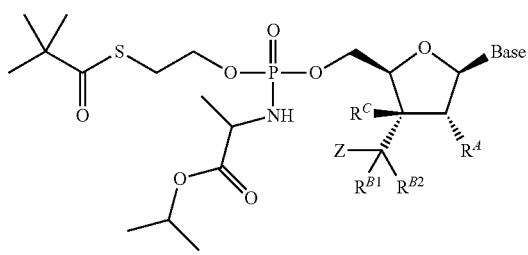

(VIIa)

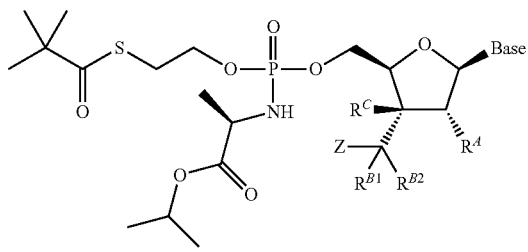

(VIIb)

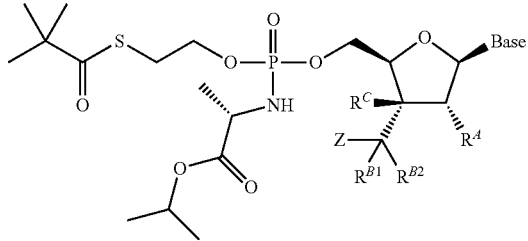

(VIIai)

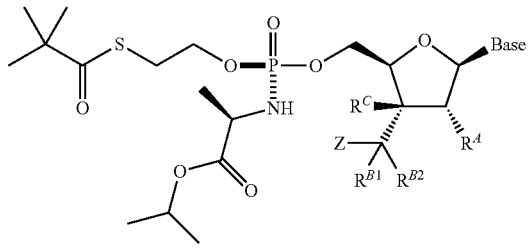

(VIIaii)

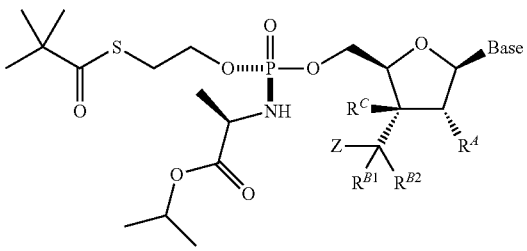

(VIIbi)

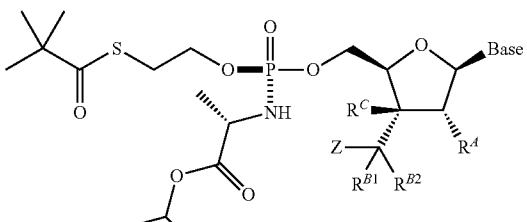

(VIIbii)

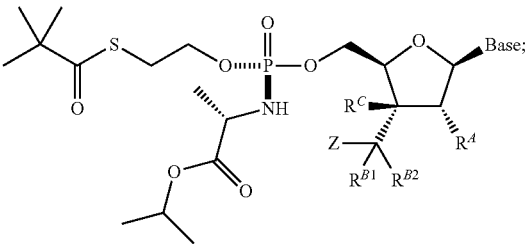

or a pharmaceutically acceptable salt thereof, wherein Base, Z, $R^A$, $R^{B1}$, $R^{B2}$ and $R^C$ are as described in the context of Formula I.

In certain embodiments, provided herein are compounds according to any of Formulas XLII-XLIIbii:

(XLII)

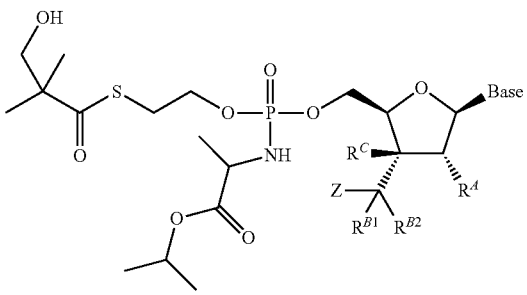

(XLIIa)

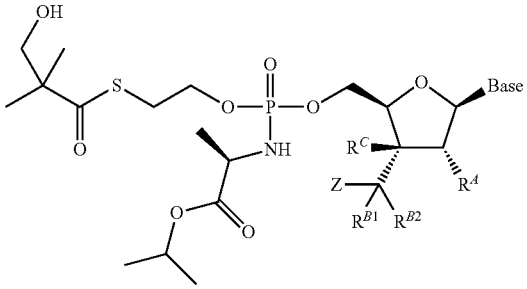

-continued
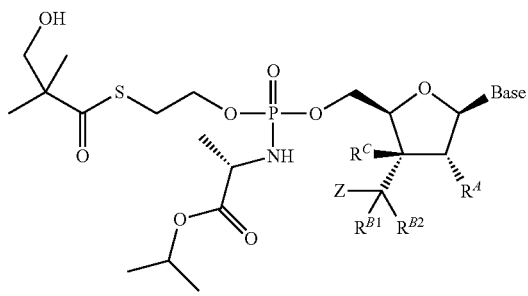
(XLIIb)
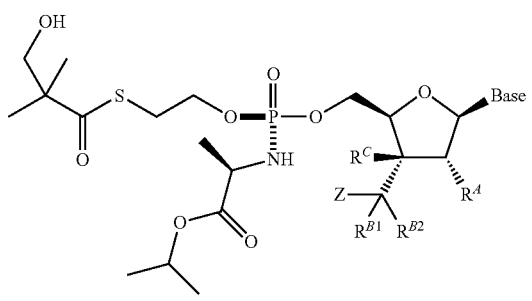
(XLIIai)
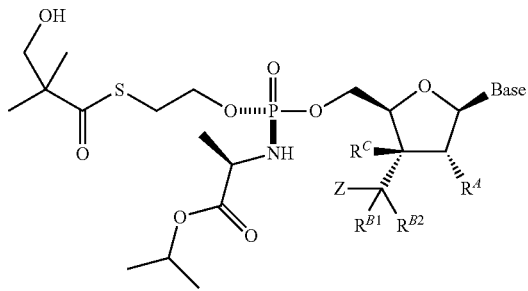
(XLIIaii)

(XLIIbi)
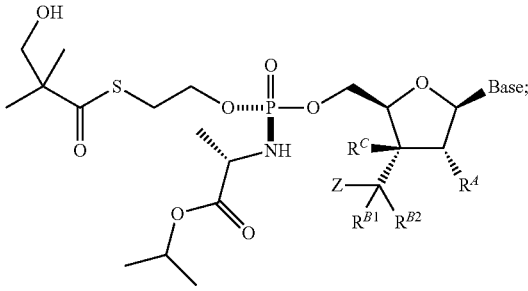
(XLIIbii)
or a pharmaceutically acceptable salt thereof, wherein Base, Z, $R^A$, $R^{B1}$, $R^{B2}$ and $R^C$ are as described in the context of Formula I.
In certain embodiments, provided herein are compounds according to any of Formulas VIII-VIIIbii:
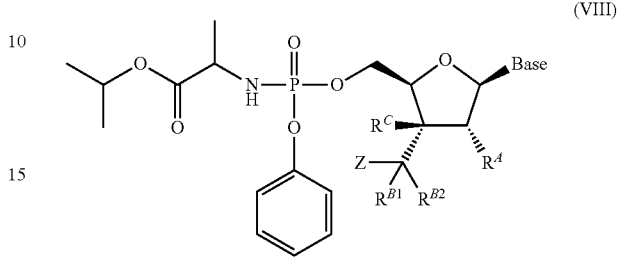
(VIII)
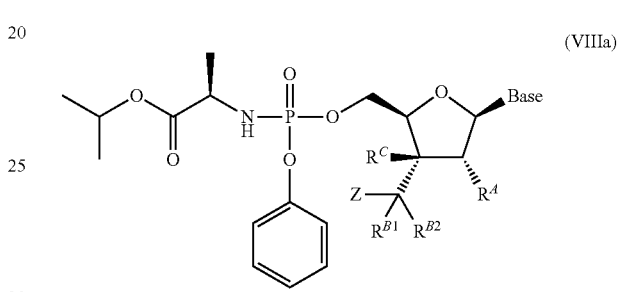
(VIIIa)
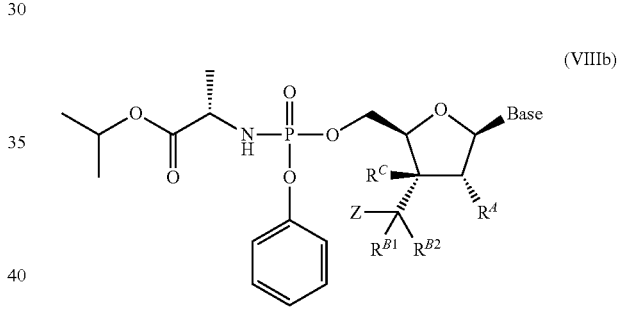
(VIIIb)
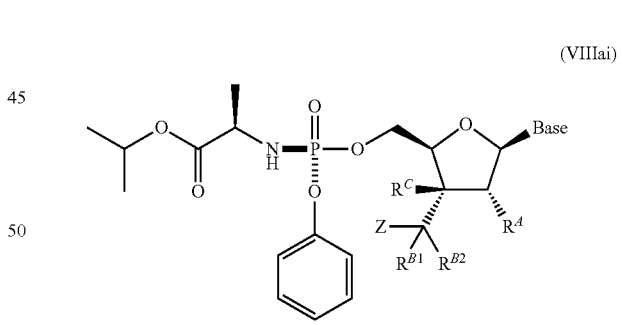
(VIIIai)
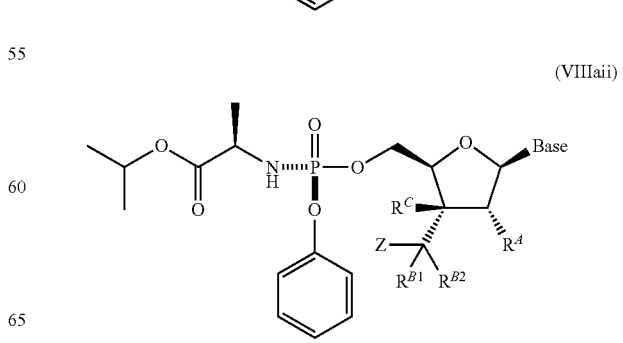
(VIIIaii)

(VIIIbi)

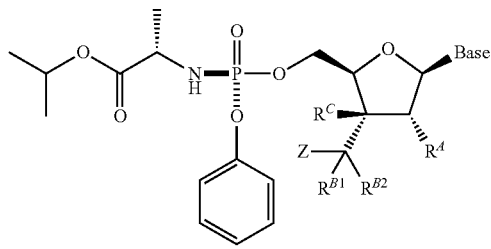

(VIIIbii)

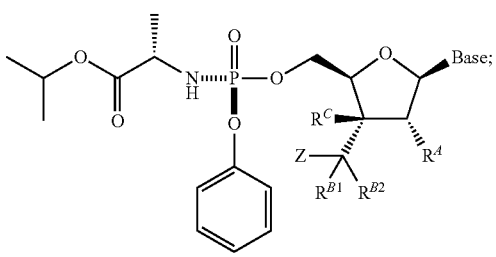

or a pharmaceutically acceptable salt thereof, wherein Base, Z, $R^A$, $R^{B1}$, $R^{B2}$ and $R^C$ are as described in the context of Formula I.

In certain embodiments, provided herein are compounds according to any of Formulas XXXV-XXXVbii:

(XXXV)

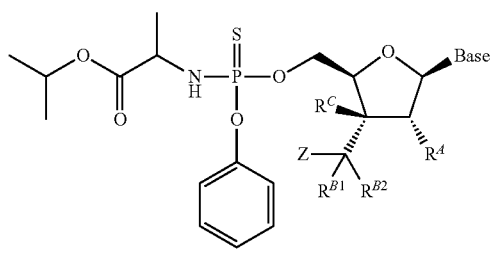

(XXXVa)

(XXXVb)

(XXXVai)

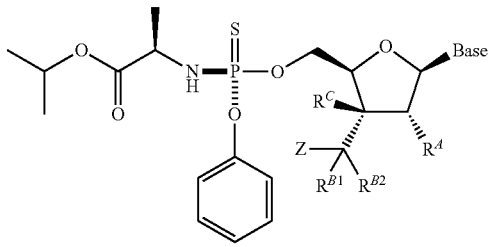

(XXXVaii)

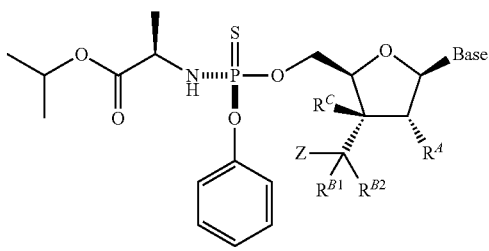

(XXXVbi)

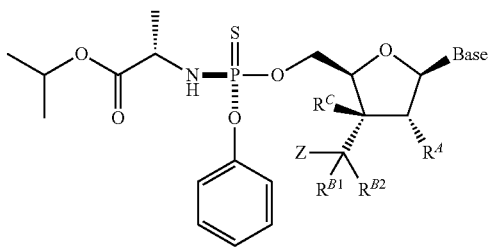

(XXXVbii)

or a pharmaceutically acceptable salt thereof, wherein Base, Z, $R^A$, $R^{B1}$, $R^{B2}$ and $R^C$ are as described in the context of Formula I.

In certain embodiments, provided herein are compounds according to any of Formulas VII-1 to VII-1bii:

(VII-1)

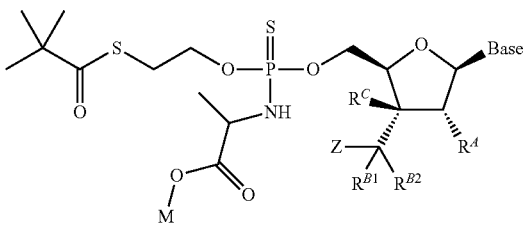

-continued (VII-1a)
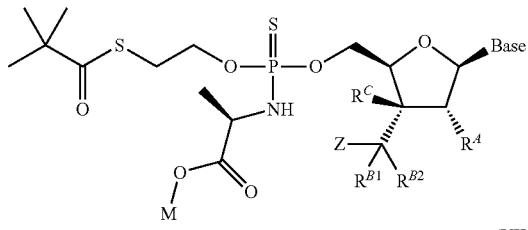

(VII-1b)
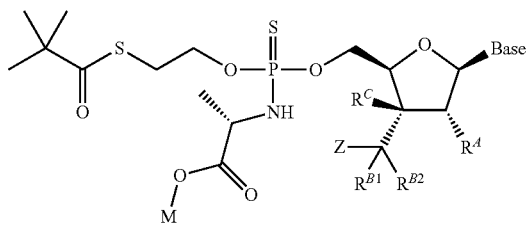

(VII-1ai)
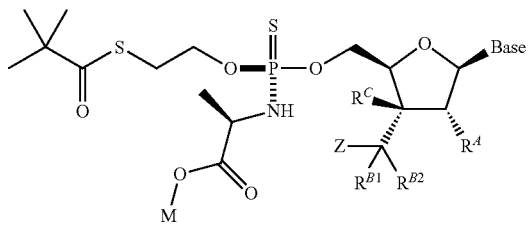

(VII-1aii)
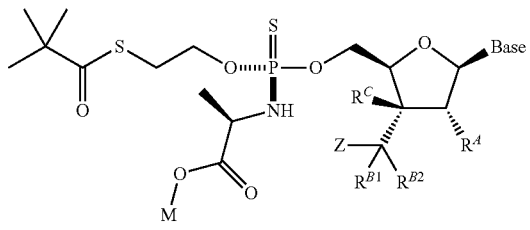

(VII-1bi)
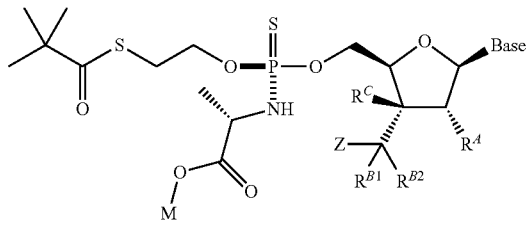

(VII-1bii)
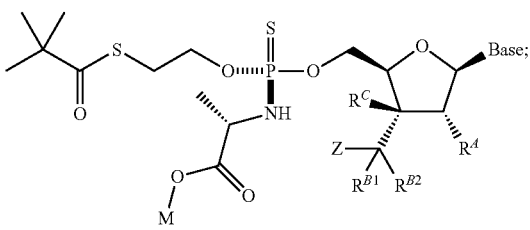

or a pharmaceutically acceptable salt thereof, wherein Base, Z, $R^A$, $R^{B1}$, $R^{B2}$ and $R^C$ are as described in the context of Formula I, and wherein M is unsubstituted $C_1$-$C_6$ alkyl or unsubstituted benzyl group. In some embodiments, M is unsubstituted isopropyl.

In certain embodiments, provided herein are compounds according to any of Formulas XLII-1 to XLII-1bii:

(XLII-1)
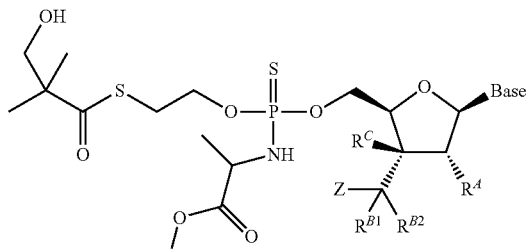

(XLII-1a)
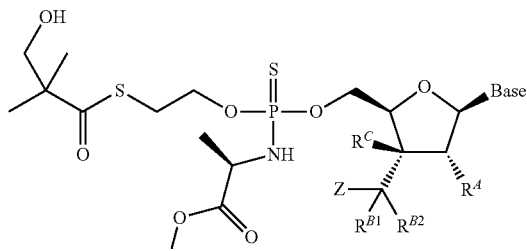

(XLII-1b)
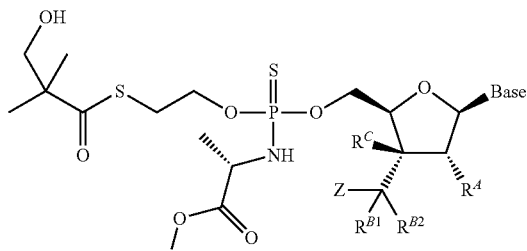

(XLII-1ai)
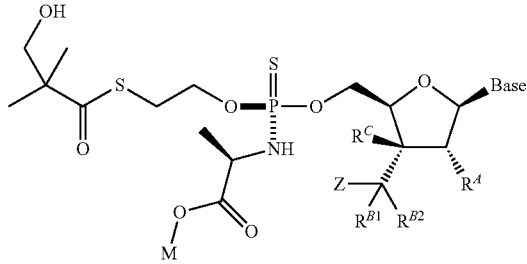

(XLII-1aii)
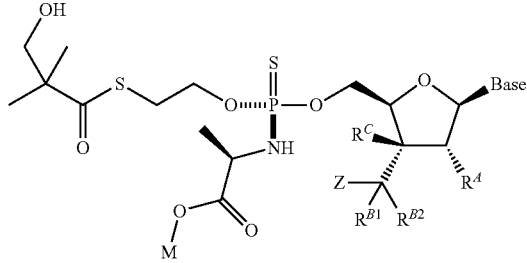

(XLII-1bi)

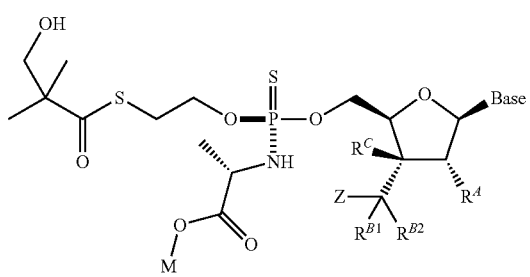

(XLIIb-1ii)

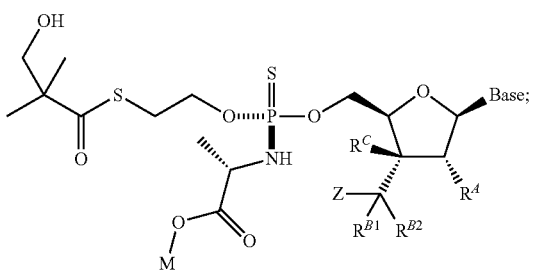

or a pharmaceutically acceptable salt thereof, wherein Base, Z, $R^A$, $R^{B1}$, $R^{B2}$ and $R^C$ are as described in the context of Formula I, and wherein M is unsubstituted $C_1$-$C_6$ alkyl or unsubstituted benzyl group. In some embodiments, M is unsubstituted isopropyl.

In certain embodiments, provided herein are compounds according to any of Formulas VIII-1-VIII-1bii:

(VIII-1)

(VIII-1a)

(VIII-1b)

(VIII-1ai)

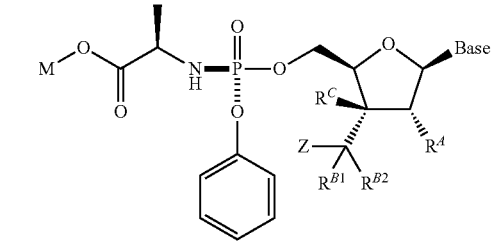

(VIII-1aii)

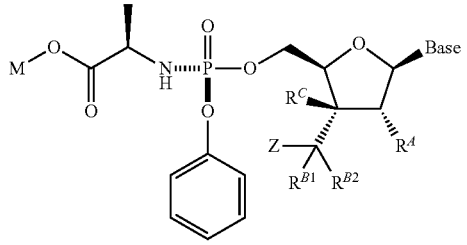

(VIII-1bi)

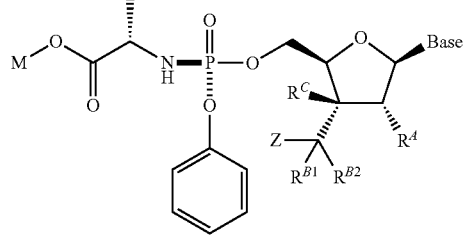

(VIII-1bii)

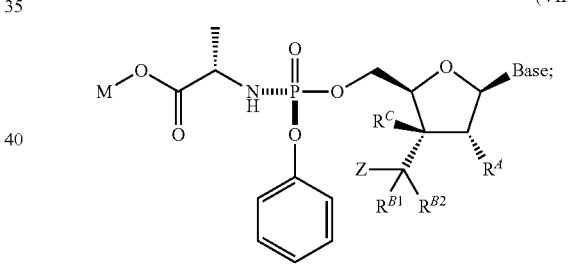

or a pharmaceutically acceptable salt thereof, wherein Base, Z, $R^A$, $R^{B1}$, $R^{B2}$ and $R^C$ are as described in the context of Formula I, and wherein M is unsubstituted $C_1$-$C_6$ alkyl or unsubstituted benzyl group. In some embodiments, M is unsubstituted isopropyl.

In certain embodiments, provided herein are compounds according to any of Formulas XXXV-1-XXXV-1bii:

(XXXV-1)

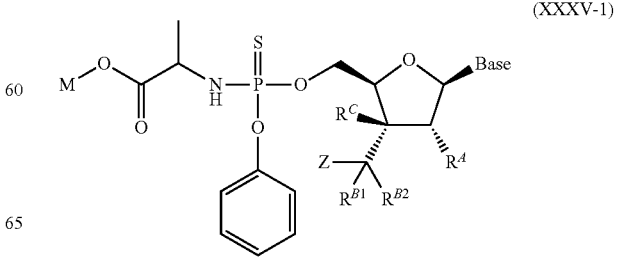

-continued (XXXV-1a)
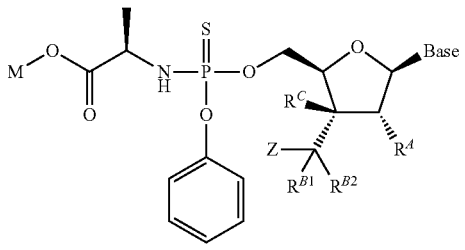

(XXXV-1b)
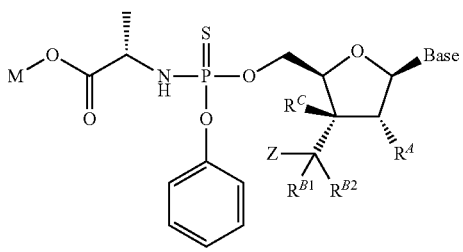

(XXXV-1ai)
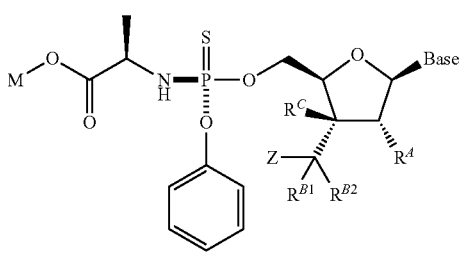

(XXXV-1aii)

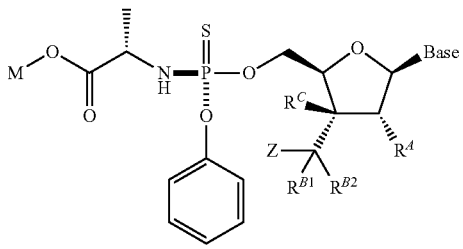

(XXXV-1bi)

(XXXV-1bii)
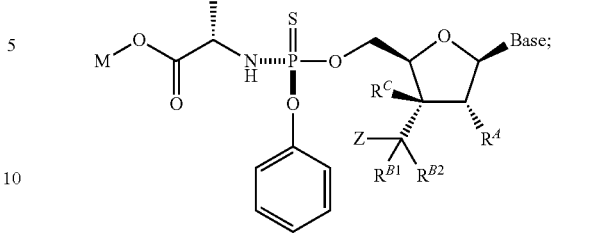

or a pharmaceutically acceptable salt thereof, wherein Base, Z, $R^A$, $R^{B1}$, $R^{B2}$ and $R^C$ are as described in the context of Formula I, and wherein M is unsubstituted $C_1$-$C_6$ alkyl or unsubstituted benzyl group. In some embodiments, M is unsubstituted isopropyl.

In certain embodiments, provided herein are compounds according to any of Formulas I-VIIIbii or XXXV-XLIIbii, wherein Base is:

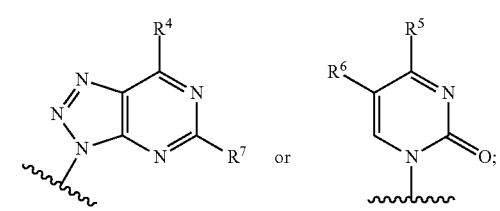

or tautomeric form thereof, wherein: $R^4$ is hydrogen, hydroxyl, alkylthio, alkoxyl, halo, amino, or aminoalkyl; $R^5$ is hydrogen, hydroxyl, amino, or alkoxyl; $R^6$ is hydrogen, halogen, or alkyl; and $R^7$ is hydrogen, hydroxyl or amino. In some embodiments, $R^4$ is hydroxy and $R^7$ is hydrogen; $R^4$ is hydroxy and $R^7$ is $NH_2$; or $R^4$ is hydroxy, alkylthio, alkoxy, halo and $R^7$ is $NH_2$; and all other groups are as defined in any Formula or embodiment herein. In some embodiments, $R^5$ and $R^6$ are hydrogen; $R^5$ is hydroxy and $R^6$ is hydrogen or halo; $R^5$ is hydroxy and $R^6$ is hydrogen or fluoro; or $R^5$ is amino and $R^6$ is hydrogen; and all other groups are as defined in any Formula or embodiment herein. In certain embodiments, provided herein are compounds according to any of Formulas I-VIIIbii or XXXV-XLIIbii, wherein each Base is independently:

or tautomeric form thereof, wherein: $R^4$ is hydrogen, hydroxyl, alkoxyl, amino or aminoalkyl; $R^5$ is hydrogen, hydroxyl, amino, or alkoxyl; $R^6$ is hydrogen, halogen, or alkyl; and $R^7$ is hydrogen, hydroxyl or amino.

In certain embodiments, provided herein are compounds according to any of Formulas IX-XII:

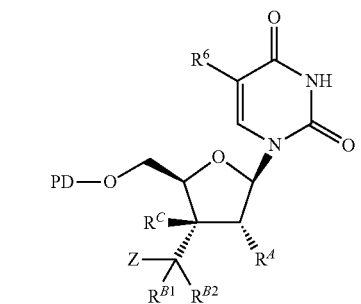
(IX)

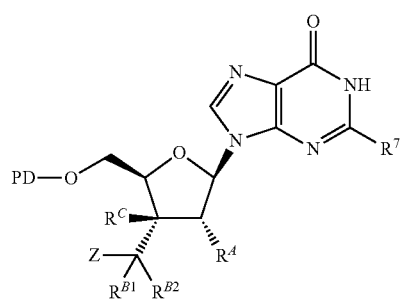
(X)

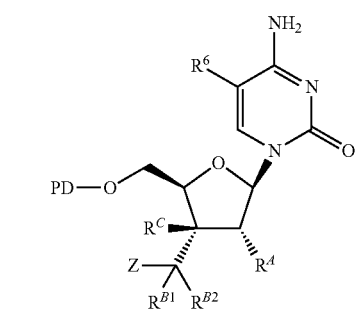
(XI)

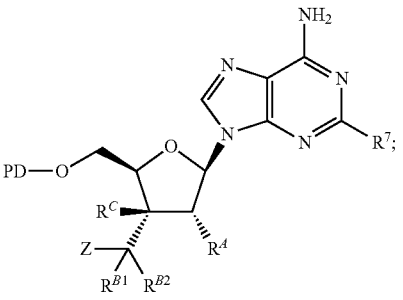
(XII)

or a pharmaceutically acceptable salt thereof, wherein: PD, $R^A$, $R^{B1}$, $R^{B2}$, $R^C$ and Z are as described in the context of Formula I; $R^6$ is hydrogen, halogen, or alkyl; and $R^7$ is hydrogen, hydroxyl, or amino.

In certain embodiments, provided herein are compounds according to any of Formulas XIII-XXI:

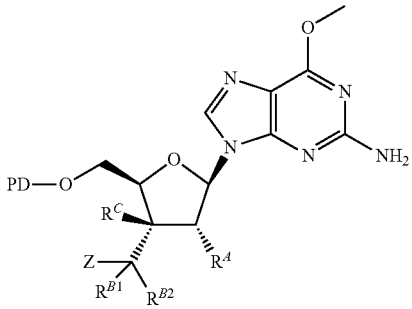
(XIII)

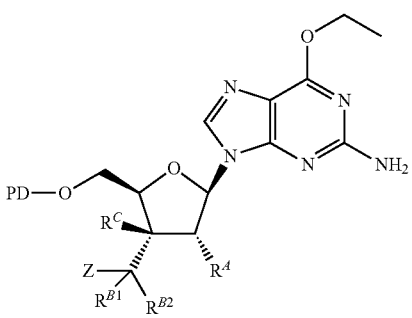
(XIV)

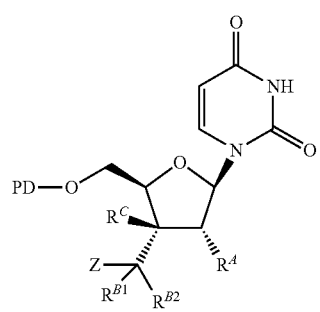
(XV)

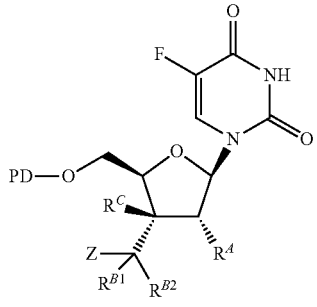
(XVI)

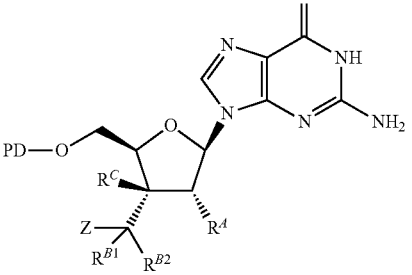
(XVII)

(XVIII)

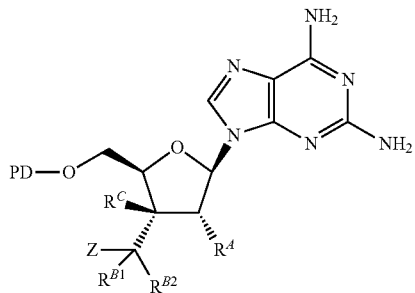

(XIX)

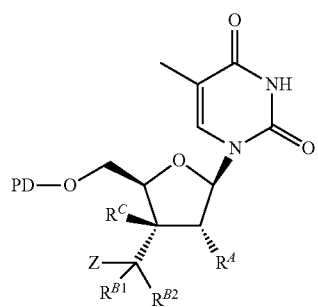

(XX)

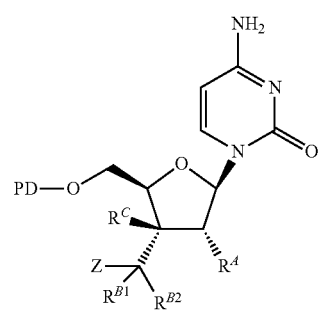

(XXI)

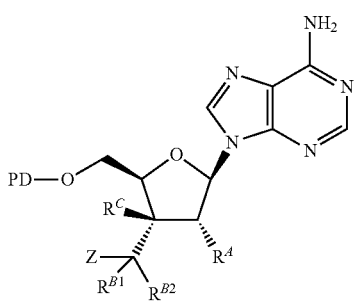

or a pharmaceutically acceptable salt thereof, wherein PD, $R^A$, $R^{B1}$, $R^{B2}$, $R^C$ and Z are as described in the context of Formula I.

In certain embodiments, provided herein are compounds according to Formula XLIII or XLIV:

(XLIII)

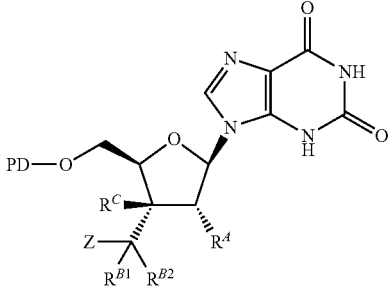

(XLIV)

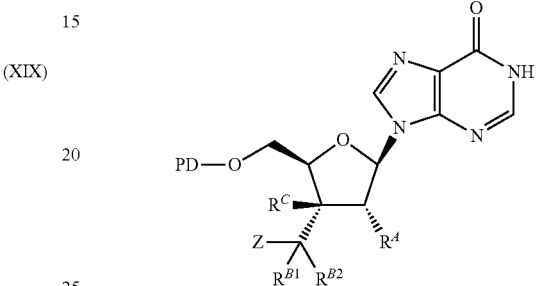

or a pharmaceutically acceptable salt thereof, wherein PD, $R^A$, $R^{B1}$, $R^{B2}$, $R^C$, and Z are as described in the context of Formula I.

In certain embodiments provided herein are compounds according to any of Formulas I-XXI or XXXV-XLIV, wherein $R^A$ is acetyloxy, fluoro, or hydroxyl. In certain embodiments provided herein are compounds according to any of Formulas I-XXI or XXXV-XLIV, wherein $R^A$ is fluoro or hydroxyl. In certain embodiments provided herein are compounds according to any of Formulas I-XXI or XXXV-XLIV, wherein $R^A$ is fluoro. In certain embodiments provided herein are compounds of any of Formulas I-XXI or XXXV-XLIV, wherein $R^A$ is hydroxyl. In certain embodiments provided herein are compounds of any of Formulas I-XXI or XXXV-XLIV, wherein $R^A$ is acetyloxy.

In certain embodiments provided herein are compounds according to any of Formulas I-XXI, XXXV, XLIII, or XLIV, wherein each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is acetyloxy, fluoro, or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is fluoro or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is fluoro. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is acetyloxy. In certain embodiments provided herein are compounds according to any of Formulas I-XXI, XXXV, XLIII, or XLIV, wherein each $R^1$ is independently alkyl, aryl, arylalkyl, cycloalkyl, heterocycloalkyl, alkoxylcarbonylalkyl, or alkylcarbonylthioalkyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; and $R^A$ is acetyloxy, fluoro, or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; and $R^A$ is fluoro or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; and $R^A$ is fluoro. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; and $R^A$ is hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; and $R^A$ is acetyloxy.

In an embodiment, a compound according to any of Formulas I-XXI, XXXV, XLIII, or XLIV is provided wherein $R^C$ is hydrogen. In certain embodiments provided herein are compounds according to any of Formulas I-XXI, XXXV, XLIII, or XLIV, wherein $R^A$ is acetyloxy, fluoro or hydroxyl; and $R^C$ is hydrogen. In certain embodiments provided herein are compounds according to any of Formulas I-XXI, XXXV, XLIII, or XLIV, wherein $R^A$ is fluoro or hydroxyl; and $R^C$ is hydrogen. In certain embodiments provided herein are compounds according to any of Formulas I-XXI, XXXV, XLIII, or XLIV, wherein $R^A$ is fluoro and $R^C$ is hydrogen. In certain embodiments provided herein are compounds of any of Formulas I-XXI, XXXV, XLIII, or XLIV, wherein $R^A$ is hydroxyl and $R^C$ is hydrogen. In certain embodiments provided herein are compounds of any of Formulas I-XXI, XXXV, XLIII, or XLIV, wherein $R^A$ is acetyloxy and $R^C$ is hydrogen.

In certain embodiments provided herein are compounds according to any of Formulas I-XXI, XXXV, XLIII, or XLIV, wherein each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl: and $R^C$ is hydrogen. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; $R^C$ is hydrogen; and $R^A$ is acetyloxy, fluoro, or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; $R^C$ is hydrogen; and $R^A$ is fluoro or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; $R^C$ is hydrogen; and $R^A$ is fluoro. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; $R^C$ is hydrogen; and $R^A$ is hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; $R^C$ is hydrogen; and $R^A$ is acetyloxy. In certain embodiments provided herein are compounds according to any of Formulas I-XXI, XXXV, XLIII, or XLIV, wherein each $R^1$ is independently alkyl, aryl, arylalkyl, cycloalkyl, heterocycloalkyl, alkoxylcarbonylalkyl, or alkylcarbonylthioalkyl: and $R^C$ is hydrogen. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; $R^C$ is hydrogen; and $R^A$ is acetyloxy, fluoro, or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; $R^C$ is hydrogen; and $R^A$ is fluoro or hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; $R^C$ is hydrogen; and $R^A$ is fluoro. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; $R^C$ is hydrogen; and $R^A$ is hydroxyl. In certain embodiments provided herein are compounds according to any of Formulas I-XXI, XXXV, XLIII, or XLIV, wherein: each $R^1$ is independently alkyl, aryl, arylalkyl, cycloalkyl, heterocycloalkyl, alkoxylcarbonylalkyl, or alkylcarbonylthioalkyl; $R^C$ is hydrogen; and $R^A$ is acetyloxy.

In some embodiments, $R^A$ is hydrogen, —OH, —OAc, azido, —NH$_2$, or —F; and all other groups are as defined in any of the formula or embodiments described herein. In some embodiments, $R^A$ is —OH; and all other groups are as defined in any of the formula or embodiments described herein. In some embodiments, $R^A$ is —OAc; and all other groups are as defined in any of the formula or embodiments described herein. In some embodiments, $R^A$ is —F; and all other groups are as defined in any of the formula or embodiments described herein.

In some embodiments, $R^C$ is hydrogen or —N$_3$; and all other groups are as defined in any of the formula or embodiments described herein. In some embodiments, $R^C$ is hydrogen; and all other groups are as defined in any of the formula or embodiments described herein. In some embodiments, $R^C$ is —N$_3$; and all other groups are as defined in any of the formula or embodiments described herein.

In some embodiments, —C($R^{B1}$)($R^{B2}$)(Z) is —CH$_2$F, —CH$_2$OH, —CHF$_2$, —CF$_3$, —C(CH$_3$)OH, —CH$_2$OAc, —CH$_2$N$_3$,

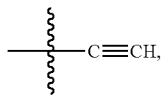 [SMILES: *C#C]

—CH$_2$CN, or —CH$_2$NH$_2$; and all other groups are as defined in any of the formula or embodiments described herein. In some embodiments, —C($R^{B1}$)($R^{B2}$)(Z) is —CH$_2$F; and all other groups are as defined in any of the formula or embodiments described herein. In some embodiments, —C($R^{B1}$)($R^{B2}$)(Z) is —CH$_2$OH; and all other groups are as defined in any of the formula or embodiments described herein. In some embodiments, —C($R^{B1}$)($R^{B2}$)(Z) is —CHF$_2$; and all other groups are as defined in any of the formula or embodiments described herein. In some embodiments, —C($R^{B1}$)($R^{B2}$)(Z) is —C(CH$_3$)OH; and all other groups are as defined in any of the formula or embodiments described herein. In some embodiments, —C($R^{B1}$)($R^{B2}$)(Z) is —C(CH$_3$)OH; and all other groups are as defined in any of the formula or embodiments described herein. In some embodiments, —C($R^{B1}$)($R^{B2}$)(Z) is —CH$_2$N$_3$; and all other groups are as defined in any of the formula or embodiments described herein. In some embodiments, —C($R^{B1}$)($R^{B2}$)(Z) is

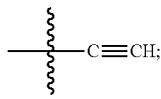

and all other groups are as defined in any of the formula or embodiments described herein. In some embodiments, —C($R^{B1}$)($R^{B2}$)(Z) is —CH$_2$CN; and all other groups are as defined in any of the formula or embodiments described herein. In some embodiments, —C($R^{B1}$)($R^{B2}$)(Z) is —CH$_2$NH$_2$; and all other groups are as defined in any of the formula or embodiments described herein.

In some embodiments, W is O; and all other groups are as defined in any of the formula or embodiments described herein. In some embodiments, W is S; and all other groups are as defined in any of the formula or embodiments described herein.

In some embodiments, Base is adeninyl, purinyl, thyminyl, cytosinyl, pyrimidinyl, uracilyl, cytidinyl, triazolopyridinyl, imidazolopyridinyl, pyrrolopyrimidinyl, triazolopyrimidinyl, pyrazolopyrimidinyl, guaninyl, adeninyl, hypoxanthinyl, 7-deazaguaninyl, 7-deazaadeninyl, or pyrrolotriazinyl; each of which is optionally substituted with 1, 2, or 3 groups independently selected from acyl (where is acyl is —C(O)R and R is alkyl, aryl, alkylaryl, or arylalkyl), hydroxy, amino, alkoxy, halo, alkyl, aminoalkyl, alkenyl, aralkyl, alkynyl, hydroxyalkyl, alkylthio, mercapto, thio, amido, cyano, and nitro; and all other groups are as defined in any of the formula or embodiments described herein.

In some embodiments, X is hydrogen, an N-linked amino acid residue or derivative thereof, or —OR$^1$ and Y is —OR$^1$ or Y and Z together with the atoms to which they are attached, combine to form a seven membered heterocyclic ring wherein Y and Z together represent a single divalent —O—; and all other groups are as defined in any of the formula or embodiments described herein. In some embodiments, R$^1$ is unsubstituted aryl; and all other groups are as defined in any of the Formula or embodiments described herein. In some embodiments, R$^1$ is unsubstituted phenyl; and all other groups are as defined in any of the Formula or embodiments described herein. In some embodiments, R$^1$ is phenyl substituted with 1, 2, or 3 groups independently selected from halo, unsubstituted C$_1$-C$_3$ alkyl, and NH$_2$; and all other groups are as defined in any of the Formula or embodiments described herein.

In some embodiments, X is hydrogen, an N-linked amino acid residue or derivative thereof, or —OR$^1$ and Y is —OR$^1$; and all other groups are as defined in any of the formula or embodiments described herein. In some embodiments, X is hydrogen and Y is OR$^1$; and all other groups are as defined in any of the formula or embodiments described herein. In some embodiments, X and Y are OR$^1$; and all other groups are as defined in any of the formula or embodiments described herein. In some embodiments, each R$^1$ is independently hydrogen or unsubstituted aryl; and all other groups are as defined in any of the Formula or embodiments described herein. In some embodiments, each R$^1$ is independently hydrogen or unsubstituted phenyl; and all other groups are as defined in any of the Formula or embodiments described herein. In some embodiments, each R$^1$ is independently hydrogen or phenyl substituted with 1, 2, or 3 groups independently selected from halo, unsubstituted C$_1$-C$_3$ alkyl, and NH$_2$; and all other groups are as defined in any of the Formula or embodiments described herein. In some embodiments, one R$^1$ is hydrogen and the other R$^1$ is phenyl substituted with 1, 2, or 3 groups independently selected from halo, unsubstituted C$_1$-C$_3$ alkyl, and NH$_2$; and all other groups are as defined in any of the Formula or embodiments described herein.

In some embodiments, X is an N-linked amino acid residue or derivative thereof and Y is OR$^1$; and all other groups are as defined in any of the formula or embodiments described herein. In some embodiments, X is —NR$^X$-G1 (S$_{C1}$)—C(O)-Q$^1$, where Q$^1$ is alkoxy, cycloalkyloxy, cycloalkylalkyloxy, aryloxy, or aralkyloxy; G1 is C$_1$-C$_2$ alkylene; R$^X$ is hydrogen and S$_{C1}$ is hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl; or R$^X$ and S$_{C1}$, together with the atoms to which they are attached, combine to form a five-membered heterocyclic ring; and Y is OR$^1$; and all other groups are as defined in any of the Formula or embodiments described herein. In some embodiments, X is —NR$^X$-G1 (S$_{C1}$)—C(O)-Q$^1$, where Q$^1$ is alkoxy, cycloalkyloxy, or aralkyloxy; G1 is C$_1$ alkylene; R$^X$ is hydrogen and S$_{C1}$ is alkyl, or arylalkyl; and Y is OR$^1$; and all other groups are as defined in any of the Formula or embodiments described herein. In some embodiments, R$^1$ is unsubstituted aryl; and all other groups are as defined in any of the Formula or embodiments described herein. In some embodiments, R$^1$ is unsubstituted phenyl; and all other groups are as defined in any of the Formula or embodiments described herein.

In some embodiments, X is hydrogen, an N-linked amino acid residue or derivative thereof, or —OR$^1$ and Y and Z together with the atoms to which they are attached, combine to form a seven membered heterocyclic ring wherein Y and Z together represent a single divalent —O—; and all other groups are as defined in any of the formula or embodiments described herein. In some embodiments, X is hydrogen and Y and Z together with the atoms to which they are attached, combine to form a seven membered heterocyclic ring wherein Y and Z together represent a single divalent —O—;

and all other groups are as defined in any of the formula or embodiments described herein. In some embodiments, X is —OR$^1$ and Y and Z together with the atoms to which they are attached, combine to form a seven membered heterocyclic ring wherein Y and Z together represent a single divalent —O—; and all other groups are as defined in any of the formula or embodiments described herein. In some embodiments, R$^1$ is unsubstituted aryl; and all other groups are as defined in any of the Formula or embodiments described herein. In some embodiments, R$^1$ is unsubstituted phenyl; and all other groups are as defined in any of the Formula or embodiments described herein.

In some embodiments, X is an N-linked amino acid residue or derivative thereof and Y and Z together with the atoms to which they are attached, combine to form a seven membered heterocyclic ring wherein Y and Z together represent a single divalent —O—; and all other groups are as defined in any of the formula or embodiments described herein. In some embodiments, X is —NR$^X$-G1(S$_{C1}$)—C(O)-Q$^1$, where Q$^1$ is alkoxy, cycloalkyloxy, cycloalkylalkyloxy, aryloxy, or aralkyloxy; G1 is C$_1$-C$_2$ alkylene; R$^X$ is hydrogen and S$_{C1}$ is hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl, or hydroxylarylalkyl; or R$^X$ and S$_{C1}$, together with the atoms to which they are attached, combine to form a five-membered heterocyclic ring; and Y and Z together with the atoms to which they are attached, combine to form a seven membered heterocyclic ring wherein Y and Z together represent a single divalent —O—; and all other groups are as defined in any of the formula or embodiments described herein. In some embodiments, X is —NR$^X$-G1(S$_{C1}$)—C(O)-Q$^1$, where Q$^1$ is alkoxy, cycloalkyloxy, or aralkyloxy; G1 is C$_1$ alkylene; R$^X$ is hydrogen and S$_{C1}$ is alkyl or, arylalkyl; and Y and Z together with the atoms to which they are attached, combine to form a seven membered heterocyclic ring wherein Y and Z together represent a single divalent —O—; and all other groups are as defined in any of the formula or embodiments described herein.

In some embodiments, the compound of Formula I is that where
R$^A$ is hydrogen, —OH, —OAc, azido, —NH$_2$, or —F;
R$^C$ is hydrogen or —N$_3$;
W is O;
Base is

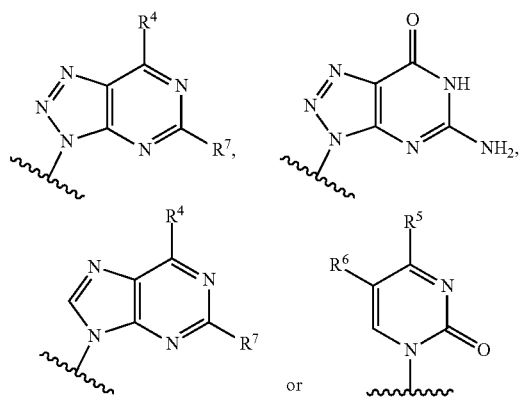

or a tautomer thereof;

R$^4$ is hydrogen, hydroxyl, unsubstituted alkylthio, hydroxyalkylthio, unsubstituted alkoxy, halo, or —NH$_2$;
R$^5$ is hydrogen, hydroxyl, or —NH$_2$;
R$^6$ is hydrogen, or halogen;
R$^7$ is hydrogen, or —NH$_2$.
—C(R$^{B1}$)(R$^{B2}$)(Z) is —CH$_2$F, —CH$_2$OH, —CHF$_2$, —C(CH$_3$)OH, —CH$_2$OAc, —CH$_2$N$_3$,

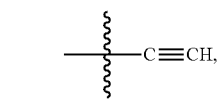

—CH$_2$CN, or —CH$_2$NH$_2$; X is hydrogen, an N-linked amino acid residue or derivative thereof, or —OR$^1$; and Y is —OR$^1$ or —C(R$^{B1}$)(R$^{B2}$) is CH$_2$; X is hydrogen, an N-linked amino acid residue or derivative thereof, or —OR$^1$; and Y and Z together with the atoms to which they are attached, combine to form a seven membered heterocyclic ring wherein Y and Z together represent a single divalent —O—;

each R$^1$ is independently hydrogen, unsubstituted alkyl, unsubstituted phenyl, unsubstituted phenylalkyl, alkylcarbonylthioalkyl, hydroxyalkylcarbonylthioalkyl, alkoxycarbonylalkyl, or alkoxycarbonyloxyalkyl. In some embodiments, X is —NR$^X$-G1(S$_{C1}$)—C(O)-Q$^1$, where Q$^1$ is alkoxy, cycloalkyloxy, or aralkyloxy; G1 is C$_1$ alkylene; R$^X$ is hydrogen and S$_{C1}$ is alkyl or, arylalkyl, In certain embodiments provided herein is a compound according to any of Formulas 101-122bii:

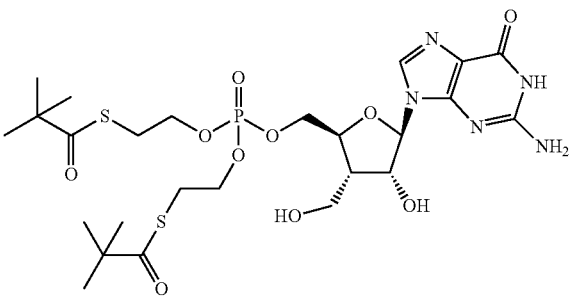

(101)

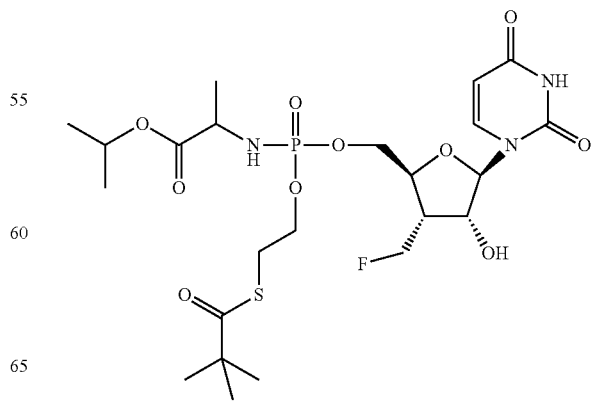

(102)

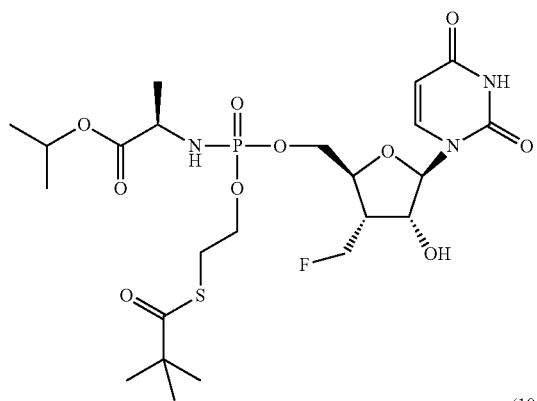
(102a)
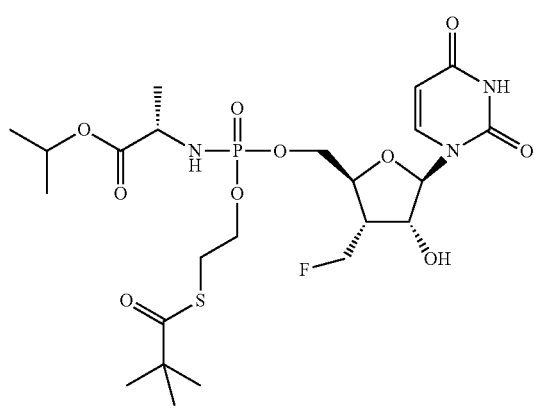
(102b)
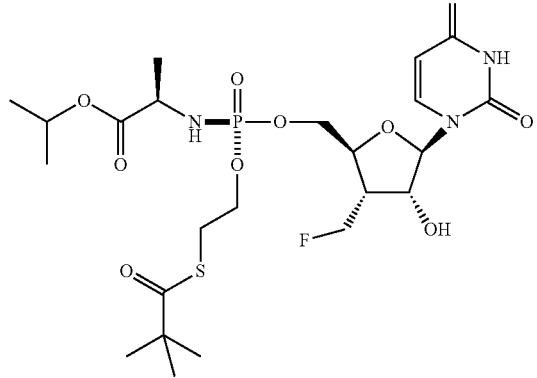
(102ai)
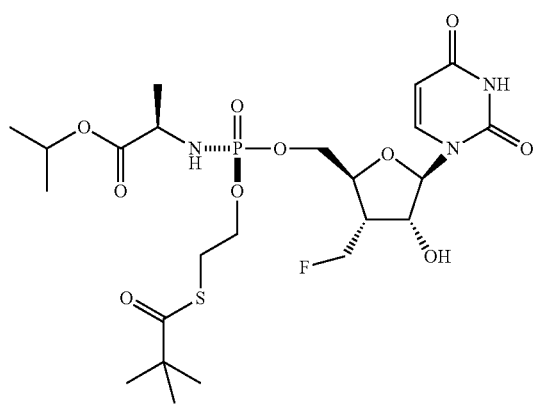
(102aii)
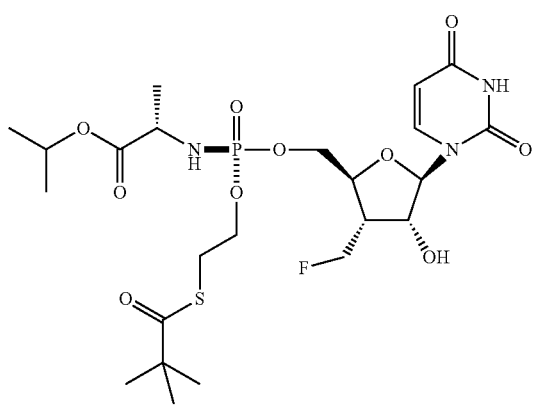
(102bi)
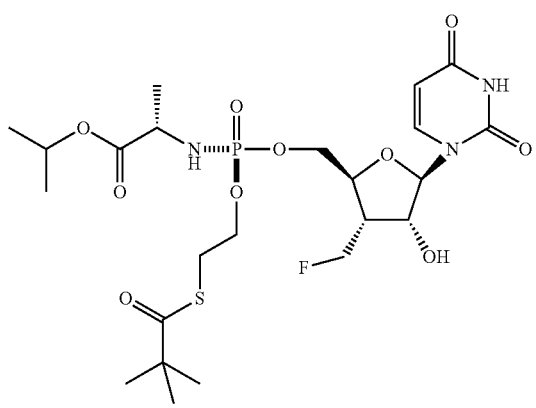
(102bii)
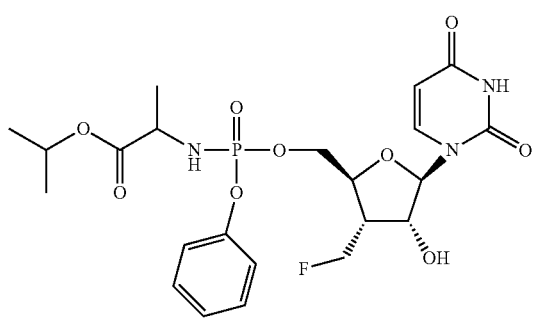
(103)
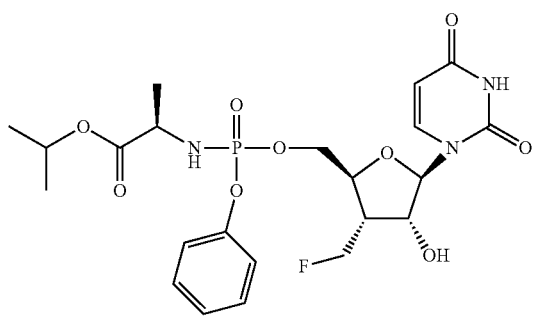
(103a)

53
-continued
(103b)
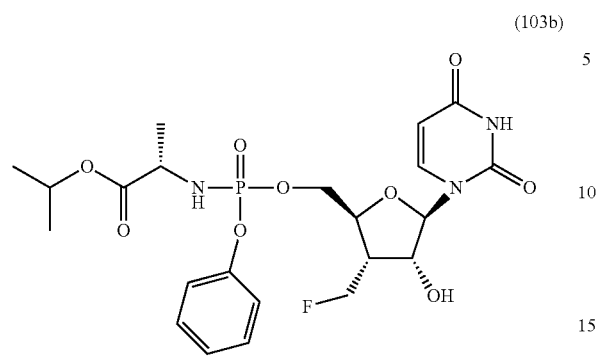
(103ai)
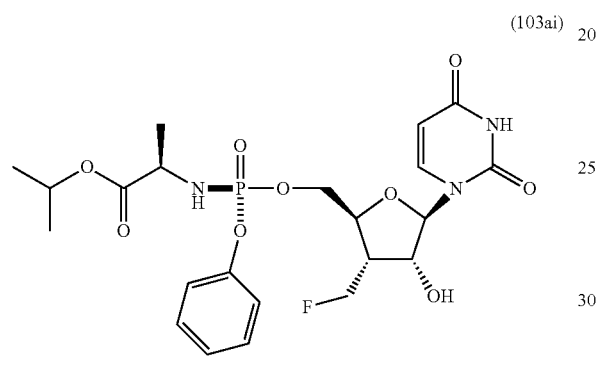
(103aii)
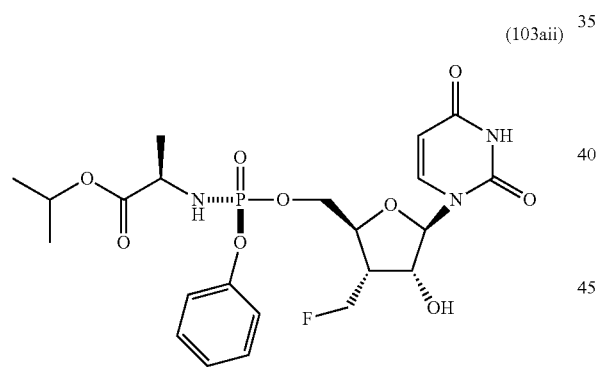
(103bi)
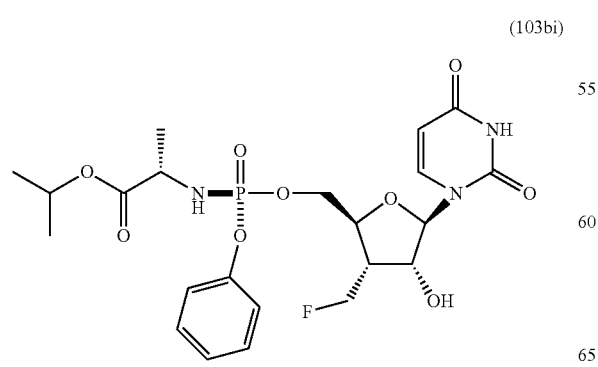
54
-continued
(103bii)
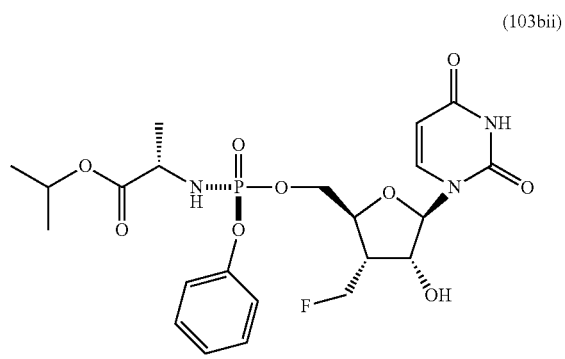
(104)
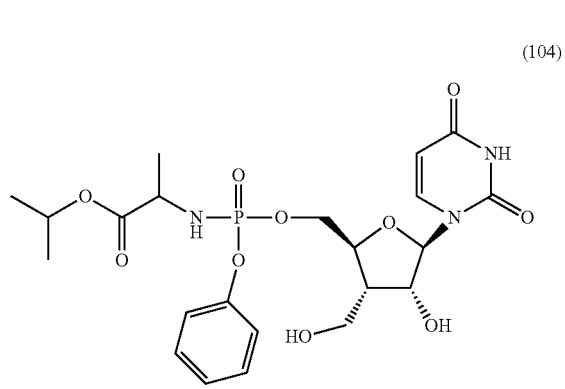
(104a)
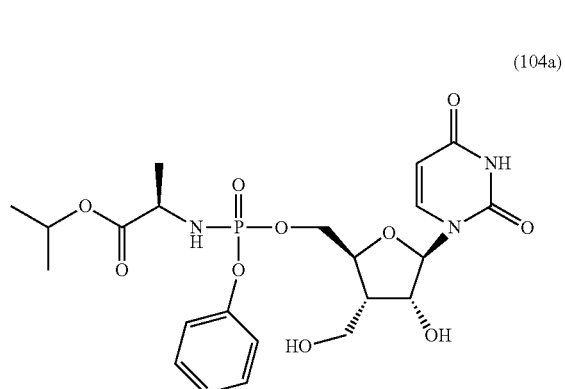
(104b)
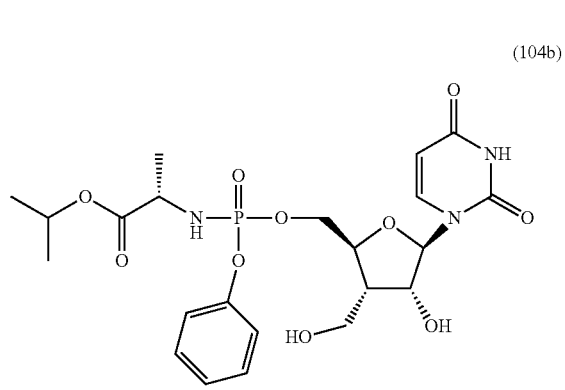

(104ai)
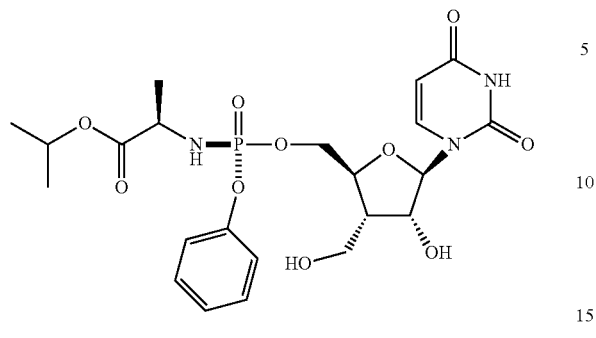
(104aii)
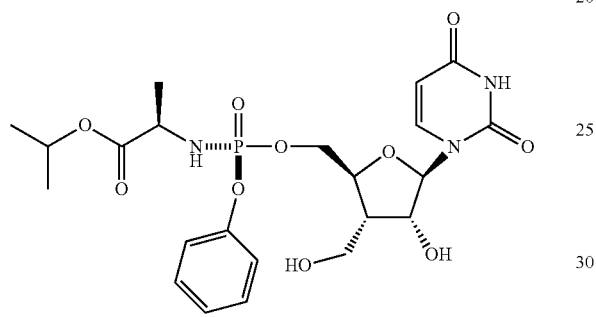
(104bi)

(104bii)
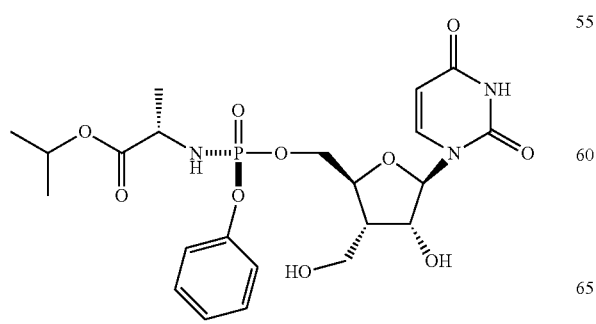
(105)
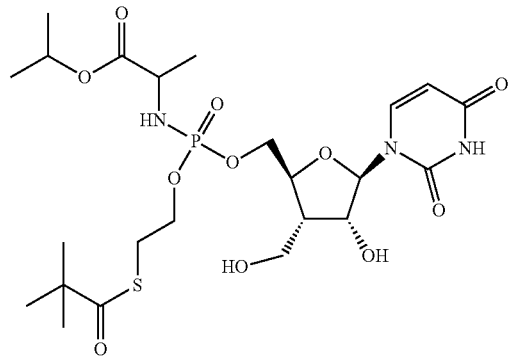
(105a)
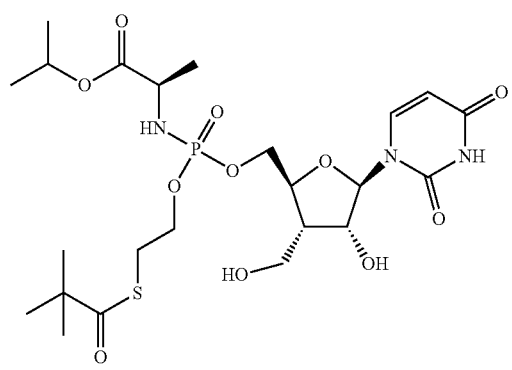
(105b)
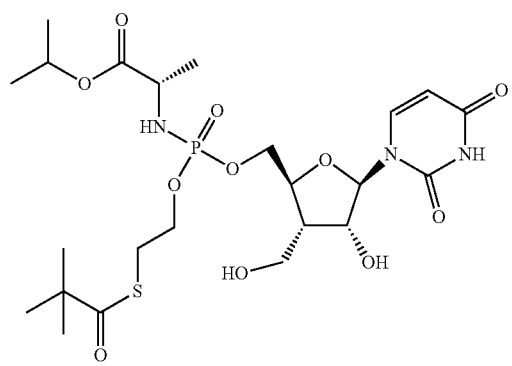
(105ai)
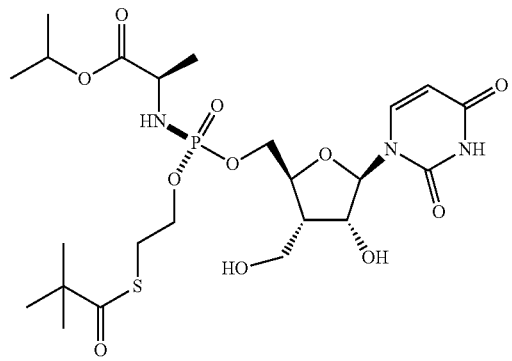

(105aii)
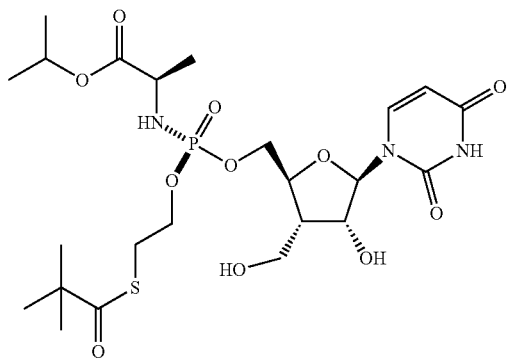
(106a)
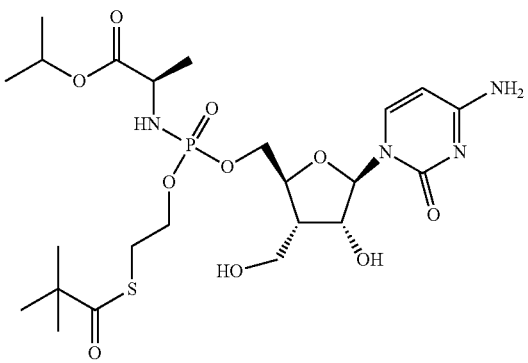
(105bi)
(106b)
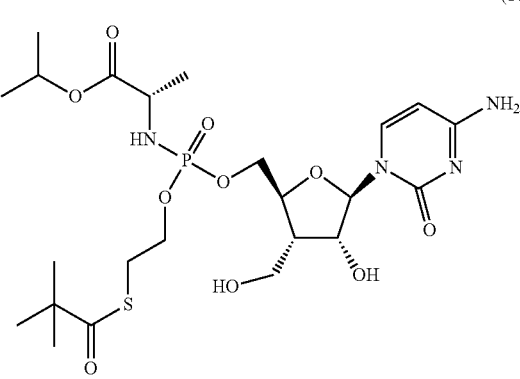
(105bii)
(106ai)
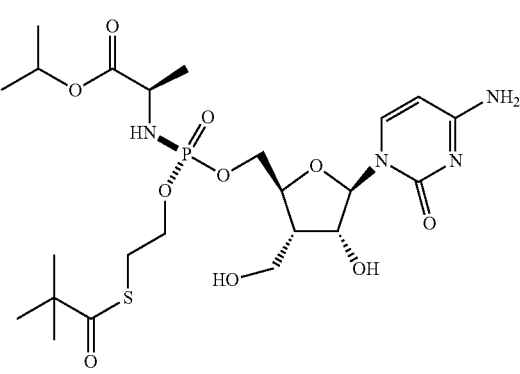
(106)
(106aii)
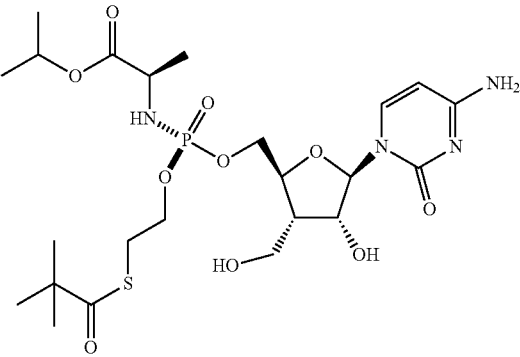

(106bi)
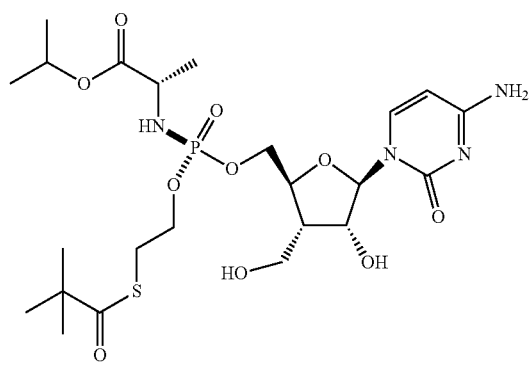
(106bii)
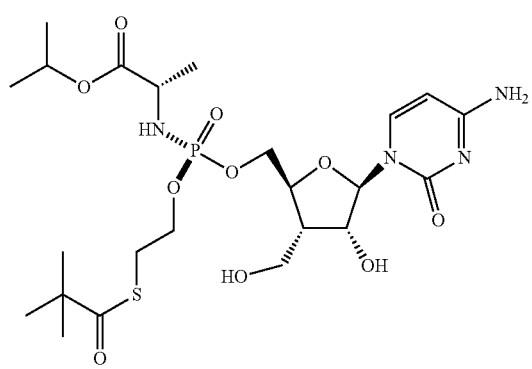
(107)
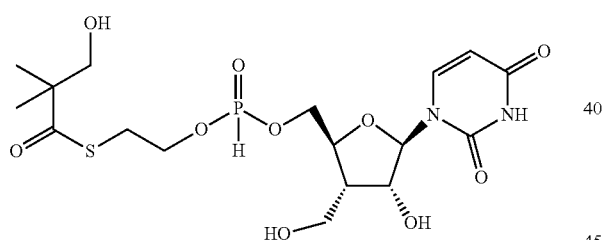
(107a)

(107b)
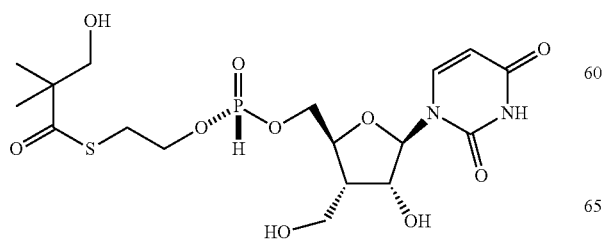
(108)
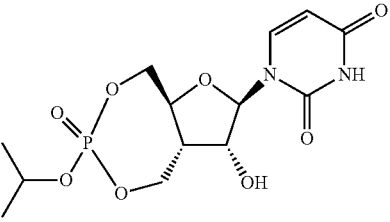
(108a)
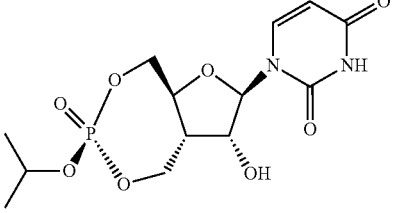
(108b)
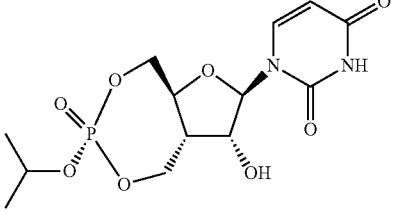
(109)
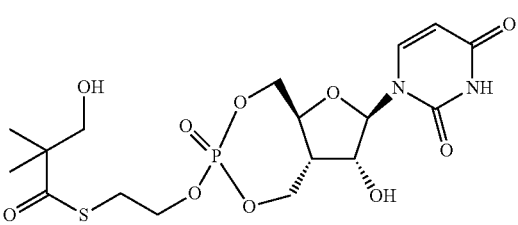
(109a)
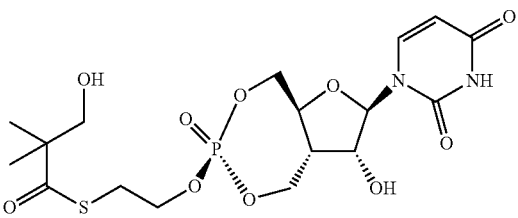
(109b)
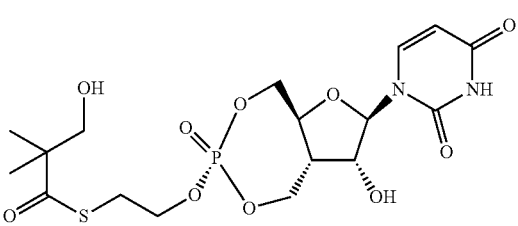

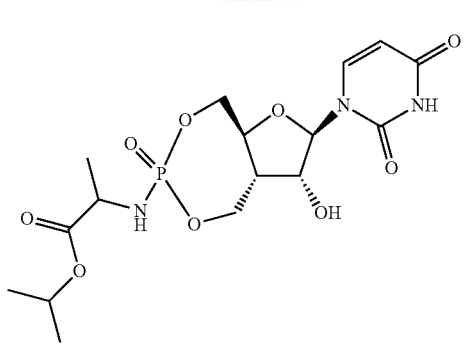
(110)
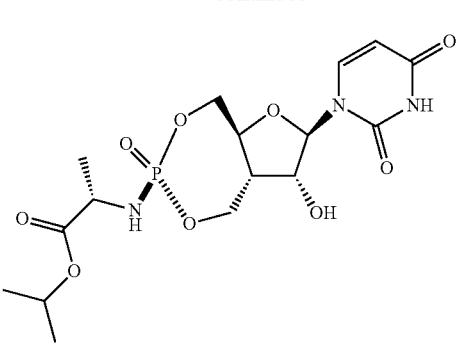
(110bi)
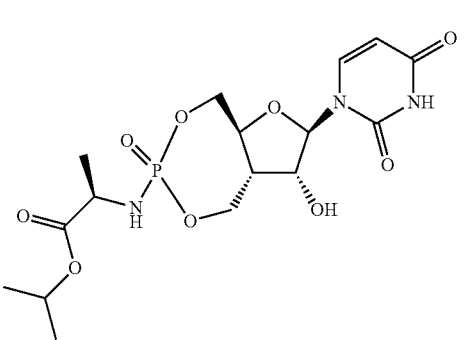
(110a)
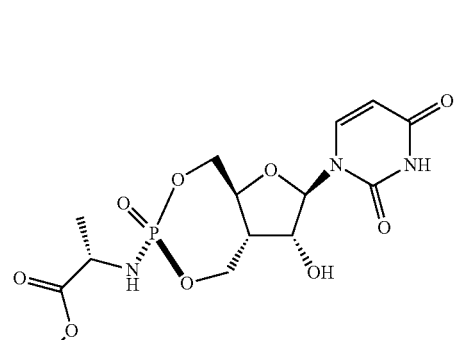
(110bii)
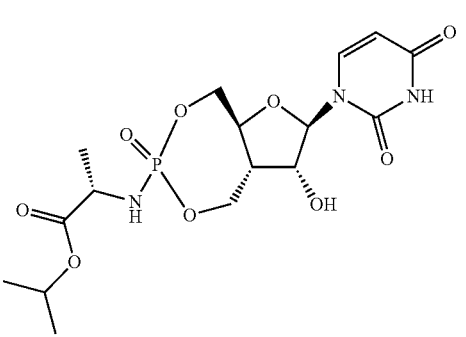
(110b)
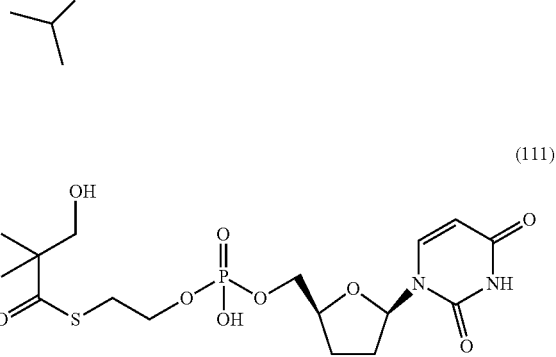
(111)
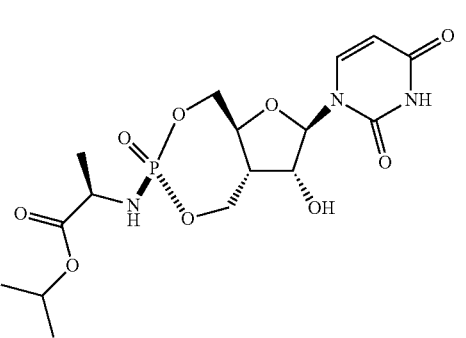
(110ai)
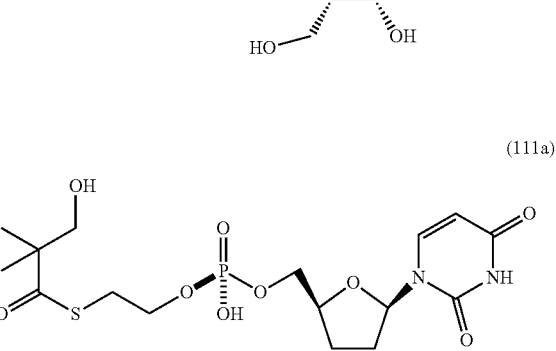
(111a)
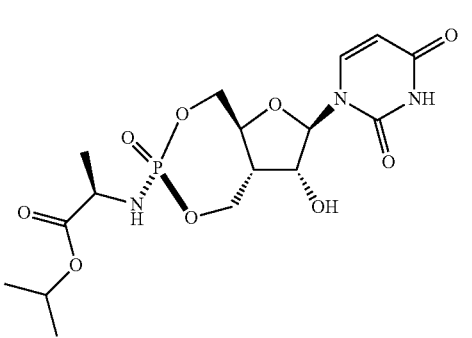
(110aii)
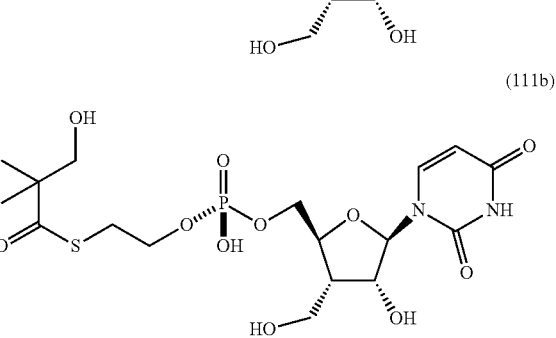
(111b)

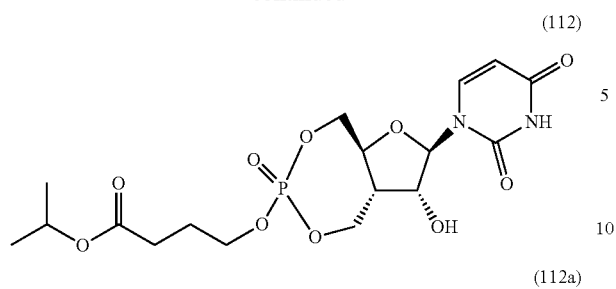
(112)
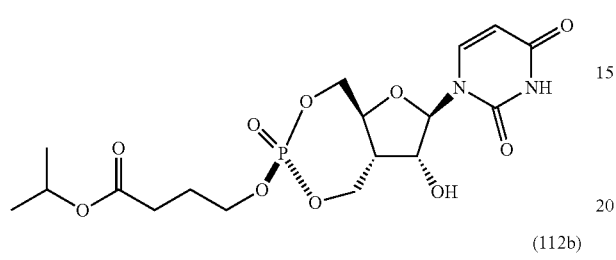
(112a)
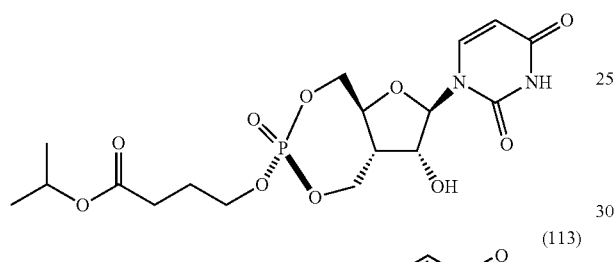
(112b)
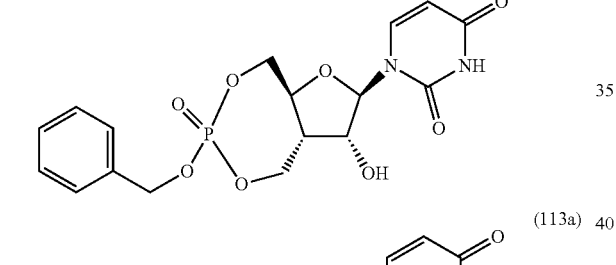
(113)
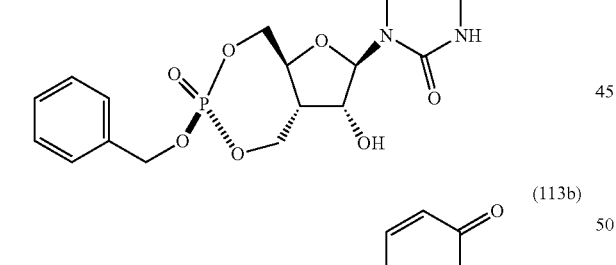
(113a)
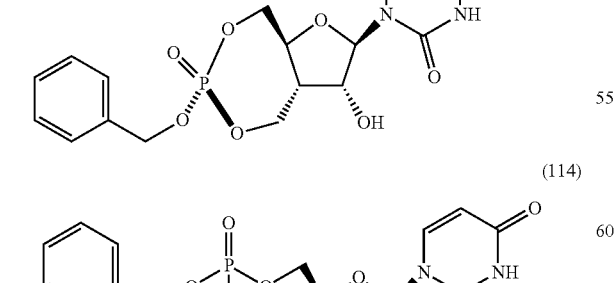
(113b)
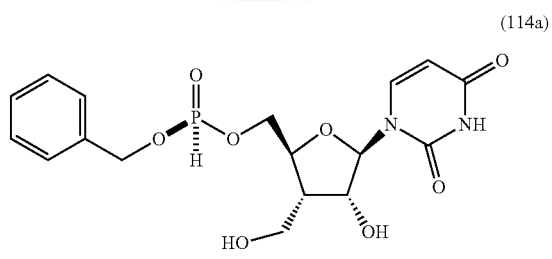
(114)
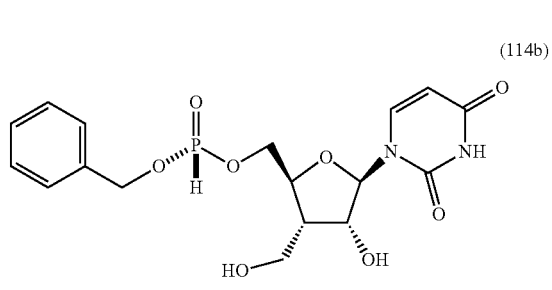
(114a)
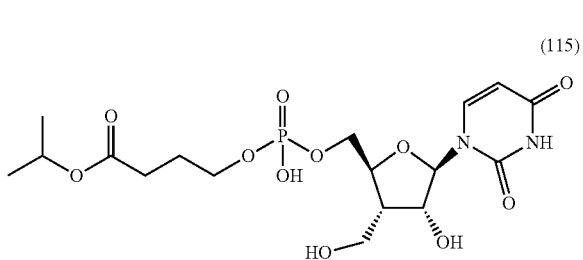
(114b)
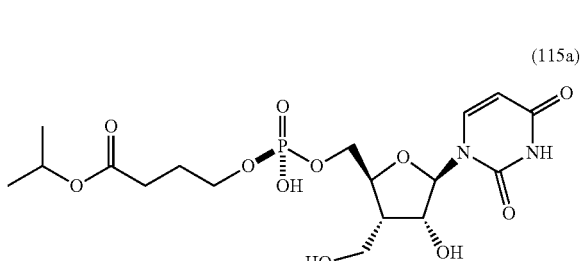
(115)
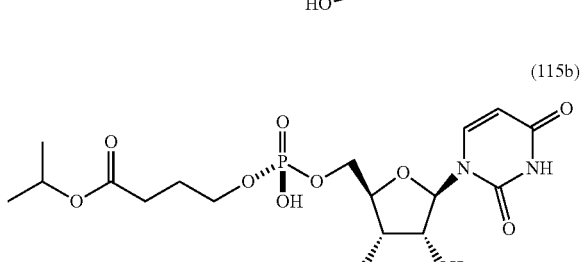
(115a)
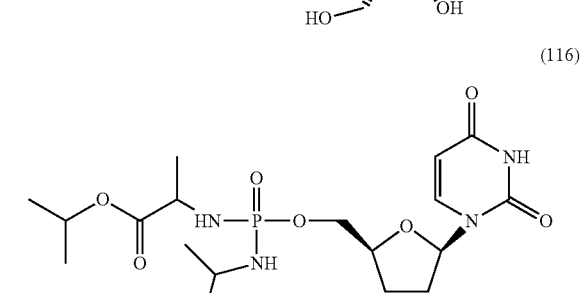
(115b)
(116)

(116a)
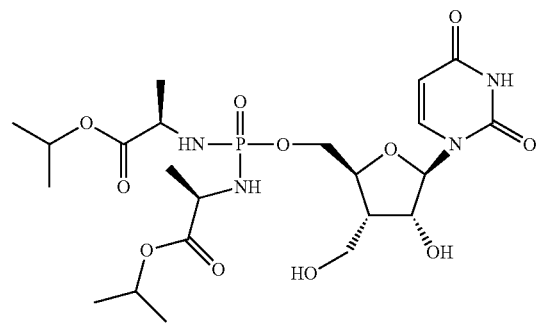
(116cii)
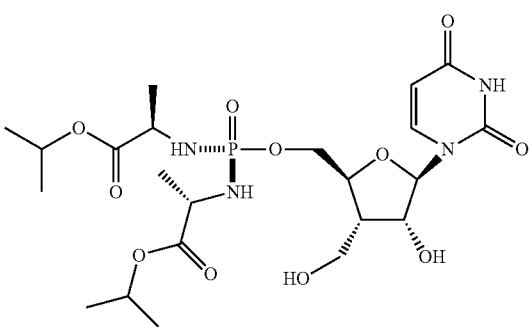
(116b)
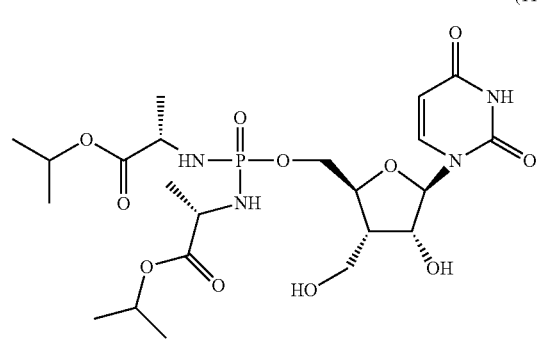
(117)
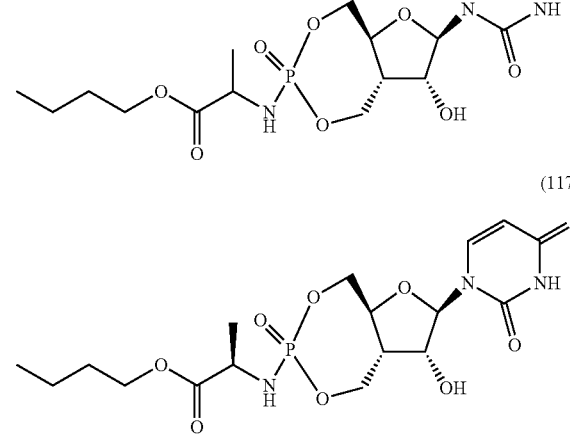
(116c)
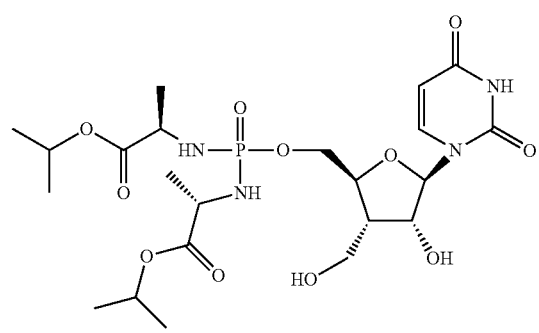
(117a)
(117b)
(117ai)
(117aii)
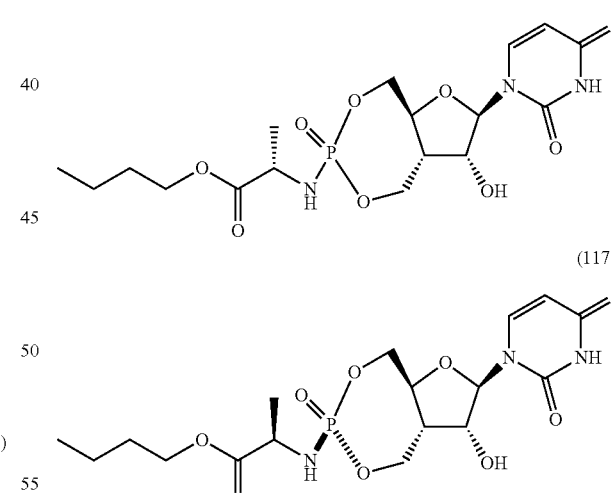
(116ci)
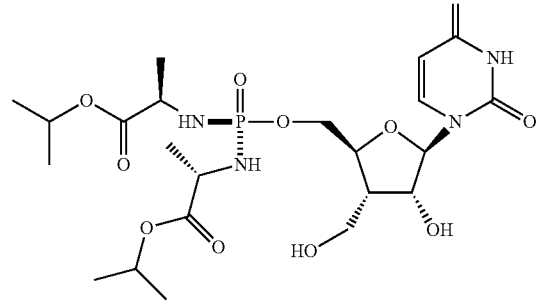
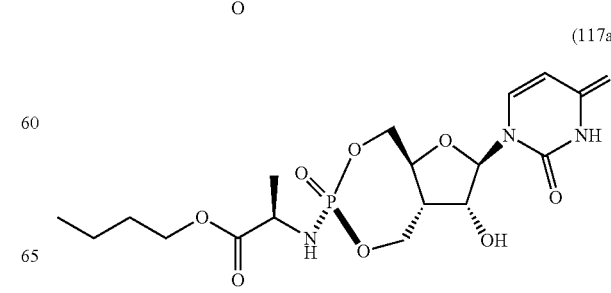

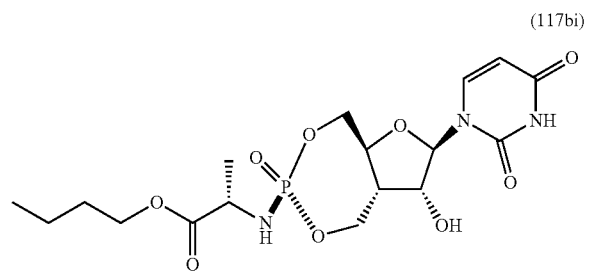
(117bi)
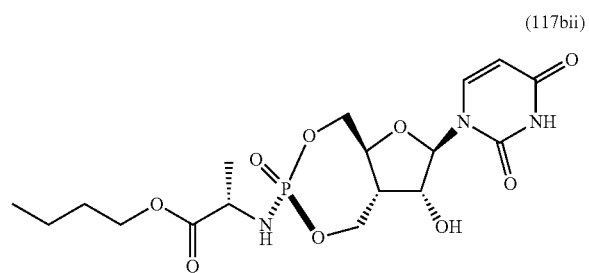
(117bii)
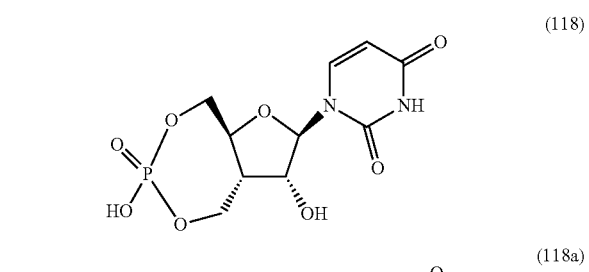
(118)
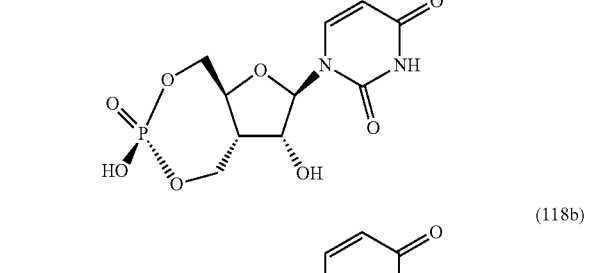
(118a)

(118b)
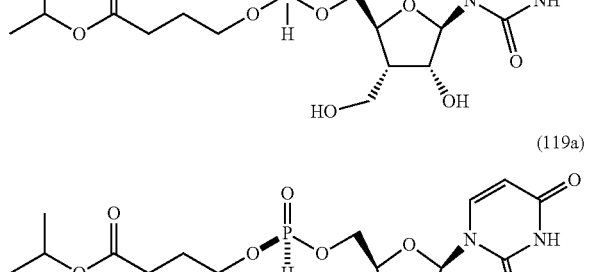
(119)
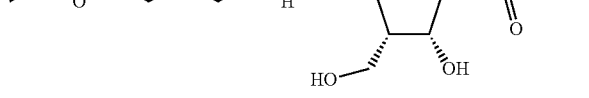
(119a)
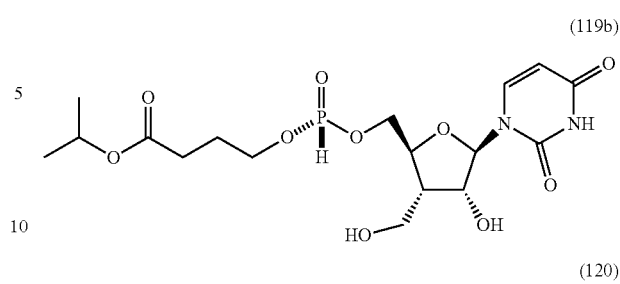
(119b)
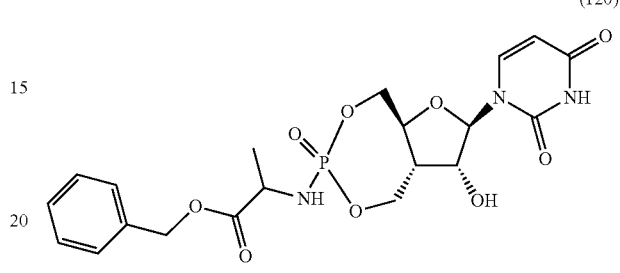
(120)
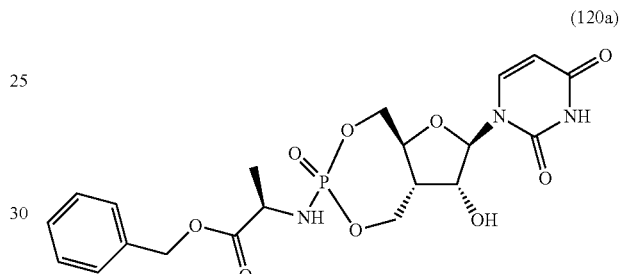
(120a)
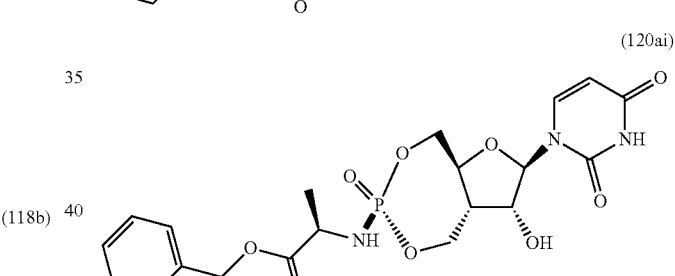
(120ai)
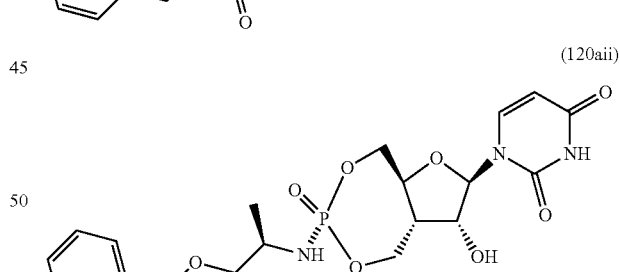
(120aii)
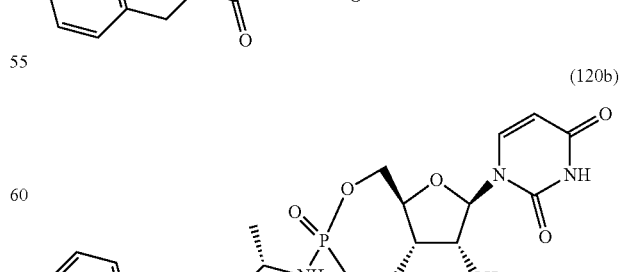
(120b)

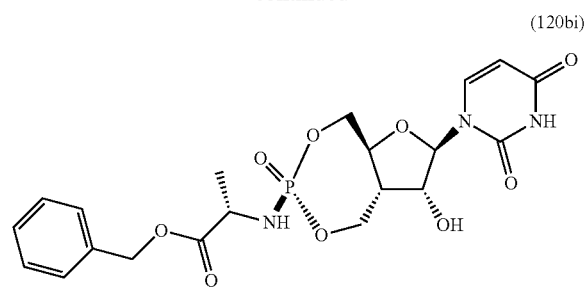
(120bi)
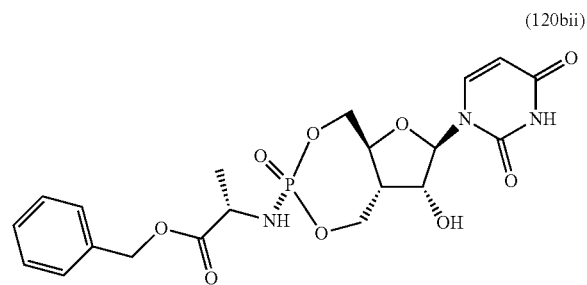
(120bii)
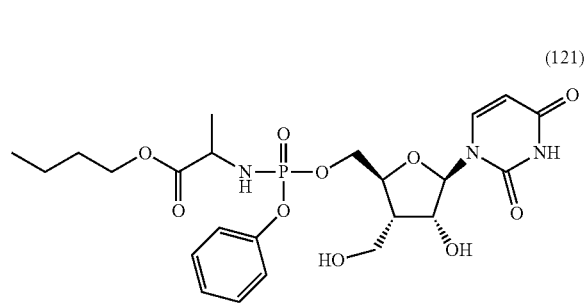
(121)
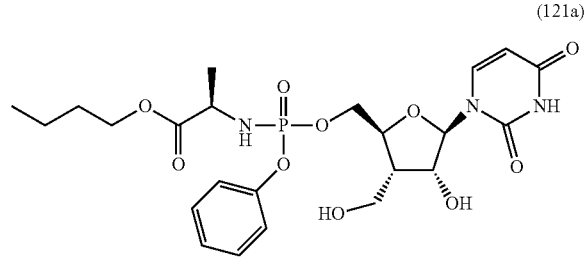
(121a)
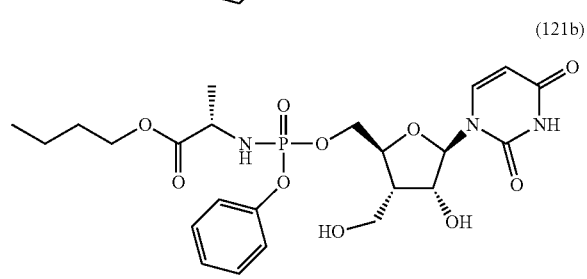
(121b)
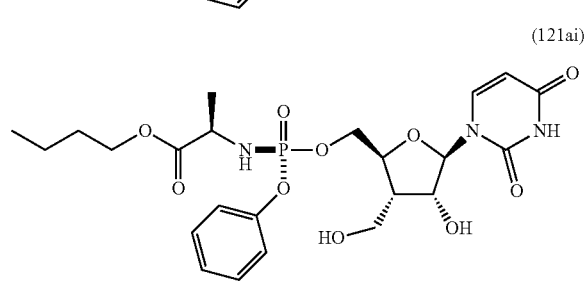
(121ai)
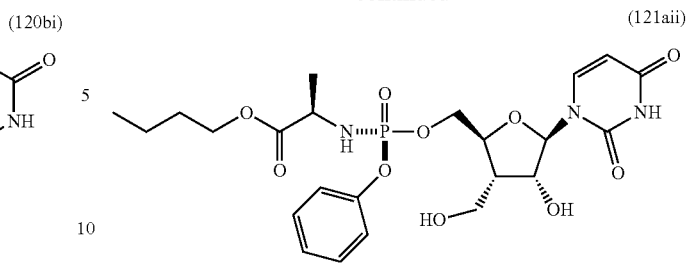
(121aii)
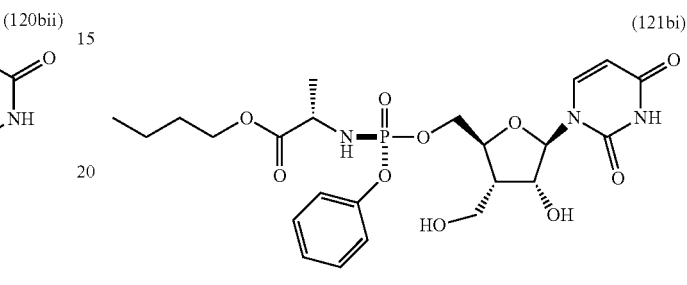
(121bi)
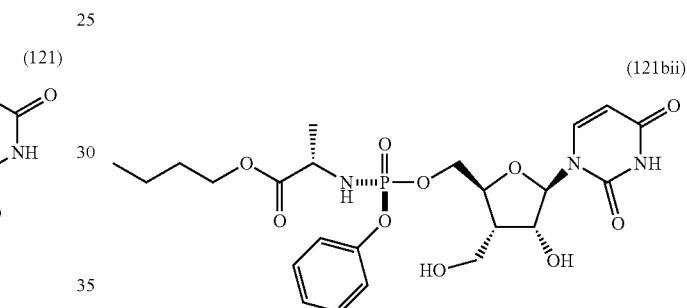
(121bii)
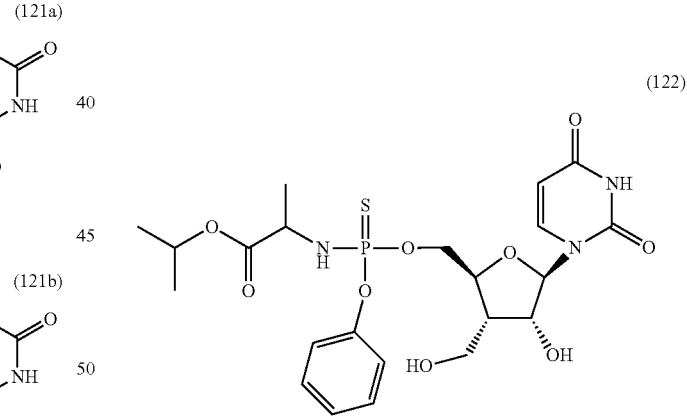
(122)
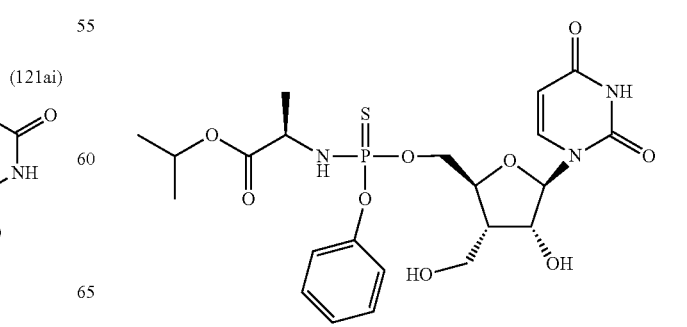
(122a)

(122b)
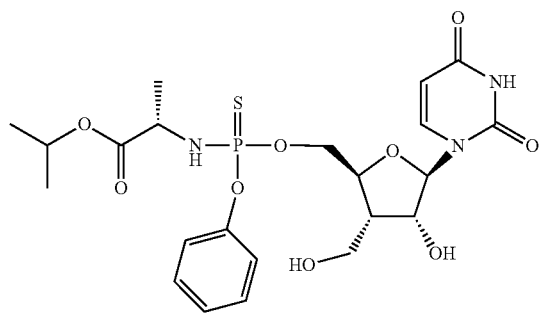
(122ai)
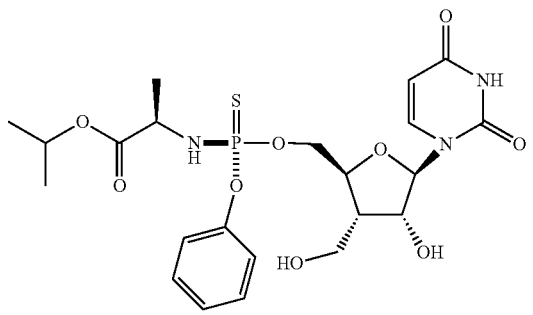
(122aii)
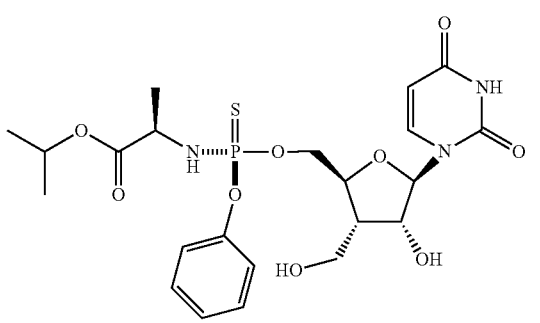
(122bi)
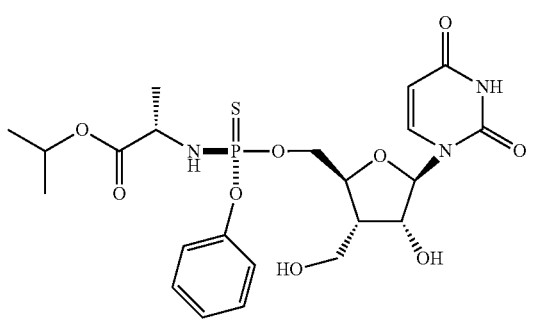
(122bii)
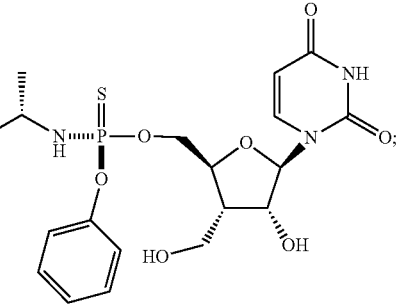
or a pharmaceutically acceptable salt thereof.
In certain embodiments provided herein is a compound according to any of Formulas 201-231:
(201)
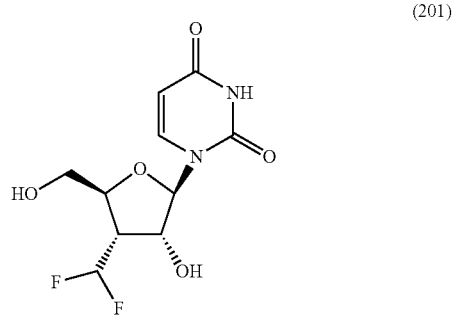
(202)
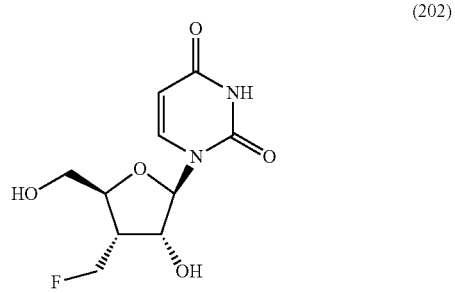
(203)
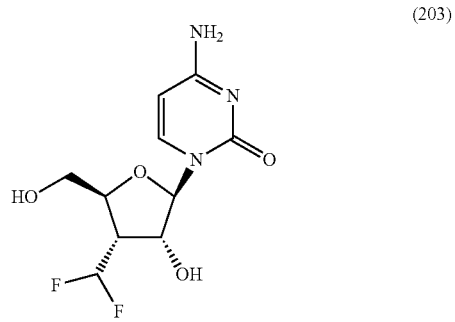

73 74
-continued -continued
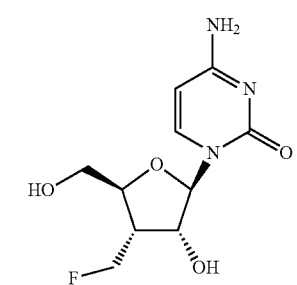 (204)
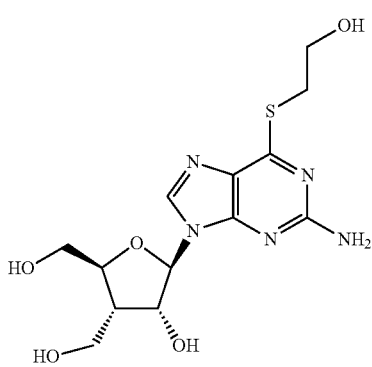 (209)
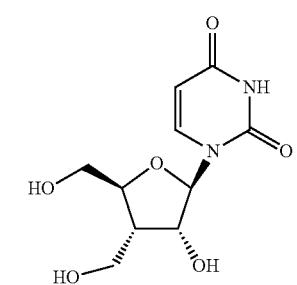 (205)
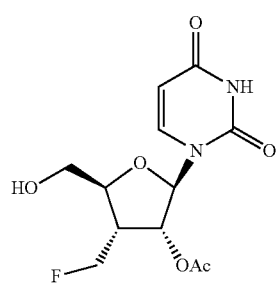 (210)
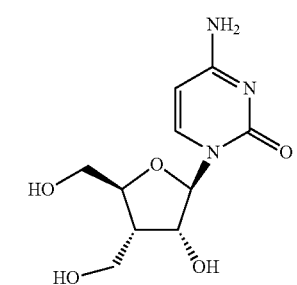 (206)
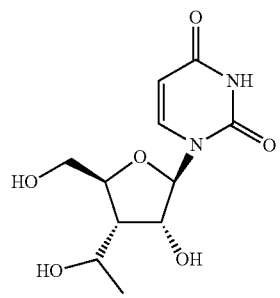 (211)
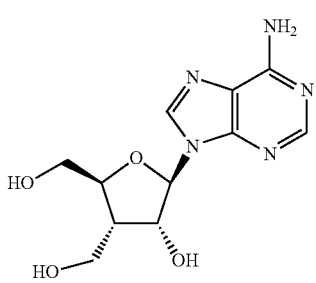 (207)
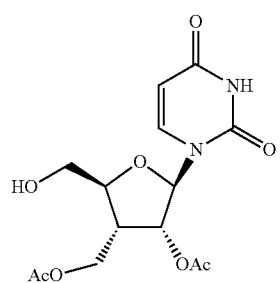 (212)
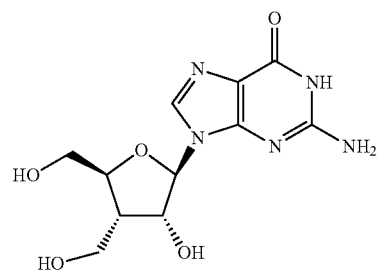 (208)
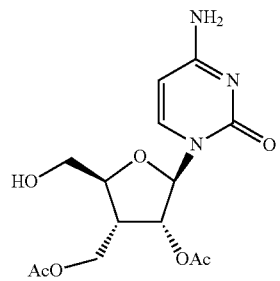 (213)

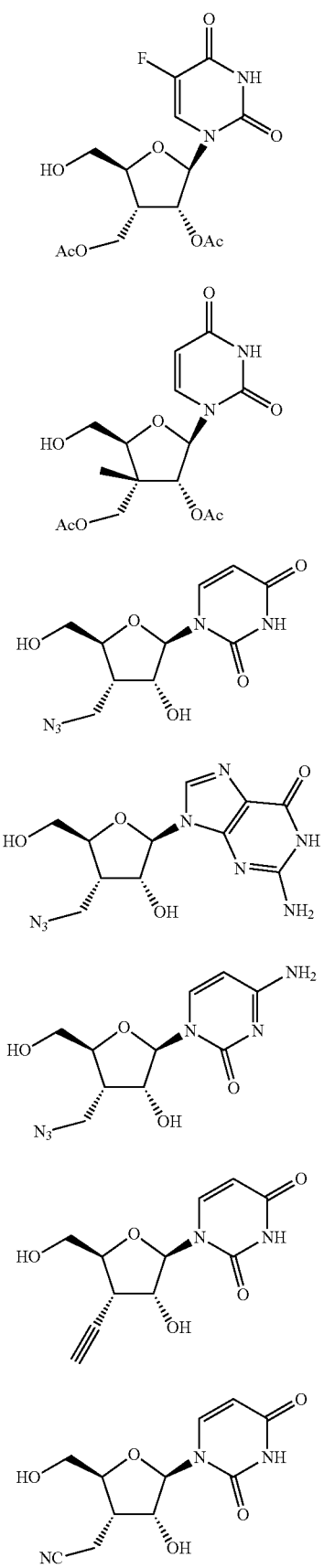
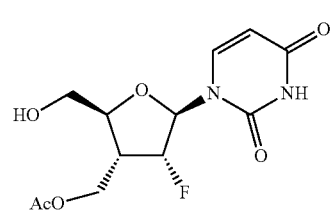
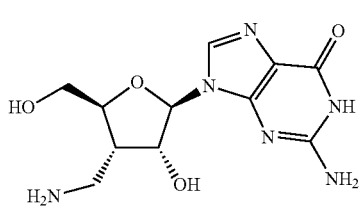
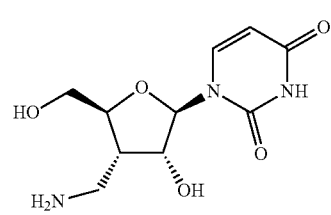
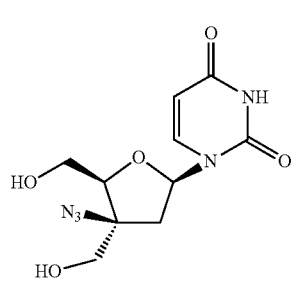
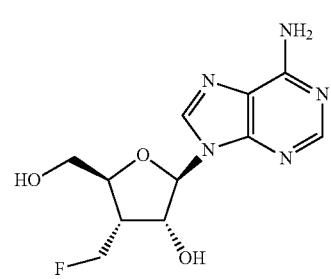
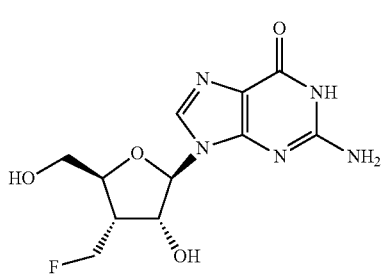

(227) 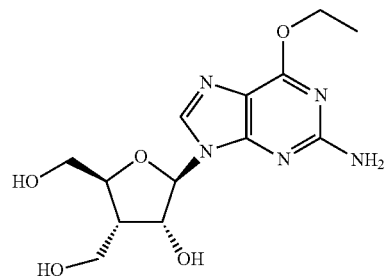
(228) 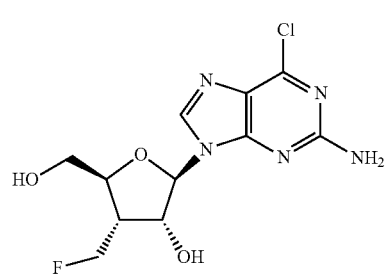
(229) 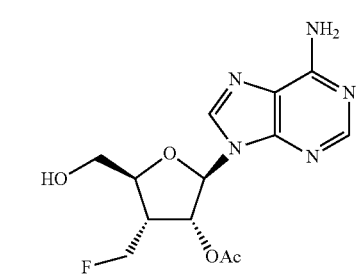
(230) 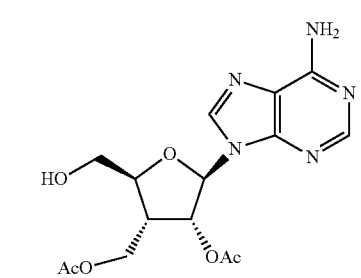
(231) 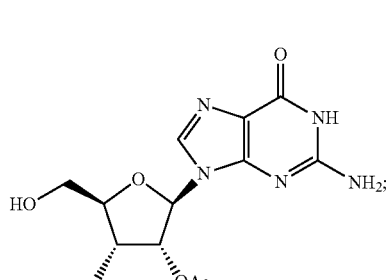
or a pharmaceutically acceptable salt thereof.
In certain embodiments provided herein is a compound according to any of Formulas 201, 203, 204, 209, 210, 211, or 224:
(201) 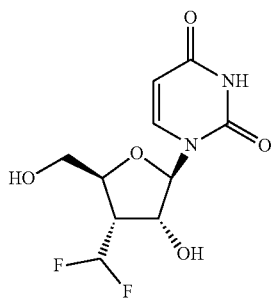
(203) 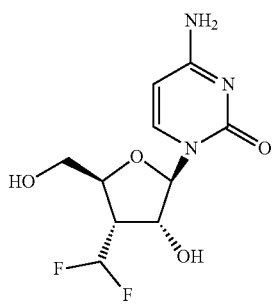
(204) 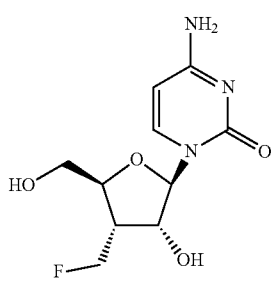
(209) 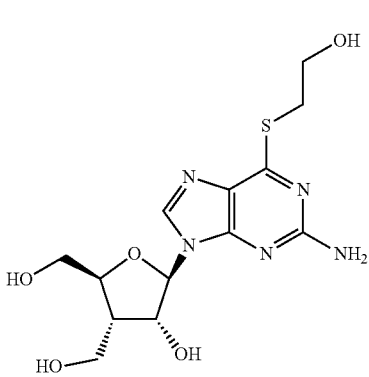
(210) 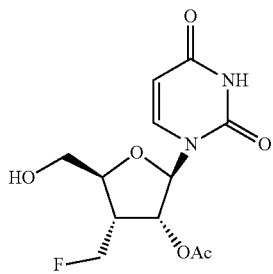

(211)
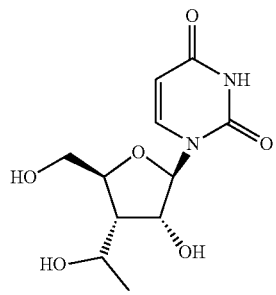
(224)
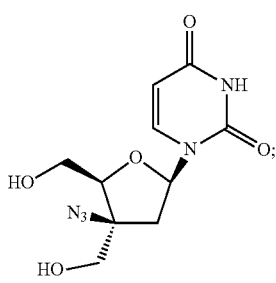
or a pharmaceutically acceptable salt thereof.
In certain embodiments provided herein is a compound according to any of Formulas 301-329:
(301)
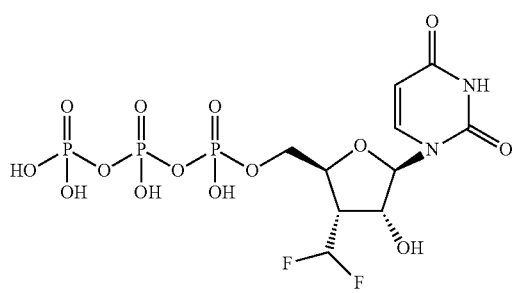
(302)
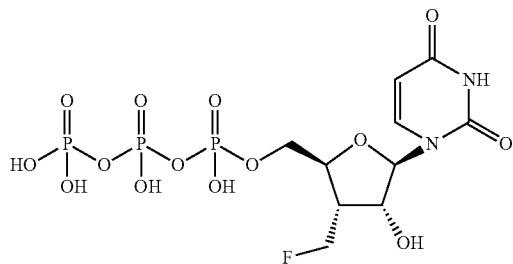
(303)
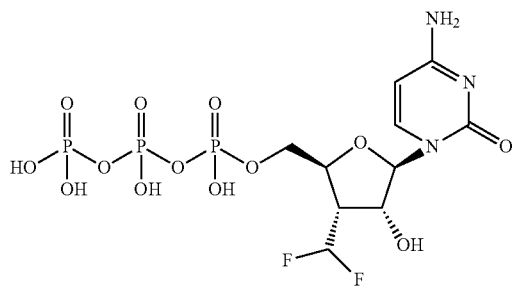
(304)
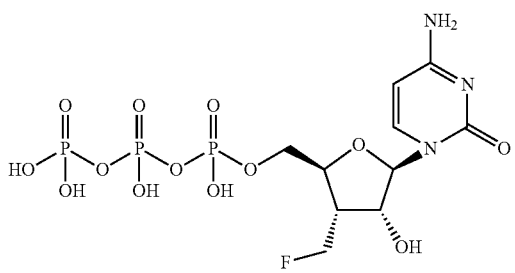
(305)
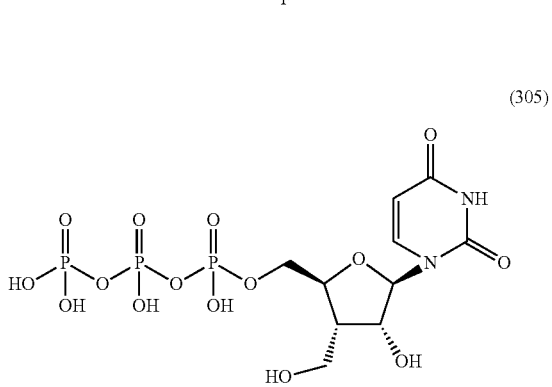
(306)
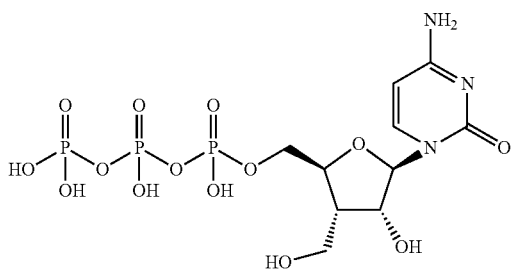
(307)
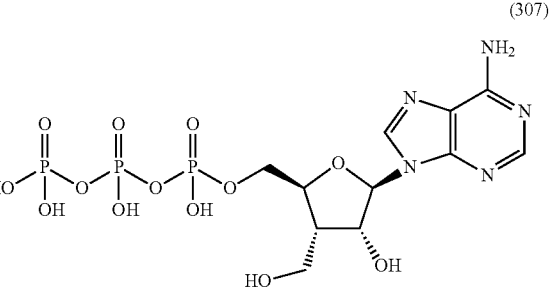
(308)

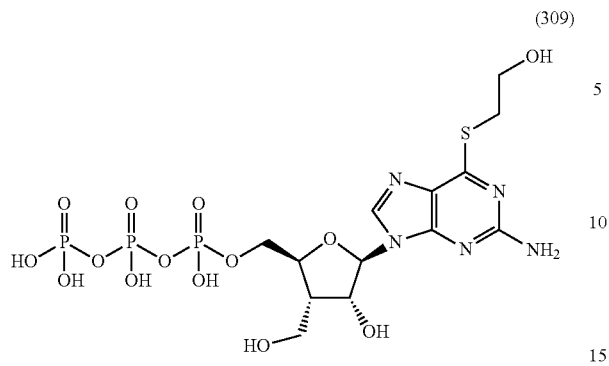
(309)
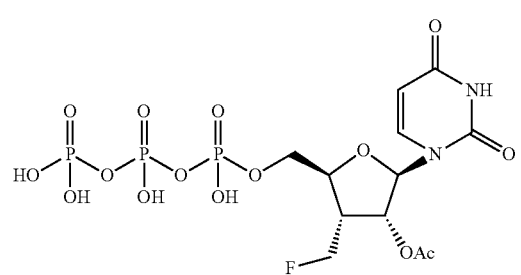
(310)
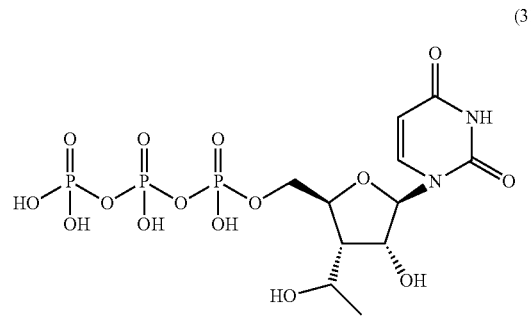
(311)
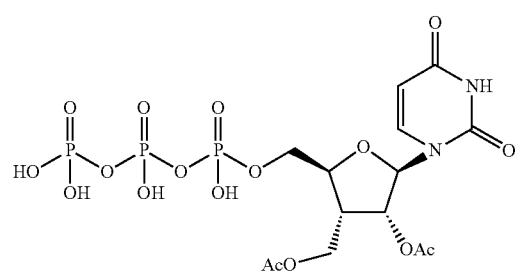
(312)
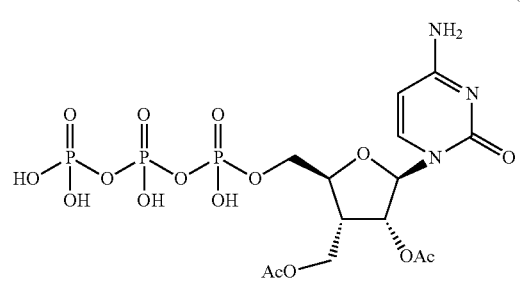
(313)
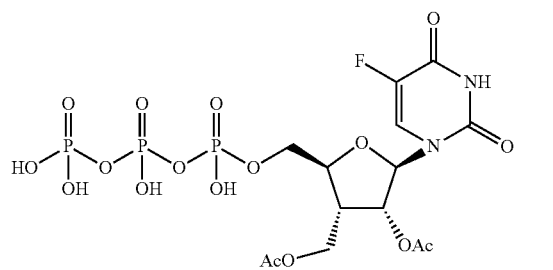
(314)
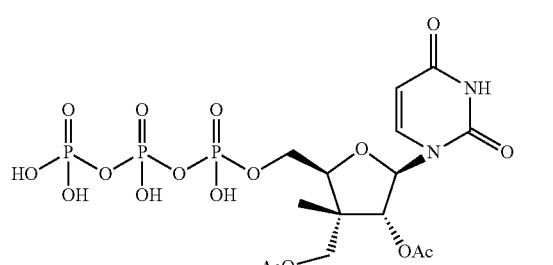
(315)
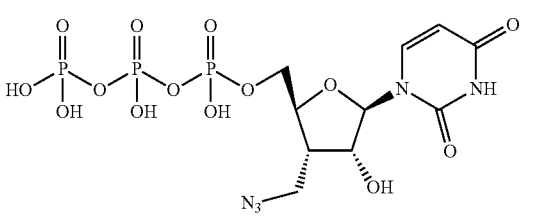
(316)
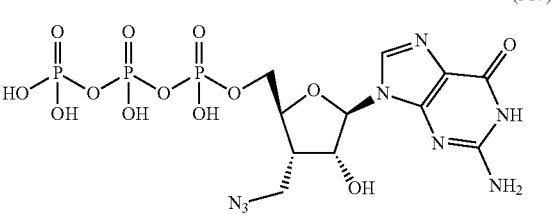
(317)
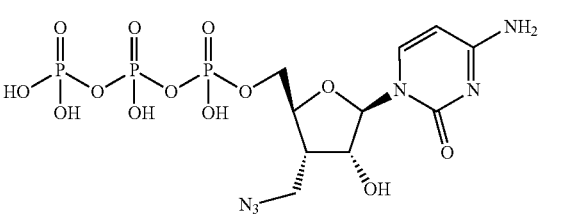
(318)
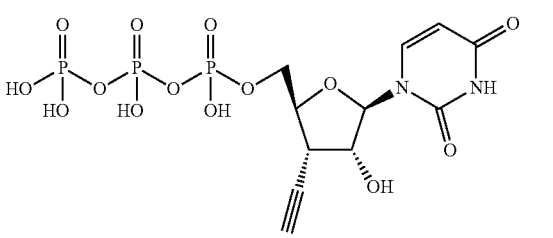
(319)

(320)
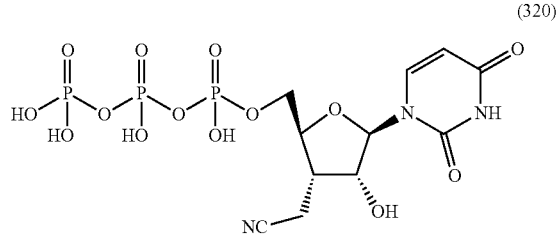
(321)
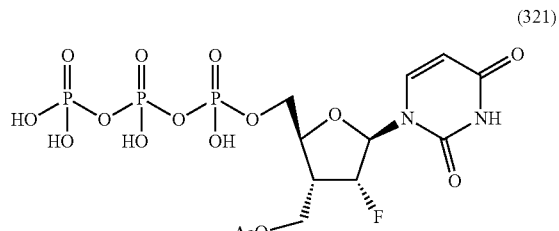
(322)
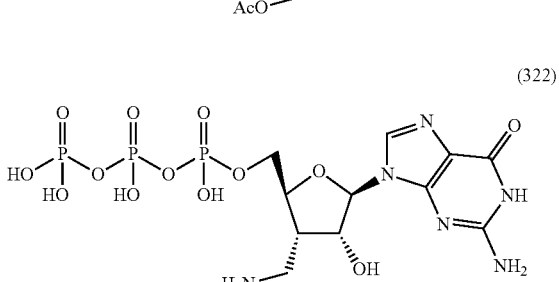
(323)
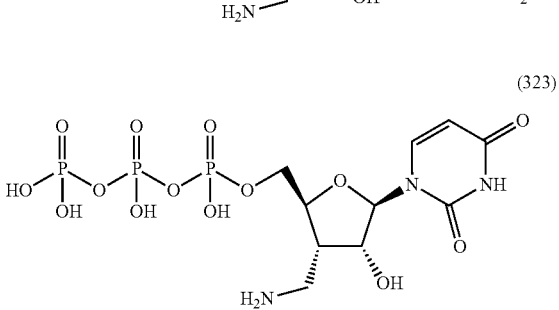
(324)
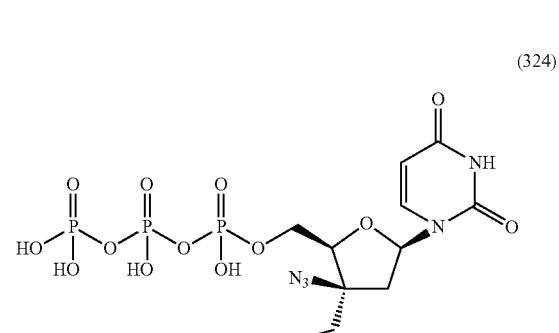
(325)
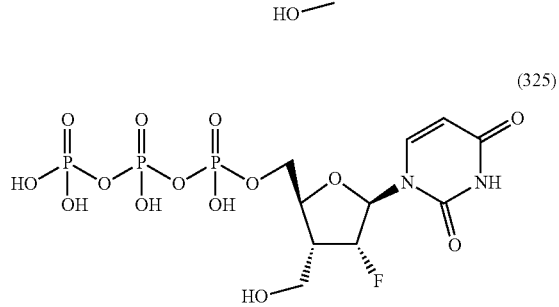
(326)
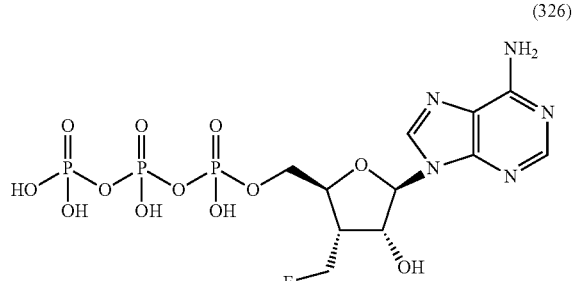
(327)
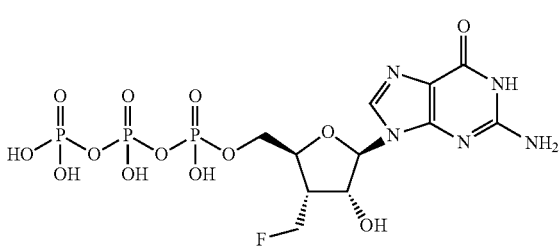
(328)
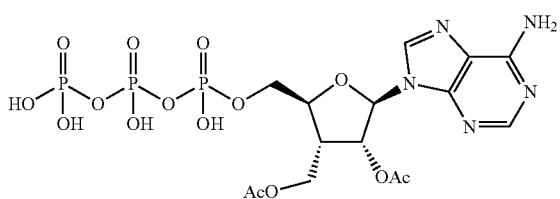
(329)
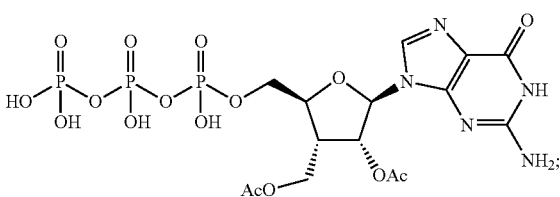
or a pharmaceutically acceptable salt thereof.
In certain embodiments, provided herein are compounds according to any of Formulas 401-404:
(401)
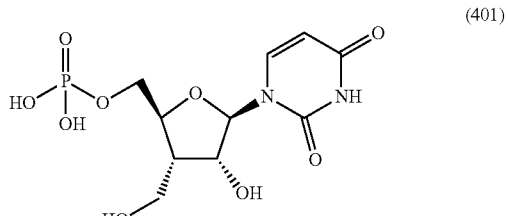
(402)
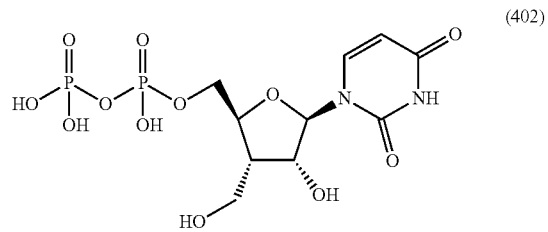

or a pharmaceutically acceptable salt thereof.

In certain embodiments, provided herein are compounds according to any of Formulae 340, 330, 341, 331, 342, 332, 343, 333, 344, 334, 345, 335, and 336:

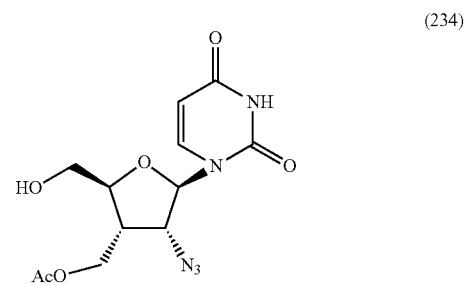
(345)
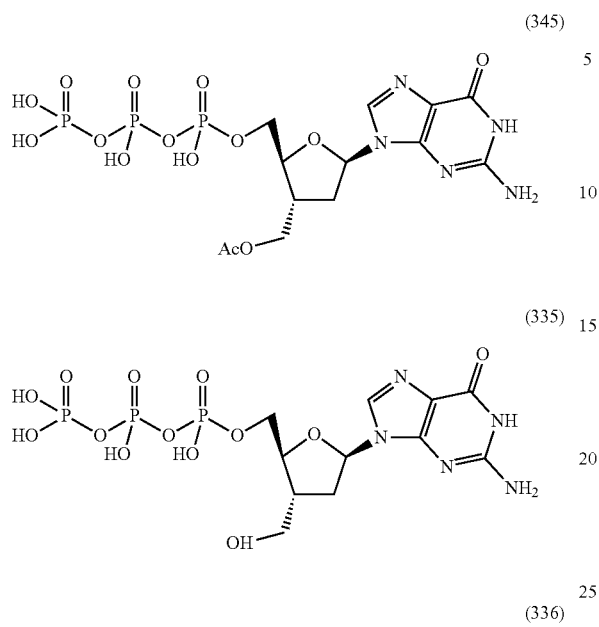
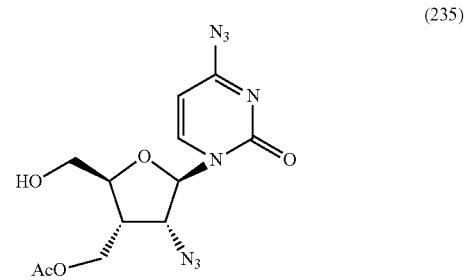
(335)
(336)
or a pharmaceutically acceptable salt thereof.
In certain embodiments, provided herein are compounds according to any of Formulae 232 to 255:
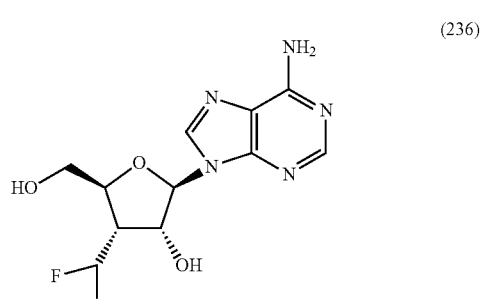
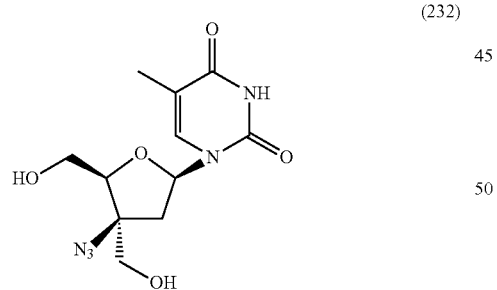
(232)
(233)
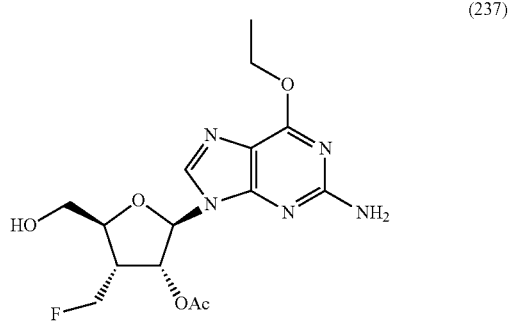
(234)
(235)
(236)
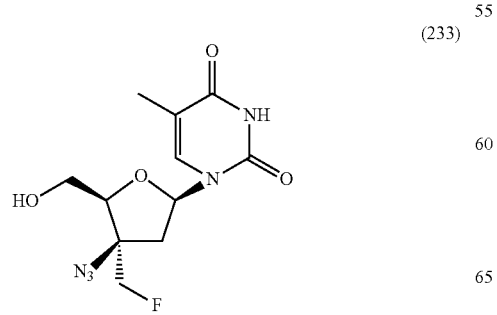
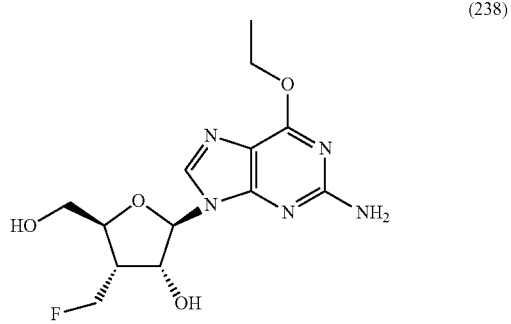
(237)
(238)

(239)
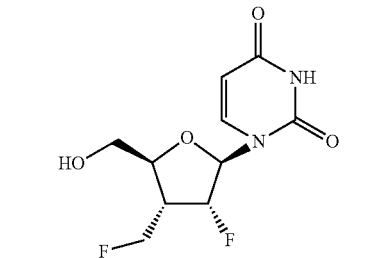
(240)
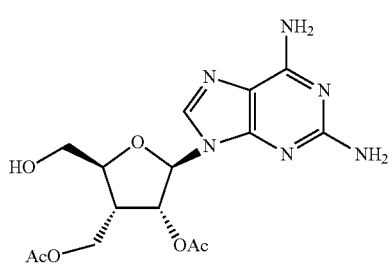
(243)
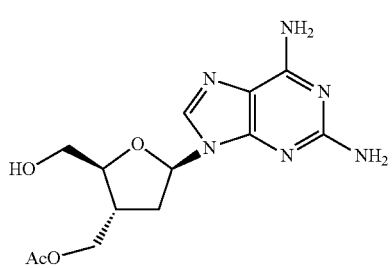
(246)
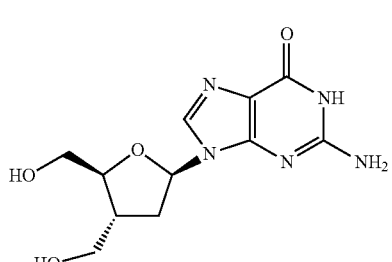
(245)
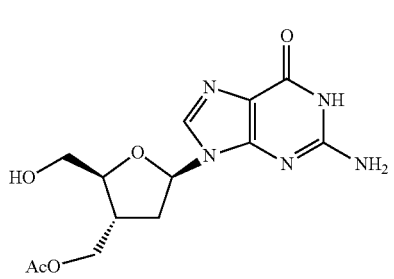
(241)

(244)
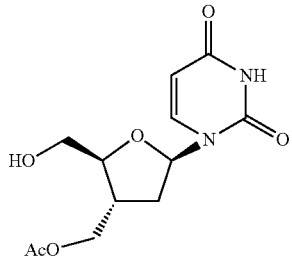
(242)
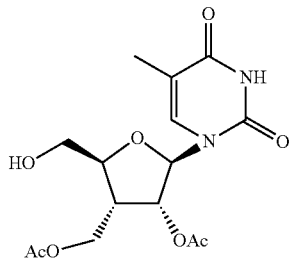
(247)
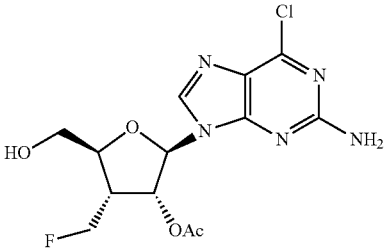
(248)
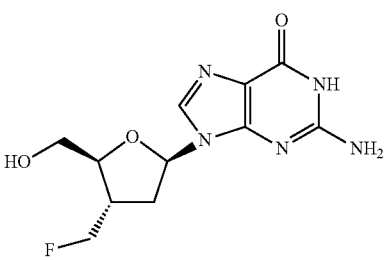
(249)
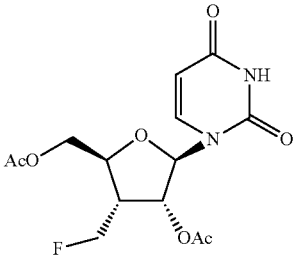

(250)
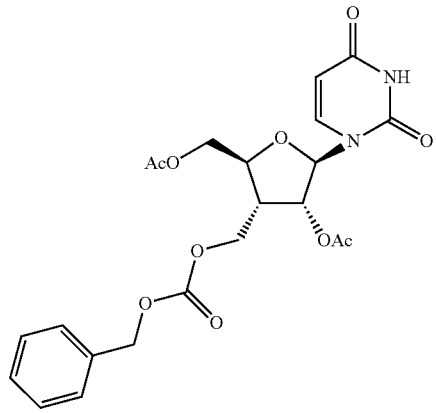
(251)
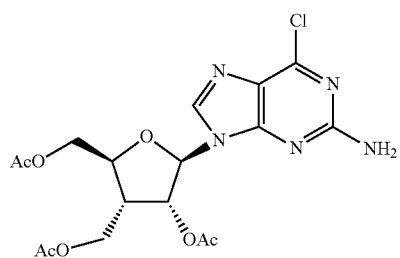
(252)
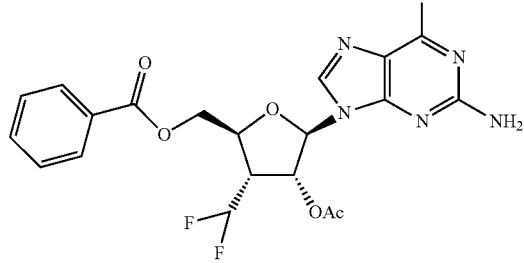
(253)
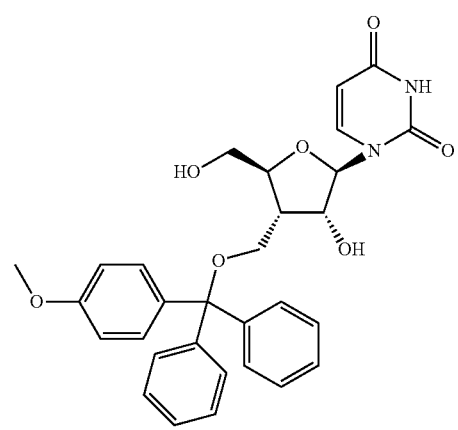
(254)
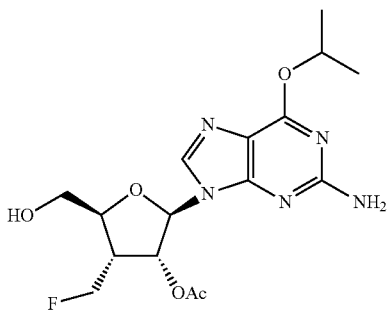
(255)
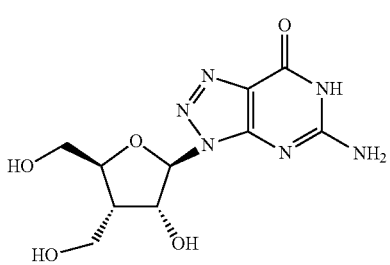
or a pharmaceutically acceptable salt thereof.
In certain embodiments, provided herein are compounds according to any of Formulae 123a to 125bii, 128a, 129a, 130a, 130ai, 130aii, 130b, 130bi, and 130bii:
(123a)
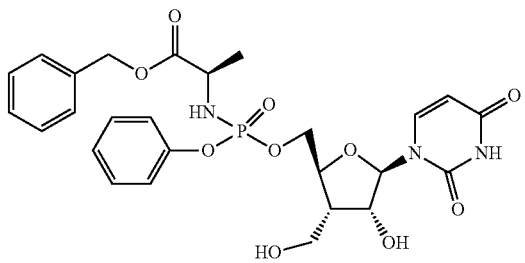
(123b)
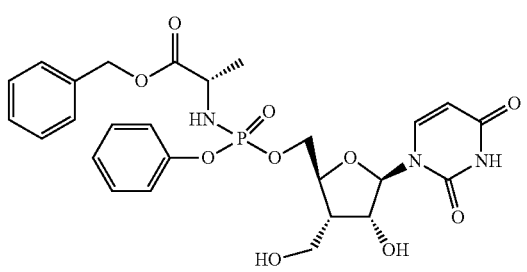
(123ai)
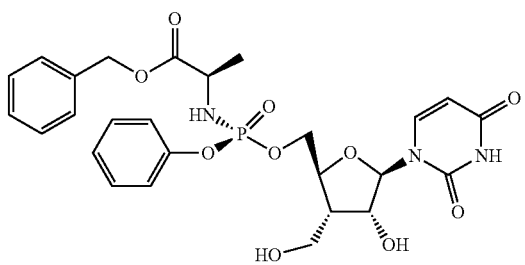

(123aii) 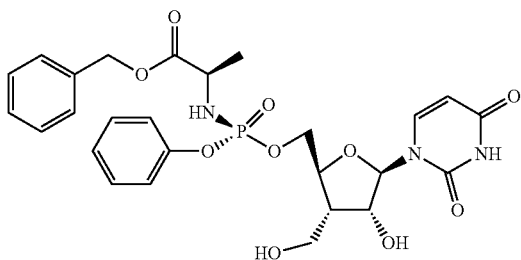
(123bi) 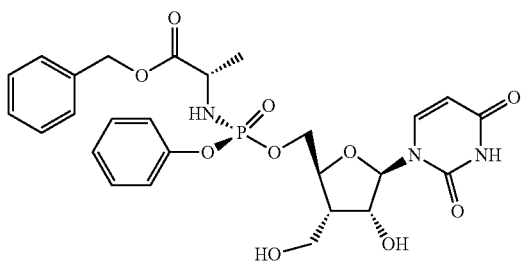
(123bii) 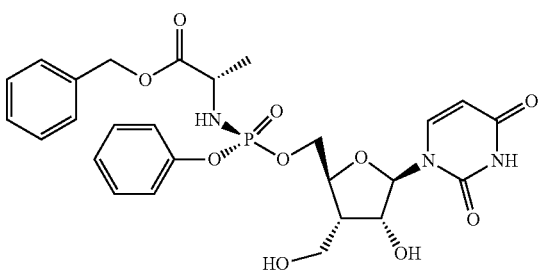
(124a) 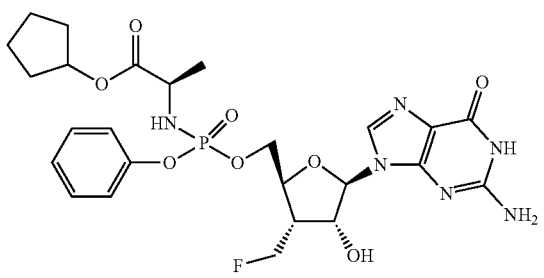
(124ai) 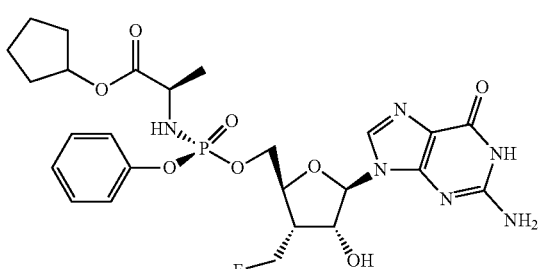
(124aii) 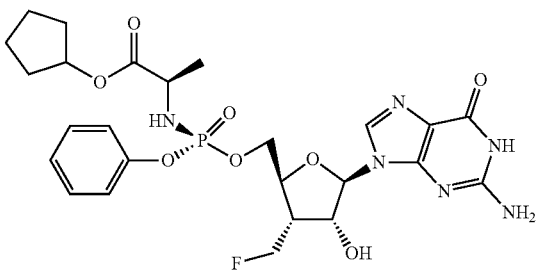
(124bi) 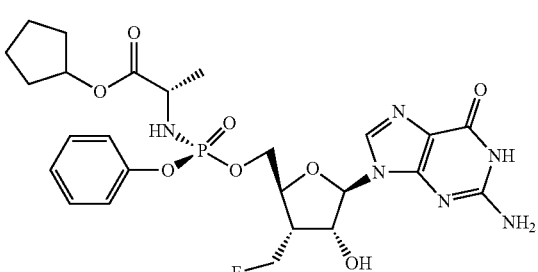
(124bii) 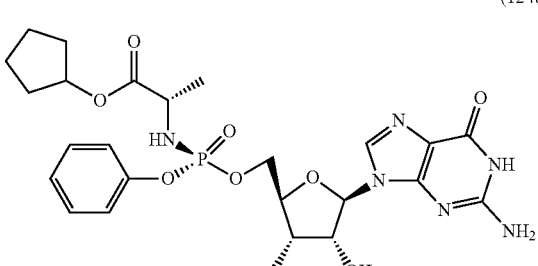
(125a) 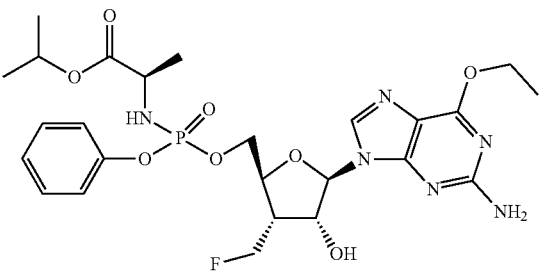
(125ai) 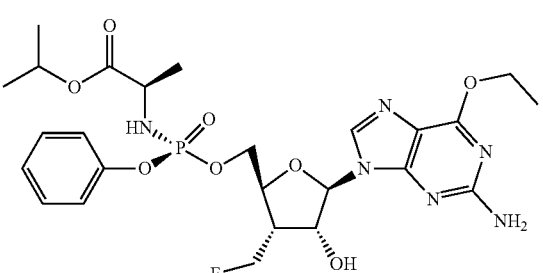

(125aii)
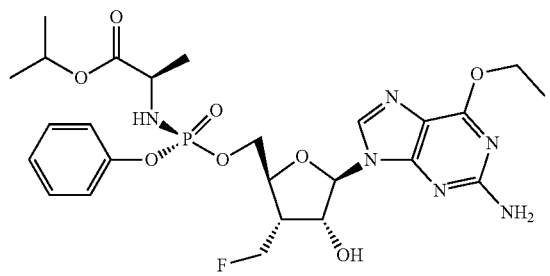
(125b)
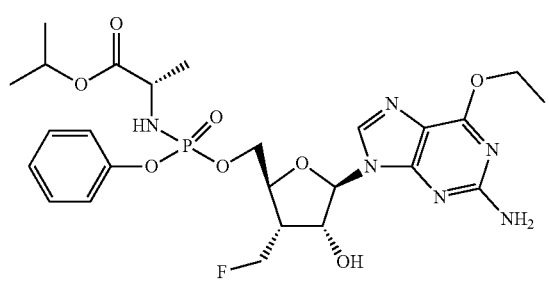
(125bi)
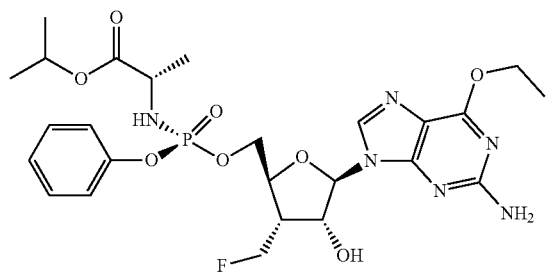
(125bii)
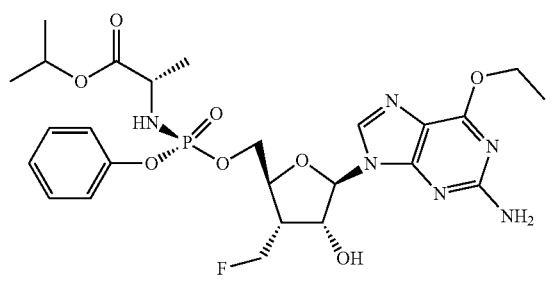
(128a)
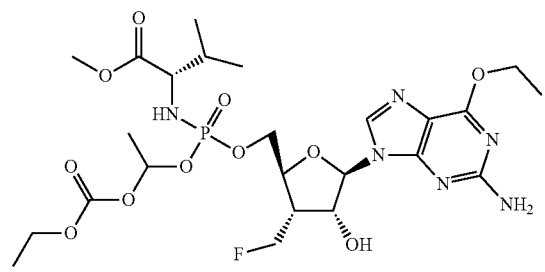
(129a)
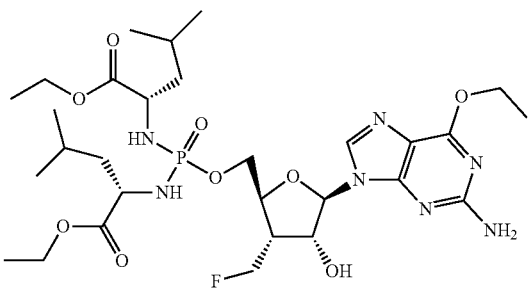
(130a)
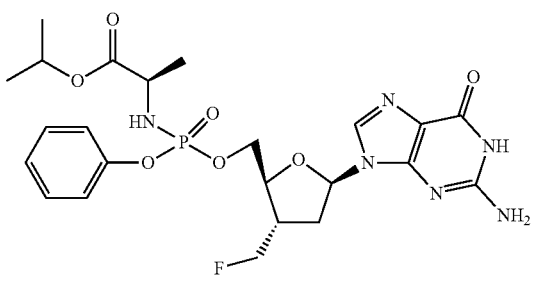
(130ai)
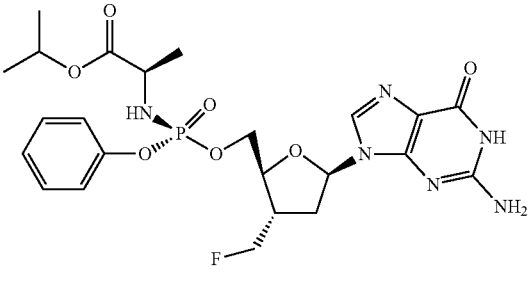
(130aii)
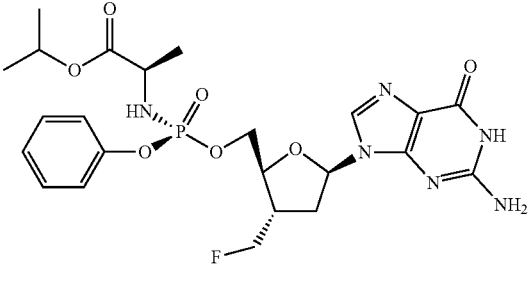
(130b)
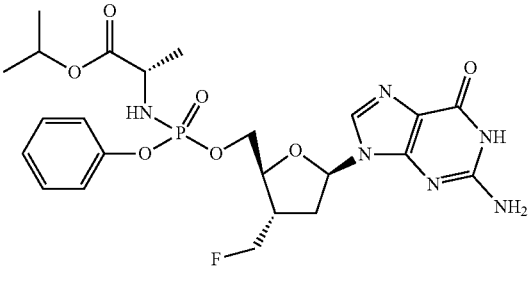

(130bi)
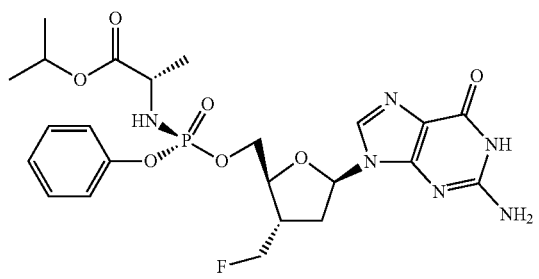
(132a)
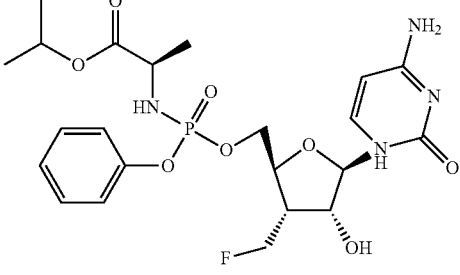
(130bii)
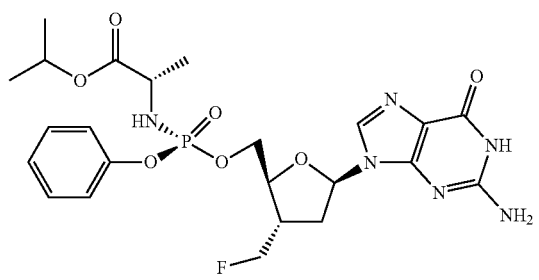
(132ai)
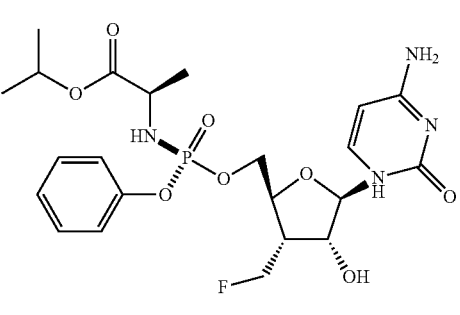
or a pharmaceutically acceptable salt thereof.
In certain embodiments, provided herein are compounds according to any of Formulae 131a to 140aii, 142 to 161b, 163a to 165, 167 to 170, and 172 to 190b:
(132aii)
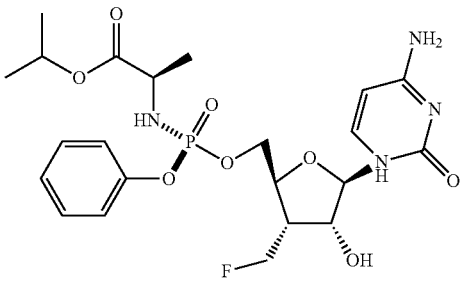
(131a)
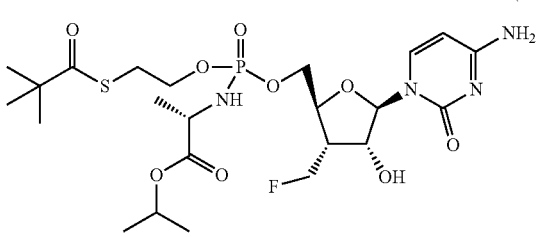
(131ai)
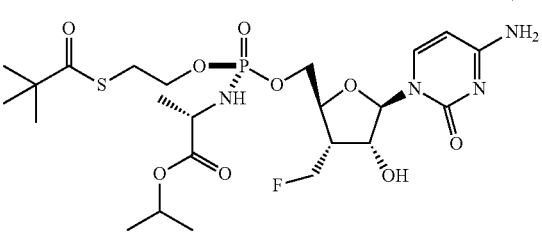
(132b)
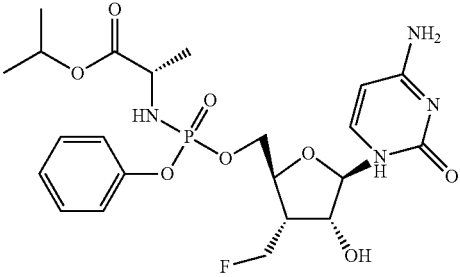
(131aii)
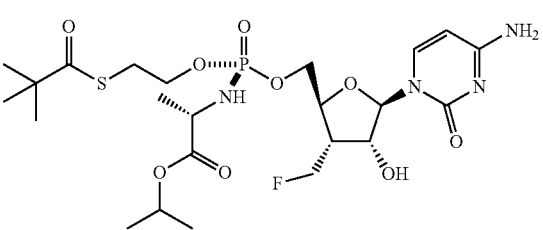
(132bi)
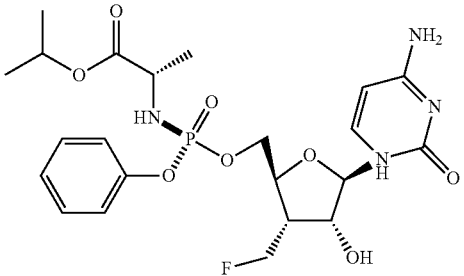

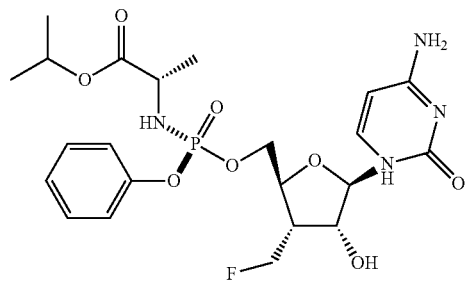
(132bii)
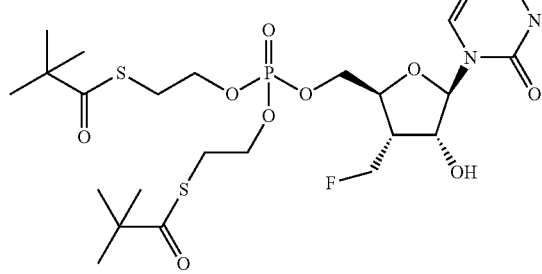
(133)
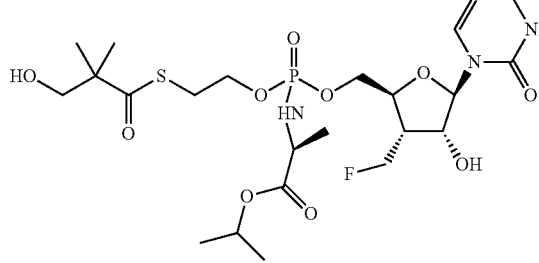
(134)
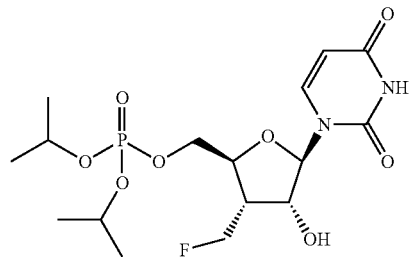
(135)
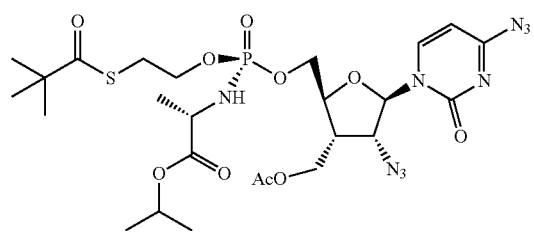
(136)
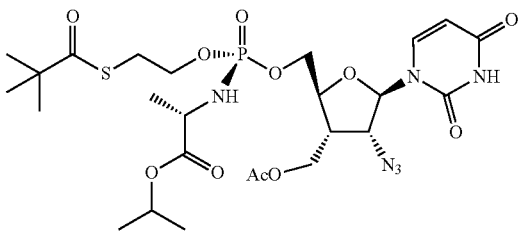
(137)
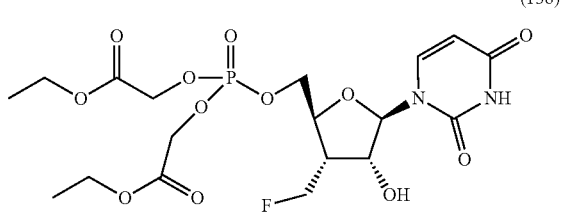
(138)
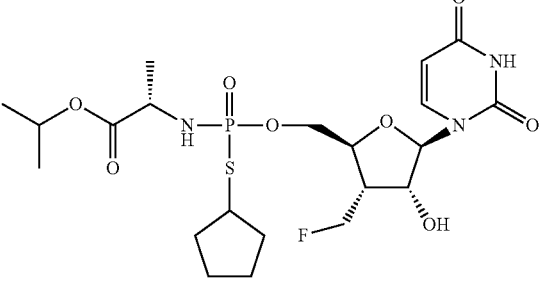
(139)
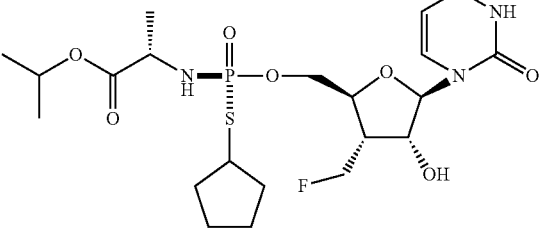
(139a)
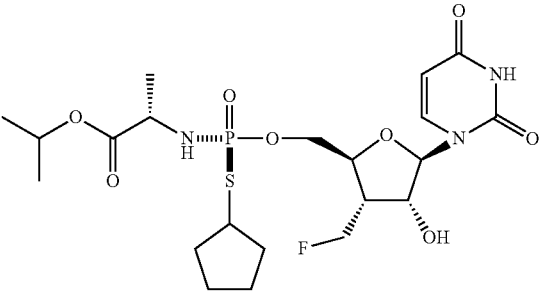
(139b)

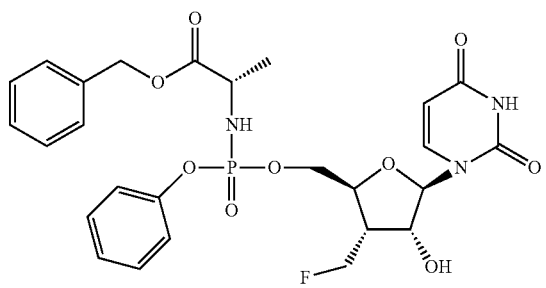
(140a)
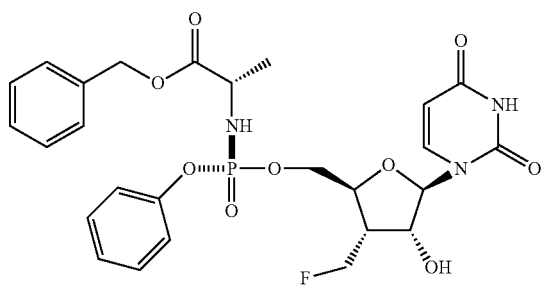
(140ai)
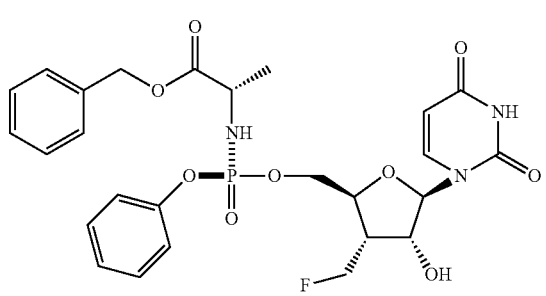
(140aii)
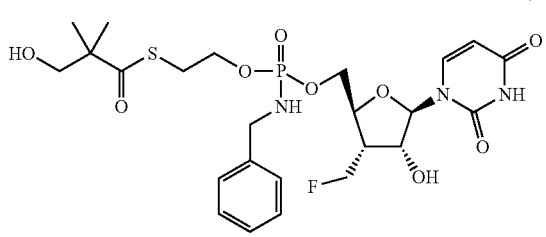
(142)
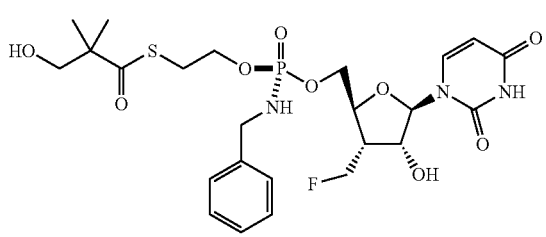
(142a)
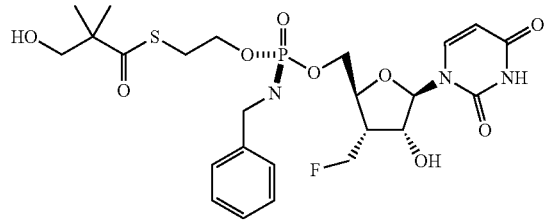
(142b)
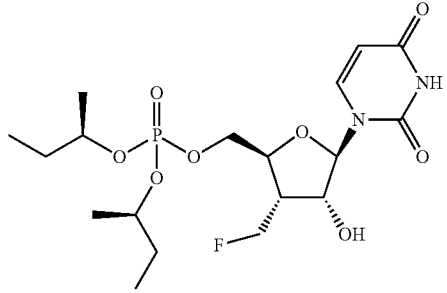
(143)
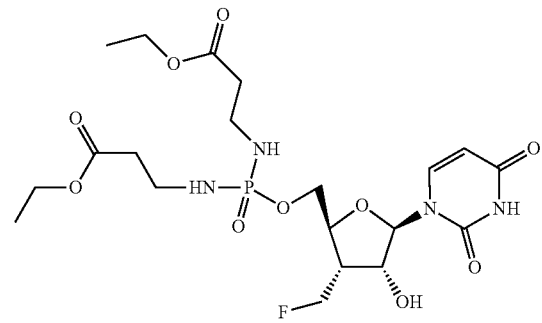
(144)
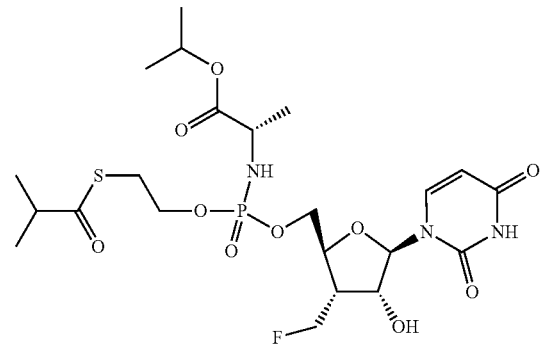
(145a)
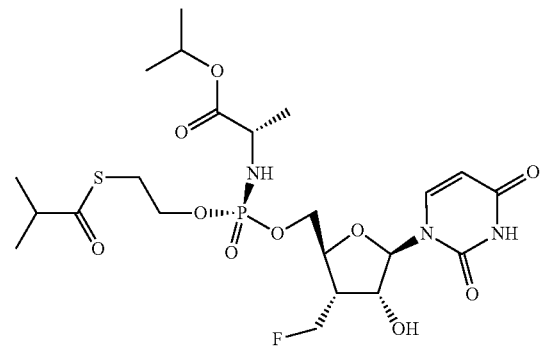
(145ai)

(145aii)
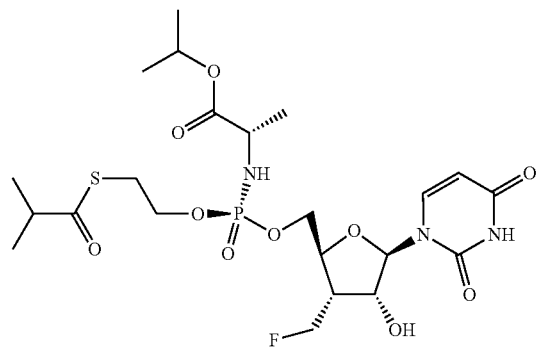
(146)
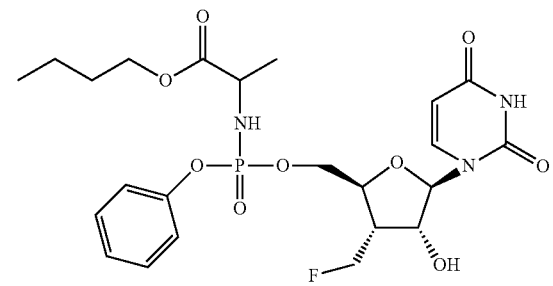
(145b)
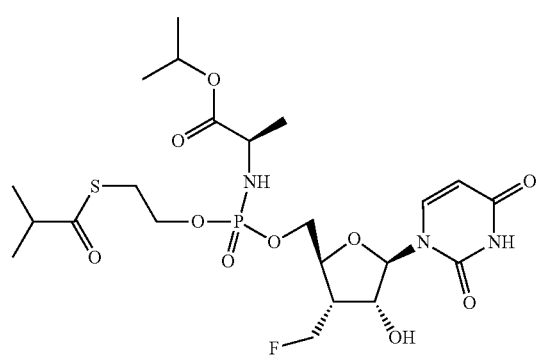
(146a)
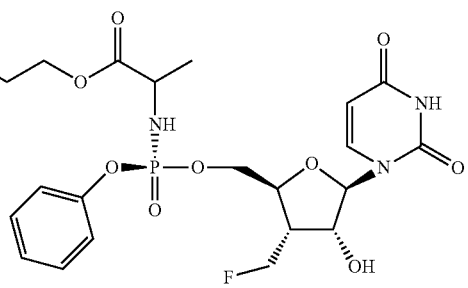
(145bi)
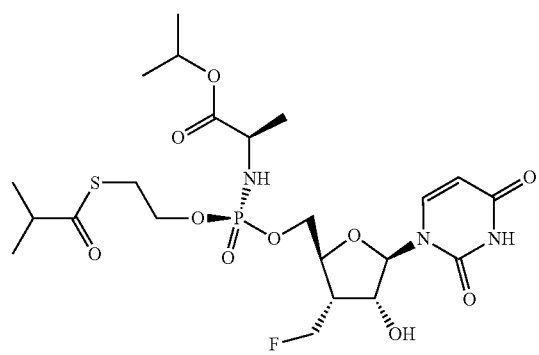
(146b)
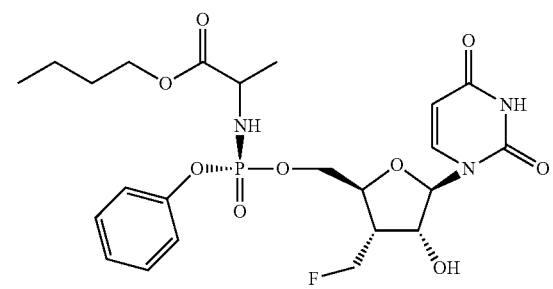
(145bii)
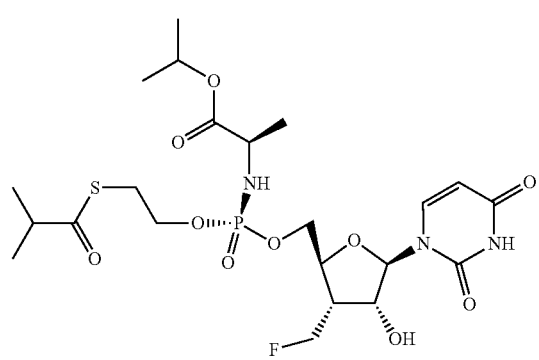
(147)
(148)
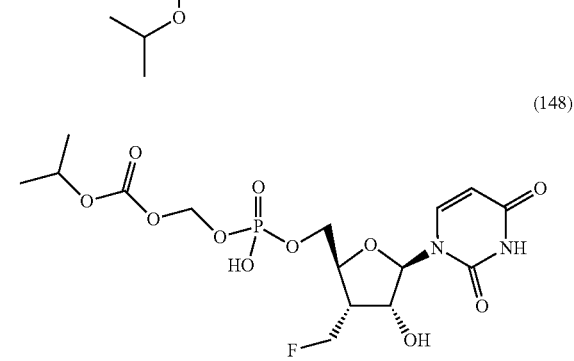

(149) 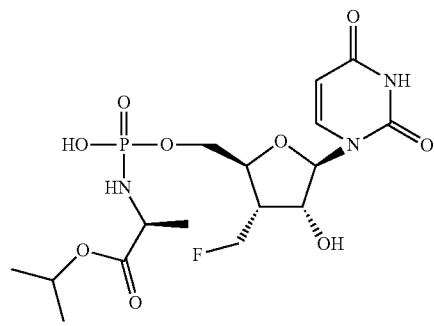
(150) 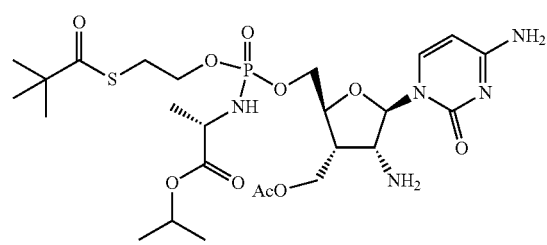
(151) 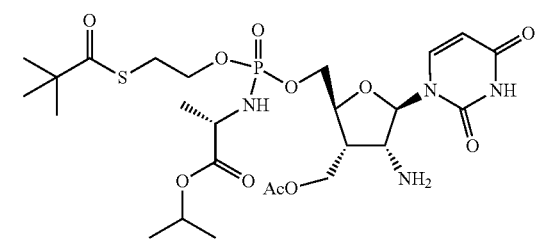
(152) 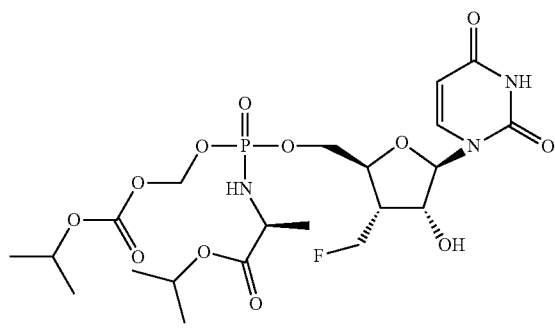
(153) 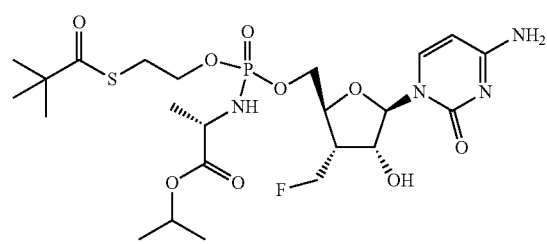
(154) 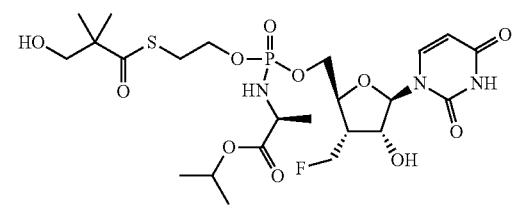
(155) 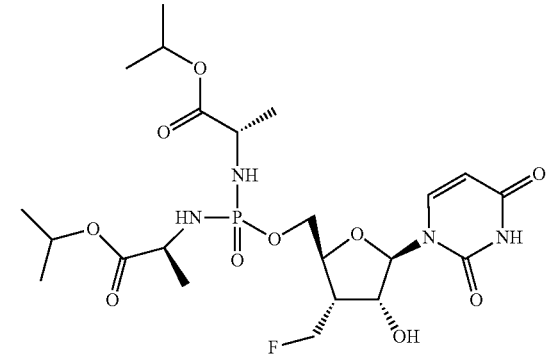
(156) 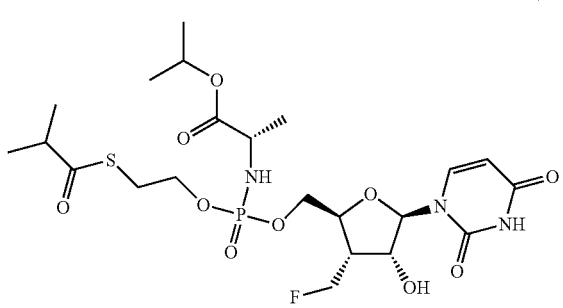
(156a) 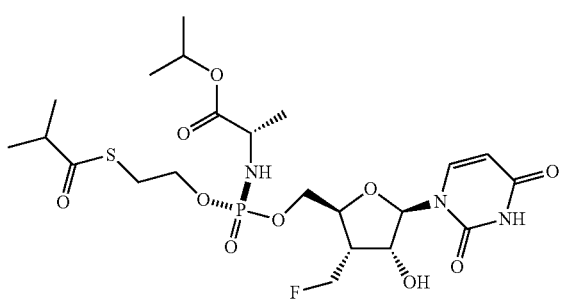
(156b) 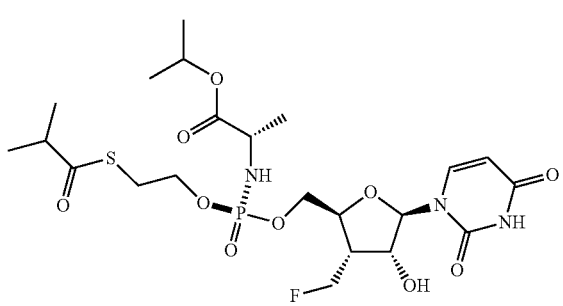

(157)
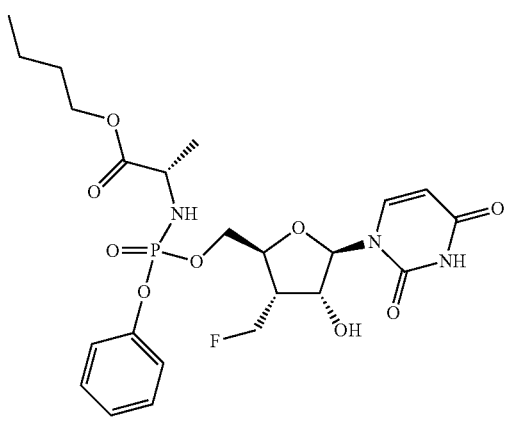
(157a)
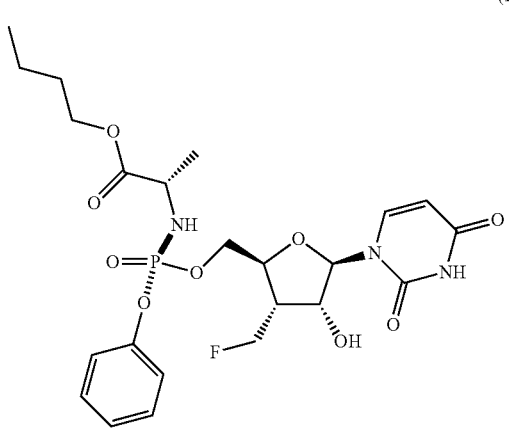
(157b)
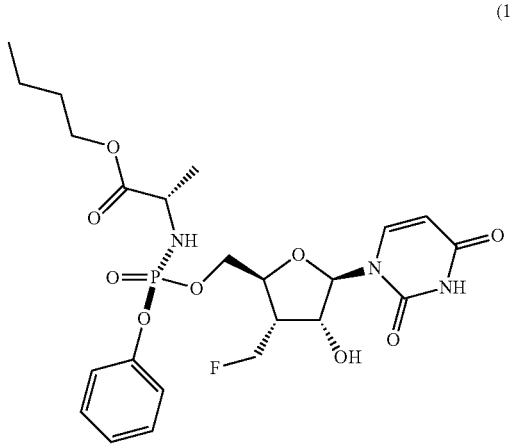
(158)
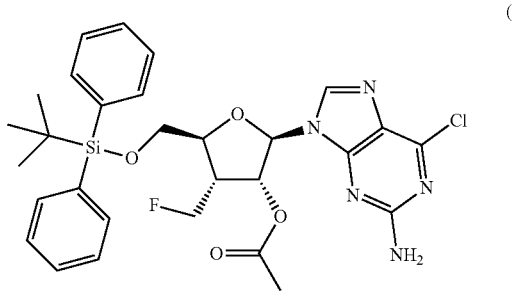
(159)
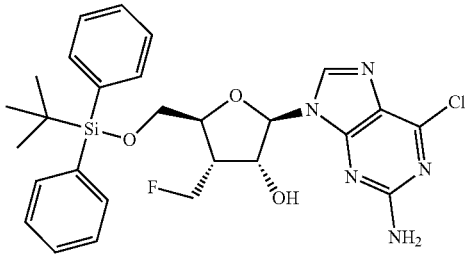
(160)
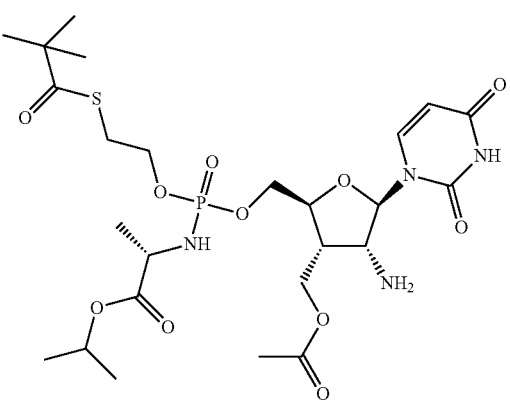
(160a)
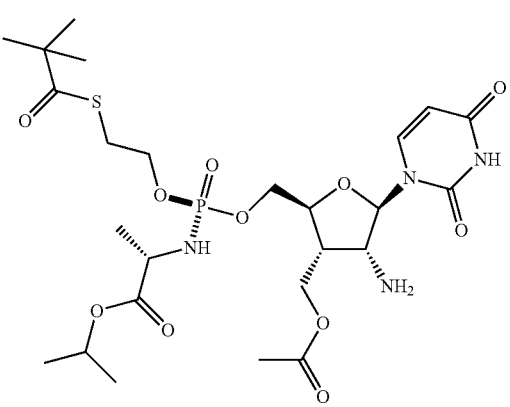
(160b)
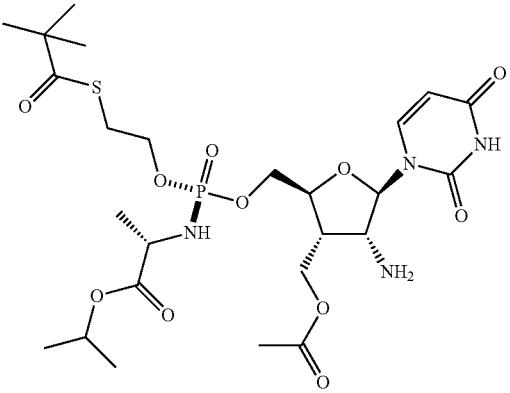

(161)
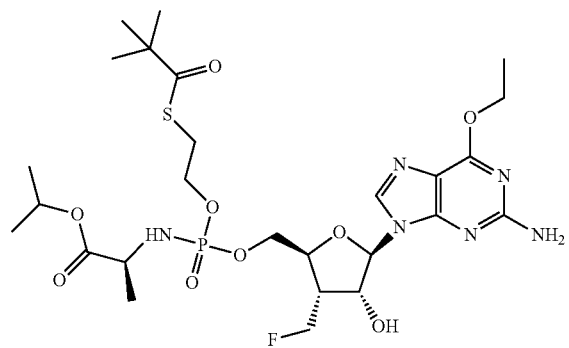
(161a)
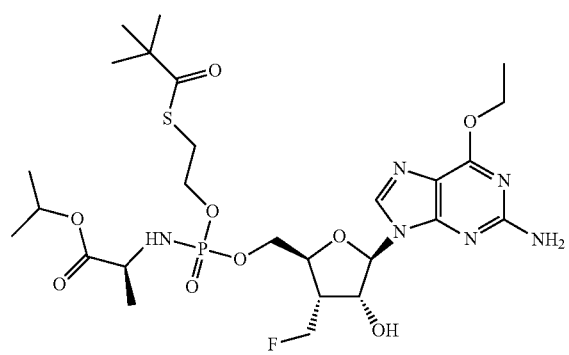
(161b)
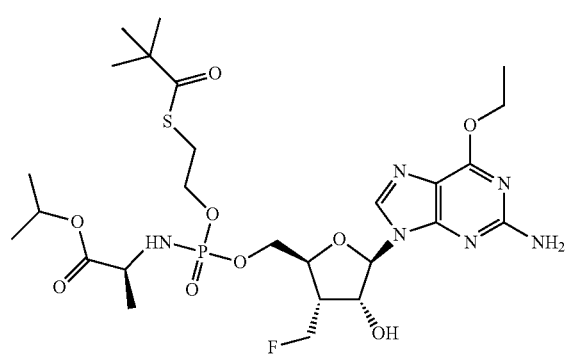
(163a)
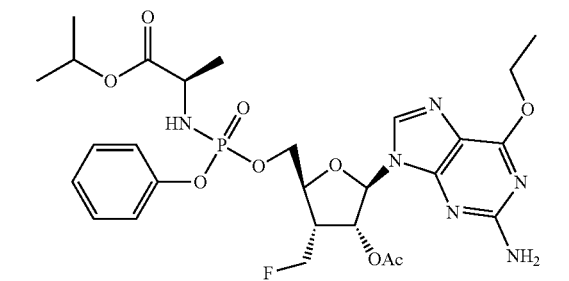
(163ai)
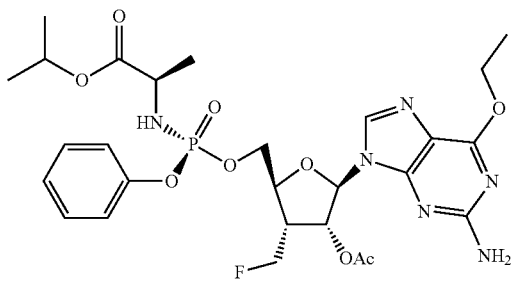
(163aii)
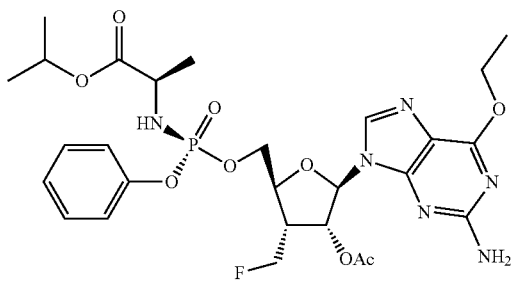
(163b)
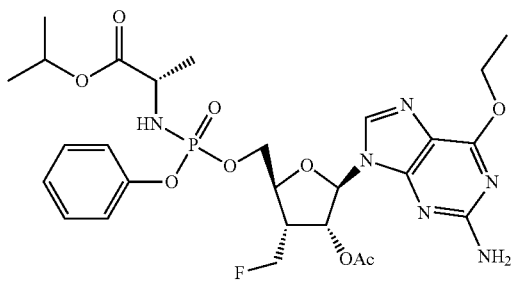
(163bi)
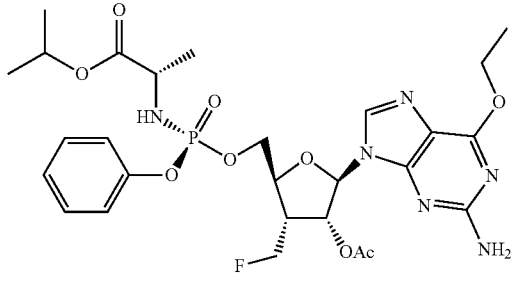
(163bii)
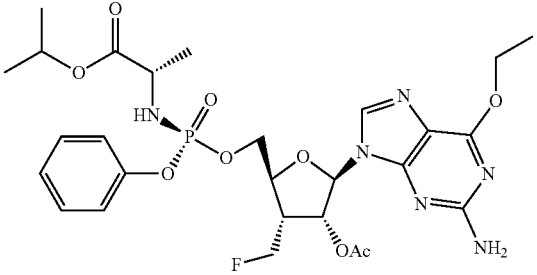

(164)
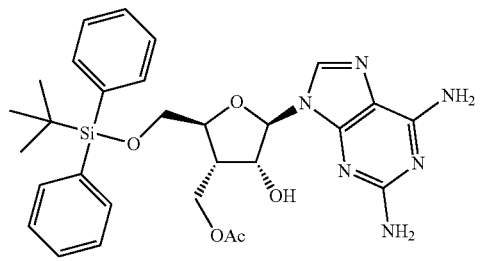
(165)
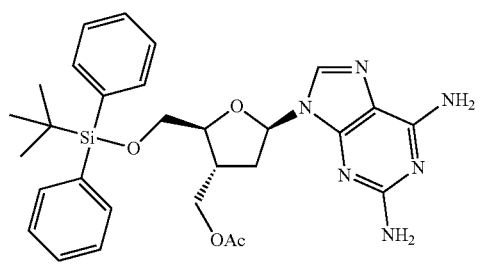
(167)
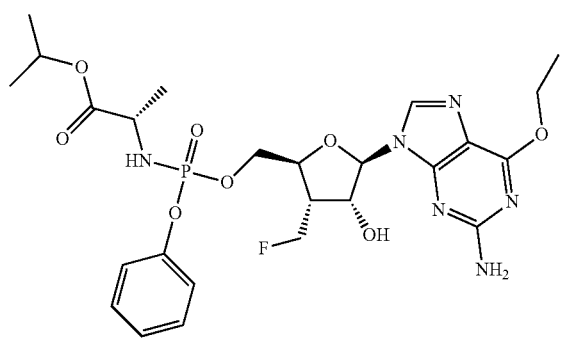
(168)
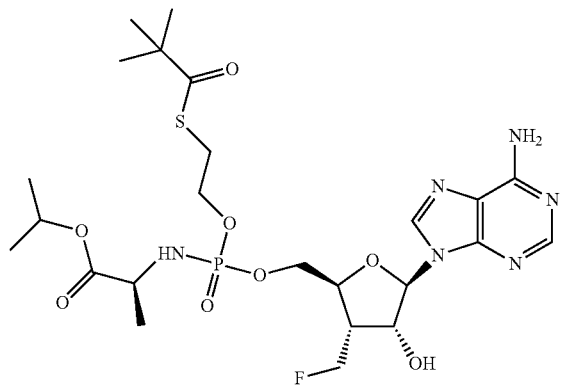
(169)
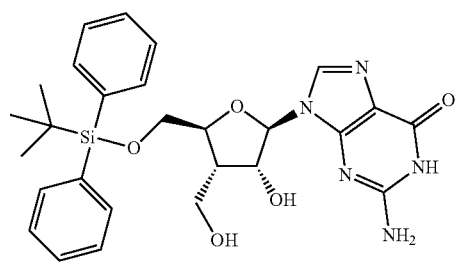
(170)
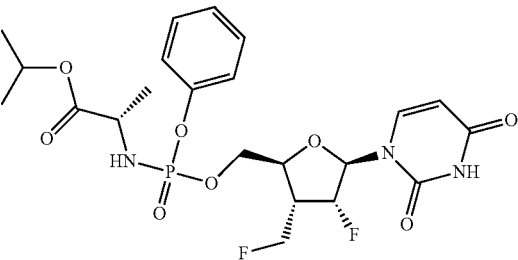
(172)
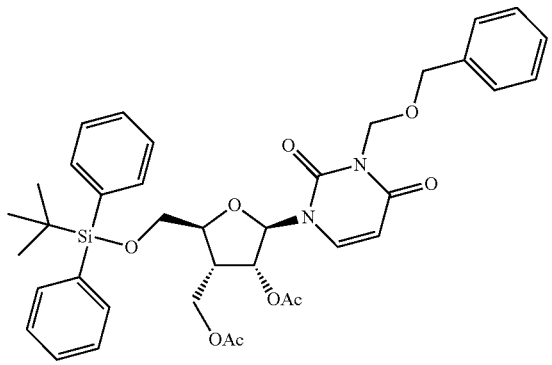
(173)
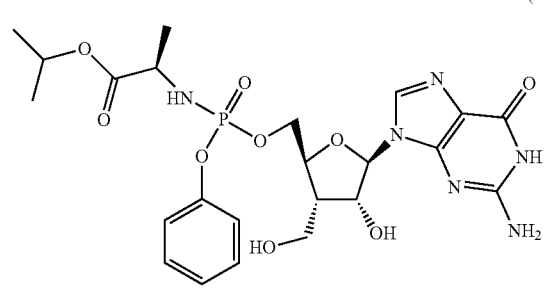
(173a)
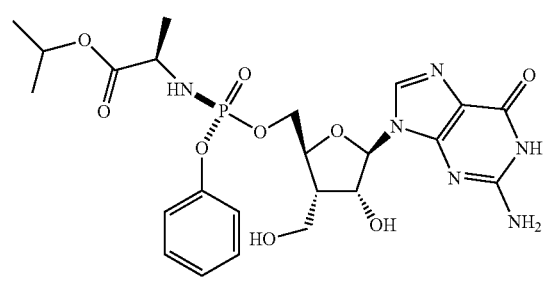
(173b)
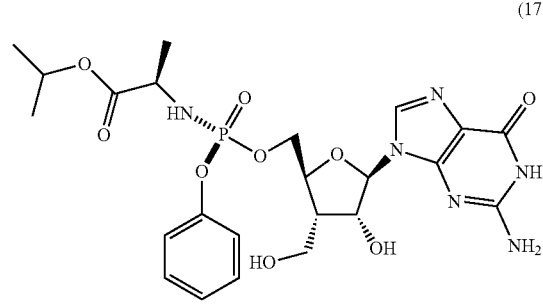

113
-continued
(174)
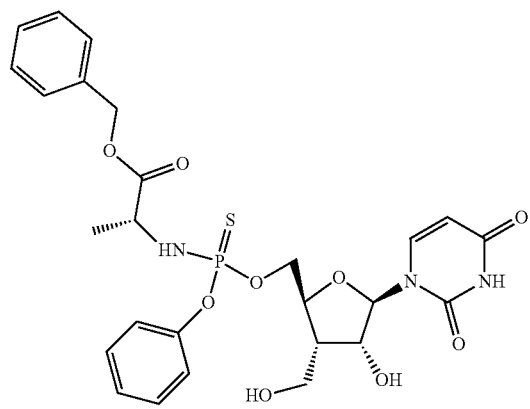
(175)
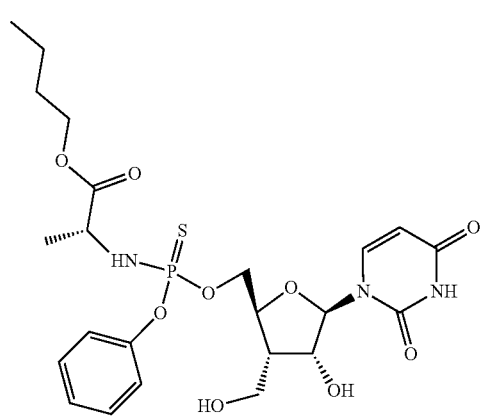
(176)
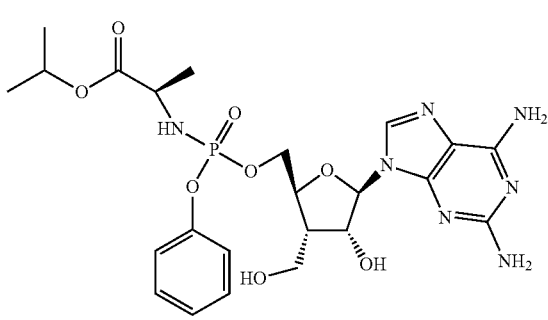
(177a)
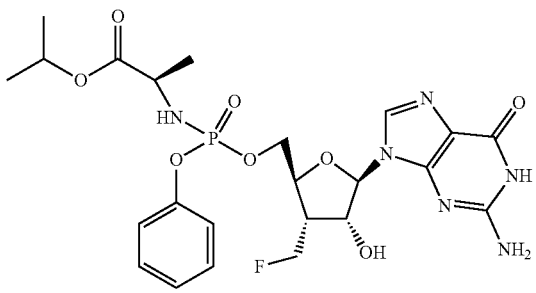
114
-continued
(177ai)
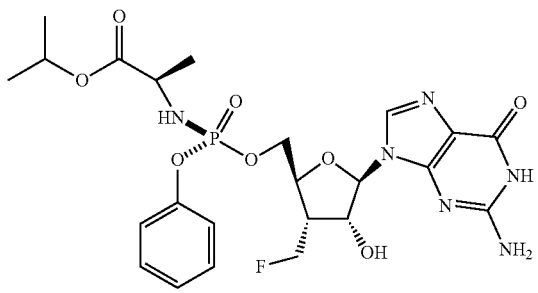
(177aii)
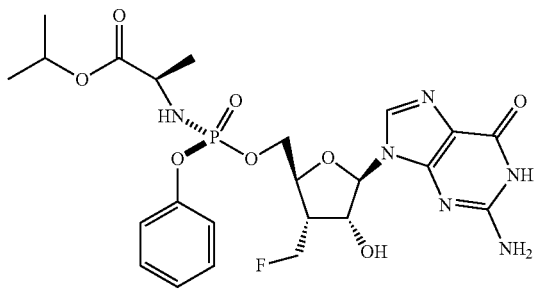
(177b)
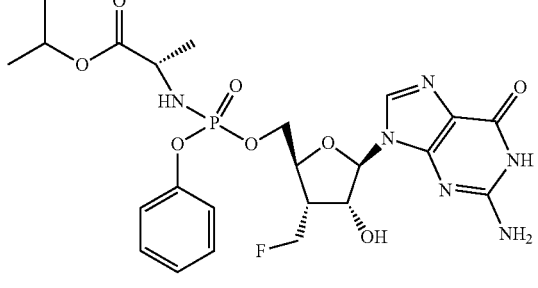
(177bi)
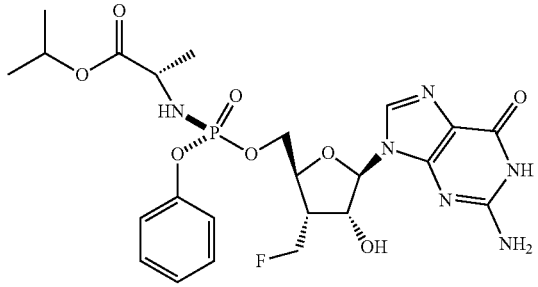
(177bii)
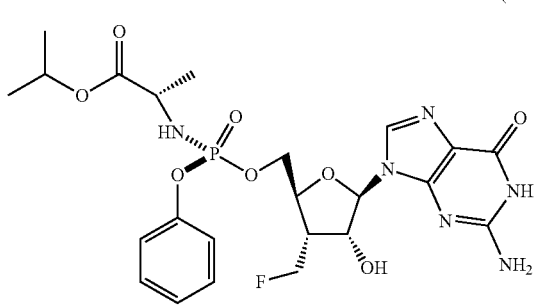

(178a)
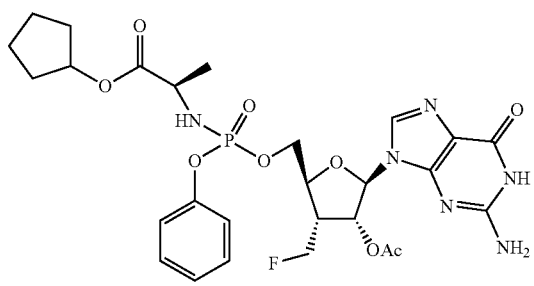
(178b)
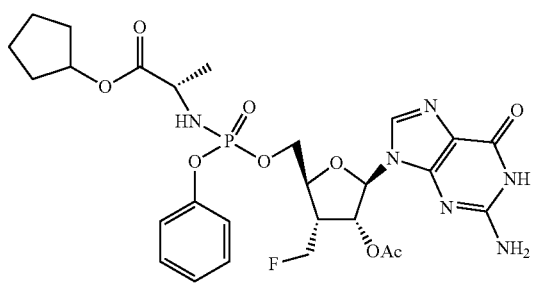
(179a)
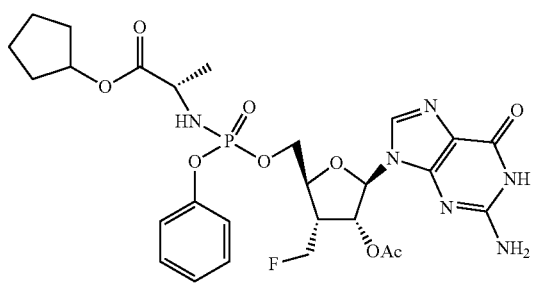
(179ai)
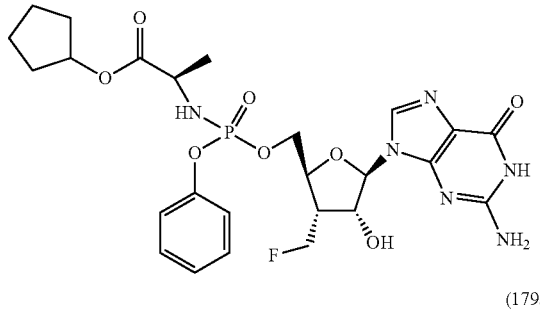
(179aii)
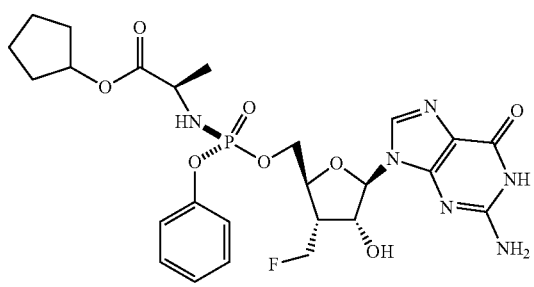
(179b)
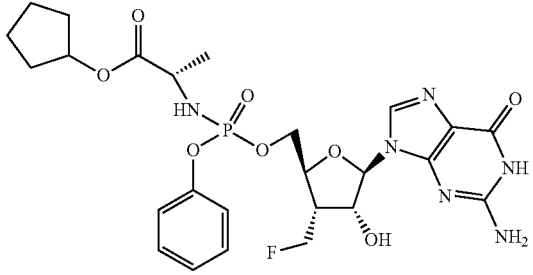
(179bi)
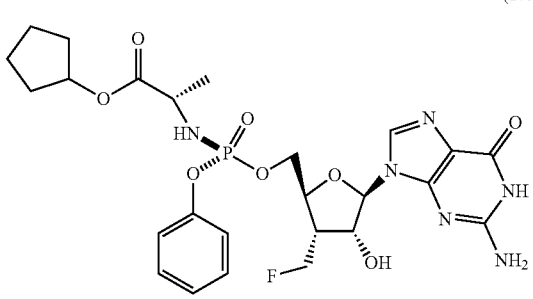
(179bii)
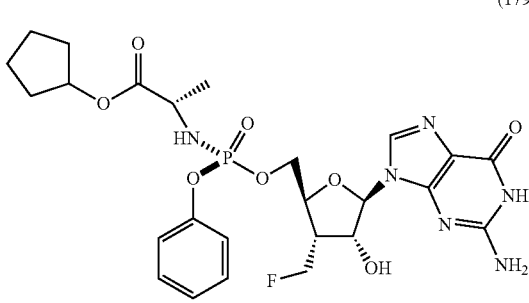
(180)
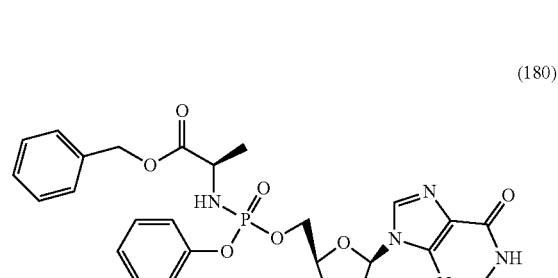
(181)
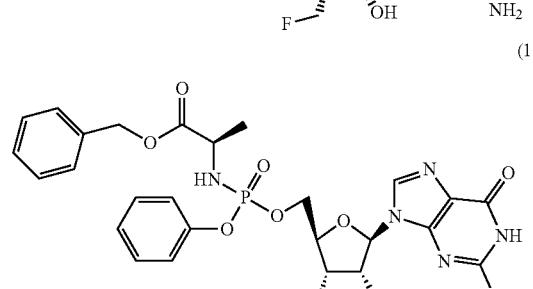

(182) 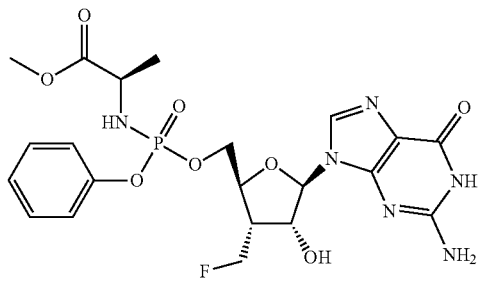
(183) 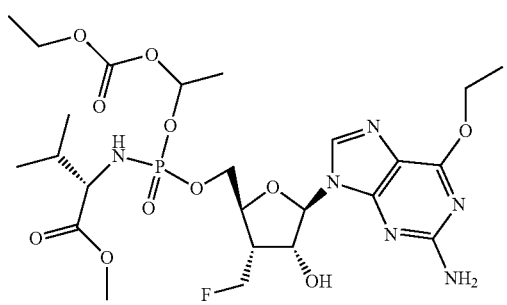
(184) 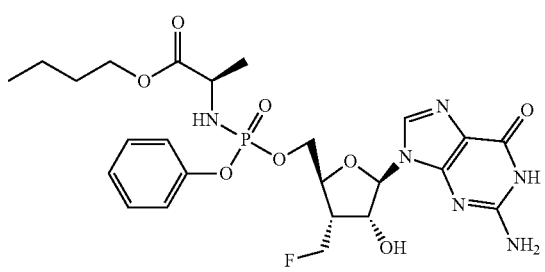
(185) 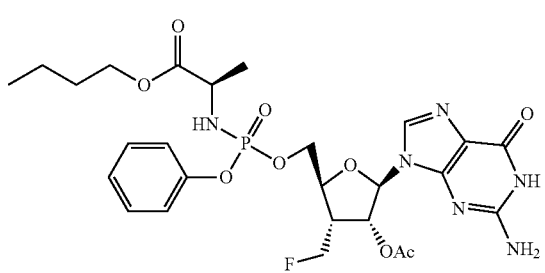
(186) 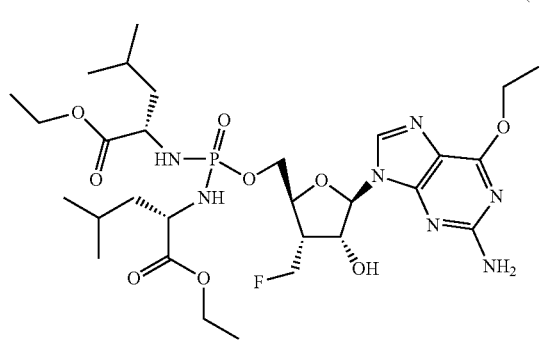
(187) 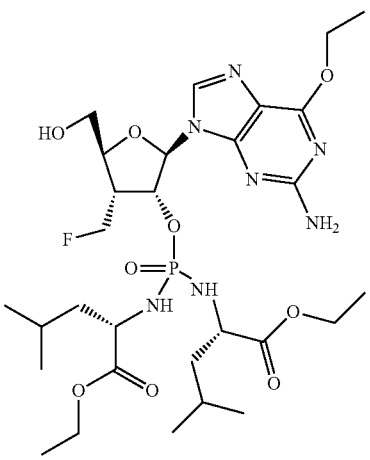
(188) 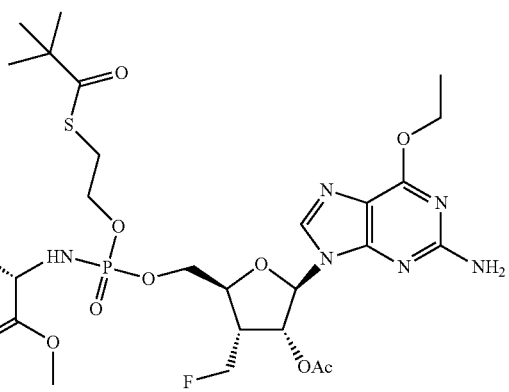
(189) 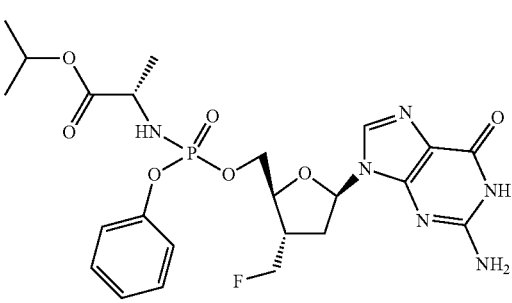
(189a) 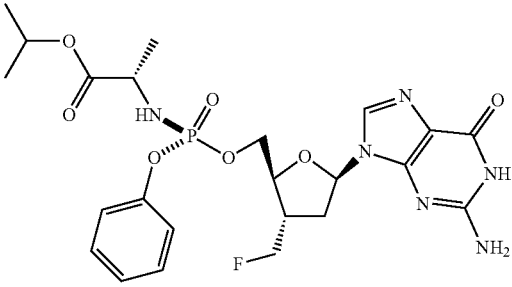

-continued
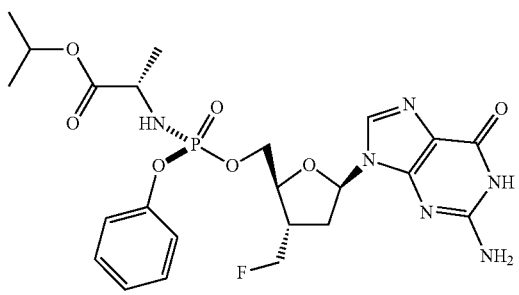
(189b)
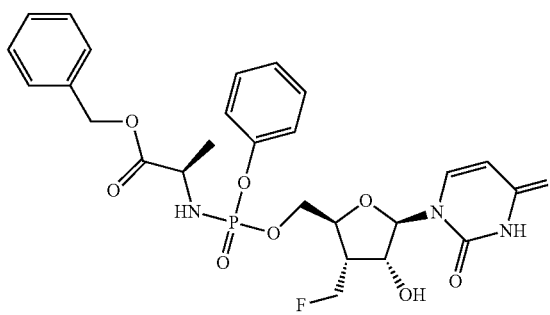
(190)
(190a)
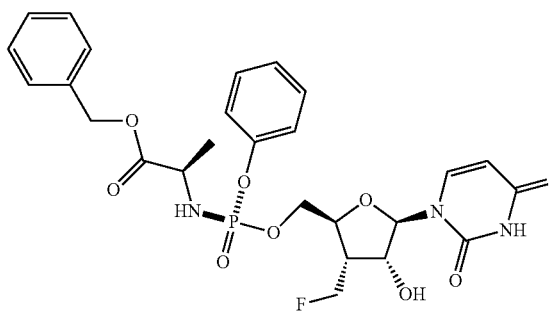
(190b)
or a pharmaceutically acceptable salt thereof.
In certain embodiments, provided herein are compounds according to any of Formulae 191 to 193:
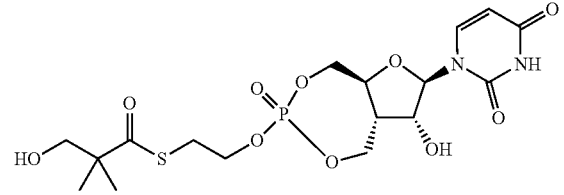
(191)
(191a)
(191b)
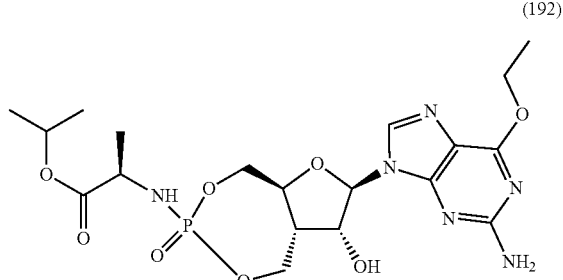
(192)
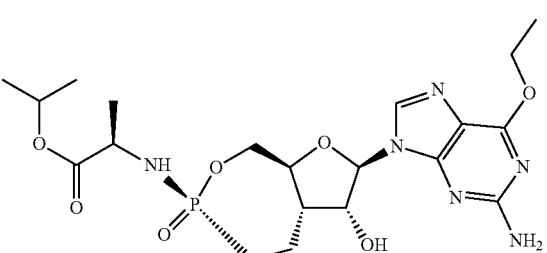
(192a)
(192b)

-continued (193)

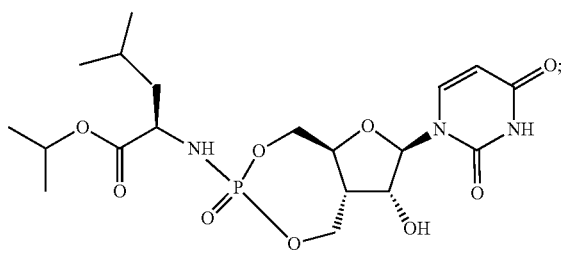

or a pharmaceutically acceptable salt thereof.

In certain embodiments, provided herein are compounds according to Formula 1001:

(1001)

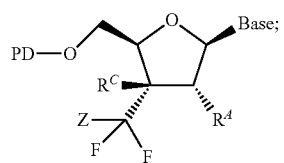

or a pharmaceutically acceptable salt thereof, wherein: $R^A$ is hydroxyl, halo, hydrogen, azido, —NH$_2$, or alkylcarbonyloxy; $R^C$ hydrogen, azido or methyl; Base is a nucleobase; PD is hydrogen, alkylcarbonyl,

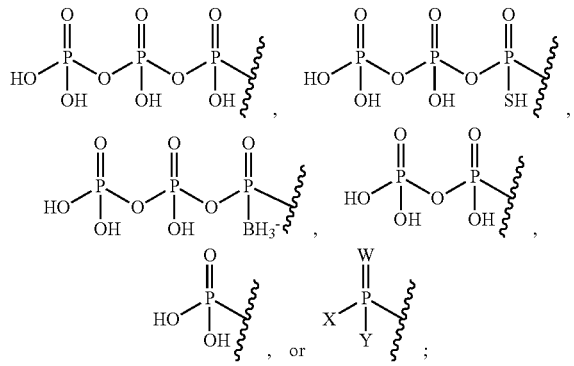

W is S or O; each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene; each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each R$^2$ is independently hydrogen, alkyl, cycloalkyl, aryl, or arylalkyl; provided that when $R^A$ is OH, $R^C$ is H and Z is fluoro, then PD is not hydrogen. In some embodiments, the compound of Formula (1001) is that where $R^A$ is hydroxyl, halo, hydrogen or alkylcarbonyloxy; $R^C$ hydrogen, azido or methyl; Base is a nucleobase; PD is hydrogen,

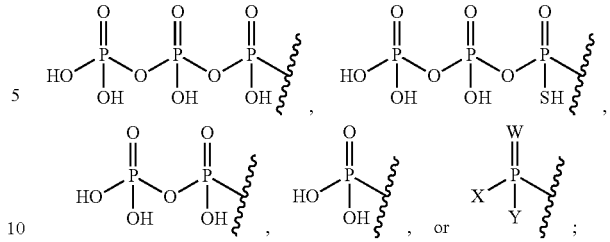

W is S or O; each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene; each R$^1$ is independently hydrogen, alkyl, aryl, arylalkyl, cycloalkyl, heterocycloalkyl, alkoxylcarbonylalkyl or alkylcarbonylthioalkyl; and each R$^2$ is independently hydrogen, alkyl, cycloalkyl, aryl, or arylalkyl. In an embodiment, a compound according to Formula 1001 is provided wherein $R^C$ is hydrogen.

In certain embodiments, provided herein are compounds according to Formula 1001, wherein Base is:

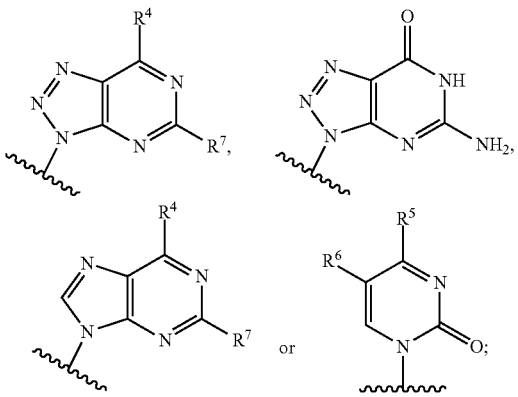

or tautomeric form thereof, wherein: $R^4$ is hydrogen, hydroxyl, alkoxyl, amino, or aminoalkyl; $R^5$ is hydrogen, hydroxyl, amino, or alkoxyl; $R^6$ is hydrogen, halogen, or alkyl; and $R^7$ is hydrogen, hydroxyl or amino. In certain embodiments, provided herein are compounds according to Formula 1001, wherein Base is:

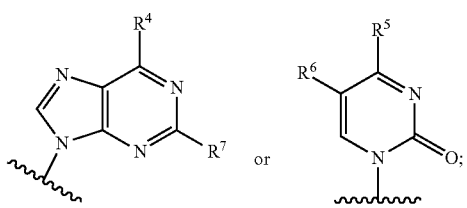

or tautomeric form thereof, wherein: $R^4$ is hydrogen, hydroxyl, alkoxyl, amino or aminoalkyl; $R^5$ is hydrogen, hydroxyl, amino, or alkoxyl; $R^6$ is hydrogen, halogen, or alkyl; and $R^7$ is hydrogen, hydroxyl or amino.

In certain embodiments, provided herein are compounds according to any of Formulas XXII-XXV:

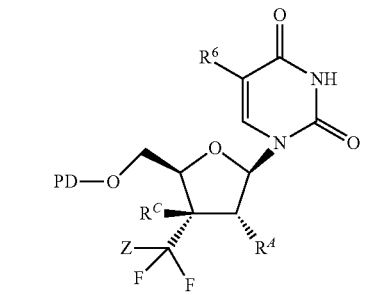
(XXII)

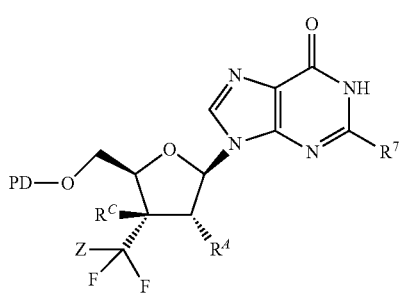
(XXIII)

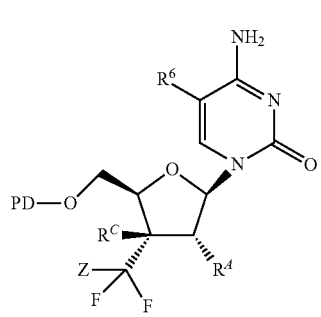
(XXIV)

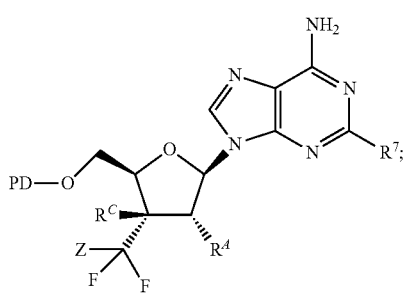
(XXV)

or a pharmaceutically acceptable salt thereof, wherein: PD, $R^A$, $R^C$ and Z are as described in the context of Formula 1001; $R^6$ is hydrogen, halogen, or alkyl; and $R^7$ is hydrogen, hydroxyl, or amino.

In certain embodiments, provided herein are compounds according to any of Formulas XXVI-XLVI:

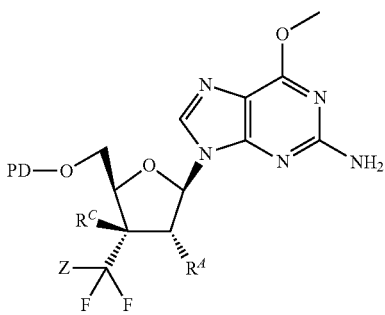
(XXVI)

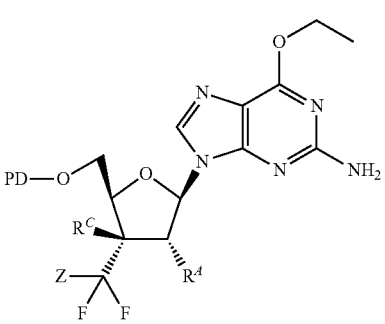
(XXVII)

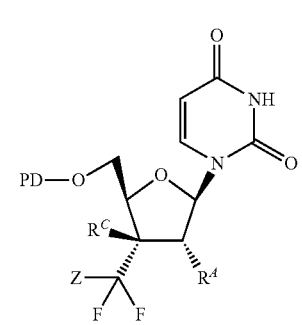
(XXVIII)

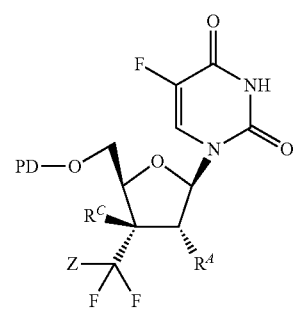
(XXIX)

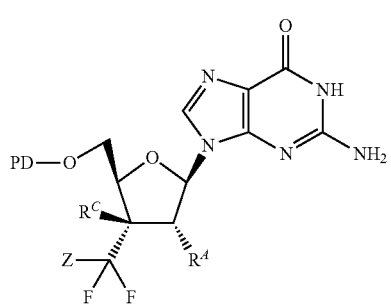
(XXX)

(XXXI)
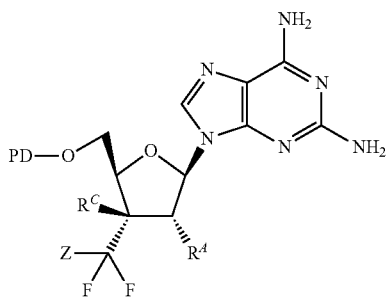

(XXXII)
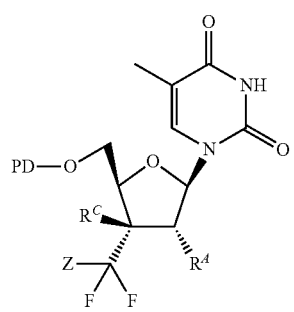

(XXXIII)
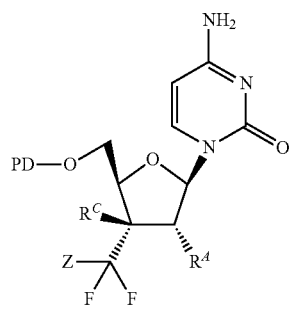

(XXXIV)
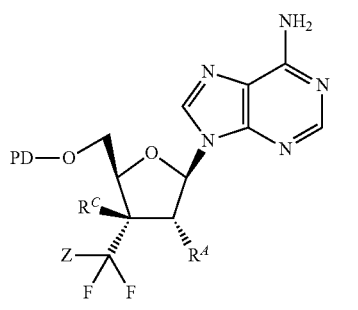

(XLV)
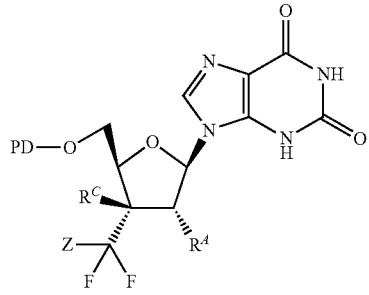

(XLVI)
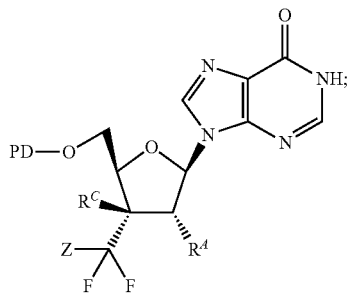

or a pharmaceutically acceptable salt thereof, wherein PD, $R^A$, $R^C$ and Z are as described in the context of Formula 1001.

In certain embodiments provided herein are compounds according to any of Formulas 1001, XXII-XXXIV, XLV, or XLVI, wherein $R^A$ is acetyloxy, fluoro, or hydroxyl. In certain embodiments provided herein are compounds according to any of Formulas 1001, XXII-XXXIV, XLV, or XLVI, wherein $R^A$ is fluoro or hydroxyl. In certain embodiments provided herein are compounds according to any of Formulas 1001, XXII-XXXIV, XLV, or XLVI, wherein $R^A$ is fluoro. In certain embodiments provided herein are compounds of any of Formulas 1001, XXII-XXXIV, XLV, or XLVI, wherein $R^A$ is hydroxyl. In certain embodiments provided herein are compounds of any of Formulas 1001, XXII-XXXIV, XLV, or XLVI, wherein $R^A$ is acetyloxy.

In certain embodiments provided herein are compounds according to any of Formulas 1001, XXII-XXXIV, XLV, or XLVI, wherein each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is acetyloxy, fluoro, or hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is fluoro or hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is fluoro. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl, alkoxycarbonyloxyalkyl, or alkylcarbonylthioalkyl; and $R^A$ is acetyloxy. In certain embodiments provided herein are compounds according to any of Formulas 1001, XXII-XXXIV, XLV, or XLVI, wherein each $R^1$ is independently alkyl, aryl, arylalkyl, cycloalkyl, heterocycloalkyl, alkoxylcarbonylalkyl or alkylcarbonylthioalkyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl or alkylcarbonylthioalkyl; and $R^4$ is acetyloxy, fluoro or hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl or alkylcarbonylthioalkyl; and $R^4$ is fluoro or hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl or alkylcarbonylthioalkyl; and $R^4$ is fluoro. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl or alkylcarbonylthioalkyl; and $R^4$ is hydroxyl. In certain embodiments provided herein are compounds according to any of Formulas 1001, XXII-XXXIV, XLV, or XLVI, wherein: each $R^1$ is independently alkyl, aryl, arylalkyl, cycloalkyl, heterocycloalkyl, alkoxylcarbonylalkyl or alkylcarbonylthioalkyl; and $R^4$ is acetyloxy.

In some embodiments, provided herein are:
(a) compounds as described herein, e.g., of Formula 1001, I-XLVI, 101-122bii, 201-255, 301-336, 340-345, 123a to 125bii, 128a-130bii, 131a to 140aii, 142 to 161b, 163a-165, 167-170, 172-190b, 191 to 193, and 401-404, and pharmaceutically acceptable salts and compositions thereof;
(b) compounds as described herein, e.g., of Formula 1001, I-XLVI, 101-122bii, 201-255, 301-336, 340-345, 123a to 125bii, 128a-130bii, 131a to 140aii, 142 to 161b, 163a-165, 167-170, 172-190b, 191 to 193, and 401-404, and pharmaceutically acceptable salts and compositions thereof for use in the treatment and/or prophylaxis of a liver disorder including Flaviviridae infection, especially in individuals diagnosed as having a Flaviviridae infection or being at risk of becoming infected by hepatitis C;
(c) processes for the preparation of compounds as described herein, e.g., of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, as described in more detail elsewhere herein;
(d) pharmaceutical formulations comprising a compound as described herein, e.g., of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt thereof together with a pharmaceutically acceptable carrier or diluent;
(e) pharmaceutical formulations comprising a compound as described herein, e.g., of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt thereof together with one or more other effective anti-HCV agents, optionally in a pharmaceutically acceptable carrier or diluent;
(f) a method for the treatment and/or prophylaxis of a host infected with Flaviviridae that includes the administration of an effective amount of a compound as described herein, e.g., of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, its pharmaceutically acceptable salt or composition; or
(g) a method for the treatment and/or prophylaxis of a host infected with Flaviviridae that includes the administration of an effective amount of a compounds as described herein, e.g., of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, its pharmaceutically acceptable salt or composition in combination and/or alternation with one or more effective anti-HCV agent.

Optically Active Compounds

It is appreciated that compounds provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

In particular, since the 1' and 4' carbons of a nucleoside are chiral, their non-hydrogen substituents (the base and the CHOR groups, respectively) can be either cis (on the same side) or trans (on opposite sides) with respect to the sugar ring system. The four optical isomers therefore are represented by the following configurations (when orienting the sugar moiety in a horizontal plane such that the oxygen atom is in the back): cis (with both groups "up", which corresponds to the configuration of naturally occurring ß-D nucleosides), cis (with both groups "down", which is a non-naturally occurring ß-L configuration), trans (with the C2' substituent "up" and the C4' substituent "down"), and trans (with the C2' substituent "down" and the C4' substituent "up"). The "D-nucleosides" are cis nucleosides in a natural configuration and the "L-nucleosides" are cis nucleosides in the non-naturally occurring configuration.

Likewise, most amino acids are chiral (designated as L or D, wherein the L enantiomer is the naturally occurring configuration) and can exist as separate enantiomers.

The compounds of and formula described herein may have one or more chiral (asymmetric) centers. Unless specified, the present invention encompasses all stereoisomeric forms of the compounds. Unspecified centers of asymmetry that are present in the compounds can all independently of one another have (R) or (S) configuration. When bonds to a chiral atom are depicted as straight lines in a provide structure, or when a compound name is recited without an (R) or (S) chiral designation for a chiral atom, it is understood that both the (R) and (S) configurations of each such chiral atom, and hence each enantiomer or diastereomer and mixtures thereof, are embraced.

Examples of methods to obtain optically active materials are known in the art, and include at least the following.
  i) physical separation of crystals—a technique whereby macroscopic crystals of the individual stereoisomers are manually separated. This technique can be used if crystals of the separate stereoisomers exist, i.e., the material is a conglomerate, and the crystals are visually distinct;
  ii) simultaneous crystallization—a technique whereby the individual stereoisomers are separately crystallized from a solution of the racemate, possible only if the latter is a conglomerate in the solid state;

iii) enzymatic resolutions—a technique whereby partial or complete separation of a racemate by virtue of differing rates of reaction for the stereoisomers with an enzyme;

iv) enzymatic asymmetric synthesis—a synthetic technique whereby at least one step of the synthesis uses an enzymatic reaction to obtain a stereoisomerically pure or enriched synthetic precursor of the desired stereoisomer;

v) chemical asymmetric synthesis—a synthetic technique whereby the desired enantiomer or diastereomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual isomers to diastereomers. The resulting diastereomers are then separated by chromatography or crystallization by virtue of their now more distinct structural differences and the chiral auxiliary later removed to obtain the desired isomer;

vii) first- and second-order asymmetric transformations—a technique whereby diastereomers from the racemate equilibrate to yield a preponderance in solution of the diastereomer from the desired isomer or where preferential crystallization of the diastereomer from the desired isomer perturbs the equilibrium such that eventually in principle all the material is converted to the crystalline diastereomer from the desired isomer. The desired isomer is then released from the diastereomer;

viii) kinetic resolutions—this technique refers to the achievement of partial or complete resolution of a racemate (or of a further resolution of a partially resolved compound) by virtue of unequal reaction rates of the stereoisomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the stereoisomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and stereoisomers are separated by virtue of their differing interactions in the gaseous mobile phase with a column containing a fixed non-racemic chiral adsorbent phase;

xii) extraction with chiral solvents—a technique whereby the stereoisomers are separated by virtue of preferential dissolution of one stereoisomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one stereoisomer of the racemate to pass through.

In some embodiments, provided is a composition of a 3'-substituted methyl or alkynyl nucleoside compound that comprises a substantially pure designated stereoisomers of the 3'-substituted methyl or alkynyl nucleoside compound. In certain embodiments, in the methods and compounds of this invention, the compounds are substantially free of other stereoisomers. In some embodiments, a composition includes a compound that is at least 85%, 90%, 95%, 98%, 99% or 100% by weight, of the compound, the remainder comprising other chemical species or stereoisomers.

Isotopically Enriched Compounds

Also provided herein are isotopically enriched compounds, including but not limited to isotopically enriched 3'-substituted methyl or alkynyl nucleoside compounds.

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

Preparation of Compounds

The compounds provided herein can be prepared, isolated, or obtained, in certain instances, by a method apparent to those of skill in the art. Compounds provided herein can be prepared according to the Exemplary Preparation Schemes provided below. Reaction conditions, steps, and reactants not provided in the Exemplary Preparation Schemes would be apparent to, and known by, those skilled in the art.

Exemplary Preparation Schemes

Exemplary Preparation Scheme 1

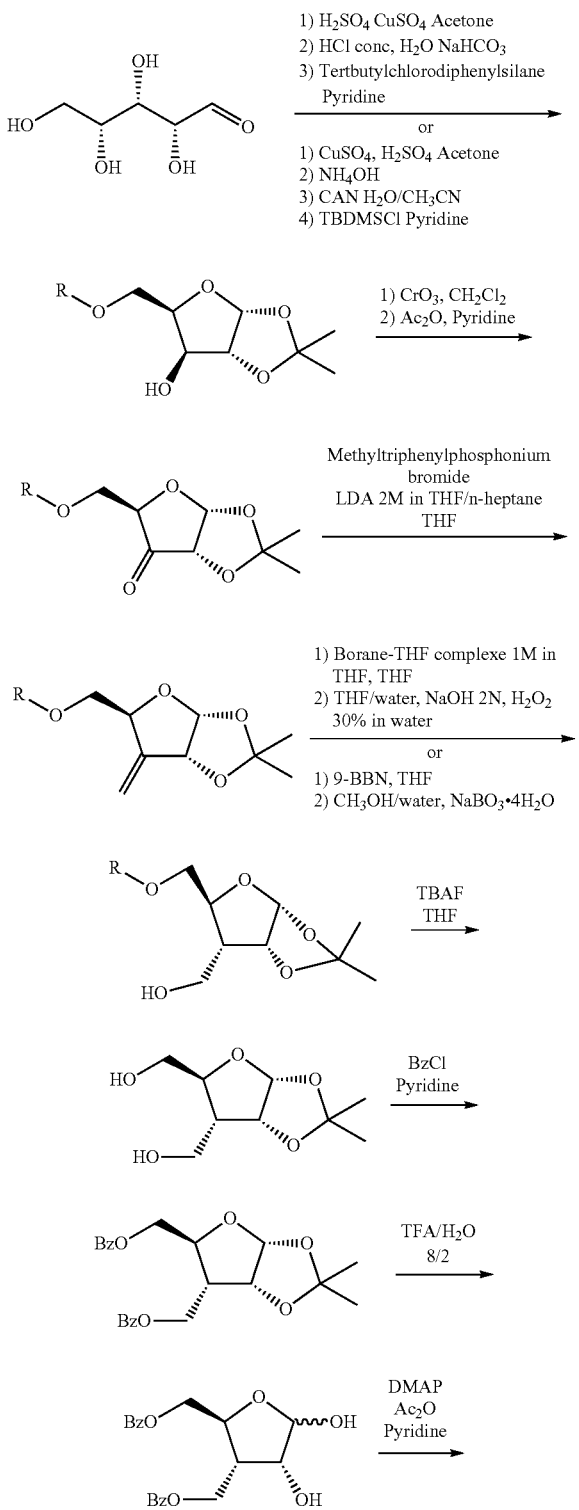

133
-continued
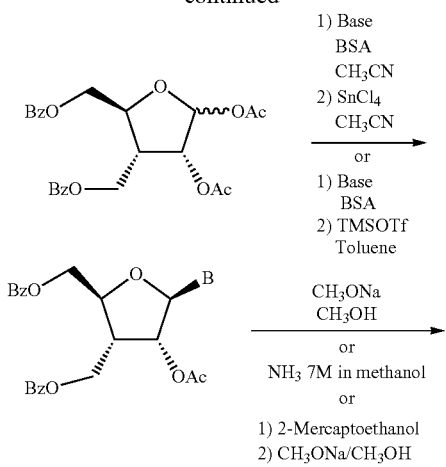
134
-continued
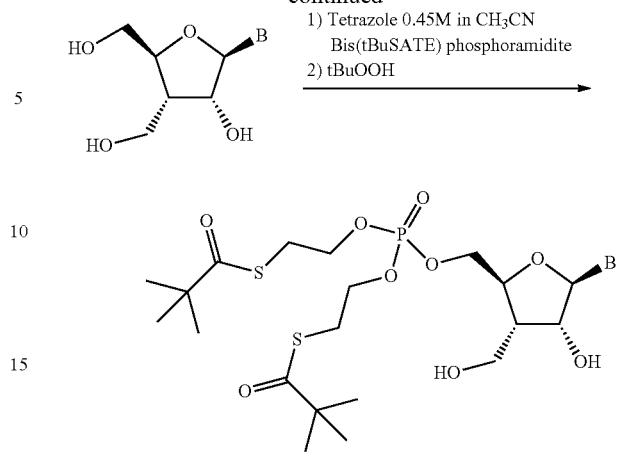
Exemplary Preparation Scheme 2
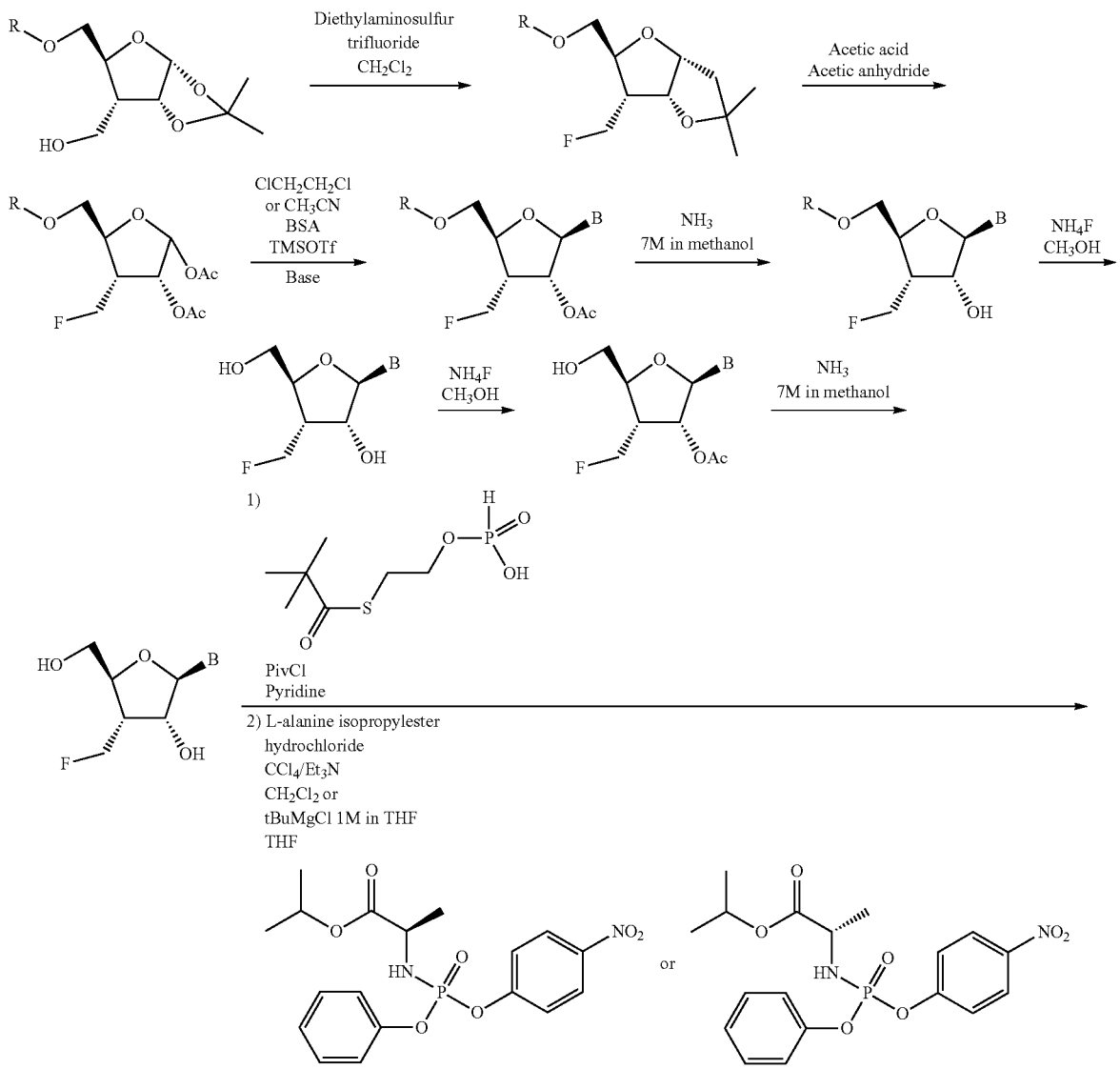

-continued
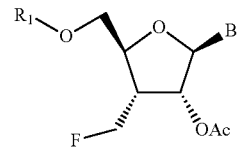
$R_1 =$ 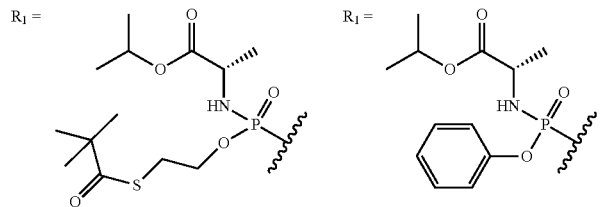 $R_1 =$ 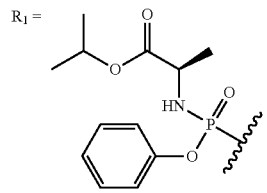
Exemplary Preparation Scheme 3
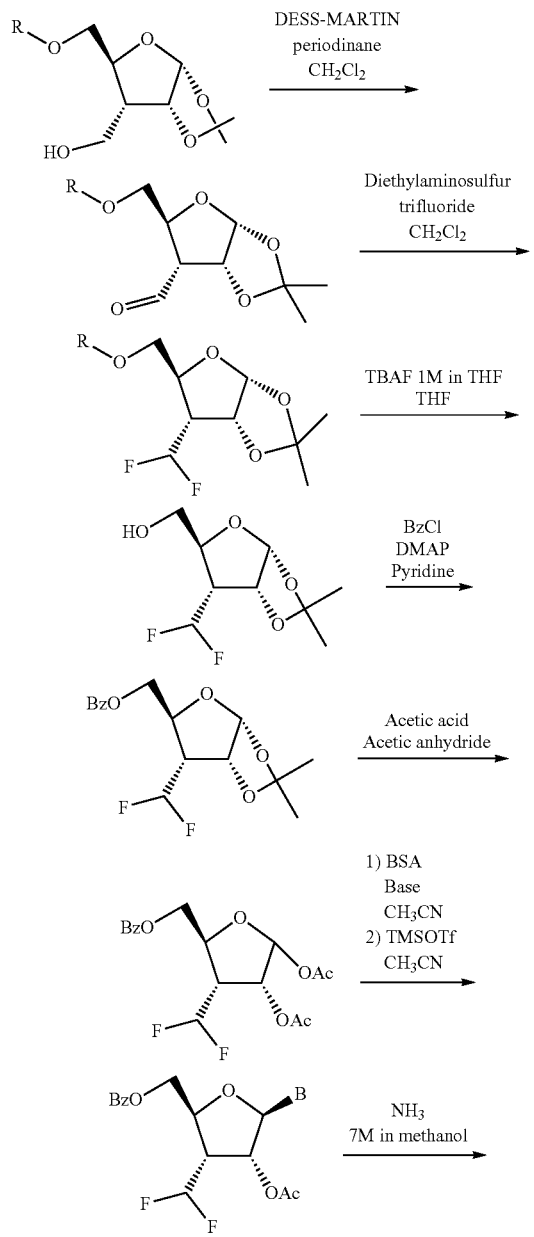
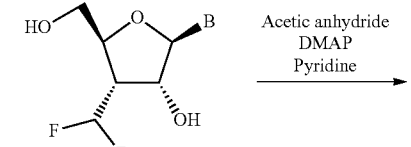
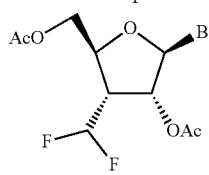
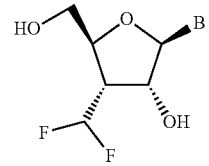
Exemplary Preparation Scheme 4
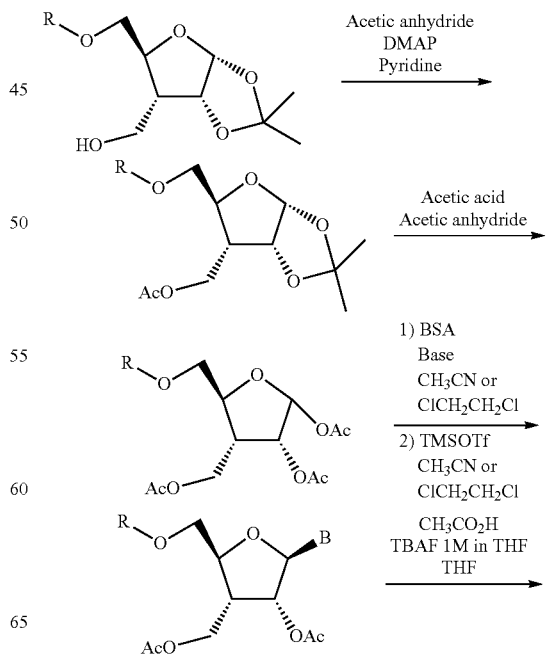

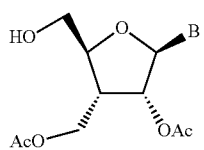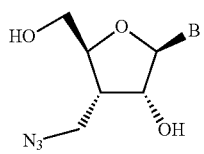
Exemplary Preparation Scheme 5
Exemplary Preparation Scheme 6
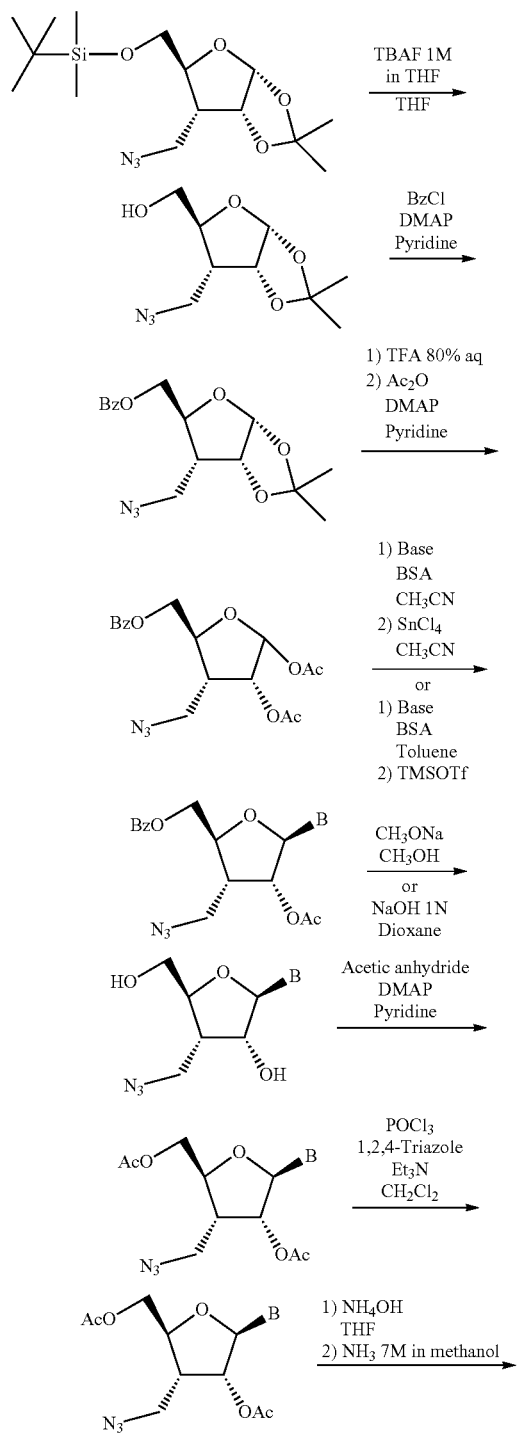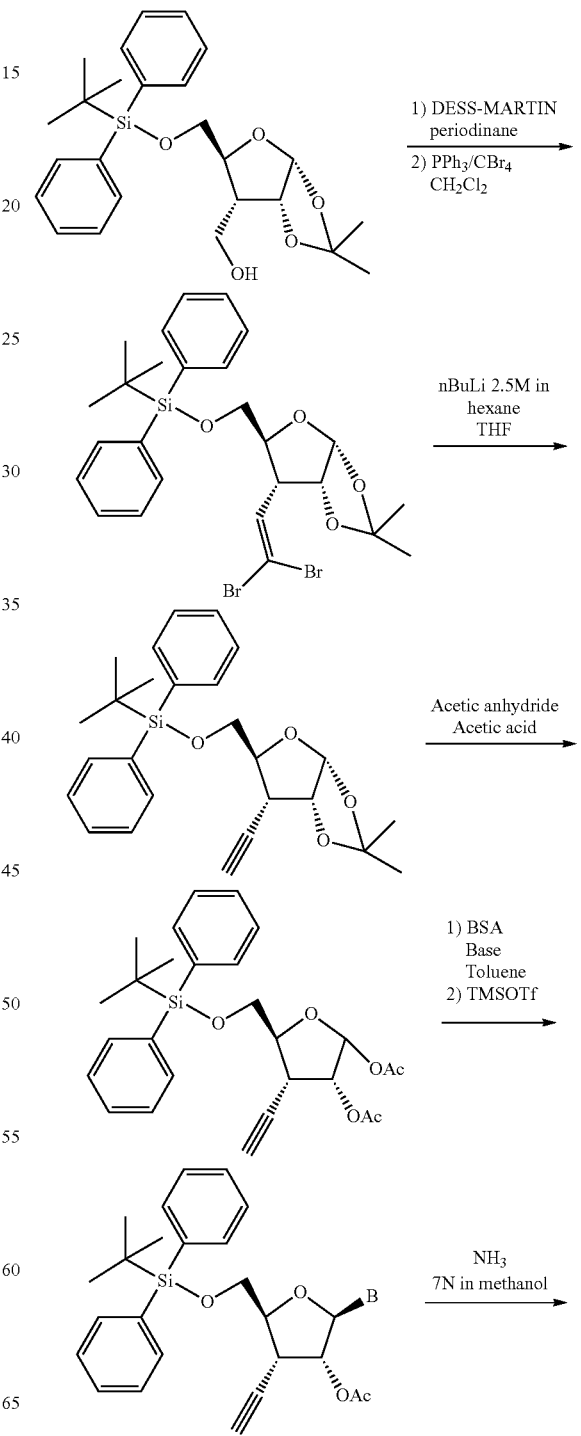

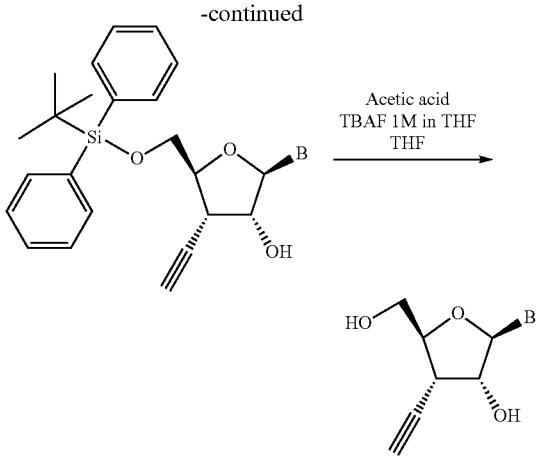

In the Exemplary Preparation Schemes, B is a nucleobase as described herein and R is a protecting group as known to those of skill in the art. Additional steps and reagents not provided in the Exemplary Preparation Schemes would be known to those of skill in the art. Exemplary methods of preparation are described in detail in the Examples herein.

Pharmaceutical Compositions and Methods of Administration

3'-substituted methyl or alkynyl nucleoside compounds can be formulated into pharmaceutical compositions using methods available in the art and those disclosed herein. Any of the compounds disclosed herein can be provided in the appropriate pharmaceutical composition and be administered by a suitable route of administration.

The methods provided herein encompass administering pharmaceutical compositions containing at least one compound as described herein, including a compound of general Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, if appropriate in the salt form, either used alone or in the form of a combination with one or more compatible and pharmaceutically acceptable carriers, such as diluents or adjuvants, or with another anti-HCV agent.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular orally, parenterally, rectally or by inhalation (e.g. in the form of aerosols). In certain embodiments, the compound provided herein is administered orally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, for example wetting, sweetening or flavoring products.

The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, for example, in the U.S. Pharmocopia (USP) SP (XXI)/NF (XVI). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, for example, an animal subject, such as a mammalian subject, for example, a human subject.

A pharmaceutical composition is formulated to be compatible with its intended route of administration. Examples of routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intratumoral, intra-synovial and rectal administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of viral infection may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington's Pharmaceutical Sciences, 20th ed., Mack Publishing, Easton Pa. (2000).

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable salt, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 20th ed., Mack Publishing, Easton Pa. (2000).

In certain embodiments, the oral dosage forms are solid and prepared under anhydrous conditions with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

Examples of excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gelcaps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, $16^{th}$, 18th and $20^{th}$ eds., Mack Publishing, Easton Pa. (1980, 1990 & 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16$^{th}$, 18th and 20$^{th}$ eds., Mack Publishing, Easton Pa. (1980, 1990 & 2000).

Depending on the specific tissue to be treated, additional components may be used prior to, in conjunction with, or subsequent to treatment with active ingredients provided. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different salts, hydrates or solvates of the active ingredients can be used to further adjust the properties of the resulting composition.

Dosage and Unit Dosage Forms

In human therapeutics, the doctor will determine the posology which he considers most appropriate according to a preventive or curative treatment and according to the age, weight, stage of the infection and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating or preventing an HCV infection in a subject by administering, to a subject in need thereof, an effective amount of a compound provided herein, or a pharmaceutically acceptable salt thereof. The amount of the compound or composition which will be effective in the prevention or treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, or between 0.30 mg/kg and 1.50 mg/kg of the subject's body weight.

In certain embodiments, the recommended daily dose range of a composition provided herein for the conditions described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiment, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, or from about 600 to about 1200 ng/mL. In some embodiments, loading doses can be administered to achieve steady-state blood or serum concentrations of about 1200 to about 8000 ng/mL, or about 2000 to about 4000 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable salt thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosages of the second agents are to be used in the combination therapies provided herein. In certain embodiments, dosages lower than those which have been or are currently being used to prevent or treat HCV infection are used in the combination therapies provided herein. The recommended dosages of second agents can be obtained from the knowledge of those of skill. For those second agents that are approved for clinical use, recommended dosages are described in, for example, Hardman et al., eds., 1996, Goodman & Gilman's The Pharmacological Basis Of Basis Of Therapeutics 9$^{th}$ Ed, Mc-Graw-Hill, N.Y.; Physician's Desk Reference (PDR) 57$^{th}$ Ed., 2003, Medical Economics Co., Inc., Montvale, N.J., which are incorporated herein by reference in its entirety.

In various embodiments, the therapies (e.g., a compound provided herein and the second agent) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In various embodiments, the therapies are administered no more than 24 hours apart or no more than 48 hours apart. In certain embodiments, two or more therapies are administered within the same patient visit. In other embodiments, the compound provided herein and the second agent are administered concurrently.

In other embodiments, the compound provided herein and the second agent are administered at about 2 to 4 days apart, at about 4 to 6 days apart, at about 1 week part, at about 1 to 2 weeks apart, or more than 2 weeks apart.

In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months.

In certain embodiments, a compound provided herein and a second agent are administered to a patient, for example, a mammal, such as a human, in a sequence and within a time interval such that the compound provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In certain embodiments, the compound provided herein and the second active agent exert their effect at times which overlap. Each second active agent can be administered separately, in any appropriate form and by any suitable route. In other embodiments, the compound provided herein is administered before, concurrently or after administration of the second active agent.

In certain embodiments, the compound provided herein and the second agent are cyclically administered to a patient. Cycling therapy involves the administration of a first agent (e.g., a first prophylactic or therapeutic agents) for a period of time, followed by the administration of a second agent and/or third agent (e.g., a second and/or third prophylactic or therapeutic agents) for a period of time and repeating this sequential administration. Cycling therapy can reduce the development of resistance to one or more of the therapies, avoid or reduce the side effects of one of the therapies, and/or improve the efficacy of the treatment.

In certain embodiments, the compound provided herein and the second active agent are administered in a cycle of less than about 3 weeks, about once every two weeks, about once every 10 days or about once every week. One cycle can comprise the administration of a compound provided herein and the second agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second agent can act additively or synergistically with the compound provided herein. In certain embodiments, the compound provided herein is administered concurrently with one or more second agents in the same pharmaceutical composition. In another embodiment, a compound provided herein is administered concurrently with one or more second agents in separate pharmaceutical compositions. In still another embodiment, a compound provided herein is administered prior to or subsequent to administration of a second agent. Also contemplated are administration of a compound provided herein and a second agent by the same or different routes of administration, e.g., oral and parenteral. In certain embodiments, when the compound provided herein is administered concurrently with a second agent that potentially produces adverse side effects including, but not limited to, toxicity, the second active agent can advantageously be administered at a dose that falls below the threshold that the adverse side effect is elicited.

Kits

Also provided are kits for use in methods of treatment of a liver disorder such as HCV infections. The kits can include a compound or composition provided herein, a second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Methods of Use

Provided herein is a method for inhibiting replication of a virus in a host, which comprises contacting the host with a therapeutically effective amount of a 3'-substituted methyl or alkynyl nucleoside disclosed herein, e.g., a 3'-substituted methyl or alkynyl nucleoside compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404 or according to any of the embodiments, or a pharmaceutically acceptable salt or active metabolite thereof. In certain embodiments, the 3'-substituted methyl or alkynyl nucleoside is of Formula I:

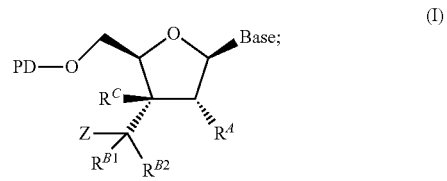

or a pharmaceutically acceptable salt thereof, wherein: $R^A$ hydroxyl, halo, hydrogen, azido, —NH$_2$, or alkylcarbonyloxy; $R^{B1}$ is hydroxyl, $C_2$-$C_6$alkenyl, $C_2$-$C_6$alkynyl, fluoro, azido, —NH$_2$, CN, benzyloxycarbonyloxy, or alkylcarbonyloxy; $R^{B2}$ is hydrogen, methyl, or fluoro; $R^C$ is hydrogen, azido or methyl; Base is a nucleobase; PD is alkylcarbonyl,

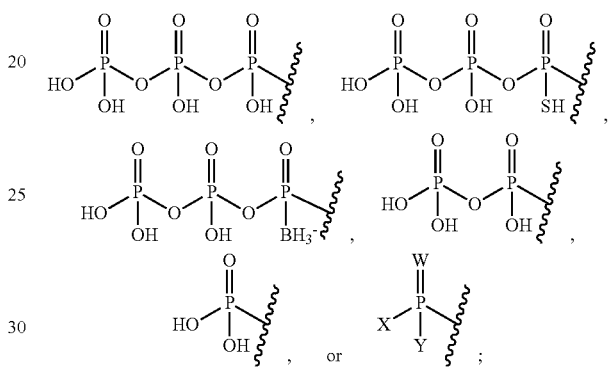

W is S or O; each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, $R^{B1}$ and $R^{B2}$ combine to form $C_{2-6}$ alkenylene or $C_{2-6}$ alkynylene; each $R^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each $R^2$ is independently hydrogen, alkyl, cycloalkyl, aryl, or arylalkyl;

with the proviso that when: PD is

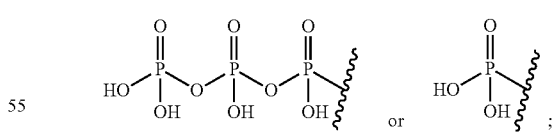

$R^A$ is hydroxyl; $R^{B1}$ is fluoro; $R^{B2}$ is hydrogen; $R^C$ is hydrogen; and Z is hydrogen; then Base is other than guanine; and provided that when $R^{B1}$, $R^{B2}$, and Z are fluoro and $R^A$ is OH, then PD is not hydrogen.

In some embodiments, the 3'-substituted methyl or alkynyl nucleoside is of Formula I is that where $R^A$ hydroxyl, halo, hydrogen or alkylcarbonyloxy; $R^{B1}$ is hydroxyl, fluoro or alkylcarbonyloxy; PD is

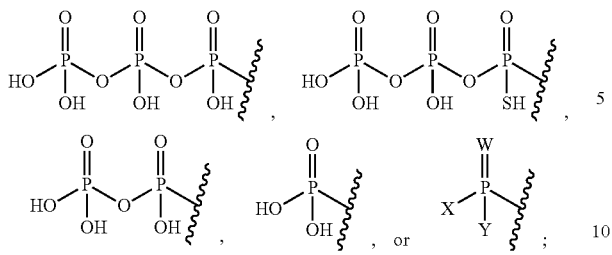

each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene; each R$^1$ is independently hydrogen, alkyl, aryl, arylalkyl, cycloalkyl, heterocycloalkyl, alkoxylcarbonylalkyl or alkylcarbonylthioalkyl; with the proviso that when: PD is

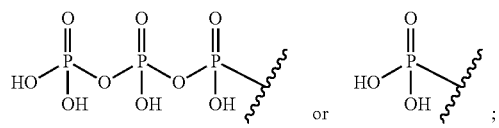 [SMILES: *P(=O)(O)OP(=O)(O)OP(=O)(O)O ; *P(=O)(O)O]

R$^A$ is hydroxyl; R$^{B1}$ is fluoro; R$^{B2}$ is hydrogen; R$^C$ is hydrogen; and Z is hydrogen; then Base is other than guanine Provided herein is a method for inhibiting replication of a virus in a cell, which comprises contacting the cell with a therapeutically effective amount of a 3'-substituted methyl or alkynyl nucleoside compound disclosed herein, e.g., a 3'-substituted methyl or alkynyl nucleoside compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt or active metabolite thereof. In certain embodiments, the 3'-substituted methyl or alkynyl nucleoside is of Formula I:

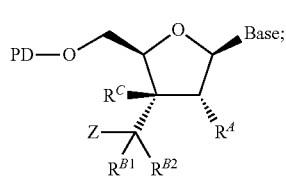

or a pharmaceutically acceptable salt thereof, wherein: R$^A$ hydroxyl, halo, hydrogen, azido, —NH$_2$, or alkylcarbonyloxy; R$^{B1}$ is hydrogen, C$_2$-C$_6$alkenyl, C$_2$-C$_6$alkynyl, hydroxyl, fluoro, azido, —NH$_2$, CN, benzyloxycarbonyloxy, or alkylcarbonyloxy; R$^{B2}$ is hydrogen, methyl or fluoro; R$^C$ is hydrogen, azido or methyl; Base is a nucleobase; PD is alkylcarbonyl,

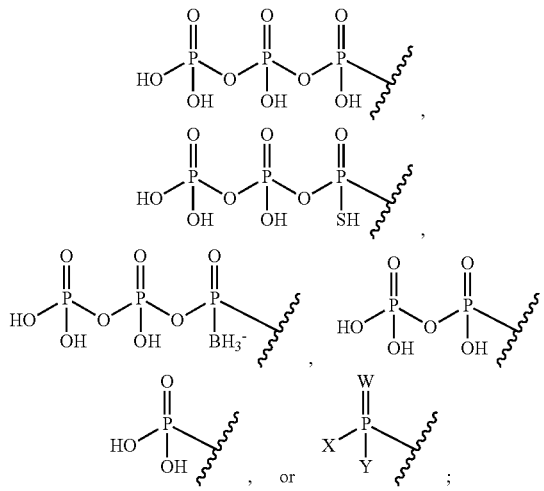

W is S or O; each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene; each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each R$^2$ is independently hydrogen, alkyl, cycloalkyl, aryl, or arylalkyl; with the proviso that when: PD is

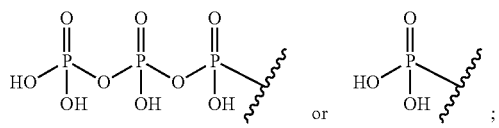

A is hydroxyl; R$^{B1}$ is fluoro; R$^{B2}$ is hydrogen; R$^C$ is hydrogen; and Z is hydrogen; then Base is other than guanine. In some embodiments, R$^A$ hydroxyl, halo, hydrogen or alkylcarbonyloxy; R$^{B1}$ is hydroxyl, fluoro or alkylcarbonyloxy; PD is

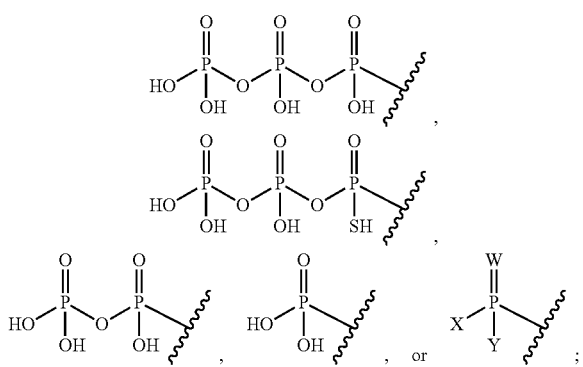

each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene; each R$^1$ is independently hydrogen, alkyl, aryl, arylalkyl, cycloalkyl, heterocycloalkyl, alkoxylcarbonylalkyl or alkylcarbonylthioalkyl; with the proviso that when: PD is

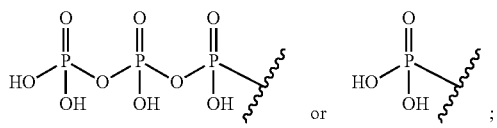 [SMILES: *P(=O)(O)OP(=O)(O)OP(=O)(O)O ; *P(=O)(O)O]

R$^A$ is hydroxyl; R$^{B1}$ is fluoro; R$^{B2}$ is hydrogen; R$^C$ is hydrogen; and Z is hydrogen; then Base is other than guanine.

Provided herein is a method for inhibiting replication of a virus, which comprises contacting the virus with a therapeutically effective amount of a 3'-substituted methyl or alkynyl nucleoside compound disclosed herein, e.g., a 3'-substituted methyl or alkynyl nucleoside compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, thereof; or a pharmaceutically acceptable salt or active metabolite thereof. In certain embodiments, the 3'-substituted methyl or alkynyl nucleoside is of Formula I:

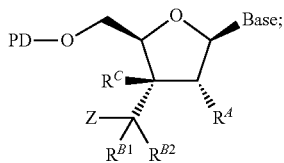

or a pharmaceutically acceptable salt thereof, wherein: R$^A$ hydroxyl, halo, hydrogen, azido, —NH$_2$, or alkylcarbonyloxy; R$^{B1}$ is hydrogen, C$_2$-C$_6$alkenyl, C$_2$-C$_6$alkynyl, hydroxyl, fluoro, azido, —NH$_2$, CN, benzyloxycarbonyloxy, or alkylcarbonyloxy; R$^{B2}$ is hydrogen, methyl or fluoro; R$^C$ is hydrogen, azido or methyl; Base is a nucleobase; PD is alkylcarbonyl,

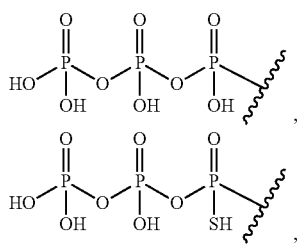

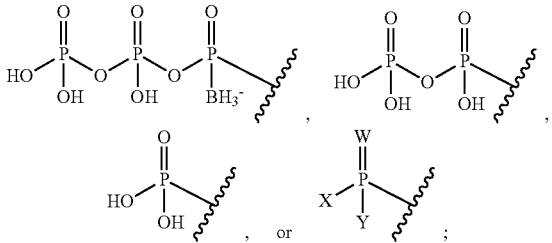

W is S or O; each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene; each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each R$^2$ is independently hydrogen, alkyl, cycloalkyl, aryl, or arylalkyl;

with the proviso that when: PD is

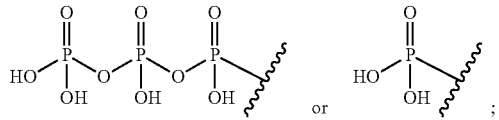 [SMILES: *P(=O)(O)OP(=O)(O)OP(=O)(O)O ; *P(=O)(O)O]

R$^A$ is hydroxyl; R$^{B1}$ is fluoro; R$^{B2}$ is hydrogen; R$^C$ is hydrogen; and Z is hydrogen; then Base is other than guanine. In some embodiments, R$^A$ hydroxyl halo hydrogen or alkylcarbonyloxy; R is hydroxyl, fluoro or alkylcarbonyloxy; PD is

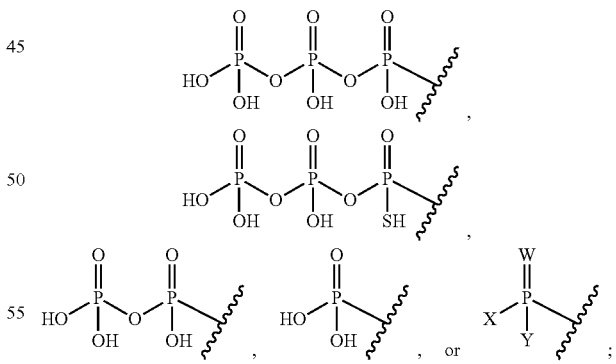

each of X and Y is independently hydrogen, —OR$^1$, —SR$^1$, —NR$^1$R$^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene; each $R^1$ is independently hydrogen, alkyl, aryl, arylalkyl, cycloalkyl, heterocycloalkyl, alkoxylcarbonylalkyl or alkylcarbonylthioalkyl; with the proviso that when: PD is

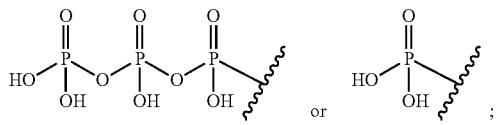 [SMILES: *P(=O)(O)OP(=O)(O)OP(=O)(O)O ; *P(=O)(O)O]

$R^A$ is hydroxyl; $R^{B1}$ is fluoro; $R^{B2}$ is hydrogen; $R^C$ is hydrogen; and Z is hydrogen; then Base is other than guanine.

Provided herein is a method for inhibiting the activity of a polymerase, which comprises contacting the polymerase with a 3'-substituted methyl or alkynyl nucleoside compound disclosed herein, e.g., a 3'-substituted methyl or alkynyl nucleoside compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, thereof; or a pharmaceutically acceptable salt or active metabolite thereof. In certain embodiments, the 3'-substituted methyl or alkynyl nucleoside is of Formula I:

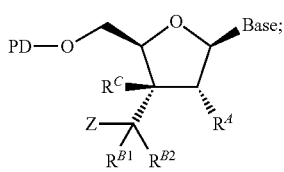

or a pharmaceutically acceptable salt thereof, wherein: $R^A$ hydroxyl, halo, hydrogen, azido, —$NH_2$, or alkylcarbonyloxy; $R^{B1}$ is hydrogen, $C_2$-$C_6$alkenyl, $C_2$-$C_6$alkynyl, hydroxyl, fluoro, azido, —$NH_2$, CN, benzyloxycarbonyloxy, or alkylcarbonyloxy; $R^{B2}$ is hydrogen, methyl or fluoro; $R^C$ is hydrogen, azido or methyl; Base is a nucleobase; PD is alkylcarbonyl,

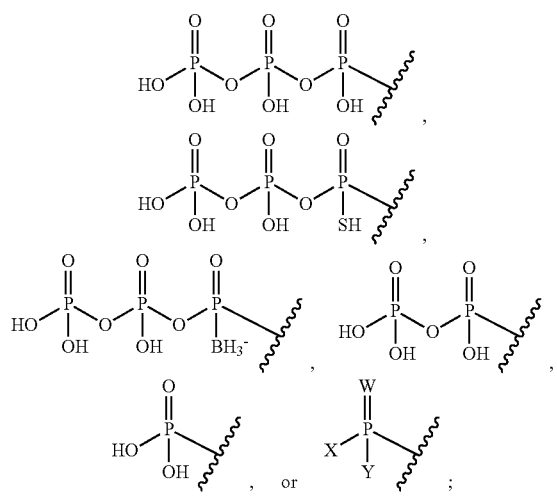

W is S or O; each of X and Y is independently hydrogen, —$OR^1$, —$SR^1$, —$NR^1R^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkenylene or $C_{2-6}$ alkynylene; each $R^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each $R^2$ is independently hydrogen, alkyl, cycloalkyl, aryl, or arylalkyl; with the proviso that when: PD is

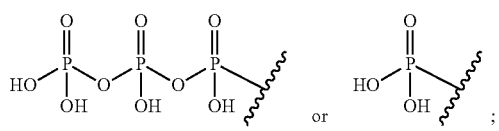 [SMILES: *P(=O)(O)OP(=O)(O)OP(=O)(O)O ; *P(=O)(O)O]

$R^A$ is hydroxyl; $R^{B1}$ is fluoro; $R^{B2}$ is hydrogen; $R^C$ is hydrogen; and Z is hydrogen; then Base is other than guanine. In some embodiments, $R^A$ hydroxyl, halo, hydrogen or alkylcarbonyloxy; $R^{B1}$ is hydroxyl, fluoro or alkylcarbonyloxy; each of X and Y is independently hydrogen, —$OR^1$, —$SR^1$, —$NR^1R^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkynylene; each $R^1$ is independently hydrogen, alkyl, aryl, arylalkyl, cycloalkyl, heterocycloalkyl, alkoxylcarbonylalkyl or alkylcarbonylthioalkyl; with the proviso that when: PD is

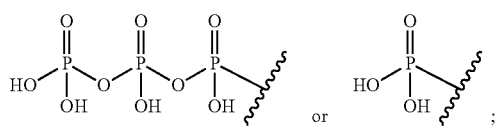 [SMILES: *P(=O)(O)OP(=O)(O)OP(=O)(O)O ; *P(=O)(O)O]

$R^A$ is hydroxyl; $R^{B1}$ is fluoro; $R^{B2}$ is hydrogen; $R^C$ is hydrogen; and Z is hydrogen; then Base is other than guanine In certain embodiments, provided herein are methods for the treatment and/or prophylaxis of a host infected with Flaviviridae that includes the administration of an effective amount of a 3'-substituted methyl or alkynyl nucleoside compound disclosed herein, e.g., a 3'-substituted methyl or alkynyl nucleoside compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt or active metabolite thereof. In certain embodiments, the 3'-substituted methyl or alkynyl nucleoside is of Formula I:

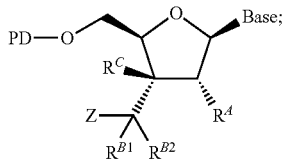 (I)

or a pharmaceutically acceptable salt thereof, wherein: $R^A$ hydroxyl, halo, hydrogen, azido, —$NH_2$, or alkylcarbonyloxy; $R^{B1}$ is hydrogen, $C_2$-$C_6$alkenyl, $C_2$-$C_6$alkynyl, hydroxyl, fluoro, azido, —$NH_2$, CN, benzyloxycarbonyloxy, or alkylcarbonyloxy; $R^{B2}$ is hydrogen, methyl, or fluoro; $R^C$ is hydrogen, azido or methyl; Base is a nucleobase; PD is alkylcarbonyl,

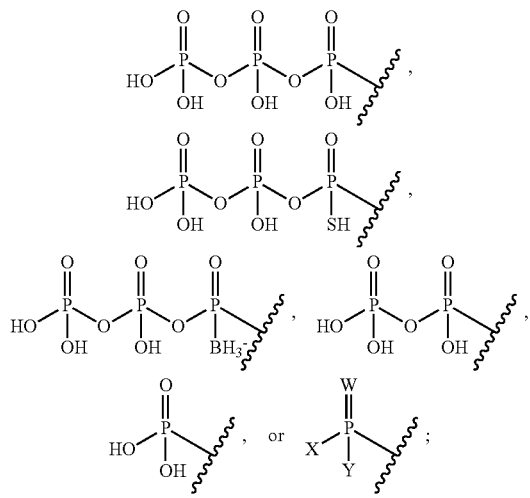

W is S or O; each of X and Y is independently hydrogen, —$OR^1$, —$SR^1$, —$NR^1R^2$, or an N-linked or O-linked amino acid residue, or derivative thereof; Z is hydrogen, methyl, azido, amino, cyano, or fluoro; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkenylene or $C_{2-6}$ alkynylene; each $R^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and each $R^2$ is independently hydrogen, alkyl, cycloalkyl, aryl, or arylalkyl; with the proviso that when: PD is

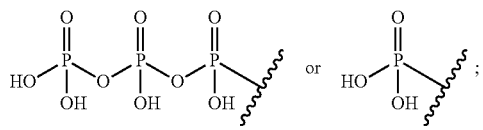 [SMILES: *P(=O)(O)OP(=O)(O)OP(=O)(O)O ; *P(=O)(O)O]

$R^A$ is hydroxyl; $R^{B1}$ is fluoro; $R^{B2}$ is hydrogen; $R^C$ is hydrogen; and Z is hydrogen; then Base is other than guanine. In some embodiments, $R^A$ hydroxyl, halo, hydrogen or alkylcarbonyloxy; $R^{B1}$ is hydroxyl, fluoro or alkylcarbonyloxy; PD is

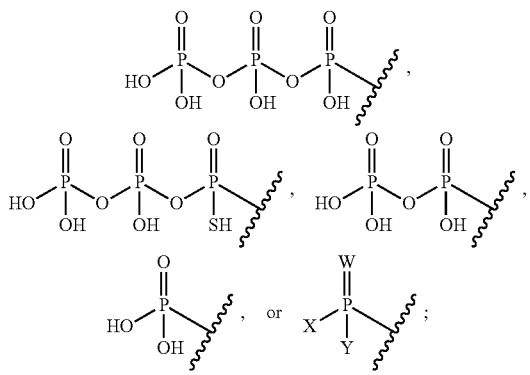

each of X and Y is independently hydrogen, —$OR^1$, —$SR^1$, —$NR^1R^2$, or an N-linked or O-linked amino acid residue, or derivative thereof; Z is hydrogen, methyl, azido, amino, cyano or fluoro; or, in the alternative, Y and Z, together with the atoms to which they are attached, combine to form a seven-membered heterocyclic ring wherein Y and Z together represent a single divalent —O—, and X is —$OR^1$, —$SR^1$, —$NR^1R^2$, or an N-linked or O-linked amino acid residue, or derivative thereof; or Z, $R^{B1}$ and $R^{B2}$ combine to form $C_{2-6}$ alkynylene; each $R^1$ is independently hydrogen, alkyl, aryl, arylalkyl, cycloalkyl, heterocycloalkyl, alkoxylcarbonylalkyl or alkylcarbonylthioalkyl; with the proviso that when: PD is

$R^A$ is hydroxyl; $R^{B1}$ is fluoro; $R^{B2}$ is hydrogen; $R^C$ is hydrogen; and Z is hydrogen; then Base is other than guanine.

In certain embodiments, provided herein are methods for treating an HCV infection in a subject. In certain embodiments, the methods encompass the step of administering to the subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

In certain embodiments, provided herein are methods for the treatment and/or prophylaxis of a host infected with Flaviviridae that includes the administration of an effective amount of a compounds provided herein, or a pharmaceutically acceptable salt thereof. In certain embodiments, provided herein are methods for treating an HCV infection in a subject. In certain embodiments, the methods encompass the step of administering to the subject in need thereof an amount of a compound effective for the treatment or prevention of an HCV infection in combination with a second agent effective for the treatment or prevention of the infection. The compound can be any compound as described herein, and the second agent can be any second agent described in the art or herein. In certain embodiments, the compound is in the form of a pharmaceutical composition or dosage form, as described elsewhere herein.

Flaviviridae which can be treated are, e.g., discussed generally in *Fields Virology*, Fifth Ed., Editors: Knipe, D. M., and Howley, P. M., Lippincott Williams & Wilkins Publishers, Philadelphia, Pa., Chapters 33-35, 2006. In a particular embodiment of the invention, the Flaviviridae is HCV. In an alternate embodiment, the Flaviviridae is a flavivirus or pestivirus. In certain embodiments, the Flaviviridae can be from any class of Flaviviridae. In certain embodiments, the Flaviviridae is a mammalian tick-borne virus. In certain embodiments, the Flaviviridae is a seabird tick-borne virus. In certain embodiments, the Flaviviridae is a mosquito-borne virus. In certain embodiments, the Flaviviridae is an Aroa virus. In certain embodiments, the Flaviviridae is a Dengue virus. In certain embodiments, the Flaviviridae is a Japanese encephalitis virus. In certain embodiments, the Flaviviridae is a Kokobera virus. In certain embodiments, the Flaviviridae is a Ntaya virus. In certain embodiments, the Flaviviridae is a Spondweni virus. In certain embodiments, the Flaviviridae is a Yellow fever virus. In certain embodiments, the Flaviviridae is a Entebbe virus. In certain embodiments, the Flaviviridae is a Modoc virus. In certain embodiments, the Flaviviridae is a Rio Bravo virus.

Specific flaviviruses which can be treated include, without limitation: Absettarov, Aedes, Alfuy, Alkhurma, Apoi, Aroa, Bagaza, Banzi, Bukalasa bat, Bouboui, Bussuquara, Cacipacore, Calbertado, Carey Island, Cell fusing agent, Cowbone Ridge, Culex, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Kamiti River, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Nakiwogo, Naranjal, Negishi, Ntaya, Omsk hemorrhagic fever, Phnom-Penh bat, Powassan, Quang Binh, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tick-borne encephalitis, Turkish sheep encephalitis, Tyuleniy, Uganda S, Usutu, Wesselsbron, West Nile, Yaounde, Yellow fever, Yokose, and Zika.

Pestiviruses which can be treated are discussed generally in *Fields Virology*, Fifth Ed., Editors: Knipe, D. M., and Howley, P. M., Lippincott Williams & Wilkins Publishers, Philadelphia, Pa., Chapters 33-35, 2006. Specific pestiviruses which can be treated include, without limitation: bovine viral diarrhea virus ("BVDV"), classical swine fever virus ("CSFV," also called hog cholera virus), and border disease virus ("BDV").

In certain embodiments, the subject can be any subject infected with, or at risk for infection with, HCV. Infection or risk for infection can be determined according to any technique deemed suitable by the practitioner of skill in the art. In certain embodiments, subjects are humans infected with HCV.

In certain embodiments, the subject has never received therapy or prophylaxis for an HCV infection. In further embodiments, the subject has previously received therapy or prophylaxis for an HCV infection. For instance, in certain embodiments, the subject has not responded to an HCV therapy. For example, under current interferon therapy, up to 50% or more HCV subjects do not respond to therapy. In certain embodiments, the subject can be a subject that received therapy but continued to suffer from viral infection or one or more symptoms thereof. In certain embodiments, the subject can be a subject that received therapy but failed to achieve a sustained virologic response. In certain embodiments, the subject has received therapy for an HCV infection but has failed to show, for example, a 2 $\log_{10}$ decline in HCV RNA levels after 12 weeks of therapy. It is believed that subjects who have not shown more than 2 $\log_{10}$ reduction in serum HCV RNA after 12 weeks of therapy have a 97-100% chance of not responding.

In certain embodiments, the subject is a subject that discontinued an HCV therapy because of one or more adverse events associated with the therapy. In certain embodiments, the subject is a subject where current therapy is not indicated. For instance, certain therapies for HCV are associated with neuropsychiatric events. Interferon (IFN)-alfa plus ribavirin is associated with a high rate of depression. Depressive symptoms have been linked to a worse outcome in a number of medical disorders. Life-threatening or fatal neuropsychiatric events, including suicide, suicidal and homicidal ideation, depression, relapse of drug addiction/overdose, and aggressive behavior have occurred in subjects with and without a previous psychiatric disorder during HCV therapy. Interferon-induced depression is a limitation for the treatment of chronic hepatitis C, especially for subjects with psychiatric disorders. Psychiatric side effects are common with interferon therapy and responsible for about 10% to 20% of discontinuations of current therapy for HCV infection.

Accordingly, provided are methods of treating or preventing an HCV infection in subjects where the risk of neuropsychiatric events, such as depression, contraindicates treatment with current HCV therapy. In certain embodiments, provided are methods of treating or preventing HCV infection in subjects where a neuropsychiatric event, such as depression, or risk of such indicates discontinuation of treatment with current HCV therapy. Further provided are methods of treating or preventing HCV infection in subjects where a neuropsychiatric event, such as depression, or risk of such indicates dose reduction of current HCV therapy.

Current therapy is also contraindicated in subjects that are hypersensitive to interferon or ribavirin, or both, or any other component of a pharmaceutical product for administration of interferon or ribavirin. Current therapy is not indicated in subjects with hemoglobinopathies (e.g., thalassemia major, sickle-cell anemia) and other subjects at risk from the hematologic side effects of current therapy. Common hematologic side effects include bone marrow suppression, neutropenia and thrombocytopenia. Furthermore, ribavirin is toxic to red blood cells and is associated with hemolysis. Accordingly, in certain embodiments, provided are methods of treating or preventing HCV infection in subjects hypersensitive to interferon or ribavirin, or both, subjects with a hemoglobinopathy, for instance thalassemia major subjects and sickle-cell anemia subjects, and other subjects at risk from the hematologic side effects of current therapy.

In certain embodiments, the subject has received an HCV therapy and discontinued that therapy prior to administration of a method provided herein. In further embodiments, the subject has received therapy and continues to receive that therapy along with administration of a method provided herein. The methods can be co-administered with other therapy for HBC and/or HCV according to the judgment of one of skill in the art. In certain embodiments, the methods or compositions provided herein can be co-administered with a reduced dose of the other therapy for HBC and/or HCV.

In certain embodiments, provided are methods of treating a subject that is refractory to treatment with interferon. For instance, in some embodiments, the subject can be a subject that has failed to respond to treatment with one or more agents. In certain embodiments, the one or more agent is an interferon, interferon α, pegylated interferon α, interferon plus ribavirin, interferon α plus ribavirin, pegylated interferon α plus ribavirin, or a combination thereof. In some embodiments, the subject can be a subject that has responded poorly to treatment with one or more agents. In certain embodiments, the one or more agent is interferon, interferon α, pegylated interferon α, interferon plus ribavirin, interferon α plus ribavirin, pegylated interferon α plus ribavirin, or a combination thereof. A pro-drug form of ribavirin, such as taribavirin, may also be used.

In certain embodiments, the subject has, or is at risk for, co-infection of HCV with HIV. For instance, in the United States, 30% of HIV subjects are co-infected with HCV and evidence indicates that people infected with HIV have a much more rapid course of their hepatitis C infection. Maier and Wu, 2002, *World J Gastroenterol* 8:577-57. The methods provided herein can be used to treat or prevent HCV infection in such subjects. It is believed that elimination of HCV in these subjects will lower mortality due to end-stage liver disease. Indeed, the risk of progressive liver disease is higher in subjects with severe AIDS-defining immunodeficiency than in those without. See, e.g., Lesens et al., 1999, *J Infect Dis* 179:1254-1258. In certain embodiments, compounds provided herein have been shown to suppress HIV in HIV subjects. Thus, in certain embodiments, provided are methods of treating or preventing HIV infection and HCV infection in subjects in need thereof.

In certain embodiments, the compounds or compositions are administered to a subject following liver transplant. Hepatitis C is a leading cause of liver transplantation in the U.S., and many subjects that undergo liver transplantation remain HCV positive following transplantation. In certain embodiments, provided are methods of treating such recurrent HCV subjects with a compound or composition provided herein. In certain embodiments, provided are methods of treating a subject before, during or following liver transplant to prevent recurrent HCV infection.

Assay Methods

Compounds can be assayed for HCV activity according to any assay known to those of skill in the art.

Further, compounds can be assayed for accumulation in liver cells of a subject according to any assay known to those of skill in the art. In certain embodiments, a compound can be administered to the subject, and a liver cell of the subject can be assayed for the compound or a derivative thereof, e.g. a nucleoside, nucleoside phosphate or nucleoside triphosphate derivative thereof.

In certain embodiments, a 3'-substituted methyl or alkynyl nucleoside compound is administered to cells, such as liver cells, in vivo or in vitro, and the nucleoside triphosphate levels delivered intracellularly are measured, to indicate delivery of the compound and triphosphorylation in the cell. The levels of intracellular nucleoside triphosphate can be measured using analytical techniques known in the art. Methods of detecting ddATP are described herein below by way of example, but other nucleoside triphosphates can be readily detected using the appropriate controls, calibration samples and assay techniques.

In certain embodiments, ddATP concentrations are measured in a sample by comparison to calibration standards made from control samples. The ddATP concentrations in a sample can be measured using an analytical method such as HPLC LC MS. In certain embodiments, a test sample is compared to a calibration curve created with known concentrations of ddATP to thereby obtain the concentration of that sample.

In certain embodiments, the samples are manipulated to remove impurities such as salts ($Na^-$, $K^+$, etc.) before analysis. In certain embodiments, the lower limit of quantitation is about ~0.2 pmol/mL for hepatocyte cellular extracts particularly where reduced salt is present.

In certain embodiments, the method allows successfully measuring triphosphate nucleotides formed at levels of 1-10,000 pmol per million cells in e.g. cultured hepatocytes and HepG2 cells.

Second Therapeutic Agents

In certain embodiments, the compounds and compositions provided herein are useful in methods of treatment of a liver disorder, that comprise further administration of a second agent effective for the treatment of the disorder, such as HCV infection in a subject in need thereof. The second agent can be any agent known to those of skill in the art to be effective for the treatment of the disorder, including those currently approved by the FDA.

In certain embodiments, a compound provided herein is administered in combination with one second agent. In further embodiments, a second agent is administered in combination with two second agents. In still further embodiments, a second agent is administered in combination with two or more second agents.

As used herein, the term "in combination" includes the use of more than one therapy (e.g., one or more prophylactic and/or therapeutic agents). The use of the term "in combination" does not restrict the order in which therapies (e.g., prophylactic and/or therapeutic agents) are administered to a subject with a disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to a subject with a disorder.

As used herein, the term "synergistic" includes a combination of a compound provided herein and another therapy (e.g., a prophylactic or therapeutic agent) which has been or is currently being used to prevent, manage or treat a disorder, which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention or treatment of a disorder). In addition, a synergistic effect can result in improved efficacy of agents in the prevention or treatment of a disorder. Finally, a synergistic effect of a combination of therapies (e.g., a combination of prophylactic or therapeutic agents) may avoid or reduce adverse or unwanted side effects associated with the use of either therapy alone.

The active compounds provided herein can be administered in combination or alternation with another therapeutic agent, in particular an anti-HCV agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In certain embodiments, an anti-HCV (or anti-pestivirus or anti-flavivirus) compound that exhibits an $EC_{50}$ of 10-15 µM. In certain embodiments, less than 1-5 µM, is desirable.

It has been recognized that drug-resistant variants of flaviviruses, pestiviruses or HCV can emerge after prolonged treatment with an antiviral agent. Drug resistance most typically occurs by mutation of a gene that encodes for an enzyme used in viral replication. The efficacy of a drug against the viral infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the viral treatments described in the Background of the Invention can be used in combination or alternation with the compounds described in this specification. Non-limiting examples of second agents include:

HCV Protease inhibitors: Examples include Medivir HCV Protease Inhibitor TMC 435 (simeprevir, Medivir, Tibotec, Johnson & Johnson); MK-7009 (Merck), RG7227 (ITMN-191) (Roche/Pharmasset/InterMune), boceprevir (SCH 503034) (Schering), SCH 446211 (Schering), narlaprevir SCH900518 (Schering/Merck), ABT-450 (Abbott/Enanta), ACH-1625 (Achillion), BI 201335 (Boehringer Ingelheim), PHX1766 (Phenomix), VX-500 (Vertex) and telaprevir (VX-950) (Vertex). Further examples of protease inhibitors include substrate-based NS3 protease inhibitors (Attwood et al., Antiviral peptide derivatives, PCT WO 98/22496, 1998; Attwood et al., Antiviral Chemistry and Chemotherapy 1999, 10, 259-273; Attwood et al., Preparation and use of amino acid derivatives as anti-viral agents, German Patent Pub. DE 19914474; Tung et al., Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734); Non-substrate-based NS3 protease inhibitors such as 2,4,6-trihydroxy-3-nitro-benzamide derivatives (Sudo K. et al., Biochemical and Biophysical Research Communications, 1997, 238, 643-647; Sudo K. et al., Antiviral Chemistry and Chemotherapy, 1998, 9, 186), including RD3-4082 and RD3-4078, the former substituted on the amide with a 14 carbon chain and the latter processing a para-phenoxyphenyl group; and Sch 68631, a phenanthrenequinone, an HCV protease inhibitor (Chu M. et al., Tetrahedron Letters 37:7229-7232, 1996);

SCH 351633, isolated from the fungus *Penicillium griseofulvum*, was identified as a protease inhibitor (Chu M. et al., Bioorganic and Medicinal Chemistry Letters 9:1949-1952). Eglin c, isolated from leech, is a potent inhibitor of several serine proteases such as *S. griseus* proteases A and B, α-chymotrypsin, chymase and subtilisin. Qasim M. A. et al., Biochemistry 36:1598-1607, 1997;

U.S. patents disclosing protease inhibitors for the treatment of HCV include, for example, U.S. Pat. No. 6,004,933 to Spruce et al., which discloses a class of cysteine protease inhibitors for inhibiting HCV endopeptidase 2; U.S. Pat. No. 5,990,276 to Zhang et al., which discloses synthetic inhibitors of hepatitis C virus NS3 protease; U.S. Pat. No. 5,538,865 to Reyes et a; WO 02/008251 to Corvas International, Inc., and U.S. Pat. No. 7,169,760, US2005/176648, WO 02/08187 and WO 02/008256 to Schering Corporation. HCV inhibitor tripeptides are disclosed in U.S. Pat. Nos. 6,534,523, 6,410,531, and 6,420,380 to Boehringer Ingelheim and WO 02/060926 to Bristol Myers Squibb. Diaryl peptides as NS3 serine protease inhibitors of HCV are disclosed in WO 02/48172 and U.S. Pat. No. 6,911,428 to Schering Corporation. Imidazoleidinones as NS3 serine protease inhibitors of HCV are disclosed in WO 02/08198 and U.S. Pat. No. 6,838,475 to Schering Corporation and WO 02/48157 and U.S. Pat. No. 6,727,366 to Bristol Myers Squibb. WO 98/17679 and U.S. Pat. No. 6,265,380 to Vertex Pharmaceuticals and WO 02/48116 and U.S. Pat. No. 6,653,295 to Bristol Myers Squibb also disclose HCV protease inhibitors. Further examples of HCV serine protease inhibitors are provided in U.S. Pat. No. 6,872,805 (Bristol-Myers Squibb); WO 2006000085 (Boehringer Ingelheim); U.S. Pat. No. 7,208,600 (Vertex); US 2006/0046956 (Schering-Plough); WO 2007/001406 (Chiron); US 2005/0153877; WO 2006/119061 (Merck); WO 00/09543 (Boehringer Ingelheim), U.S. Pat. No. 6,323,180 (Boehringer Ingelheim) WO 03/064456 (Boehringer Ingelheim), U.S. Pat. No. 6,642,204 (Boehringer Ingelheim), WO 03/064416 (Boehringer Ingelheim), U.S. Pat. No. 7,091,184 (Boehringer Ingelheim), WO 03/053349 (Bristol-Myers Squibb), U.S. Pat. No. 6,867,185, WO 03/099316 (Bristol-Myers Squibb), U.S. Pat. No. 6,869,964, WO 03/099274 (Bristol-Myers Squibb), U.S. Pat. No. 6,995,174, WO 2004/032827 (Bristol-Myers Squibb), U.S. Pat. No. 7,041,698, WO 2004/043339 and U.S. Pat. No. 6,878,722 (Bristol-Myers Squibb);

Thiazolidine derivatives which show relevant inhibition in a reverse-phase HPLC assay with an NS3/4A fusion protein and NS5A/5B substrate (Sudo K. et al., Antiviral Research, 1996, 32, 9-18), especially compound RD-1-6250, possessing a fused cinnamoyl moiety substituted with a long alkyl chain, RD4 6205 and RD4 6193;

Thiazolidines and benzanilides identified in Kakiuchi N. et al., J. EBS Letters 421, 217-220; Takeshita N. et al., Analytical Biochemistry, 1997, 247, 242-246;

A phenanthrenequinone possessing activity against protease in a SDS-PAGE and autoradiography assay isolated from the fermentation culture broth of *Streptomyces* sp., SCH 68631 (Chu M. et al., Tetrahedron Letters, 1996, 37, 7229-7232), and SCH 351633, isolated from the fungus *Penicillium griseofulvum*, which demonstrates activity in a scintillation proximity assay (Chu M. et al., Bioorganic and Medicinal Chemistry Letters 9, 1949-1952);

Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

HCV polymerase inhibitors, including nucleoside and non-nucleoside polymerase inhibitors, such as ribavirin, viramidine, clemizole, filibuvir (PF-00868554), HCV POL, NM 283 (valopicitabine), MK-0608, 7-Fluoro-MK-0608, MK-3281, IDX-375, ABT-072, ABT-333, ANA598, BI 207127, GS 9190, PSI-6130, R1626, PSI-6206, PSI-938, PSI-7851, GS-7977 (sofosbuvir, Pharmasset, Gilead), RG1479, RG7128, HCV-796 VCH-759 or VCH-916;

Gliotoxin (Ferrari R. et al., *Journal of Virology*, 1999, 73, 1649-1654), and the natural product cerulenin (Lohmann V. et al., *Virology*, 1998, 249, 108-118);

Interfering RNA (iRNA) based antivirals, including short interfering RNA (siRNA) based antivirals, such as Sirna-034 and others described in International Patent Publication Nos. WO/03/070750 and WO 2005/012525, and US Patent Publication No. US 2004/0209831;

HCV NS5A inhibitors, such as BMS-790052 (daclatasvir, Bristol-Myers Squibb), PPI-461 (Presidio Pharmaceuticals), PPI-1301 (Presidio Pharmaceuticals), samatasvir (IDX-719, Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead);

Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 1999, 181, 251-257);

Inhibitors of IRES-dependent translation (Ikeda N et al., Agent for the prevention and treatment of hepatitis C, Japanese Patent Pub. JP-08268890; Kai Y. et al., Prevention and treatment of viral diseases, Japanese Patent Pub. JP-10101591);

HCV entry inhibitors, such as celgosivir (MK-3253) (MIGENIX Inc.), SP-30 (Samaritan Pharmaceuticals), ITX4520 (iTherX), ITX5061 (iTherX), PRO-206 (Progenics Pharmaceuticals) and other entry inhibitors by Progenics Pharmaceuticals, e.g., as disclosed in U.S. Patent Publication No. 2006/0198855;

Ribozymes, such as nuclease-resistant ribozymes (Maccjak, D. J. et al., *Hepatology* 1999, 30, abstract 995) and those disclosed in U.S. Pat. No. 6,043,077 to Barber et al., and U.S. Pat. Nos. 5,869,253 and 5,610,054 to Draper et al.; and Nucleoside analogs developed for the treatment of Flaviviridae infections.

In certain embodiments, the compounds provided herein can be administered in combination with any of the compounds described by Idenix Pharmaceuticals in International Publication Nos. WO 01/90121, WO 01/92282, WO 2004/003000, 2004/002422 and WO 2004/002999.

Other patent applications disclosing the use of certain nucleoside analogs that can be used as second agents to treat hepatitis C virus include: PCT/CA00/01316 (WO 01/32153; filed Nov. 3, 2000) and PCT/CA01/00197 (WO 01/60315; filed Feb. 19, 2001) filed by BioChem Pharma, Inc. (now Shire Biochem, Inc.); PCT/US02/01531 (WO 02/057425; filed Jan. 18, 2002); PCT/US02/03086 (WO 02/057287; filed Jan. 18, 2002); U.S. Pat. Nos. 7,202,224; 7,125,855; 7,105,499 and 6,777,395 by Merck & Co., Inc.; PCT/EP01/09633 (WO 02/18404; published Aug. 21, 2001); US 2006/0040890; 2005/0038240; 2004/0121980; U.S. Pat. Nos. 6,846,810; 6,784,166 and 6,660,721 by Roche; PCT Publication Nos. WO 01/79246 (filed Apr. 13, 2001), WO 02/32920 (filed Oct. 18, 2001) and WO 02/48165; US 2005/0009737; US 2005/0009737; U.S. Pat. Nos. 7,094,770 and 6,927,291 by Pharmasset, Ltd.

Further compounds that can be used as second agents to treat hepatitis C virus are disclosed in PCT Publication No. WO 99/43691 to Emory University, entitled "2'-Fluoronucleosides". The use of certain 2'-fluoronucleosides to treat HCV is disclosed.

Other compounds that can be used as second agents include 1-amino-alkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056,961), and piperidines (U.S. Pat. No. 5,830,905 to Diana et al.).

In certain embodiments, a compound of Formula 1001, I-XLVI, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt thereof, or a composition comprising a compound of Formula 1001, I-XLVI, 101-122bii, 201-255, 301-336, 340-345, 123a to 125bii, 128a-130bii, 131a to 140aii, 142 to 161b, 163a-165, 167-170, 172-190b, 191 to 193, and 401-404, or a pharmaceutically acceptable salt thereof is administered in combination or alternation with a second anti-viral agent. In certain embodiments, the second anti-viral agent is an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, or a combination thereof.

Exemplary Second Therapeutic Agents for Treatment of HCV

In certain embodiments, one or more compounds provided herein can be administered in combination or alternation with an anti-hepatitis C virus interferon, such as Intron A® (interferon alfa-2b) and; Roferon A® (Recombinant interferon alfa-2a), Infergen® (consensus interferon; interferon alfacon-1), PEG-Intron® (pegylated interferon alfa-2b), and Pegasys® (pegylated interferon alfa-2a). In certain embodiments, one or more compounds provided herein can be administered in combination or alternation with ribavirin and in combination or alternation with an anti-hepatitis C virus interferon. In certain embodiments, one or more compounds provided herein can be administered in combination or alternation with ribavirin, in combination or alternation with an anti-hepatitis C virus interferon, and in combination or alternation with an anti-hepatitis C virus protease inhibitor. In certain embodiments, one or more compounds provided herein can be administered in combination or alternation with ribavirin. In certain embodiments, one or more compounds provided herein can be administered in combination or alternation with an anti-hepatitis C virus interferon and without ribavirin. In certain embodiments, one or more compounds provided herein can be administered in combination or alternation with an anti-hepatitis C virus interferon, in combination or alternation with an anti-hepatitis C virus protease inhibitor, and without ribavirin.

In certain embodiments, the anti-hepatitis C virus interferon is infergen, IL-29 (PEG-Interferon lambda), R7025 (Maxy-alpha), Belerofon, Oral Interferon alpha, BLX-883 (Locteron), omega interferon, multiferon, medusa interferon, Albuferon or REBIF®.

In certain embodiments, one or more compounds provided herein can be administered in combination or alternation with an anti-hepatitis C virus polymerase inhibitor, such as ribavirin, viramidine, HCV POL, NM 283 (valopicitabine), MK-0608, 7-Fluoro-MK-0608, PSI-6130, R1626, PSI-6206, PSI-938, R1479, HCV-796, VX-950 (Telaprevir, Vertex), GS 9190 NN (Gilead), GS 9256 (Gilead), PSI-7792 (BMS), BI 207127 (BI), R7128 (Roche), GS-7977 (sofosbuvir, Pharmasset, Gilead), PSI-938 (Pharmasset), VX-222 (Vertex), ALS-2200 (Vertex), ALS-2158 (Vertex), MK-0608 (Merck), TMC649128 (Medivir), PF-868554 (Pfizer), PF-4878691 (Pfizer), ANA598 (Roche), VCH-759 (Vertex), IDX184 (Idenix), IDX375 (Idenix), A-837093 (Abbott), GS 9190 (Gilead), GSK625433 (GlaxoSmithKline), ABT-072 (Abbott), ABT-333 (Abbott), INX-189 (Inhibitex), or EDP-239 (Enanta).

In certain embodiments, the one or more compounds provided herein can be administered in combination with ribavarin and an anti-hepatitis C virus interferon, such as Intron A® (interferon alfa-2b) and Pegasys® (Peginterferon alfa-2a); Roferon A® (Recombinant interferon alfa-2a), Infergen® (consensus interferon; interferon alfacon-1), PEG-Intron® (pegylated interferon alfa-2b), Zalbin (albinterferon alfa-2b), omega interferon, pegylated interferon lambda, and Pegasys® (pegylated interferon alfa-2a).

In certain embodiments, one or more compounds provided herein can be administered in combination or alternation with an anti-hepatitis C virus protease inhibitor such as ITMN-191, SCH 503034 (boceprevir), VX950 (telaprevir), VX985, VX500, VX813, PHX1766, BMS-650032, GS 9256, BI 201335, IDX320, R7227, MK-7009 (vaniprevir), TMC 435 (simeprevir, Medivir, Tibotec, Johnson & Johnson), BMS-791325, ACH-1625, ACH-2684, ABT-450, or AVL-181.

In certain embodiments, one or more compounds provided herein can be administered in combination or alternation with an HCV NS5A inhibitor, such as BMS-790052 (daclatasvir, Bristol-Myers Squibb), PPI-461 (Presidio Pharmaceuticals), PPI-1301 (Presidio Pharmaceuticals), samatasvir (IDX-719, Idenix Pharmaceuticals), AZD7295 (Arrow Therapeutics, AstraZeneca), EDP-239 (Enanta), ACH-2928 (Achillion), ACH-3102 (Achillion), ABT-267 (Abbott), or GS-5885 (Gilead).

In certain embodiments, one or more compounds provided herein can be administered in combination or alternation with an anti-hepatitis C virus vaccine, such as TG4040, PeviPROTM, CGI-5005, HCV/MF59, GV1001, IC41, GNI-103, GenPhar HCV vaccine, C-Vaxin, CSL123, Hepavaxx C, ChronVac-C® or INNO0101 (E1).

In certain embodiments, one or more compounds provided herein can be administered in combination or alternation with an anti-hepatitis C virus monoclonal antibody, such as MBL-HCV1, AB68 or XTL-6865 (formerly HepX-C); or an anti-hepatitis C virus polyclonal antibody, such as cicavir.

In certain embodiments, one or more compounds provided herein can be administered in combination or alternation with an anti-hepatitis C virus immunomodulator, such as Zadaxin® (thymalfasin), SCV-07, NOV-205 or Oglufanide.

In certain embodiments, one or more compounds provided herein can be administered in combination or alternation with cyclophilin inhibitor, such as Enanta cyclophilin binder, SCY-635, or Debio-025.

In certain embodiments, one or more compounds provided herein can be administered in combination or alternation with Nexavar, doxorubicin, PI-88, amantadine, JBK-122, VGX-410C, MX-3253 (Ceglosivir), Suvus (BIVN-401 or virostat), PF-03491390 (formerly IDN-6556), G126270, UT-231B, DEBIO-025, EMZ702, ACH-0137171, MitoQ, ANA975, AVI-4065, Bavituxinab (Tarvacin), Alinia (nitrazoxanide) or PYN17.

In certain embodiments, one or more compounds provided herein can be administered in combination or alternation with telaprevir, boceprevir, simeprevir, interferon alfacon-1, interferon alfa-2b, pegylated interferon alpha 2a, pegylated interferon alpha 2b, ribavirin, or combinations thereof.

In certain embodiments, one or more compounds provided herein can be administered in combination or alternation with a protease inhibitor. In certain embodiments, one or more compounds provided herein can be administered in combination or alternation with telaprevir. In certain embodiments, one or more compounds provided herein can be administered in combination or alternation with boceprevir.

In certain embodiments, one or more compounds provided herein can be administered in combination or alternation with a protease inhibitor and in combination or alternation with ribavirin. In certain embodiments, one or more compounds provided herein can be administered in combination or alternation with telaprevir and in combination or alternation with ribavirin. In certain embodiments, one or more compounds provided herein can be administered in combination or alternation with boceprevir and in combination or alternation with ribavirin.

In certain embodiments, one or more compounds provided herein can be administered in combination or alternation with a protease inhibitor and not in combination or alternation with ribavirin. In certain embodiments, one or more compounds provided herein can be administered in combination or alternation with telaprevir and not in combination or alternation with ribavirin. In certain embodiments, one or more compounds provided herein can be administered in combination or alternation with boceprevir and not in combination or alternation with ribavirin.

In certain embodiments, one or more compounds provided herein can be administered in combination or alternation with an interferon. In certain embodiments, one or more compounds provided herein can be administered in combination or alternation with interferon alfacon-1. In certain embodiments, one or more compounds provided herein can be administered in combination or alternation with interferon alfa-2b. In certain embodiments, one or more compounds provided herein can be administered in combination or alternation with pegylated interferon alpha 2a. In certain embodiments, one or more compounds provided herein can be administered in combination or alternation with pegylated interferon alpha 2b.

In certain embodiments, one or more compounds provided herein can be administered in combination or alternation with an interferon and in combination or alternation with ribavirin. In certain embodiments, one or more compounds provided herein can be administered in combination or alternation with interferon alfacon-1 and in combination or alternation with ribavirin. In certain embodiments, one or more compounds provided herein can be administered in combination or alternation with interferon alfa-2b and in combination or alternation with ribavirin. In certain embodiments, one or more compounds provided herein can be administered in combination or alternation with pegylated interferon alpha 2a and in combination or alternation with ribavirin. In certain embodiments, one or more compounds provided herein can be administered in combination or alternation with pegylated interferon alpha 2b and in combination or alternation with ribavirin.

In certain embodiments, one or more compounds can be administered in combination or alternation with one or more of the second agents provided herein and not in combination or alternation with ribavirin. In certain embodiments, one or more compounds provided herein can be administered in combination or alternation with an interferon and not in combination or alternation with ribavirin. In certain embodiments, one or more compounds provided herein can be administered in combination or alternation with interferon alfacon-1 and not in combination or alternation with ribavirin. In certain embodiments, one or more compounds provided herein can be administered in combination or alternation with interferon alfa-2b and not in combination or alternation with ribavirin. In certain embodiments, one or more compounds provided herein can be administered in combination or alternation with pegylated interferon alpha 2a and not in combination or alternation with ribavirin. In certain embodiments, one or more compounds provided herein can be administered in combination or alternation with pegylated interferon alpha 2b and not in combination or alternation with ribavirin.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: Ac (acetyl); g (grams); mg (milligrams); mL (milliliters); μL (microliters); mM (millimolar); μM (micromolar); Hz (Hertz); MHz (megahertz); mmol (millimoles); hr or hrs (hours); min (minutes); MS (mass spectrometry); ESI (electrospray ionization); TLC (thin layer chromatography); HPLC (high pressure liquid chromatography); THF (tetrahydrofuran); $CDCl_3$ (deuterated chloroform); AcOH (acetic acid); DCM (dichloromethane); DMSO (dimethylsulfoxide); DMSO-$d_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 3'-Substituted Methyl or Alkynyl Nucleosides

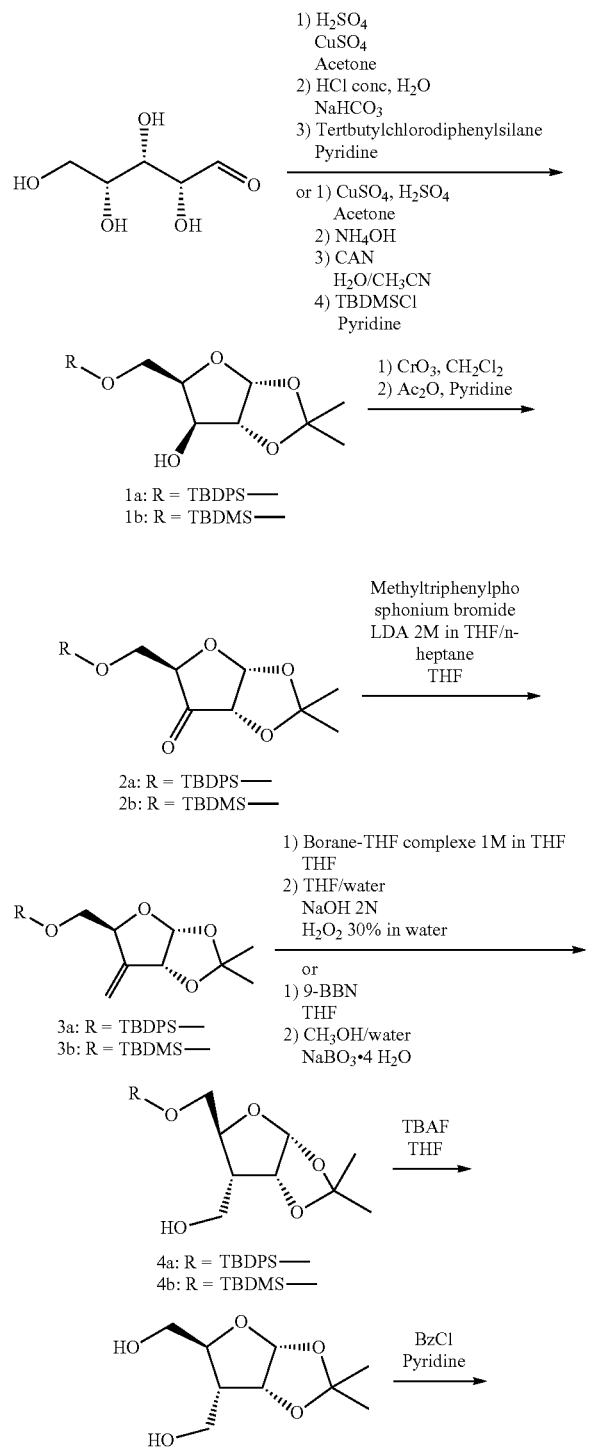

173

-continued

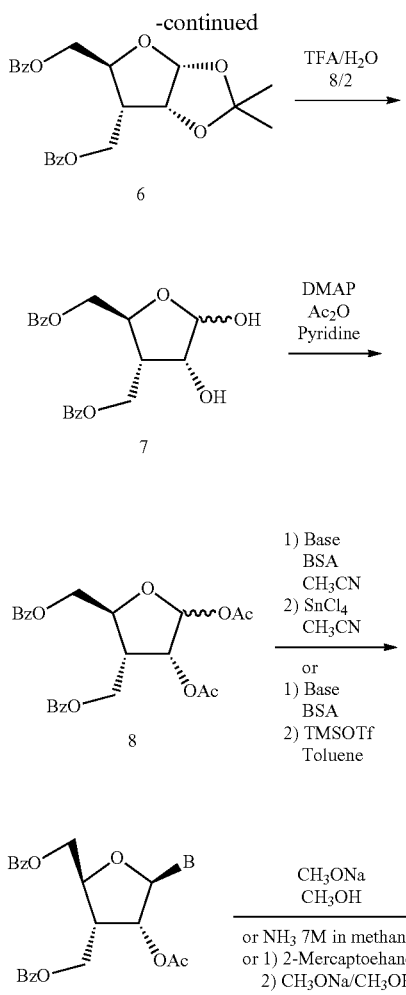

9a: B = Uracile
9b: B = 6-Chloropurine
9c: B = Cytosine
9d: B = 2-Amino-6-chloropurine

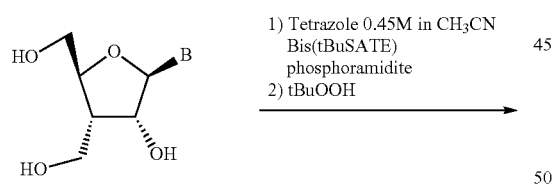

205: B = Uracile
207: B = Adenine
206: B = Cytosine
208: B = Guanine
209: B = 2-Amino-6-thioethanolpurine

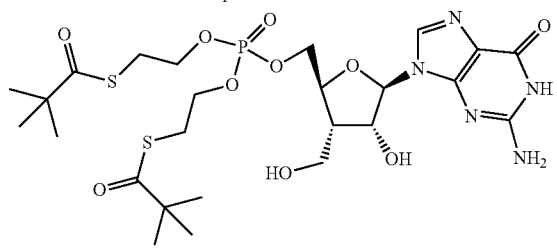

101

174

Preparation of Compound 1a

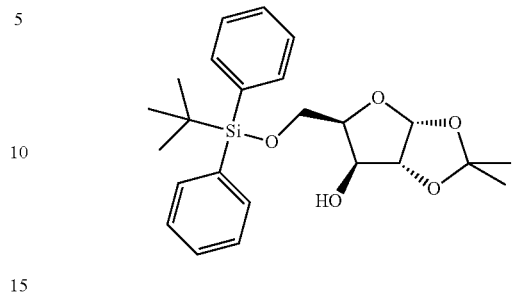

To a stirred solution of (2R,3S,4R)-2,3,4,5-tetrahydroxypentanal D-xylose (666 mmol) in acetone (2000 mL) were added anhydrous copper(2) sulfate (1139 mmol) and sulfuric acid 95% (10 mL). The reaction mixture was stirred at room temperature overnight, then filtered and neutralized with ammonium hydroxide. After filtration, the mixture was concentrated under reduced pressure. The crude mixture was dissolved in a mixture of water (1750 mL) and concentrated HCl (9 mL) and was stirred at room temperature during 2 hours. The reaction mixture was neutralized by addition of bicarbonate and evaporated to dryness. The crude residue was dissolved with dichloromethane and the organic layer was dried on $Na_2SO_4$, filtered and concentrated under reduced pressure. The crude mixture was dissolved in anhydrous pyridine (1200 mL) and tert-butylchlorodiphenylsilane (679 mmol) was added at 0° C. The reaction mixture was stirred at room temperature overnight. Methanol (20 mL) was added and the mixture was concentrated under reduced pressure. The organic layer was washed successively with HCl 0.5N, a saturated aqueous solution of $NaHCO_3$ and brine, dried over $Na_2SO_4$ and concentrated under reduced pressure to give the expected crude compound in 69% yield. $^1$H NMR ($CDCl_3$, 400 MHz) δ (ppm) 1.05 (s, 9H), 1.33 (s, 3H), 1.47 (s, 3H), 4.03 (brs, 1H), 4.1-4.15 (m, 3H), 4.37 (brs, 1H), 4.55 (d, J=3.67 Hz, 1H), 6 (d, J=3.67 Hz, 1H), 7.38-7.47 (m, 6H), 7.66-7.72 (m, 4H).

Preparation of Compound 1b

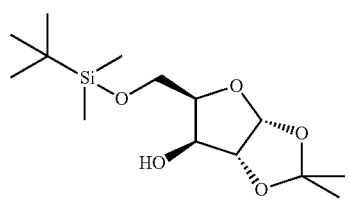 [SMILES: CC1(C)O[C@H]2O[C@H](CO[Si](C)(C)C(C)(C)C)[C@H](O)[C@H]2O1]

To a suspension of (2R,3S,4R)-2,3,4,5-tetrahydroxypentanal D-xylose (333 mmol) and $CuSO_4$ (633 mmol) in acetone (1000 mL) was added sulfuric acid (5 mL). The reaction mixture was stirred at room temperature overnight, then filtered on celite. $NH_4OH$ was added to the filtrate until pH=7 and the mixture (white precipitate) was filtered again on celite. The filtrate was concentrated under reduced pressure. The crude was diluted in a mixture of acetonitrile (330 mL) and water (330 mL) and cerium ammonium nitrate (3% mol) was added. The reaction mixture was stirred at room temperature during 6.5 hours, then stopped by addition of $NH_4OH$ (25 mL) and filtered on celite. The filtrate was diluted with ethyl acetate and washed with water. The aqueous layer was extracted with ethyl acetate and the combined organic layers were dried over Na₂SO₄, filtered and concentrated under reduced pressure. The crude mixture was dissolved in anhydrous pyridine (600 mL) and TBDM-SCl (1.1 eq) was added. The reaction mixture was stirred at room temperature overnight and concentrated under reduced pressure. The residue was diluted in dichloromethane and washed with HCl 1N and saturated aqueous solution of NaHCO₃. The organic layer was dried over Na₂SO₄, filtered and concentrated under reduced pressure to give the expected compound as an orange oil in 74% (over 3 steps).

Preparation of Compound 2a

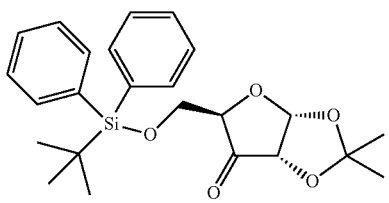 [SMILES: CC1(C)O[C@H]2O[C@H](CO[Si](c3ccccc3)(c3ccccc3)C(C)(C)C)C(=O)[C@H]2O1]

To a stirred solution of chromium (VI) oxide (500 mmol) in anhydrous dichloromethane (1400 mL) were added dropwise at 0° C. acetic anhydride (524 mmol) and anhydrous pyridine (86 mL). The reaction mixture was stirred at room temperature during 30 minutes. Compound 1a (163 mmol) in dichloromethane (200 mL) was added dropwise and the reaction mixture was stirred at room temperature overnight. The mixture was poured on cold ethyl acetate (2000 mL) and precipitated salts were filtered on a silica gel cake. The filtrate was concentrated under reduced pressure and co-evaporated with toluene and dried under high vacuum overnight to give the expected compound as an oil in quantitative yield (TLC control).

Preparation of Compound 2b

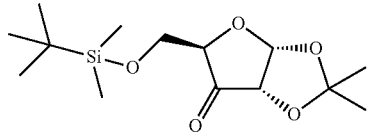 [SMILES: CC1(C)O[C@H]2O[C@H](CO[Si](C)(C)C(C)(C)C)C(=O)[C@H]2O1]

Compound 2b was synthesized from compound 1b (32.9 mmol) in 95% yield as described for compound 2a (in this case, after addition of compound 1b in dichloromethane, the reaction mixture was stirred during 2.5 hours).

Preparation of Compound 3a

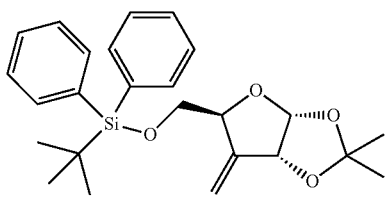 [SMILES: C=C1[C@H]2OC(C)(C)O[C@H]2O[C@@H]1CO[Si](c1ccccc1)(c1ccccc1)C(C)(C)C]

To a stirred solution of lithium diisopropylamide 2M in a mixture of THF/n-heptane (175.3 mmol) in anhydrous tetrahydrofuran (1200 mL) was added portionwise methyltriphenylphosphonium bromide (199.2 mmol). The reaction mixture was heated at 50° C. during 30 minutes. Then, a solution of compound 2a (159.4 mmol) in anhydrous tetrahydrofuran (300 mL) was added dropwise during 20 minutes. The reaction mixture was heated at 50° C. during 1 hour. The reaction mixture was poured on a saturated NH₄Cl solution (1500 mL). The 2 layers were separated and the aqueous layer was extracted with ethyl acetate (2000 mL). The organic layers were washed with water, dried, filtered and concentrated under reduced pressure. The crude residue was purified by chromatography on silica gel column (eluent: petroleum ether/ethyl acetate 0 to 70%) to give the expected compound in 92% yield. ¹H NMR (DMSO-d₆, 400 MHz) δ (ppm) 0.97 (s, 9H), 1.29 (s, 3H), 1.37 (s, 3H), 3.65 (dd, J=10.86 Hz and 4.20 Hz, 1H), 3.77 (dd, J=10.85 Hz and 3.57 Hz, 1H), 4.73-4.75 (m, 1H), 4.93-4.95 (m, 1H), 5.22-5.23 (m, 1H), 5.40-5.41 (m, 1H), 5.80 (d, J=4.15 Hz, 1H), 7.36-7.48 (m, 6H), 7.60-7.64 (m, 4H).

Preparation of Compound 3b

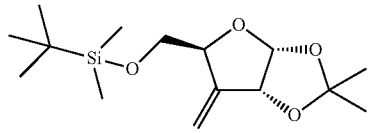 [SMILES: C=C1[C@H]2OC(C)(C)O[C@H]2O[C@@H]1CO[Si](C)(C)C(C)(C)C]

Compound 3b was synthesized from compound 2b (30.79 mmol) in 41% yield as described for compound 3a (eluent of purification: hexane/ethyl acetate).

Preparation of Compound 4a

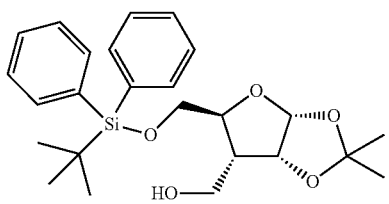 [SMILES: CC1(C)O[C@H]2O[C@H](CO[Si](c3ccccc3)(c3ccccc3)C(C)(C)C)[C@@H](CO)[C@H]2O1]

In a 3-neck round bottom flask equipped with a dropping funnel, a thermometer and a condenser, was introduced under nitrogen borane-THF complex 1M in THF (85.18 mmol) by a cannula. The reaction mixture was stirred at 0° C. under nitrogen and a solution of compound 3a (36.25 mmol) in anhydrous tetrahydrofuran (2.1 mL/mmol) was added dropwise at a rate that kept the reaction temperature between 0-5° C. The reaction mixture was then stirred at room temperature during 3 hours. The reaction mixture was cooled down to 0° C. under nitrogen and successively treated with THF/water 1:1 (58 mL), 2N NaOH (67 mL) and hydrogen peroxide 30% in water (1.6 mL/mmol). The reaction mixture was stirred at room temperature during 2 hours then extracted twice with diethyl ether. The organic layers were combined, dried and evaporated under vacuum. The crude residue was purified by chromatography on silica gel column (eluent: petroleum ether/diethyl ether) to give the expected compound as a yellow oil in 72% yield. ¹H NMR (DMSO-d$_6$, 400 MHz) δ (ppm) 0.98 (s, 9H), 1.24 (s, 3H), 1.38 (s, 3H), 2.14-2.21 (m, 1H), 3.34-3.46 (m, 1H), 3.59-3.69 (m, 2H), 3.81-3.88 (m, 2H), 4.58-4.60 (m, 1H), 4.67-4.69 (m, 1H), 5.74 (d, J=3.46 Hz, 1H), 7.39-7.46 (m, 6H), 7.60-7.65 (m, 4H); MS (ESI) m/z=465.2 (MNa$^+$).

Preparation of Compound 4b

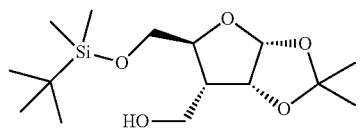 [SMILES: CC1(C)O[C@H]2O[C@H](CO[Si](C)(C)C(C)(C)C)[C@@H](CO)[C@H]2O1]

To a solution of compound 3b (1 mmol) in anhydrous tetrahydrofuran (8.3 mL) was added 9-BBN (6 mmol). The reaction mixture was stirred at room temperature during the week-end. Methanol (2 mL) and water (4 mL) were added, followed by addition of NaBO$_3$.4H$_2$O (24 mmol). The reaction mixture was stirred at room temperature during 24 hours then filtered. The filtrate was washed with water and brine, dried over Na$_2$SO$_4$ and concentrated under reduced pressure. The crude residue was purified by chromatography on silica gel column (eluent: hexane/ethyl acetate 10 to 20%) to give the expected compound in quantitative yield. $^1$H NMR (CDCl$_3$, 300.133 MHz) δ (ppm) 0 (s, 6H), 0.82 (s, 9H), 1.2 (s, 3H), 1.35 (s, 3H), 1.9-2.1 (m, 1H), 3.38 (m, 1H), 3.54-3.62 (m, 1H), 3.67-3.78 (m, 3H), 4.53-4.58 (m, 1H), 4.60-4.63 (m, 1H), 5.67 (d, J=3.62 Hz, 1H).

Preparation of Compound 5

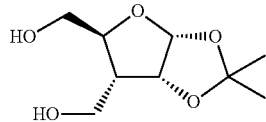

To a solution of compound 4a (0.868 mmol) in anhydrous tetrahydrofuran (3 mL) was added TBAF 1M in THF (3 mL). The reaction mixture was stirred at room temperature during 15 minutes and concentrated under reduced pressure. The crude residue was purified by chromatography on silica gel column (eluent: hexane/ethyl acetate) to give the expected compound in 47% yield. $^1$H NMR (DMSO-d$_6$, 250 MHz) δ (ppm) 1.23 (s, 3H), 1.38 (s, 3H), 1.93-2.05 (m, 1H), 3.35-3.75 (m, 5H), 4.63-4.71 (m, 3H), 5.71 (d, J=3.6 Hz, 1H).

Preparation of Compound 6

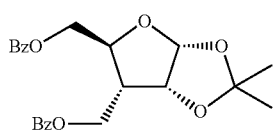

To a solution of compound 5 (6.62 mmol) in anhydrous pyridine (33 mL) was added at 0° C. benzoyl chloride (16.54 mmol). The reaction mixture was stirred at 0° C. during 10 minutes then at room temperature for 1.5 hours. The reaction mixture was diluted with ethyl acetate and washed with aqueous solutions of bicarbonate 5%, HCl 0.5N and brine. The organic layer was dried over Na$_2$SO$_4$, filtered and concentrated under reduced pressure. The crude residue was purified by chromatography on silica gel column (eluent: petroleum ether/diethyl ether 20%) to give the expected compound as a white powder in 84% yield. $^1$H NMR (CDCl$_3$, 250 MHz) δ (ppm) 1.36 (s, 3H), 1.56 (s, 3H), 2.50-2.68 (m, 1H), 4.35-4.51 (m, 3H), 4.70-4.86 (m, 3H), 5.92 (d, J=3.65 Hz, 1H), 7.37-7.56 (m, 6H), 7.97-8.04 (m, 4H).

Preparation of Compound 7

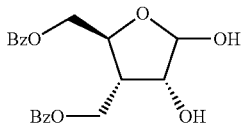

A solution of compound 6 (5.58 mmol) in a mixture of trifluoroacetic acid/water (8/2) was stirred at room temperature during 1.5 hours. The reaction mixture was concentrated under reduced pressure and co-evaporated with toluene. The crude compound was used for the next step without purification.

Preparation of Compound 8

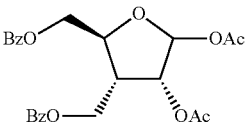

To a solution of compound 7 (5.58 mmol) and DMAP (11.16 mmol) in anhydrous pyridine (19 mL) was added under argon acetic anhydride (111.6 mmol). The reaction mixture was stirred at room temperature during 2 hours then diluted with ethyl acetate, washed with aqueous solutions of NaHCO$_3$ 5%, HCl 0.5N and brine. The organic layer was dried over Na$_2$SO$_4$, filtered and concentrated under reduced pressure. The crude residue was purified by chromatography on silica gel column (eluent: hexane/ethyl acetate 10 to 20%) to give the expected compound in 88% yield. $^1$H NMR (CDCl$_3$, 250 MHz) δ (ppm) 1.98 (s, 3H), 2.05 (s, 3H), 2.95-3.05 (m, 1H), 4.34-4.64 (m, 5H), 5.36-5.43 (m, 1H), 6.1 (s, 0.89H), 6.41-6.43 (m, 0.11H), 7.35-7.54 (m, 6H), 7.92-8.04 (m, 4H).

Preparation of Compound 9a

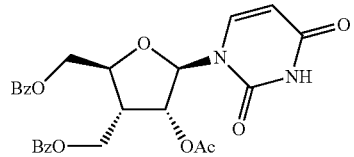

To a solution of uracil (1.09 mmol) in anhydrous acetonitrile (10 mL/mmol) was added BSA (2.96 mmol). The reaction mixture was stirred at reflux during 2 hours. Then, compound 8 (0.99 mmol) and SnCl$_4$ (1.77 mmol) were added at room temperature and the reaction mixture was stirred at reflux during 2 hours. The mixture was diluted with ethyl acetate and a saturated solution of NaHCO$_3$ was added. The resulting mixture was filtered on celite and the filtrate was washed with aqueous solution of NaHCO$_3$ 5%. The layers were separated and the organic layer was dried over Na$_2$SO$_4$, filtered and concentrated under reduced pressure to give the expected compound used in the next step without purification.

Preparation of Compound 9b

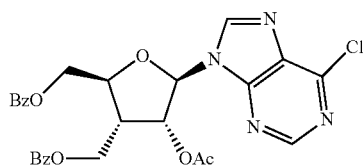

To a solution of 6-chloropurine (0.81 mmol) in anhydrous toluene (3.8 mL) was added BSA (2.30 mmol). The reaction mixture was stirred at reflux during 1.5 hours. The reaction mixture was cooled down to room temperature and a solution of compound 8 (0.77 mmol) in anhydrous toluene was added followed by addition of TMSOTf (0.92 mmol). The reaction mixture was stirred at reflux during 30 minutes. The mixture was diluted with ethyl acetate and washed successively with a saturated solution of NaHCO$_3$ and a mixture of H$_2$O/NaCl (1/1). The organic layer was dried over Na$_2$SO$_4$, filtered and concentrated under reduced pressure to give the expected crude compound in 95% yield.

Preparation of Compound 9c

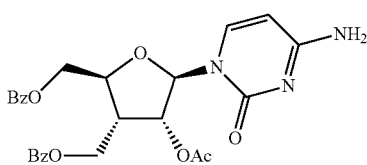

Compound 9c was synthesized from compound 8 (0.658 mmol) as described for compound 9a (purity control by HPLC).

Preparation of Compound 9d

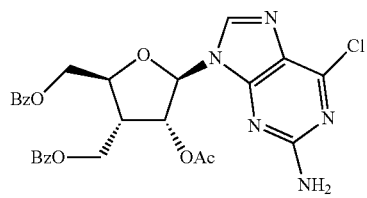

Compound 9d was synthesized from compound 8 as described for compound 9b (second reflux time=2 hours) in 97% yield; MS=566 (MH$^+$).

Preparation of Compound 205

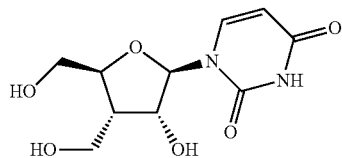 [SMILES: O=c1ccn([C@@H]2O[C@H](CO)[C@@H](CO)[C@H]2O)c(=O)[nH]1]

To a solution of compound 9a (0.99 mmol) in methanol (6 mL) was added CH$_3$ONa (3.26 mmol). The reaction mixture was stirred at room temperature during 20 minutes. The mixture was neutralized to pH=6-7 with acetic acid and concentrated under reduced pressure. The crude residue was purified by C18 chromatography (eluent: H$_2$O/CH$_3$CN 0 to 15%) to give the expected compound in 62% yield (over 2 steps). $^1$H NMR (DMSO-d$_6$, 400 MHz) δ (ppm) 2.13-2.2 (m, 1H), 3.45-3.50 (m, 1H), 3.57 (dd, J=12.18 Hz and 2.89 Hz, 1H), 3.66 (dd, J=10.64 Hz and 6.86 Hz, 1H), 3.78 (dd, J=12.14 Hz and 1.87 Hz, 1H), 3.98 (td, J=9.12 Hz and 2.76 Hz, 1H), 4.19 (d, J=4.37 Hz, 1H), 4.54 (brs, 1H), 5.13 (brs, 1H), 5.58 (d, J=8.09 Hz, 1H), 5.6 (brs, 1H), 5.65 (d, J=1.9 Hz, 1H), 8.1 (d, J=8 Hz, 1H), 11.25 (brs, 1H); MS=259 (MH$^+$).

Preparation of Compound 207

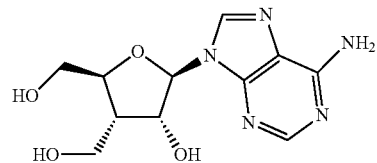 [SMILES: Nc1ncnc2c1ncn2[C@@H]1O[C@H](CO)[C@@H](CO)[C@H]1O]

A solution of compound 9b (0.73 mmol) in ammonia solution 7N in methanol (20 mL) was stirred in a pressure vessel at 90° C. overnight. The reaction mixture was concentrated under reduced pressure and the crude residue was purified by C18 chromatography (eluent: H$_2$O/CH$_3$CN 0 to 15%) to give the expected compound as a light yellow solid in 11% yield. NMR (DMSO-d$_6$, 400 MHz) δ (ppm) 2.42-2.52 (m, 1H), 3.53-3.60 (m, 2H), 3.70-3.78 (m, 2H), 4.05-4.1 (m, 1H), 4.56-4.57 (m, 2H), 5.23 (brs, 1H), 5.71 (brs, 1H), 5.9 (d, J=2.52 Hz, 1H), 7.28 (brs, 2H), 8.14 (s, 1H), 8.41 (s, 1H); MS=282 (MH$^+$).

Preparation of Compound 206

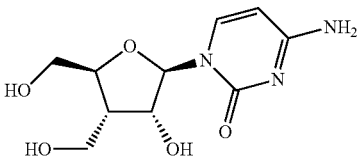 [SMILES: Nc1ccn([C@@H]2O[C@H](CO)[C@@H](CO)[C@H]2O)c(=O)n1]

Compound 206 was synthesized from compound 9c as described for compound 205 in 51% yield (over 2 steps). $^1$H NMR (DMSO-d$_6$+D$_2$O, 400 MHz) δ (ppm) 2.07-2.11 (m, 1H), 3.41-3.66 (m, 3H), 3.78 (dd, J=12.26 Hz and 2.36 Hz, 1H), 3.92-3.96 (m, 1H), 4.08 (d, J=4.75 Hz, 1H), 5.61 (d, J=0.83 Hz, 1H), 5.69 (d, J=7.43 Hz, 1H), 8.06 (d, J=7.44 Hz, 1H); MS=258 (MH+).

Preparation of Compounds 208 and 209

(DMSO-d$_6$, 400 MHz) δ (ppm) 2.41-2.48 (m, 1H), 3.30-3.40 (m, 2H), 3.53-3.75 (m, 6H), 4.01-4.04 (m, 1H), 4.49 (s, 1H), 4.6 (brs, 1H), 4.98 (brs, 1H), 5.07 (brs, 1H), 5.65-5.66 (m, 1H), 5.82 (d, J=2.23 Hz, 1H), 6.51 (brs, 2H), 8.25 (s, 1H); MS=358.13 (MH+).

Preparation of Compound 101

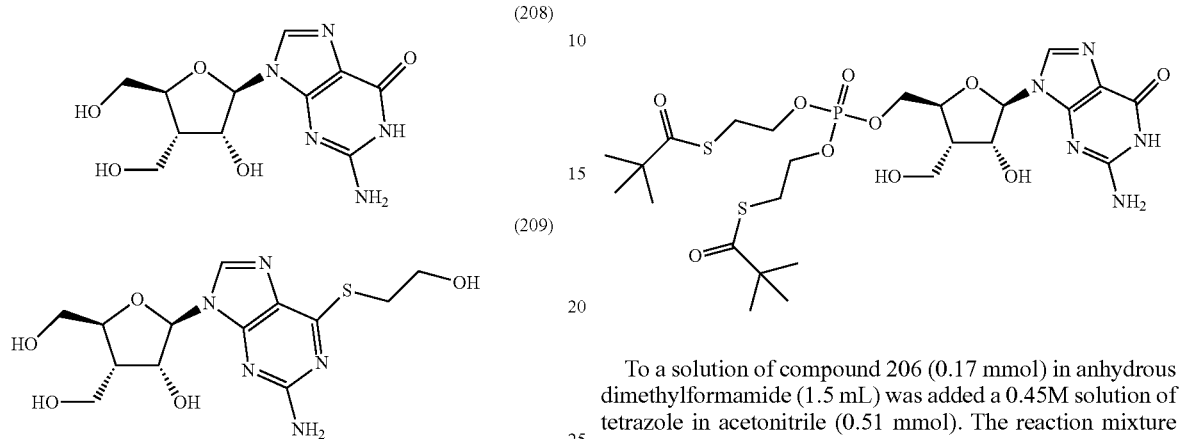

To a solution of compound 9d (1.39 mmol) in methanol (17 mL) were added 2-mercaptoethanol (5.56 mmol) and CH$_3$ONa (5.56 mmol). The reaction mixture was stirred at reflux overnight. The mixture was filtered, washed with methanol and the precipitate was dried to give the expected compound 208 as beige solid in 27% yield. NMR (DMSO-d$_6$, 400 MHz) δ (ppm) 2.45-2.52 (m, 1H), 3.54-3.63 (m, 2H), 3.75-3.79 (m, 2H), 4.06-4.08 (m, 2H), 4.55-4.57 (m, 2H), 5.55 (brs, 2H), 5.75 (d, J=3.1 Hz, 1H), 6.84 (brs, 2H), 7.85 (s, 1H); MS=298 (MH+).

The filtrate was concentrated under reduced pressure and purified to give the compound 209 as yellow solid. NMR To a solution of compound 206 (0.17 mmol) in anhydrous dimethylformamide (1.5 mL) was added a 0.45M solution of tetrazole in acetonitrile (0.51 mmol). The reaction mixture was cooled down to 0° C. and bis(tBuSATE) phosphoramidite (0.34 mmol) dissolved in anhydrous dimethylformamide (0.150 mL) was added. The reaction mixture was stirred under microwave irradiations at 65° C. during 14 minutes. The reaction mixture was cooled down again and tBuOOH (5M) (0.250 mL) was added at 0° C. The reaction mixture was stirred during 40 minutes and the solvents were concentrated under reduced pressure. The reaction mixture was purified successively by chromatography on silica gel column and C18 chromatography to give the expected compound as a white powder in 2% yield.

Preparation of Compounds 202, 204, 210, 225, 226, 228, 229, 102b, 103a and 103b

Scheme 2

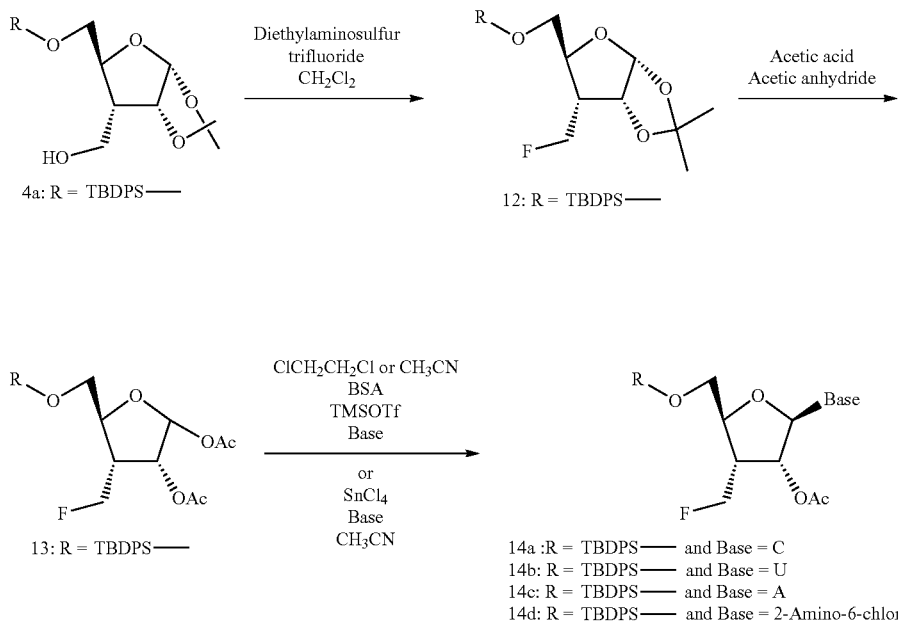

-continued
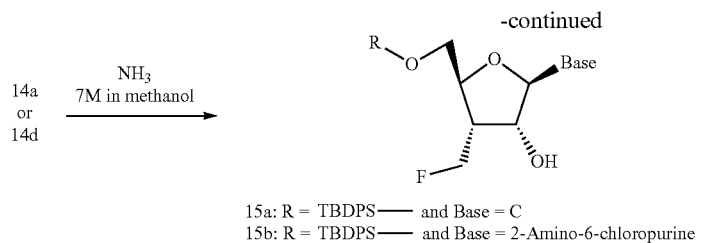
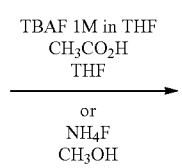
15a: R = TBDPS— and Base = C
15b: R = TBDPS— and Base = 2-Amino-6-chloropurine
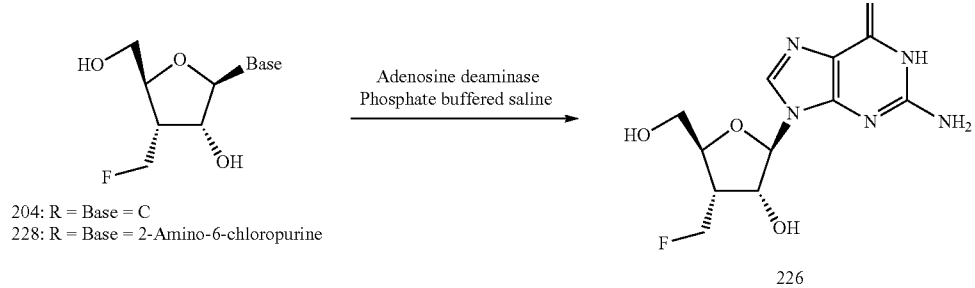
204: R = Base = C
228: R = Base = 2-Amino-6-chloropurine
226
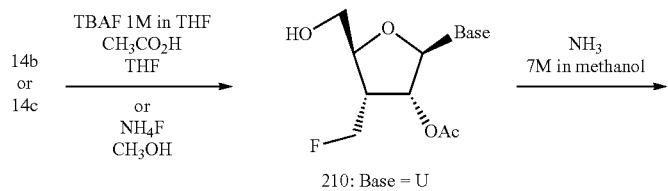
210: Base = U
229: Base = A
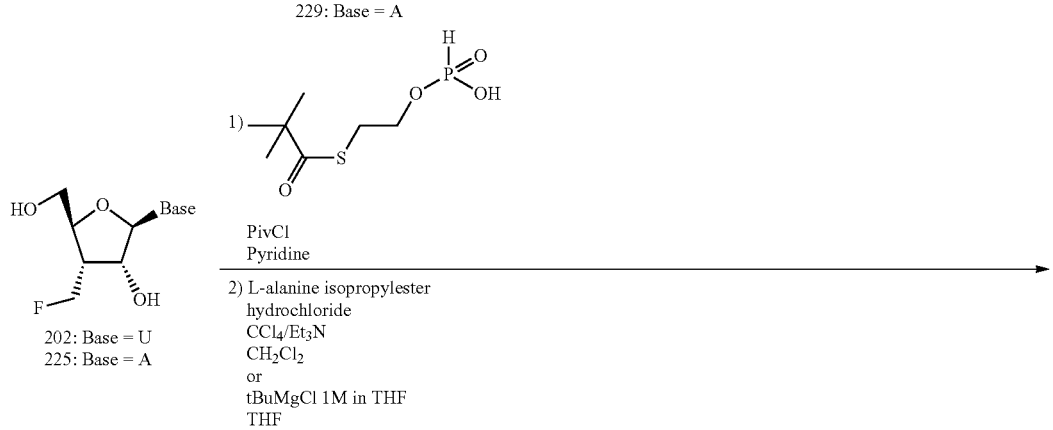
202: Base = U
225: Base = A
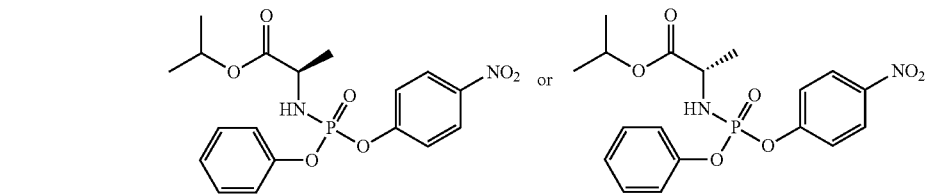
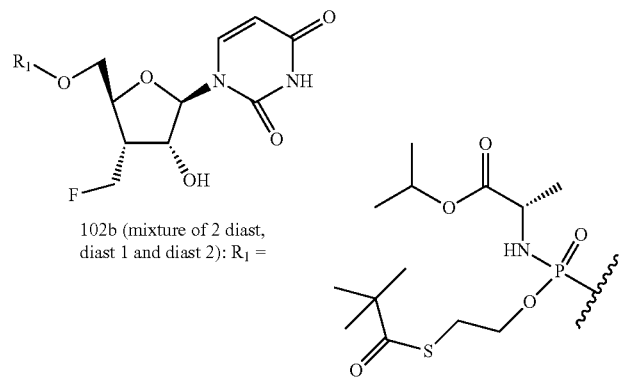
102b (mixture of 2 diast, diast 1 and diast 2): $R_1$ =

103a: R₁ = 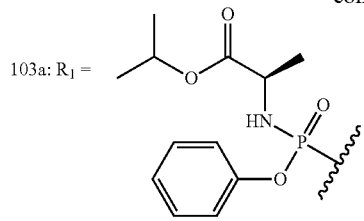

103b (diast 1 and diast 2): R₁ = 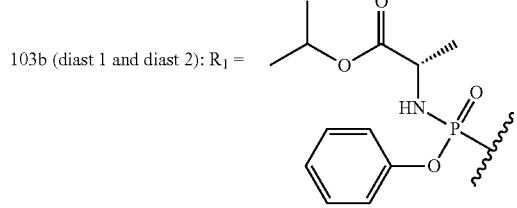

Preparation of Compound 12

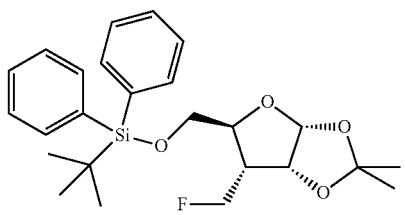 [SMILES: CC1(C)O[C@H]2O[C@H](CO[Si](c3ccccc3)(c3ccccc3)C(C)(C)C)[C@@H](CF)[C@H]2O1]

To a solution of compound 4a (20.33 mmol) in anhydrous dichloromethane (10 mL/mmol) under nitrogen was added dropwise diethylaminosulfur trifluoride (40.67 mmol) at 0° C. The reaction mixture was stirred at 0° C. during 2 hours and poured on buffer phosphate pH=7 (0.5M). The 2 layers were separated and the organic layer was washed with water, dried over $Na_2SO_4$, filtered and concentrated under reduced pressure. The residue was purified by chromatography on silica gel column (eluent: petroleum ether/ethyl acetate 0 to 25%) to give the expected compound as a white solid in 29% yield. $^1H$ NMR ($CDCl_3$, 400 MHz) δ (ppm) 1.05 (s, 9H), 1.34 (s, 3H), 1.51 (s, 3H), 2.59-2.70 (m, 1H), 3.80 (ddd, J=53.15 Hz and 11.23 Hz and 3.65 Hz, 2H), 3.99 (td, J=9.83 Hz and 3.62 Hz, 1H), 4.46-4.50 (m, 0.5H), 4.57-4.61 (m, 0.5H), 4.66-4.70 (m, 0.5H), 4.75-4.82 (m, 1.5H), 5.86 (d, J=3.67 Hz, 1H), 7.36-7.45 (m, 6H), 7.65-7.69 (m, 4H); $^{19}F$ NMR ($CDCl_3$, 376.5 MHz) δ (ppm) −223.7 (s, 1F).

Preparation of Compound 13

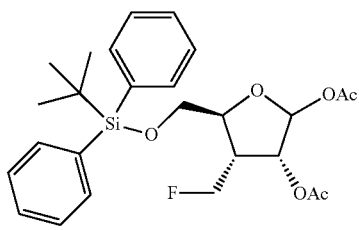 [SMILES: CC(=O)OC1O[C@H](CO[Si](c2ccccc2)(c2ccccc2)C(C)(C)C)[C@@H](CF)[C@H]1OC(C)=O]

To a solution of compound 12 (4.86 mmol) in acetic acid (2 mL/mmol) were added acetic anhydride (19.2 mmol) and a drop of $H_2SO_4$ concentrated. The reaction mixture was stirred at room temperature during 2 hours and diluted with ethyl acetate. The organic layer was washed successively with water, and a saturated solution of sodium bicarbonate, dried over $Na_2SO_4$, filtered and concentrated under reduced pressure. The crude residue was purified by chromatography on silica gel column (eluent: petroleum ether/ethyl acetate 0 to 25%) to give the expected compound as a pale yellow oil in 84% yield. MS (ESI) m/z=511.2 ($MNa^+$).

Preparation of Compound 14a

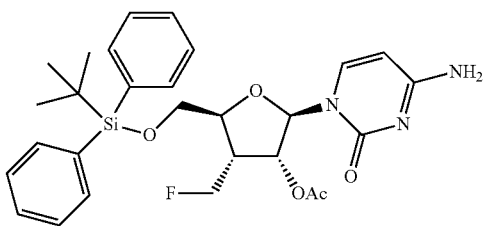 [SMILES: CC(=O)O[C@@H]1[C@H](CF)[C@@H](CO[Si](c2ccccc2)(c2ccccc2)C(C)(C)C)O[C@H]1n1ccc(N)nc1=O]

To a suspension of cytosine (4.71 mmol) in anhydrous 1,2-dichloroethane (10 mL/mmol) was added dropwise at room temperature N,O-bis(trimethylsilyl)acetamide (10.83 mmol). The reaction mixture was heated at reflux during 2 hours (colorless solution). Then, a solution of compound 13 (2.05 mmol) in anhydrous 1,2-dichloroethane (10 mL/mmol) was added at room temperature followed by trimethylsilyl trifluoromethanesulfonate (4.71 mmol) and the reaction mixture was heated at reflux during 2 hours. The reaction mixture was poured on a saturated solution of bicarbonate and the organic layer was washed with brine, dried over $Na_2SO_4$, filtered and concentrated under reduced pressure. The crude residue was purified by chromatography on silica gel column (eluent: $CH_2Cl_2/CH_3OH$ 0 to 5%) to give the expected compound as a colorless foam in quantitative yield. MS (ESI) m/z=540.09 ($MH^+$).

Preparation of Compound 14b

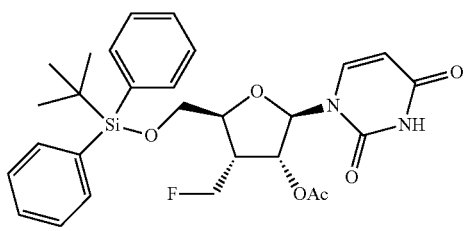 [SMILES: CC(=O)O[C@@H]1[C@H](CF)[C@@H](CO[Si](c2ccccc2)(c2ccccc2)C(C)(C)C)O[C@H]1n1ccc(=O)[nH]c1=O]

To a suspension of uracil (4.9 mmol) in anhydrous acetonitrile (10 mL/mmol) was added dropwise at room temperature N,O-bis(trimethylsilyl)acetamide (9.4 mmol). The reaction mixture was refluxed during 1 hour. Then, a solution of compound 13 (4.1 mmol) in anhydrous acetonitrile (10 mL/mmol) was added at room temperature followed by trimethylsilyl trifluoromethanesulfonate (6.1 mmol). The reaction mixture was heated at reflux overnight, then diluted with ethyl acetate. The organic layer was washed with a saturated solution of bicarbonate and brine, dried over $Na_2SO_4$, filtered and concentrated under reduced pressure. The crude residue was purified by chromatography on silica gel column (eluent: $CH_2Cl_2/CH_3CH_2OH$ 0 to 5%) to give the expected compound as a white foam in 54% yield. $^1H$ NMR ($CDCl_3$, 400 MHz) δ (ppm) 1.11 (s, 9H), 2.14 (s, 3H), 2.92-3.03 (m, 1H), 3.77 (d, J=11.87 Hz, 1H), 4.16 (d, J=11.99 Hz, 1H), 4.25 (d, J=8.06, 1H), 4.38-4.60 (m, 2H), 5.37 (d, J=8.19 Hz, 1H), 5.49 (dd, J=2.84 Hz and 6.50 Hz, 1H), 5.99 (d, J=2.81 Hz, 1H), 7.38-7.48 (m, 6H), 7.63-7.67 (m, 4H), 7.83 (d, J=8.23 Hz, 1H), 8.36 (s, 1H); MS (ESI) m/z=539.2 (MH⁻).

Preparation of Compound 15

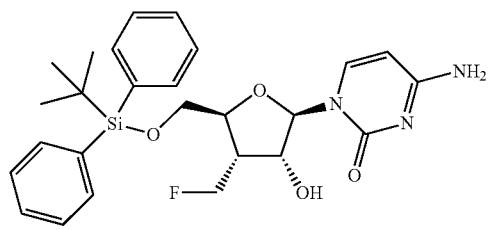 [SMILES: CC(C)(C)[Si](OC[C@H]1O[C@@H](n2ccc(N)nc2=O)[C@H](O)[C@@H]1CF)(c1ccccc1)c1ccccc1]

A solution of compound 14a (2.20 mmol) in ammonia solution 7N in methanol (2 mL/mmol) was stirred at room temperature during 6 hours. The solvent was removed under reduced pressure at room temperature to give the expected crude compound as a white solid in quantitative yield. MS (ESI) m/z=498.

Preparation of Compound 204

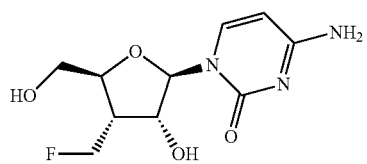 [SMILES: Nc1ccn([C@@H]2O[C@H](CO)[C@@H](CF)[C@H]2O)c(=O)n1]

To a solution of compound 15 (2.20 mmol) in anhydrous methanol (5 mL/mmol) was added ammonium fluoride (17.7 mmol) at room temperature and under nitrogen atmosphere. The reaction mixture was heated at reflux during 2 hours and concentrated under reduced pressure. The crude residue was purified by chromatography on silica gel column (eluent: $CH_2Cl_2/CH_3CH_2OH$ 0 to 15%) followed by C18 chromatography (eluent: $H_2O/CH_3CN$ 0 to 8%) to give after lyophilisation the expected compound as a white solid in 23% yield. $^1H$ NMR (DMSO-$d_6$, 400 MHz) δ (ppm) 3.54 (dd, J=12.32 Hz and 2.71 Hz, 1H), 3.76-3.79 (m, 1H), 4.01 (td, J=9.64 Hz and 2.80 Hz, 1H), 4.14 (d, J=5.04 Hz, 1H), 4.41-4.45 (m, 0.5H), 4.53-4.63 (m, 1H), 4.71-4.75 (m, 0.5H), 5.13 (brs, 1H), 5.64 (brs, 1H), 5.66 (d, J=7.48 Hz, 1H), 5.83 (brs, 1H), 7.01 (brs, 1H), 7.1 (brs, 1H), 8.0 (d, J=7.34 Hz, 1H); MS (ESI) m/z=260.2 (MH⁺).

Preparation of Compound 210

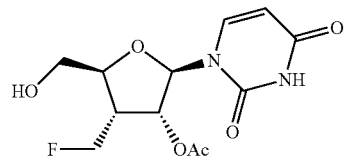 [SMILES: CC(=O)O[C@@H]1[C@H](CF)[C@@H](CO)O[C@H]1n1ccc(=O)[nH]c1=O]

Compound 210 was synthesized from compound 14b (2.20 mmol) as described for compound 204 (without C18 purification) as a white foam in 54% yield. MS (ESI) m/z=303 (MH⁺).

Preparation of Compound 202

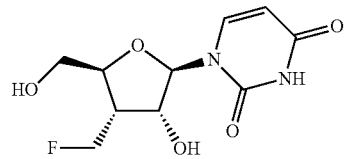 [SMILES: O=c1ccn([C@@H]2O[C@H](CO)[C@@H](CF)[C@H]2O)c(=O)[nH]1]

A solution of compound 210 (1.2 mmol) in ammonia solution 7N in MeOH (2 mL/mmol) was stirred at room temperature during 3 hours. The reaction mixture was concentrated under reduced pressure and gathered with an impure fraction of another reaction. This mixture was diluted in water and purified by prepMS to give the expected compound as a white solid. $^1H$ NMR (DMSO-$d_6$, 400 MHz) δ (ppm) 3.50-3.57 (m, 1H), 3.71-3.78 (m, 1H), 4-4.06 (m, 1H), 4.22-4.27 (m, 1H), 4.45-4.50 (m, 0.5H), 4.56-4.61 (m, 1H), 4.68-4.74 (m, 0.5H), 5.15-5.20 (m, 1H), 5.56-5.59 (m, 1H), 5.65 (brs, 1H), 5.83-5.85 (m, 1H), 8.01-8.05 (m, 1H), 11.27 (brs, 1H); MS (ESI) m/z=261 (MH⁺).

Preparation of Compound 228

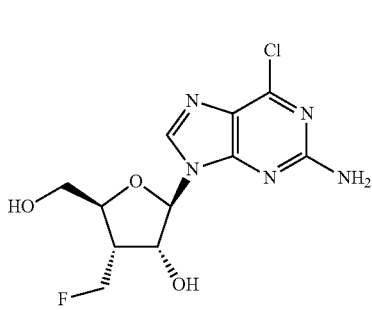 [SMILES: Nc1nc(Cl)c2ncn([C@@H]3O[C@H](CO)[C@@H](CF)[C@H]3O)c2n1]

Compound 228 was synthesized according to Scheme 2.

Preparation of Compound 226

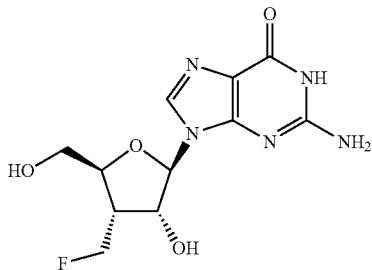 [SMILES: Nc1nc2c(ncn2[C@@H]2O[C@H](CO)[C@@H](CF)[C@H]2O)c(=O)[nH]1]

Compound 226 was synthesized according to Scheme 2.

MS (ESI) m/z=300.1 (MH⁻). $^1$H NMR (400 MHz, DMSO) δ (ppm) 10.84 (brs, 1H), 7.97 (s, 1H), 6.70 (brs, 2H), 5.93 (brs, 1H), 5.69 (d, J=2.94 Hz, 1H), 5.12 (brs, 1H), 4.77-4.50 (m, 3H), 4.08-4.04 (m, 1H), 3.68 (dd, J=2.85 Hz and 12.03 Hz, 1H), 3.52 (dd, J=3.88 Hz and 11.96 Hz, 1H), 2.78-2.66 (m, 1H). $^{19}$F NMR (362 MHz, DMSO) δ (ppm) −224.87 (s, 1F).

Preparation of Compound 229

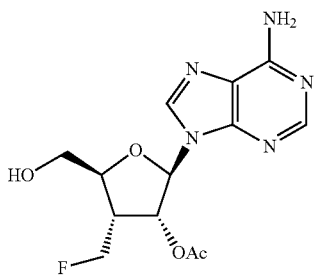 [SMILES: CC(=O)O[C@@H]1[C@H](CF)[C@@H](CO)O[C@H]1n1cnc2c(N)ncnc21]

Compound 229 was synthesized according to Scheme 2.

Preparation of Compound 225

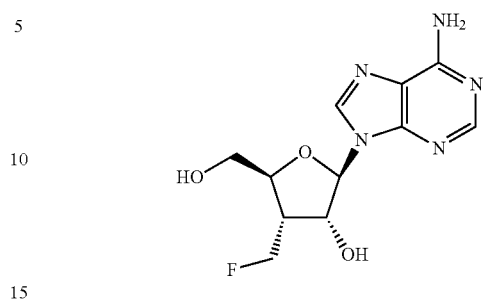

Compound 225 was synthesized according to Scheme 2.
MS (ESI) m/z=284 (MH⁻). $^1$H NMR (400 MHz, DMSO) δ (ppm) 8.40 (s, 1H), 8.14 (s, 1H), 7.30 (brs, 2H), 5.96 (d, J=2.94 Hz, 1H), 5.89 (d, J=2.72 Hz, 1H), 5.30 (t, J=5.70 Hz, 1H), 4.80-4.56 (m, 3H), 4.16-4.12 (m, 1H), 3.77-3.72 (m, 1H), 3.57-3.52 (m, 1H), 2.85-2.73 (m, 1H). $^{19}$F NMR (362 MHz, DMSO) δ (ppm) −224.91 (s, 1F).

Preparation of Compound 102b (Two Diastereomers)

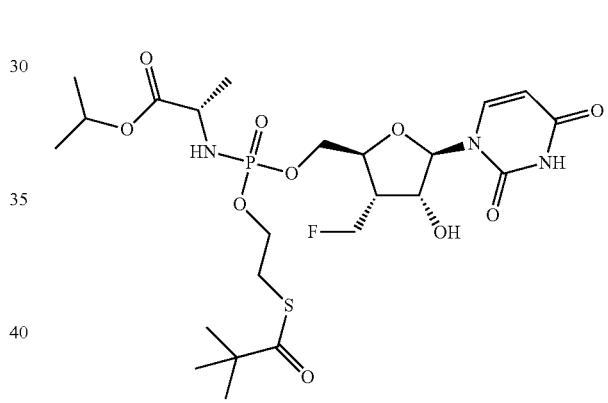

To a solution of compound 202 (1.02 mmol) and 2-(2,2-dimethylpropanoylsulfanyl)ethoxy phosphinic acid (1.53 mmol) in anhydrous pyridine (12 mL/mmol) was slowly added trimethylacetyl chloride (2.044 mmol) at 0° C. The reaction mixture was stirred during 1 hour at 0° C. and 2 hours at room temperature. The reaction mixture was quenched with NH₄Cl 1M (100 mL) and extracted with ethyl acetate. The organic layer was dried over Na₂SO₄, filtered and concentrated under reduced pressure. The crude residue was diluted in dichloromethane (10 mL/mmol). Carbon tetrachloride (5 mL/mmol) was added followed by addition of triethylamine (6.123 mmol) and H-Ala-OiPr.HCl (3.061 mmol) at room temperature. The reaction mixture was stirred overnight at room temperature. The mixture was directly purified by chromatography on silica gel column (eluent: CH₂Cl₂/CH₃OH 0 to 20%) to give the mixture of diastereoisomers as a white powder in 47% yield. MS (ESI) m/z=598.2 (MH⁻).

The 2 diastereoisomers were separated by PrepMS and each diastereoisomer was purified again by chromatography on silica gel column (eluent: CH₂Cl₂/CH₃OH 0 to 20%).

102b (diastereoisomer 1): white lyophilized solid; 5%; $^1$H NMR (CD₃OD, 400 MHz) δ (ppm) 1.23 (s, 9H), 1.25-1.28

(m, 6H), 1.38-1.40 (m, 3H), 2.61-2.72 (m, 1H), 3.15 (t, J=6.65 Hz, 2H), 3.84-3.89 (m, 1H), 4.03-4.08 (m, 2H), 4.20-4.27 (m, 1H), 4.39-4.45 (m, 3H), 4.70-4.74 (m, 1H), 5.02 (septuplet, J=6.22 Hz, 1H), 5.76-5.78 (m, 2H), 7.90 (d, J=8.12 Hz, 1H); $^{31}$P NMR (CD$_3$OD, 162 MHz) δ (ppm) 8.19 (s, 1P); $^{19}$F NMR (CD$_3$OD, 376.5 MHz) δ (ppm) −228.61 (s, F); MS (ESI) m/z=598.2 (MH$^+$).

102b (diastereoisomer 2): white lyophilized solid; 6%; $^1$H NMR (CD$_3$OD, 400 MHz) δ (ppm) 1.24 (s, 9H), 1.25 (d, J=6.28 Hz, 3H), 1.26 (d, J=6.28 Hz, 3H), 1.38-1.40 (m, 3H), 2.57-2.68 (m, 1H), 3.18 (t, J=6.54 Hz, 2H), 3.82-3.90 (m, 1H), 4.08-4.21 (m, 3H), 4.36-4.44 (m, 3H), 4.70-4.74 (m, 1H), 5.02 (septuplet, J=6.28 Hz, 1H), 5.74-5.76 (m, 2H), 7.86 (d, J=8.12 Hz, 1H); $^{31}$P NMR (CD$_3$OD, 162 MHz) δ (ppm) 8.23 (s, 1P); $^{19}$F NMR (CD$_3$OD, 376.5 MHz) δ (ppm) −228.57 (s, F); MS (ESI) m/z=598.2 (MH$^+$).

Preparation of Compound 103a

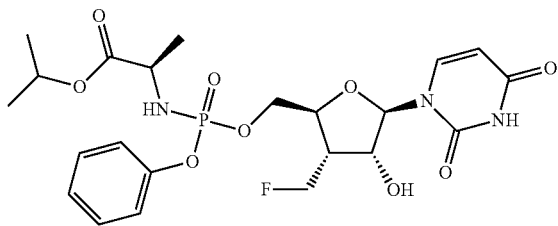 [SMILES: CC(C)OC(=O)[C@@H](C)NP(=O)(OC[C@H]1O[C@@H](n2ccc(=O)[nH]c2=O)[C@H](O)[C@@H]1CF)Oc1ccccc1]

To a stirred solution of compound 202 (1.153 mmol) in anhydrous tetrahydrofuran (20 mL/mmol) was added tert-butylmagnesium chloride 1M in THF (3.459 mmol). The reaction mixture was stirred at room temperature during 10 minutes. A solution of isopropyl (2R)-2-[[(4-nitrophenoxy)-phenoxy-phosphoryl]amino]propanoate (1.268 mmol) in anhydrous tetrahydrofuran (5 mL/mmol) was added to the reaction mixture. The reaction mixture was stirred at room temperature during 3 hours. The mixture was diluted with ethyl acetate and washed with water and brine. The organic layer was dried over Na$_2$SO$_4$, filtered and concentrated under reduced pressure. The crude residue was purified by chromatography on silica gel column (eluent: CH$_2$Cl$_2$/CH$_3$OH 0 to 20%) to give the mixture of diastereoisomers as a white lyophilized solid in 24% yield. $^1$H NMR (CD$_3$OD, 400 MHz) δ (ppm) 1.22-1.24 (m, 6H), 1.30-1.36 (m, 3H), 2.49-2.69 (m, 1H), 3.87-3.95 (m, 1H), 4.25-4.44 (m, 3H), 4.47-4.53 (m, 1H), 4.54-4.85 (m, 2H), 4.98 (septuplet, J=6.28 Hz, 1H), 5.59 (d, J=8.06 Hz, 0.45H), 5.67 (d, J=8.05 Hz, 0.55H), 5.75-5.78 (m, 1H), 7.18-7.28 (m, 3H), 7.34-7.41 (m, 2H), 7.77 (d, J=8.13 Hz, 0.55H), 7.84 (d, J=8.13 Hz, 0.45H); $^{31}$P NMR (CD$_3$OD, 162 MHz) δ (ppm) 3.44 (s, 0.55P), 4.10 (s, 0.45P); $^{19}$F NMR (CD$_3$OD, 376.5 MHz) δ (ppm) −228.79 (s, 0.55F), −228.67 (s, 0.45F); MS (ESI) m/z=530.2 (MH$^+$).

Preparation of Diastereomers of Compound 103b

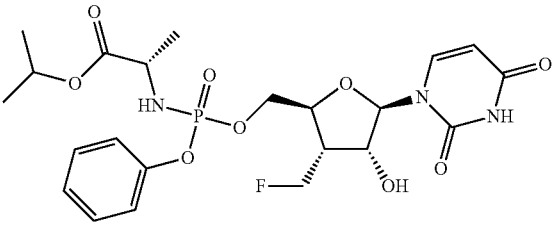 [SMILES: CC(C)OC(=O)[C@H](C)NP(=O)(OC[C@H]1O[C@@H](n2ccc(=O)[nH]c2=O)[C@H](O)[C@@H]1CF)Oc1ccccc1]

Compounds 103b (diastereomer 1) and 103b (diastereomer 2) were synthesized from compound 202 (1.153 mmol) as described for compound 103a but using isopropyl (2S)-2-[[(4-nitrophenoxy)-phenoxy-phosphoryl] amino] propanoate. In this case, the 2 diastereoisomers were separated by prepMS.

103b (diastereoisomer 1): white lyophilized solid; 4%; $^1$H NMR (CD$_3$OD, 400 MHz) δ (ppm) 1.22-1.25 (m, 6H), 1.32-1.34 (m, 3H), 2.54-2.65 (m, 1H), 3.87-3.95 (m, 1H), 4.32-4.38 (m, 2H), 4.41-4.45 (m, 1H), 4.51-4.55 (m, 1H), 4.57-4.61 (m, 0.5H), 4.68-4.72 (m, 1H), 4.79-4.83 (m, 0.5H), 4.99 (septuplet, J=6.24 Hz, 1H), 5.68 (d, J=8.10 Hz, 1H), 5.76-5.77 (m, 1H), 7.18-7.25 (m, 3H), 7.34-7.39 (m, 2H), 7.83 (d, J=8.10 Hz, 1H); $^{31}$P NMR (CD$_3$OD, 162 MHz) δ (ppm) 3.88 (s, 1P); $^{19}$F NMR (CD$_3$OD, 376.5 MHz) δ (ppm) −228.78 (s, F); MS (ESI) m/z=530.2 (MH$^+$).

103b (diastereoisomer 2): white lyophilized solid; 11%; $^1$H NMR (CD$_3$OD, 400 MHz) δ (ppm) 1.22 (d, J=6.22 Hz, 3H), 1.23 (d, J=6.22 Hz, 3H), 1.34-1.36 (m, 3H), 2.57-2.68 (m, 1H), 3.88-3.96 (m, 1H), 4.26-4.32 (m, 1H), 4.39-4.43 (m, 2H), 4.45-4.50 (m, 1H), 4.56-4.60 (m, 0.5H), 4.68-4.72 (m, 1H), 4.80-4.84 (m, 0.5H), 4.97 (septuplet, J=6.25 Hz, 1H), 5.58 (d, J=8.11 Hz, 1H), 5.75-5.76 (m, 1H), 7.19-7.23 (m, 1H), 7.25-7.29 (m, 2H), 7.36-7.41 (m, 2H), 7.79 (d, J=8.10 Hz, 1H); $^{31}$P NMR (CD$_3$OD, 162 MHz) δ (ppm) 3.75 (s, 1P); $^{19}$F NMR (CD$_3$OD, 376.5 MHz) δ (ppm) −228.65 (s, F); MS (ESI) m/z=530.2 (MH$^+$).

Preparation of Compounds 201 and 203

Scheme 3

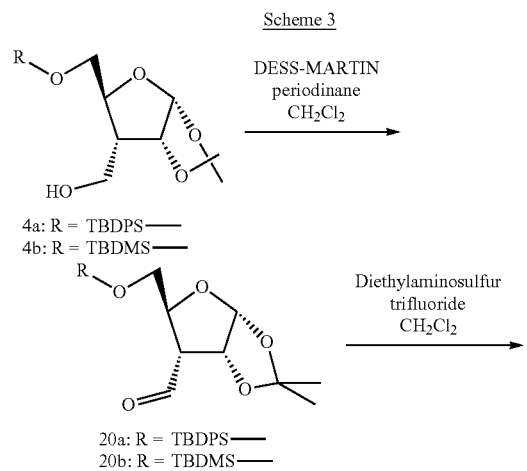

4a: R = TBDPS
4b: R = TBDMS

20a: R = TBDPS
20b: R = TBDMS

-continued

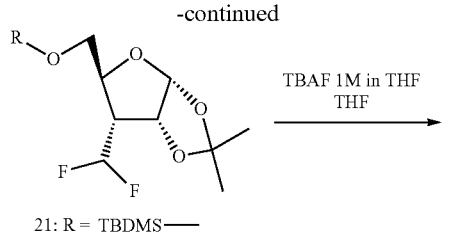

21: R = TBDMS—

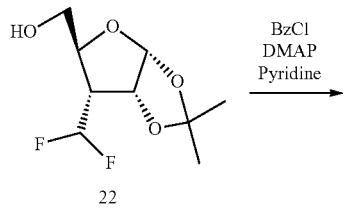

22

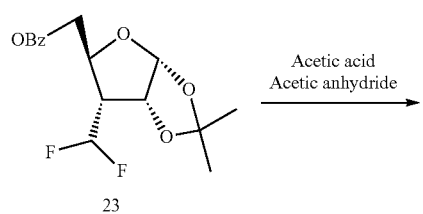

23

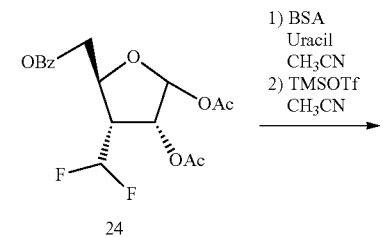

24

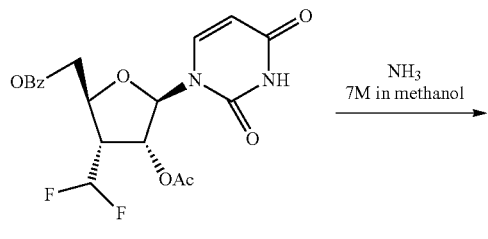

25

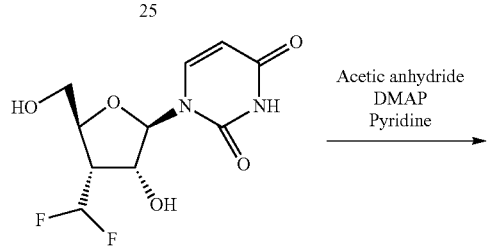

201

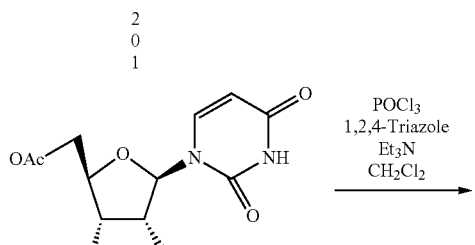

27

-continued

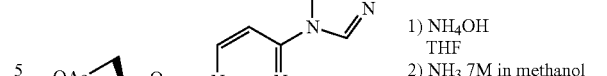

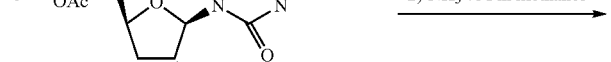

28

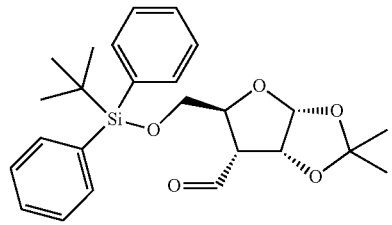 [SMILES: CC1(C)O[C@H]2O[C@H](CO[Si](c3ccccc3)(c3ccccc3)C(C)(C)C)[C@@H](C=O)[C@H]2O1]

203

Preparation of Compound 20a

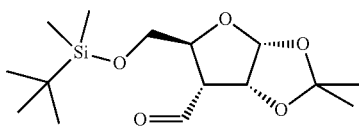

Compound 20a was synthesized from compound 4a (48.8 mmol) as described for compound 20b (no purification) as an oil in 82% yield; MS (ESI) m/z=463.2 (MNa⁺).

Preparation of Compound 20b

To a solution of DESS-MARTIN periodinane (42.3 mmol) in anhydrous dichloromethane (7.14 mL/mmol) under nitrogen atmosphere at 0° C. was added dropwise a solution of 4b (28.2 mmol) in dichloromethane (3.57 mL/mmol). The reaction mixture was stirred at room temperature during 2 hours. The reaction mixture was quenched on a mixture of a saturated solution of NaHCO$_3$ (200 ml) and Na$_2$S$_2$O$_3$ (20 g in 200 ml of water) and extracted with ethyl acetate (or dichloromethane). The organic layer was washed with brine, dried, filtered and concentrated under reduced pressure. The residue was purified by chromatography on silica gel column (eluent: petroleum ether/ethyl acetate 0 to 35%) to give the expected compound as a colorless oil in 73% yield. $^1$H NMR (CDCl$_3$, 400 MHz) δ (ppm) 0 (s, 6H), 0.83 (s, 9H), 1.29 (s, 3H), 1.46 (s, 3H), 2.94-3.01 (m, 1H), 3.70-3.84 (m, 2H), 4.47-4.53 (m, 1H), 4.96-5 (m, 1H), 5.81-5.85 (m, 1H), 9.73-9.75 (m, 1H).

Preparation of Compound 21

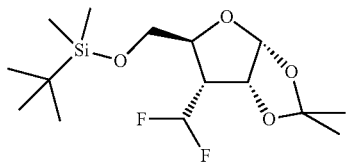 [SMILES: CC1(C)O[C@H]2O[C@H](CO[Si](C)(C)C(C)(C)C)[C@@H](C(F)F)[C@H]2O1]

To a solution of compound 20b (19 mmol) in anhydrous dichloromethane (10 mL/mmol) was added dropwise at 0° C. under nitrogen atmosphere diethylaminosulfur trifluoride (76 mmol). The reaction mixture was stirred at room temperature during 2 hours, then quenched on buffer phosphate solution pH=7 (0.5M). The 2 layers were separated and the organic layer was concentrated under reduced pressure. The residue was purified by chromatography on silica gel column (eluent: petroleum ether/diethyl ether 0 to 50%) to give the expected compound as a colorless oil in 50% yield. $^1$H NMR (CDCl$_3$, 400 MHz) δ (ppm) 0.06 (s, 6H), 0.89 (s, 9H), 1.34 (s, 3H), 1.53 (s, 3H), 2.68-2.80 (m, 1H), 3.64 (d, J=11.63 Hz, 1H), 3.92 (d, J=11.63 Hz, 1H), 4.23 (d, J=9.42 Hz, 1H), 4.74-4.77 (m, 1H), 5.82-5.84 (m, 1H), 5.87-6.17 (m, 1H); $^{19}$F NMR (CDCl$_3$, 376.5 MHz) δ (ppm) −122.04 (dd, J=297.37 Hz and 56.24 Hz, 1F), −114.25 (dd, J=297.11 Hz and 56.01 Hz, 1F).

Preparation of Compound 22

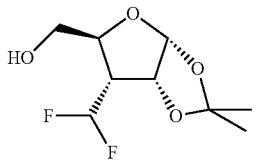

To solution of compound 21 (12.8 mmol) in anhydrous tetrahydrofuran (10 mL/mmol) under nitrogen atmosphere was added dropwise tetra-n-butylammonium fluoride 1M in THF (16.6 mmol). The reaction mixture was stirred at room temperature during 30 minutes. The reaction mixture was diluted with ethyl acetate then quenched on saturated solution of ammonium chloride. The aqueous layer was extracted with ethyl acetate and the combined organic layers were concentrated under reduced pressure. The crude residue was purified by chromatography on silica gel column (eluent: dichloromethane/ethanol 0 to 5%) to give the expected compound as a white solid in 86% yield. $^1$H NMR (CDCl$_3$, 400 MHz) δ (ppm) 1.34 (s, 3H), 1.54 (s, 3H), 1.8 (brs, 1H), 2.61-2.72 (m, 1H), 3.63 (dd, J=12.42 Hz and 3.58 Hz, 1H), 3.96 (d, J=12.37 Hz, 1H), 4.27-4.32 (m, 1H), 4.80 (t, J=4.19 Hz, 1H), 5.87 (d, J=3.62 Hz, 1H), 5.89 (d, J=7.39 Hz, 0.25H), 6.03 (dd, J=7.36 Hz and 2.25 Hz, 0.5H), 6.17 (d, J=7.38 Hz, 0.25H); $^{19}$F NMR (CDCl$_3$, 376.5 MHz) δ (ppm) −121.74 (d, J=300.16 Hz, 1F), −114.25 (d, J=299.95 Hz, 1F).

Preparation of Compound 23

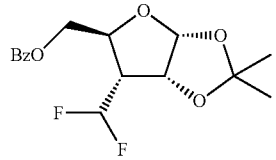

To a solution of compound 22 (11.0 mmol) in anhydrous pyridine (6 mL/mmol) was added at room temperature 4-dimethylaminopyridine (11.0 mmol) and benzoyl chloride (16.5 mmol). The white suspension was stirred during 1 hour. The reaction mixture was concentrated under reduced pressure and portioned between CH$_2$Cl$_2$/NH$_4$Cl saturated. The organic layer was washed with HCl 1N, a saturated solution of NaHCO$_3$ and brine. The organic layer was dried, filtered and concentrated under reduced pressure. The crude residue was purified by chromatography on silica gel column (eluent: petroleum ether/ethyl acetate 0 to 20%) to give the expected compound as a colorless oil in 98% yield. MS (ESI) m/z=351 (MNa$^+$).

Preparation of Compound 24

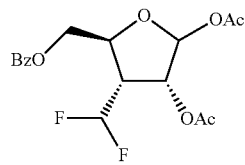

To a solution of compound 23 (10.8 mmol) in acetic acid (2.04 mL/mmol) were added acetic anhydride (42.5 mmol) and a drop of concentrated H$_2$SO$_4$. The reaction mixture was stirred at room temperature during 2 hours, diluted with ethyl acetate and washed with water and saturated NaHCO$_3$. The organic layers were dried over Na$_2$SO$_4$, filtered and concentrated under reduced pressure. The crude residue was purified by chromatography on silica gel column (eluent: petroleum ether/ethyl acetate 0 to 35%) to give the expected compound as a white solid in 52% yield. $^1$H NMR (CDCl$_3$, 400 MHz) δ (ppm) 1.92 (s, 3H), 2.14 (s, 3H), 3.05-3.16 (m, 1H), 4.34 (dd, J=11.87 Hz and 4.82 Hz, 1H), 4.68-4.75 (m, 2H), 5.38 (d, J=5.0 Hz, 1H), 5.94 (d, J=6.32 Hz, 0.25H), 6.08 (d, J=6.35 Hz, 0.5H), 6.16 (s, 1H), 6.22 (d, J=6.34 Hz, 0.25H), 7.44-7.48 (m, 2H), 7.56-7.61 (m, 1H), 8.07-8.09 (m, 2H); $^{19}$F NMR (CDCl$_3$, 376.5 MHz) δ (ppm) −121.61 (d, J=298.44 Hz, 1F), −113.63 (d, J=298.28 Hz, 1F); MS (ESI) m/z=395 (MNa$^+$).

Preparation of Compound 25

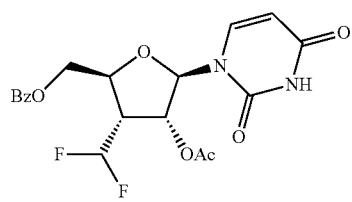

To a suspension of uracil (3.2 mmol) in anhydrous acetonitrile (10 mL/mmol) was added dropwise at room temperature BSA (6.2 mmol). The mixture was heated at reflux during 1 hour. The solution of compound 24 (2.7 mmol) in anhydrous acetonitrile (10 mL/mmol) and trimethylsilyl trifluoromethanesulfonate (4.0 mmol) were added at room temperature and the reaction mixture was heated at reflux during 5 hours. The mixture was diluted with ethyl acetate, washed with a saturated solution of NaHCO₃ and brine. The organic layer was concentrated under reduced pressure and the crude residue was purified by chromatography on silica gel column (eluent: $CH_2Cl_2/CH_3CH_2OH$ 0 to 5%) to give the expected compound as a colorless foam in 97% yield. MS (ESI) m/z=425.2 (MH⁺).

Preparation of Compound 201

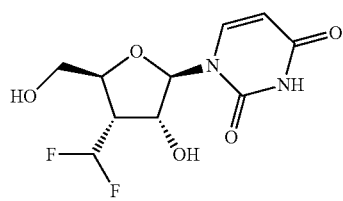 [SMILES: O=c1ccn([C@@H]2O[C@H](CO)[C@@H](C(F)F)[C@H]2O)c(=O)[nH]1]

Compound 25 (2.61 mmol) was dissolved in ammonia solution 7N in MeOH (15 mL/mmol) under nitrogen and the reaction mixture was stirred at room temperature overnight. The solvent was removed under reduced pressure and the residue was purified by reverse phase chromatography (eluent: $H_2O/CH_3CN$ 0 to 30%) to give the expected compound as a white solid in 78% yield. ¹H NMR (DMSO-d₆, 400 MHz) δ (ppm) 2.64-2.75 (m, 1H), 3.46-3.51 (m, 1H), 3.73-3.79 (m, 1H), 4.29-4.38 (m, 2H), 5.24-5.27 (m, 1H), 5.59 (d, J=8.07 Hz, 1H), 5.67-5.69 (m, 1H), 6.07 (d, J=5.18 Hz, 0.25H), 6.13-6.17 (m, 1H), 6.21 (d, J=5.03 Hz, 0.5H), 6.34 (d, J=5.19 Hz, 0.25H), 7.99 (d, J=8.15 Hz, 1H), 11.20 (brs, 1H); ¹⁹F NMR (DMSO-d₆, 376.5 MHz) δ (ppm) −123.26 (d, J=290.02 Hz, 1F), −116.94 (d, J=290.02 Hz, 1F); MS (ESI) m/z=301 (MNa⁺).

Preparation of Compound 27

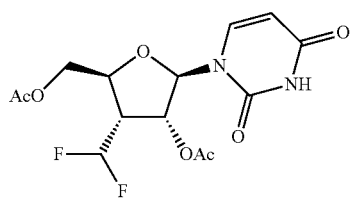

To a solution of compound 201 (1.37 mmol) in anhydrous pyridine (10 mL/mmol) were added 4-dimethylaminopyridine (0.137 mmol) and acetic anhydride (3 mmol). The reaction mixture was stirred during 1 hour at room temperature, then quenched with water and diluted in ethyl acetate. The organic layer was washed with water, dried over Na₂SO₄, filtered and concentrated under reduced pressure. The crude mixture was co-evaporated with toluene and dichloromethane and purified by chromatography on silica gel column (eluent: $CH_2Cl_2/CH_3OH$ 0 to 10%) to give the expected compound as a white solid in 87% yield. MS (ESI) m/z=363 (MH⁺).

Preparation of Compound 28

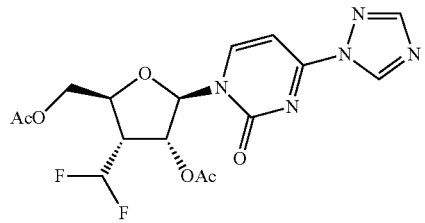 [SMILES: CC(=O)OC[C@H]1O[C@@H](n2ccc(-n3cncn3)nc2=O)[C@H](OC(C)=O)[C@@H]1C(F)F]

To a solution of compound 27 (1.19 mmol) and 1,2,4-triazole (13.41 mmol) in anhydrous dichloromethane (20 mL/mmol) and triethylamine (13.41 mmol) was added under nitrogen phosphorous oxychloride (3.09 mmol) at 0° C. The reaction mixture was stirred during 4 hours at room temperature then quenched with ice and diluted in dichloromethane. The organic layer was washed with water, dried over Na₂SO₄ and concentrated under reduced pressure. The residue was purified by chromatography on silica gel column (eluent: $CH_2Cl_2/CH_3OH$ 0 to 10%) to give the expected compound as a white solid in 39% yield. MS (ESI) m/z=414.2 (MH⁺).

Preparation of Compound 203

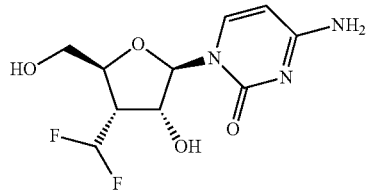 [SMILES: Nc1ccn([C@@H]2O[C@H](CO)[C@@H](C(F)F)[C@H]2O)c(=O)n1]

To a solution of compound 28 (0.46 mmol) in anhydrous tetrahydrofuran (12 mL/mmol) was added ammonium hydroxide solution (0.9 mL/mmol). The reaction mixture was stirred at room temperature during 1 hour and concentrated under reduced pressure. The crude mixture was dissolved in ammonia solution 7N in methanol (20 mL/mmol) and the reaction mixture was stirred at room temperature overnight. The mixture was concentrated and purified by C18 chromatography (eluent: $H_2O/CH_3CN$ 0 to 10%) to give the expected compound as a white solid in 57% yield. ¹H NMR (DMSO-d₆, 400 MHz) δ (ppm) 2.56-2.67 (m, 1H), 3.49 (dd, J=12.42 Hz and 2.98 Hz, 1H), 3.76-3.81 (m, 1H), 4.25 (dd, J=5.73 Hz and 1.98 Hz, 1H), 4.30-4.34 (m, 1H), 5.23 (brs, 1H), 5.66-5.68 (m, 2H), 6.04 (d, J=5.86 Hz, 0.25H), 6.13 (brs, 1H), 6.18 (d, J=5.87 Hz, 0.5H), 6.32 (d, J=5.85 Hz, 0.25H), 7.06 (brs, 1H), 7.15 (brs, 1H), 7.98 (d, J=7.46 Hz, 1H); ¹⁹F NMR (DMSO-d₆, 376.5 MHz) δ (ppm) −122.90 (d, J=290.92 Hz, 1F), −115.68 (d, J=290.08 Hz, 1F); MS (ESI) m/z=278.2 (MH⁺).

Preparation of Compound 211

Scheme 4

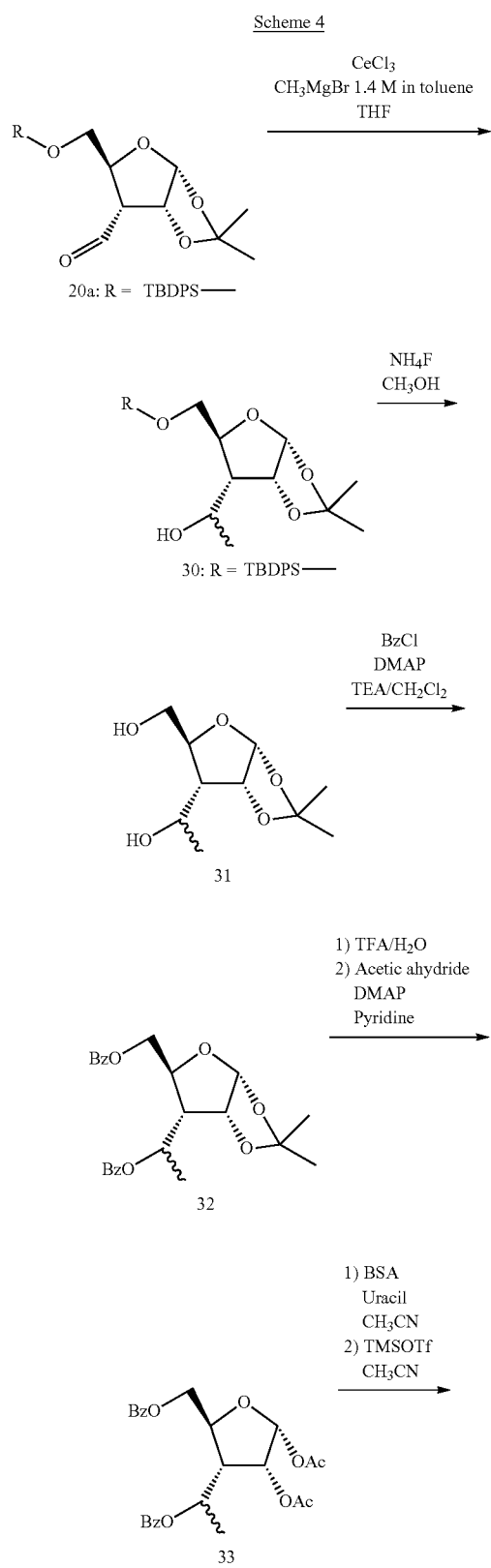

-continued

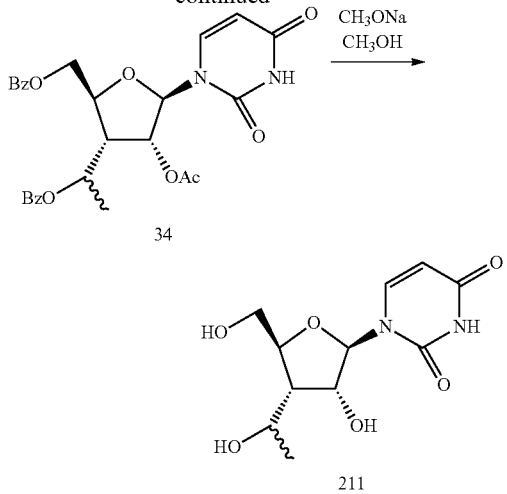

Preparation of Compound 30

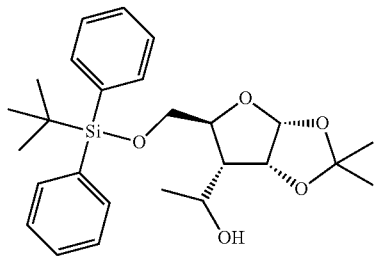 [SMILES: CC(O)[C@H]1[C@H]2OC(C)(C)O[C@H]2O[C@@H]1CO[Si](c1ccccc1)(c1ccccc1)C(C)(C)C]

A suspension of anhydrous cerium (3) chloride (26.4 mmol) in anhydrous tetrahydrofuran (7 mL/mmol) was stirred at room temperature during 15 minutes. The reaction mixture was cooled with an ice-bath and methylmagnesium bromide 1.4M in toluene (52.8 mmol) was added over 5 minutes. After stirring at 0° C. during 90 minutes, the reaction mixture was cooled down to −78° C. and a solution of compound 20a (40.0 mmol) in tetrahydrofuran (2 mL/mmol) was added. After 2 hours at −78° C., the reaction mixture was gradually warmed up to room temperature and carefully quenched with a saturated solution of ammonium chloride. The mixture was diluted with ethyl acetate and the organic layer was sequentially washed with HCl 5%, saturated sodium bicarbonate, and brine, dried over $Na_2SO_4$, filtered and concentrated under reduced pressure. The crude was purified by chromatography on silica gel column (eluent: petroleum ether/diethyl ether 0 to 50%) to give the expected compound as an oil in 73% yield. MS (ESI) m/z=479.2 (MNa$^+$).

Preparation of Compound 31

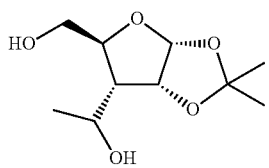

To a solution of compound 30 (29.1 mmol) in methanol (10 mL/mmol) was added ammonium fluoride (43.7 mmol) at room temperature. The reaction mixture was heated at reflux during 1 hour and concentrated under reduced pressure. The crude residue was purified by chromatography on silica gel column (eluent: CH$_2$Cl$_2$/CH$_3$OH 0 to 10%) to give the expected compound as a beige solid in 82% yield (TLC control).

Preparation of Compound 32

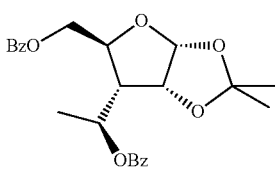

To a solution of compound 31 (24.0 mmol) and 4-dimethylaminopyridine (2.40 mmol) in anhydrous dichloromethane (5 mL/mmol) and triethylamine (120 mmol) was slowly added benzoyl chloride (83.9 mmol) at 0° C. The reaction mixture was stirred at room temperature overnight and at reflux during 5 hours. The reaction was diluted in dichloromethane and washed with water. The organic layer was dried over Na$_2$SO$_4$, filtered and concentrated under reduced pressure. The crude residue was purified by chromatography on silica gel column (eluent: petroleum ether/diethyl ether 0 to 50%) to give the expected compound as a white solid in 98% yield. MS (ESI) m/z=449.2 (MH$^+$).

Preparation of Compound 33

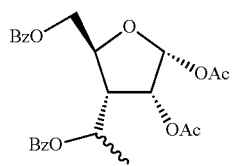

A solution of compound 32 (23.4 mmol) in trifluoroacetic acid (3.2 mL/mmol) and water (0.8 mL/mmol) was stirred at room temperature during 1 hour then concentrated under reduced pressure and co-evaporated with pyridine (2×100 ml). The crude mixture and 4-dimethylaminopyridine (23.4 mmol) was diluted in anhydrous pyridine (4 mL/mmol) and acetic anhydride (469 mmol) was added at 0° C. The reaction mixture was stirred overnight at room temperature then quenched with ice and diluted with ethyl acetate. The organic layer was washed successively with water, a saturated solution of NaHCO$_3$ and brine. The organic layer was dried over Na$_2$SO$_4$, filtered and concentrated under reduced pressure. The crude residue was purified by chromatography on silica gel column (eluent: petroleum ether/diethyl ether 0 to 100%) to give the expected compound as a white solid in 65% yield. MS (ESI) m/z=493.2 (MH$^+$).

Preparation of Compound 34

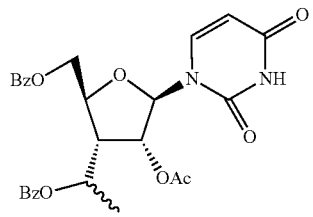

To a suspension of compound 33 (15 mmol) and uracil (18 mmol) in anhydrous acetonitrile (10 mL/mmol) was added N,O-bis-(trimethylsilyl)-acetamide (38 mmol) at room temperature. The reaction mixture was stirred during 30 minutes at 70° C. To the reaction mixture was added trimethylsilyl trifluoromethanesulfonate (23 mmol) at room temperature and the reaction mixture was stirred during 2 hours at 70° C. The reaction was diluted in ethyl acetate (300 ml) and washed with saturated solution of NaHCO$_3$ (300 ml), water (300 ml) and brine (300 ml). The organic layer was dried over Na$_2$SO$_4$, filtered and concentrated under reduced pressure. The crude residue was purified by chromatography on silica gel column (eluent: CH$_2$Cl$_2$/CH$_3$OH 0 to 5%) to give the expected compound as a white solid in 83% yield. MS (ESI) m/z=521.2 (MH$^-$).

Preparation of Compound 211

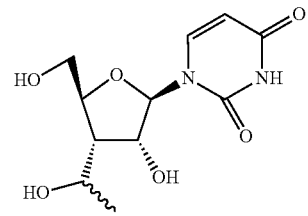 [SMILES: CC(O)[C@H]1[C@@H](O)[C@H](n2ccc(=O)[nH]c2=O)O[C@@H]1CO]

Compound 211 was synthesized from compound 34 (1.91 mmol) as described for compound 205 (purification: 100% H$_2$O) as a white solid in 88% yield; $^1$H NMR (DMSO-d$_6$, 400 MHz) δ (ppm) 1.12 (d, J=6.19 Hz, 3H), 1.86-1.91 (m, 1H), 3.69 (dd, J=11.90 Hz and 3.29 Hz, 1H), 3.78-3.88 (m, 2H), 4.07 (d, J=4.88 Hz, 1H), 4.16 (td, J=9.07 Hz and 3.0 Hz, 1H), 4.55 (brs, 1H), 4.99 (brs, 1H), 5.53 (d, J=8.07 Hz, 1H), 5.61 (d, J=1.37 Hz, 1H), 5.63 (brs, 1H), 8.07 (d, J=8.08 Hz, 1H), 11.24 (brs, 1H); MS (ESI) m/z=295 (MNa$^+$).

Preparation of Compounds 212-214, 227, 230 and 231

Scheme 5

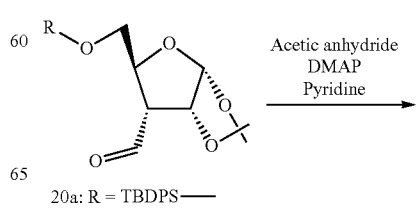

20a: R = TBDPS—

-continued

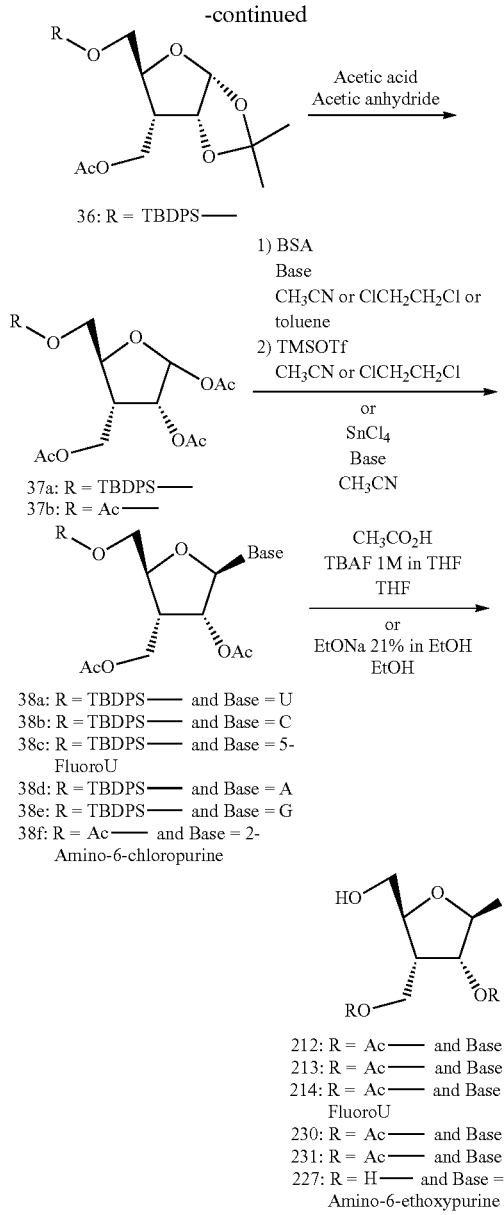

36: R = TBDPS—

1) BSA
Base
CH₃CN or ClCH₂CH₂Cl or toluene
2) TMSOTf
CH₃CN or ClCH₂CH₂Cl
or
SnCl₄
Base
CH₃CN 37a: R = TBDPS—
37b: R = Ac—

CH₃CO₂H
TBAF 1M in THF
THF
or
EtONa 21% in EtOH
EtOH

38a: R = TBDPS— and Base = U
38b: R = TBDPS— and Base = C
38c: R = TBDPS— and Base = 5-FluoroU
38d: R = TBDPS— and Base = A
38e: R = TBDPS— and Base = G
38f: R = Ac— and Base = 2-Amino-6-chloropurine 212: R = Ac— and Base = U
213: R = Ac— and Base = C
214: R = Ac— and Base = 5-FluoroU
230: R = Ac— and Base = A
231: R = Ac— and Base = G
227: R = H— and Base = 2-Amino-6-ethoxypurine Preparation of Compound 36

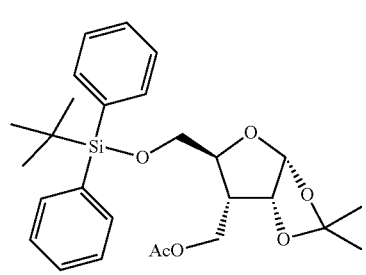 [SMILES: CC(=O)OC[C@H]1[C@H]2OC(C)(C)O[C@H]2O[C@@H]1CO[Si](c1ccccc1)(c1ccccc1)C(C)(C)C]

To a stirred solution of compound 4a (5.6 mmol) in a mixture of anhydrous pyridine (1.74 mL/mmol) and acetic anhydride (1.74 mL/mmol) was added 4-dimethylaminopyridine (0.40 mmol). The reaction mixture was stirred at room temperature during 12 hours, then concentrated under reduced pressure. The residue was dissolved in dichloromethane, washed with a saturated solution of NaHCO₃, dried over Na₂SO₄, filtered and concentrated under reduced pressure. The crude residue was purified by chromatography on silica gel column (eluent: petroleum ether/ethyl acetate 0 to 20%) to give the expected compound as a colorless oil in 83% yield. ¹H NMR (CDCl₃, 400 MHz) δ (ppm) 1.05 (s, 9H), 1.34 (s, 3H), 1.50 (s, 3H), 2 (s, 3H), 2.51-2.59 (m, 1H), 3.73 (dd, J=11.38 Hz and 3.45 Hz, 1H), 3.92 (dd, J=11.40 Hz and 3.15 Hz, 1H), 3.98 (td, J=9.90 Hz and 3.27 Hz, 1H), 4.18 (dd, J=11.10 Hz and 6.50 Hz, 1H), 4.30 (dd, J=11.08 Hz and 8.03 Hz, 1H), 4.71-4.73 (m, 1H), 5.85 (d, J=3.63 Hz, 1H), 7.35-7.44 (m, 6H), 7.66-7.70 (m, 4H); MS (ESI) m/z=507.2 (MNa⁺).

Preparation of Compound 37

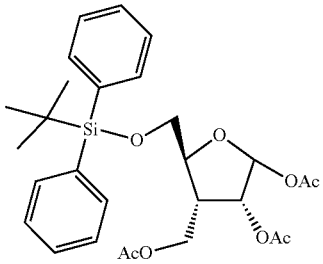 [SMILES: CC(=O)OC[C@@H]1[C@@H](CO[Si](c2ccccc2)(c2ccccc2)C(C)(C)C)OC(OC(C)=O)[C@@H]1OC(C)=O]

To a solution of compound 36 (4.68 mmol) in acetic acid (2.04 mL/mmol) were added acetic anhydride (18.5 mmol) and a drop of concentrated H₂SO₄. The reaction mixture was stirred at room temperature overnight. The mixture was diluted with ethyl acetate, washed successively with water and a saturated solution of NaHCO₃. The organic layer was dried over Na₂SO₄, filtered and concentrated under reduced pressure. The crude residue was purified by chromatography on silica gel column (eluent: petroleum ether/ethyl acetate 0 to 35%) to give the expected compound as a colorless oil in 48% yield. MS (ESI) m/z=551.2 (MNa⁺).

Preparation of Compound 38a

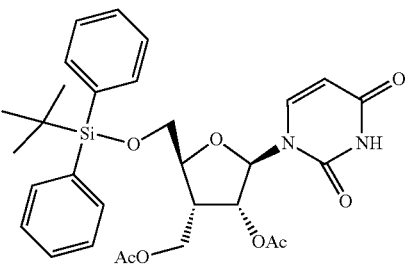 [SMILES: CC(=O)OC[C@H]1[C@@H](OC(C)=O)[C@H](n2ccc(=O)[nH]c2=O)O[C@@H]1CO[Si](c1ccccc1)(c1ccccc1)C(C)(C)C]

Compound 38a was synthesized from compound 37 (2.3 mmol) as described for compound 25 (in this case, the reaction mixture was heated at reflux overnight after addition of TMSOTf) as a colorless oil in 76% yield; MS (ESI) m/z=581.4 (MH⁺).

Preparation of Compound 38b

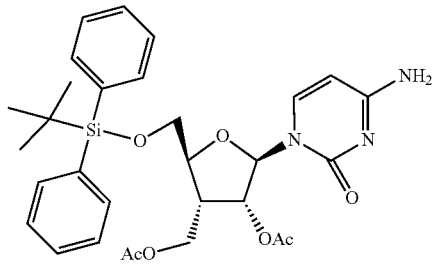 [SMILES: CC(=O)OC[C@H]1[C@@H](OC(C)=O)[C@H](n2ccc(N)nc2=O)O[C@@H]1CO[Si](c1ccccc1)(c1ccccc1)C(C)(C)C]

Compound 38b was synthesized from compound 37 (1.14 mmol) as described for compound 25 (in this case, solvent used was dichloroethane) as a colorless oil in 76% yield. $^1$H NMR (DMSO-$d_6$, 400 MHz) δ (ppm) 1.02 (s, 9H), 1.90 (s, 3H), 2.06 (s, 3H), 2.85-2.92 (m, 1H), 3.76 (dd, J=11.70 Hz and 3.70 Hz, 1H), 3.94 (dd, J=11.40 Hz and 6.03 Hz, 1H), 4 (dd, J=11.66 Hz and 2.58 Hz, 1H), 4.07-4.15 (m, 2H), 5.40 (dd, J=6.28 Hz and 2.02 Hz, 1H), 5.52 (d, J=7.42 Hz, 1H), 5.79 (d, J=2.04 Hz, 1H), 7.20 (s, 2H), 7.40 (m, 6H), 7.61-7.66 (m, 4H), 7.73 (d, J=7.42 Hz, 1H); MS (ESI) m/z=580.4 (MH$^+$).

Preparation of Compound 38c

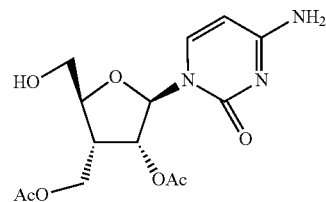

Compound 38c was synthesized from compound 37 (0.946 mmol) as described for compound 25 (in this case, the second reaction time was 1 hour) as a white solid in 53% yield. MS (ESI) m/z=621.2 (MNa$^+$).

Preparation of Compound 212

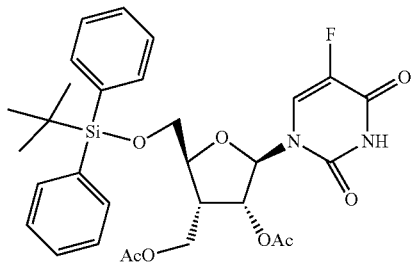 [SMILES: CC(=O)OC[C@H]1[C@@H](OC(C)=O)[C@H](n2cc(F)c(=O)[nH]c2=O)O[C@@H]1CO[Si](c1ccccc1)(c1ccccc1)C(C)(C)C]

To a solution of compound 38a (1.31 mmol) in anhydrous tetrahydrofuran (1.3 mL/mmol) with acetic acid (3.26 mmol) under nitrogen was added dropwise tetra-n-butylammonium fluoride 1M in THF (2.75 mmol). The reaction mixture was stirred during 3 hours at room temperature and was directly purified by chromatography on silica gel column (eluent: $CH_2Cl_2/CH_3OH$ 0 to 20%) and by C18 chromatography (eluent: $H_2O/CH_3CN$ 0 to 30%) to give the expected compound as a white solid in 51% yield. $^1$H NMR (DMSO-$d_6$, 400 MHz) δ (ppm) 1.98 (s, 3H), 2.05 (s, 3H), 2.73-2.80 (m, 1H), 3.53-3.59 (m, 1H), 3.71-3.77 (m, 1H), 4-4.05 (m, 2H), 4.15-4.20 (m, 1H), 5.17-5.20 (m, 1H), 5.40 (dd, J=6.50 Hz and 2.69 Hz, 1H), 5.61 (d, J=8.07 Hz, 1H), 5.76 (d, J=2.68 Hz, 1H), 7.94 (d, J=8.07 Hz, 1H), 11.32 (s, 1H); MS (ESI) m/z=343 (MH$^+$).

Preparation of Compound 213

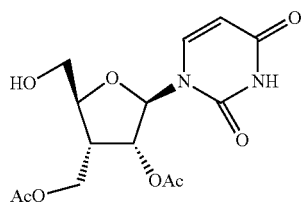 [SMILES: CC(=O)OC[C@H]1[C@@H](OC(C)=O)[C@H](n2ccc(=O)[nH]c2=O)O[C@@H]1CO]

Compound 213 was synthesized from compound 38b (0.865 mmol) as described for compound 212 as a white solid in 45% yield; $^1$H NMR (DMSO-$d_6$, 400 MHz) δ (ppm) 1.97 (s, 3H), 2.05 (s, 3H), 2.69-2.76 (m, 1H), 3.54-3.59 (m, 1H), 3.73-3.78 (m, 1H), 3.97-4 (m, 2H), 4.15 (dd, J=11.40 Hz and 7.59 Hz, 1H), 5.13 (t, J=5.32 Hz, 1H), 5.35 (dd, J=6.10 Hz and 2.18 Hz, 1H), 5.69 (d, J=7.42 Hz, 1H), 5.72 (d, J=2.21 Hz, 1H), 7.17 (brs, 1H), 7.21 (brs, 1H), 7.90 (d, J=7.41 Hz, 1H); MS (ESI) m/z=342.2 (MH$^+$).

Preparation of Compound 214

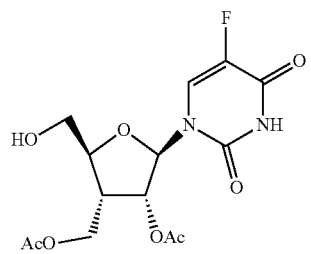 [SMILES: CC(=O)OC[C@H]1[C@@H](OC(C)=O)[C@H](n2cc(F)c(=O)[nH]c2=O)O[C@@H]1CO]

Compound 214 was synthesized from compound 38c (0.501 mmol) as described for compound 212 as a white solid in 42% yield; $^1$H NMR (DMSO-$d_6$, 400 MHz) δ (ppm) 1.98 (s, 3H), 2.06 (s, 3H), 2.73-2.80 (m, 1H), 3.57-3.62 (m, 1H), 3.78-3.83 (m, 1H), 3.99 (dd, J=11.35 Hz and 5.73 Hz, 1H), 4.03-4.06 (m, 1H), 4.17 (dd, J=11.40 Hz and 7.28 Hz, 1H), 5.39 (t, J=4.55 Hz, 1H), 5.46 (dd, J=6.08 Hz and 2.15 Hz, 1H), 5.73 (t, J=1.75 Hz, 1H), 8.41 (d, J=7.35 Hz, 1H), 11.84 (brs, 1H); MS (ESI) m/z=359 (MH$^-$).

Preparation of Compound 230

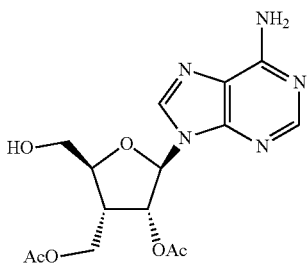 [SMILES: CC(=O)OC[C@H]1[C@@H](OC(C)=O)[C@H](n2cnc3c(N)ncnc32)O[C@@H]1CO]

Compound 230 was synthesized according to Scheme 5.

Preparation of Compound 231

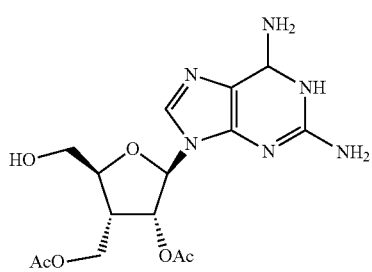 [SMILES: CC(=O)OC[C@H]1[C@@H](OC(C)=O)[C@H](n2cnc3c2N=C(N)NC3N)O[C@@H]1CO]

Compound 231 was synthesized according to Scheme 5.

Preparation of Compound 227

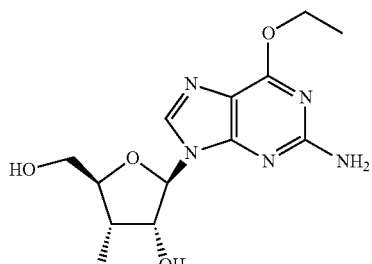

Compound 227 was synthesized according to Scheme 5.
MS (ESI) m/z=326 (MH+). $^1$H NMR (400 MHz, DMSO+ D2O) δ (ppm) 8.14 (s, 1H), 6.39 (brs, 2H), 5.79 (d, J=2.37 Hz, 1H), 4.47-4.42 (m, 3H), 4.03-3.99 (m, 1H), 3.73-3.67 (m, 2H), 3.55-3.49 (m, 2H), 2.46-2.40 (m, 1H), 1.35 (t, J=7.10 Hz, 3H).

Preparation of Compound 215

Scheme 6

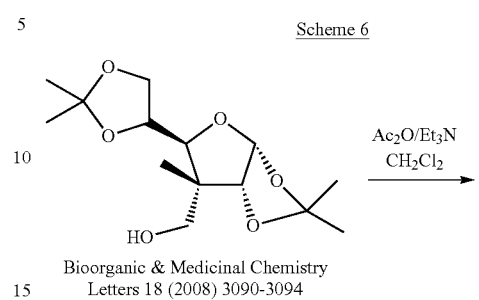

Bioorganic & Medicinal Chemistry Letters 18 (2008) 3090-3094

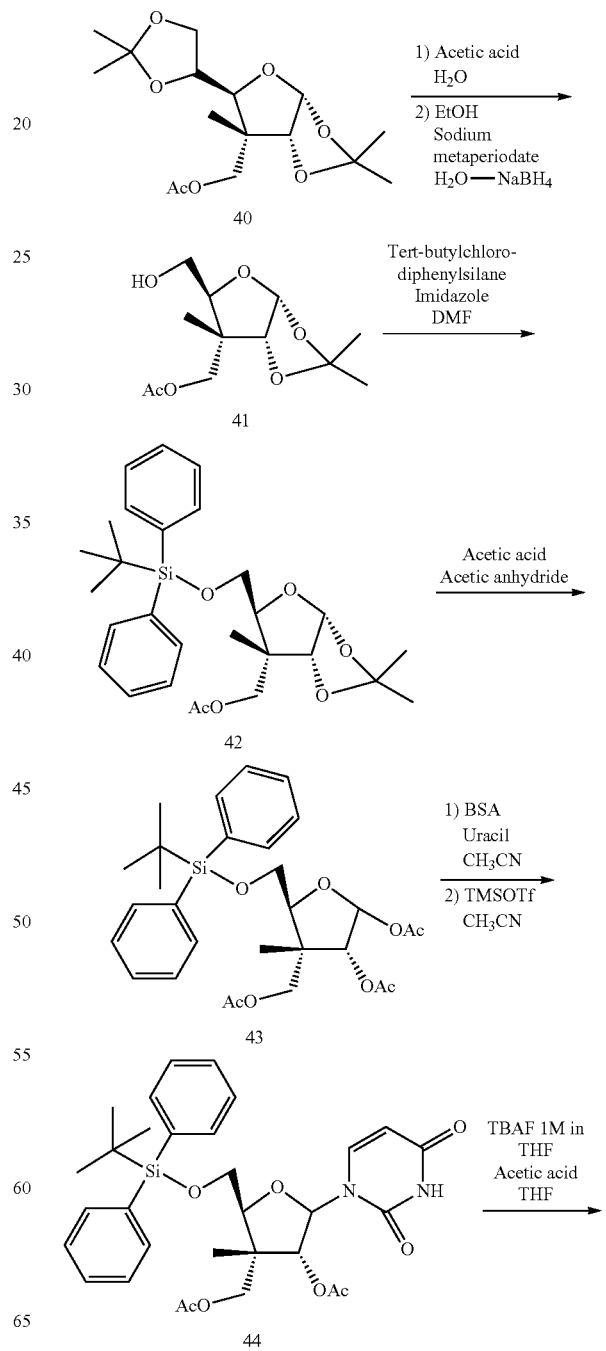

Preparation of Compound 40

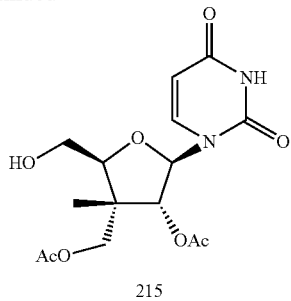 [SMILES: CC(=O)OC[C@]1(C)[C@@H](CO)O[C@@H](n2ccc(=O)[nH]c2=O)[C@@H]1OC(C)=O]

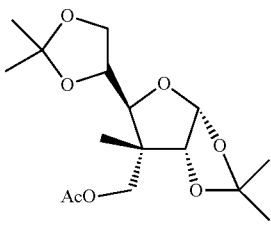

To a solution of [(3aR,5S,6R,6aR)-5-(2,2-dimethyl-1,3-dioxolan-4-yl)-2,2,6-trimethyl-5,6a-dihydro-3aH-furo[2,3-d][1,3]dioxol-6-yl]methanol, synthesized according to *Bioorganic Medicinal Chemistry Letters*, 18 (2008) 3090-3094, (34.7 mmol) and triethylamine (173 mmol) in anhydrous dichloromethane (5 mL/mmol) was slowly added acetic anhydride (69.4 mmol). The reaction mixture was stirred at room temperature during 2 days, then washed successively with HCl 1N, a saturated solution of NaHCO$_3$ and brine. The dried organic layer was concentrated under reduced pressure and the crude residue was purified by chromatography on silica gel column (eluent: petroleum ether/diethyl ether, PMA stain) to give the expected compound as a yellowish oil in 82% yield. $^1$H NMR (DMSO-d$_6$, 400 MHz) δ (ppm) 0.93 (s, 3H), 1.24 (s, 3H), 1.26 (s, 3H), 1.30 (s, 3H), 1.41 (s, 3H), 2.02 (s, 3H), 3.61 (d, J=8.23 Hz, 1H), 3.71-3.77 (m, 1H), 3.94 (d, J=10.78 Hz, 1H), 3.97-4.05 (m, 2H), 4.21 (d, J=10.78 Hz, 1H), 4.30 (d, J=3.49 Hz, 1H), 5.78 (d, J=3.44 Hz, 1H).

Preparation of Compound 41

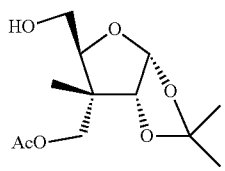 [SMILES: CC(=O)OC[C@]1(C)[C@@H](CO)O[C@@H]2OC(C)(C)O[C@@H]21]

A solution of compound 40 (28.3 mmol) in acetic acid (70 mL) and water (30 mL) was stirred at room temperature overnight. The solvents were evaporated and the residue co-evaporated with toluene to dryness. To a solution of the crude residue (28.2 mmol) in ethanol (5 mL/mmol) was slowly added at 0° C. a solution of sodium metaperiodate 98% (42.3 mmol) in water (2.5 mL/mmol). The reaction mixture was stirred at room temperature during 3 hours and cooled down at 0° C. Sodium borohydride (42.3 mmol) was added portionwise. The reaction mixture was stirred at room temperature overnight, filtered and washed with ethanol. The filtrate was evaporated to dryness and the residue was taken up in ethyl acetate and washed with a saturated aqueous solution of sodium bicarbonate, water and brine. The organic layer was dried over Na$_2$SO$_4$, filtered and concentrated under reduced pressure. The crude residue was purified by chromatography on silica gel column (eluent: petroleum ether/diethyl ether) to give the expected compound as a white crystallized solid in 62% yield. $^1$H NMR (DMSO-d$_6$, 400 MHz) δ (ppm) 0.79 (s, 3H), 1.21 (s, 3H), 1.40 (s, 3H), 3.35-3.46 (m, 3H), 3.53 (dd, J=10.45 Hz and 5.32 Hz, 1H), 3.76 (dd, J=6.79 Hz and 5.07 Hz, 1H), 4.19 (d, J=3.61 Hz, 1H), 4.61 (t, J=5.01 Hz, 1H), 4.71 (t, J=5.56 Hz, 1H), 5.72 (d, J=3.56 Hz, 1H).

Preparation of Compound 42

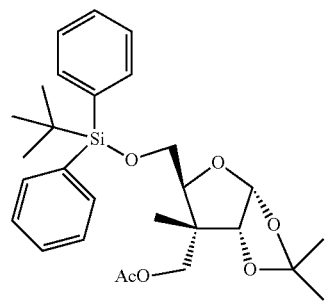 [SMILES: CC(=O)OC[C@]1(C)[C@@H](CO[Si](c2ccccc2)(c2ccccc2)C(C)(C)C)O[C@@H]2OC(C)(C)O[C@@H]21]

To a solution of compound 41 (15.4 mmol) and imidazole (23.1 mmol) in anhydrous N,N-dimethylformamide (1 mL/mmol) was added dropwise tert-butylchlorodiphenylsilane (18.4 mmol). The reaction mixture was stirred at room temperature overnight, then diluted with ethyl acetate. The organic layer was successively washed with HCl 1N, a saturated solution of NaHCO$_3$ and brine. The organic layer was dried over Na$_2$SO$_4$, filtered and concentrated under reduced pressure. The crude residue was purified by chromatography on silica gel column (eluent: petroleum ether/diethyl ether) to give the expected compound as a colorless oil in 86% yield. $^1$H NMR (CDCl$_3$, 400 MHz) δ (ppm) 0.98 (s, 3H), 1.08 (s, 9H), 1.31 (s, 3H), 1.54 (s, 3H), 2.75 (dd, J=8.80 Hz and 4.22 Hz, 1H), 3.61 (dd, J=10.51 Hz and 8.50 Hz, 1H), 3.73-3.85 (m, 3H), 4.19 (dd, J=8.47 Hz and 5.02 Hz, 1H), 4.31 (d, J=3.68 Hz, 1H), 5.75 (d, J=3.66 Hz, 1H), 7.38-7.47 (m, 6H), 7.66-7.69 (m, 4H); MS (ESI) m/z=479.2 (MNa$^+$).

Preparation of Compound 43

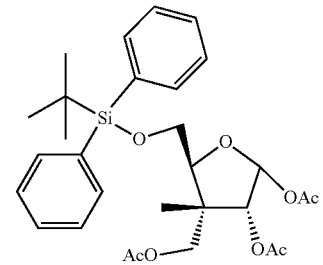 [SMILES: CC(=O)OC[C@]1(C)[C@@H](CO[Si](c2ccccc2)(c2ccccc2)C(C)(C)C)OC(OC(C)=O)[C@@H]1OC(C)=O]

Compound 43 was synthesized from compound 42 (13.2 mmol) as described for compound 13 (in this case, eluent used for purification was petroleum ether/diethyl ether) as a colorless gum (mixture of anomers). MS (ESI) m/z=565.2 (MNa+).

Preparation of Compound 44

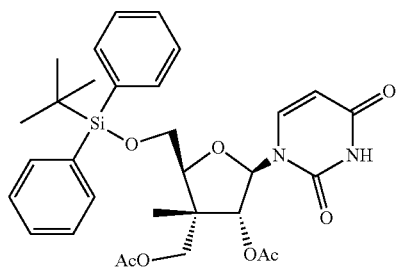 [SMILES: CC(=O)OC[C@]1(C)[C@@H](CO[Si](c2ccccc2)(c2ccccc2)C(C)(C)C)O[C@@H](n2ccc(=O)[nH]c2=O)[C@@H]1OC(C)=O]

A solution of compound 43 (3.42 mmol), uracil (6.85 mmol) and N,O-bis-(trimethylsilyl)-acetamide (12 mmol) in anhydrous acetonitrile (15 mL/mmol) was heated at reflux under nitrogen during 1 hour. The reaction mixture was cooled down to 0° C. and trimethylsilyl trifluoromethane-sulfonate (8.56 mmol) was slowly added. The reaction mixture was heated at reflux under nitrogen overnight, then concentrated under reduced pressure. The crude mixture was diluted in ethyl acetate and washed with HCl 1N, a saturated aqueous solution of NaHCO$_3$ and brine. The organic layer was dried over Na$_2$SO$_4$, filtered and concentrated under reduced pressure. The crude residue was purified by chromatography on silica gel column (eluent: petroleum ether/diethyl ether) to give the expected compound as a white solid as a mixture of 1'-anomers in a ratio 65:35 (α/β not assigned) in 70% yield. MS (ESI) m/z=617.2 (MNa+).

Preparation of Compound 215

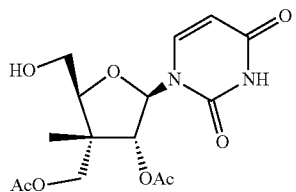

To a solution of compound 44 (2.41 mmol) and acetic acid (9.62 mmol) in anhydrous tetrahydrofuran (10 mL/mmol) was added tetra-n-butylammonium fluoride 1M in THF (4.81 mmol). The reaction mixture was stirred at room temperature overnight and concentrated under reduced pressure. The crude mixture was cleaned up through a SXC-2 cartridge with methanol to scavenge TBAF. This fraction was evaporated and the resulting crude residue was purified twice by chromatography on silica gel column (eluent: dichloromethane/ethanol) to give the expected compound as a white solid in 21% yield. $^1$H NMR (DMSO-d$_6$, 400 MHz) δ (ppm) 1.13 (s, 3H), 2.01 (s, 3H), 2.05 (s, 3H), 3.56-3.61 (m, 1H), 3.66-3.71 (m, 1H), 4.01-4.03 (m, 1H), 4.05-4.11 (m, 2H), 5.21 (d, J=6.88 Hz, 1H), 5.28-5.30 (m, 1H), 5.66 (d, J=8.12 Hz, 1H), 5.98 (d, J=6.88 Hz, 1H), 8.11 (d, J=8.16 Hz, 1H), 11.30 (s, 1H); MS (ESI) m/z=379.2 (MNa+).

Preparation of Compounds 216-218

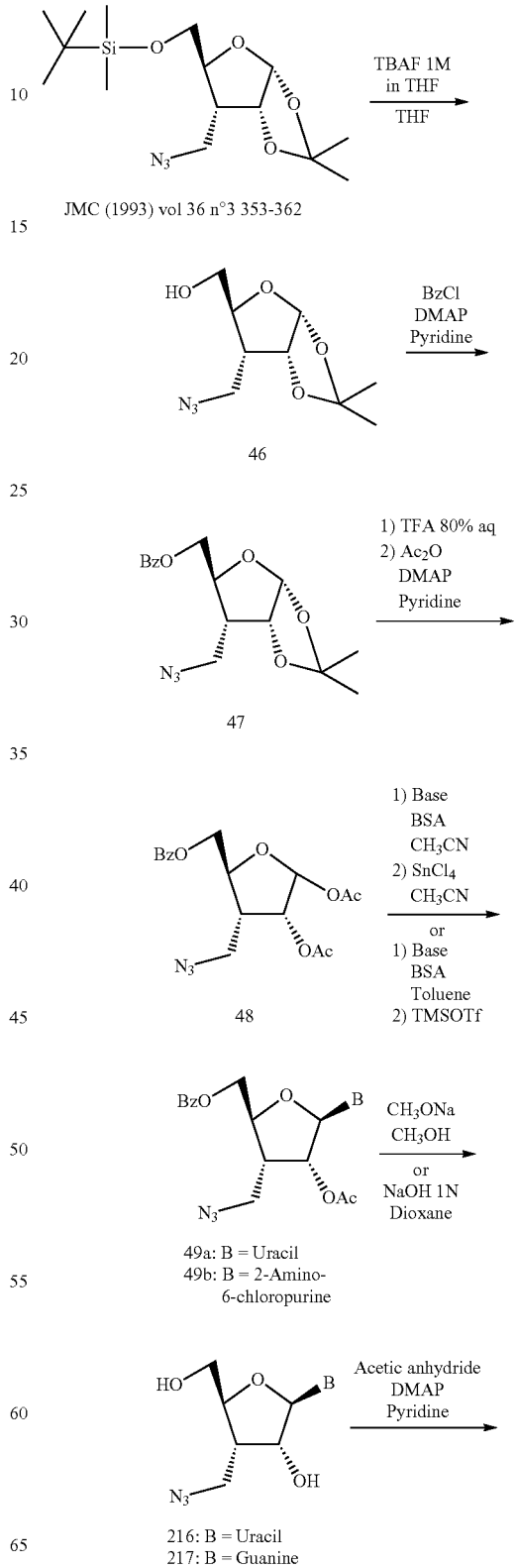

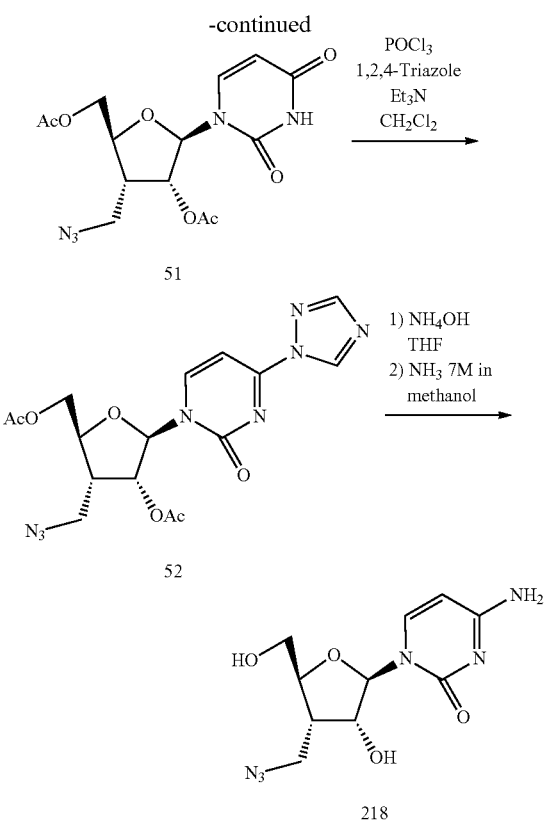

51

52

218

Preparation of Compound 46

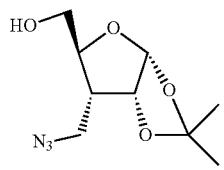 [SMILES: CC1(C)O[C@H]2O[C@H](CO)[C@@H](CN=[N+]=[N-])[C@H]2O1]

The [(3aR,5S,6R,6aR)-6-(azidomethyl)-2,2-dimethyl-3a,5,6,6a-tetrahydrofuro[2,3-d][1,3]dioxol-5-yl]methoxy-tert-butyl-dimethyl-silane (as described in JMC (1993) vol 36 no 3 353-362) (52.40 mmol) was dissolved in anhydrous tetrahydrofuran (10 mL/mmol) and tetra-butylammonium fluoride (1M in THF) (68 mL) was added dropwise at room temperature. The reaction mixture was stirred at room temperature during 30 minutes and the mixture was concentrated under reduced pressure. The crude residue was purified by chromatography on silica gel column (eluent: dichloromethane/ethyl acetate 0 to 20%) to give the expected compound.

Preparation of Compound 47

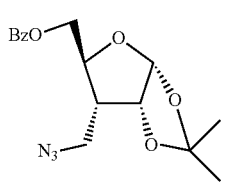

To a solution of compound 46 (54.53 mmol) and dimethylaminopyridine (54.53 mmol) in anhydrous pyridine (6 mL/mmol) was added benzoyl chloride (65.4 mmol). The reaction mixture was stirred at room temperature during 1 hour and concentrated under reduced pressure. The crude mixture was diluted with diethyl ether and washed successively with HCl 1N, a saturated solution of NaHCO₃ and brine. The organic layer was dried over Na₂SO₄, filtered and concentrated under reduced pressure. The residue was purified by chromatography on silica gel column (eluent: petroleum ether/diethyl ether 0 to 30%) to give the expected compound in 93% yield.

Preparation of Compound 48

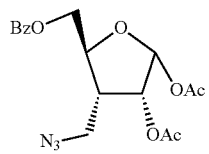

Compound 47 (50.7 mmol) was dissolved in aqueous solution of TFA 80% (4 mL/mmol) and the reaction mixture was stirred at room temperature during 1 hour. The mixture was concentrated under reduced pressure, then co-evaporated with ethanol and pyridine. The crude mixture was dissolved in anhydrous pyridine (4 mL/mmol) and dimethylaminopyridine (50.7 mmol) and acetic anhydride (1014 mmol) were added. The reaction mixture was stirred at room temperature during 2.5 hours, then neutralized with ice and diluted with ethyl acetate. The organic layer was washed successively with water, a saturated solution of NaHCO₃ and brine, dried over Na₂SO₄, filtered and concentrated under reduced pressure. The crude residue was purified by chromatography on silica gel column (petroleum ether/diethyl ether 0 to 100%) to give the expected compound in 73% yield.

Preparation of Compound 49a

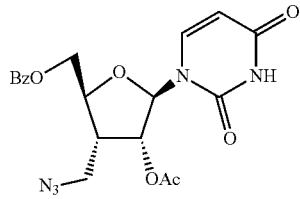

Compound 49a was synthesized from compound 48 (5.3 mmol) as described for compound 14b (in this case, the second reflux time was 2 hours) in 92% yield.

Preparation of Compound 49b

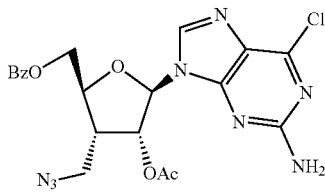

To a suspension of 2-amino-6-chloropurine (7.28 mmol) in anhydrous toluene (11 mL/mmol) was added dropwise at room temperature N,O-bis(trimethylsilyl)acetamide (15.2 mmol). The reaction mixture was heated at 120° C. during 1 hour. The solution of compound 48 (6.63 mmol) in anhydrous toluene was added at room temperature followed trimethylsilyl trifluoromethanesulfonate (20 mmol). The reaction mixture was heated at 120° C. during 3 hours, then diluted with ethyl acetate and washed with a saturated solution of bicarbonate and brine. The organic layer was dried, filtered and concentrated under reduced pressure. The crude residue was purified by 2 successive chromatographies on silica gel column (eluent: $CH_2Cl_2/CH_3OH$ 0 to 5%) to give the expected compound in 56% yield.

Preparation of Compound 216

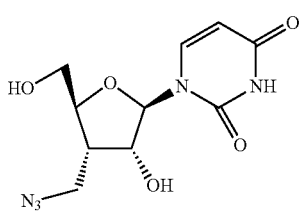 [SMILES: [N-]=[N+]=NC[C@H]1[C@@H](O)[C@H](n2ccc(=O)[nH]c2=O)O[C@@H]1CO]

Compound 216 was synthesized from compound 49a (3.96 mmol) as described for compound 205 as a white solid in 89% yield. $^1$H NMR (DMSO-$d_6$, 400 MHz) δ (ppm) 2.28-2.36 (m, 1H), 3.35 (dd, J=12.31 Hz and 5.69 Hz, 1H), 3.53-3.60 (m, 2H), 3.75 (dd, J=12.40 Hz and 2.42 Hz, 1H), 3.91 (td, J=9.40 Hz and 2.57 Hz, 1H), 4.20 (dd, J=5.43 Hz and 1.36 Hz, 1H), 5.55 (d, J=8.07 Hz, 1H), 5.64 (d, J=1.59 Hz, 1H), 6.03 (brs, 1H), 8.04 (d, J=8.08 Hz, 1H).

Preparation of Compound 217

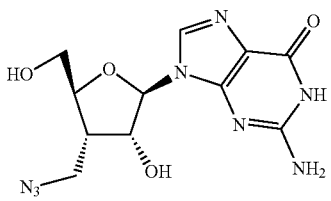 [SMILES: [N-]=[N+]=NC[C@H]1[C@@H](O)[C@H](n2cnc3c(=O)[nH]c(N)nc32)O[C@@H]1CO]

To a solution of compound 49b (2.054 mmol) in anhydrous dioxane (14 mL) was added a solution of NaOH 1N (14 mL) and the reaction mixture was stirred under microwave irradiations at 110° C. during 30 minutes. The mixture was neutralized with acetic acid (800 µl) and diluted with water. After extraction with dichloromethane, the aqueous layer was concentrated under reduced pressure. The crude residue was purified by 2 C18 chromatographies (eluent: $H_2O/CH_3CN$ 0 to 20%) and crystallization in water to give the expected compound in 23% yield. $^1$H NMR (DMSO-$d_6$, 400 MHz) δ (ppm) 2.54-2.61 (m, 1H), 3.43 (dd, J=12.27 Hz and 5.64 Hz, 1H), 3.50-3.55 (m, 1H), 3.62 (dd, J=12.27 Hz and 8.10 Hz, 1H), 3.66-3.71 (m, 1H), 3.91-3.95 (m, 1H), 4.40-4.43 (m, 1H), 5.03-5.06 (m, 1H), 5.71 (d, J=2.05 Hz, 1H), 5.92 (d, J=5.32 Hz, 1H), 6.44 (brs, 2H), 7.97 (s, 1H), 10.6 (brs, 1H).

Preparation of Compound 51

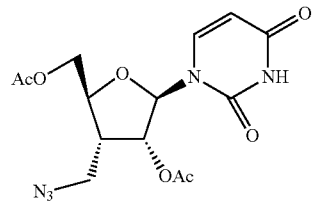 [SMILES: CC(=O)OC[C@H]1O[C@@H](n2ccc(=O)[nH]c2=O)[C@H](OC(C)=O)[C@@H]1CN=[N+]=[N-]]

Compound 51 was synthesized from compound 216 (1.06 mmol) as described for compound 27 as a white solid in 90% yield. MS (ESI) m/z=390.2 (MNa$^+$).

Preparation of Compound 52

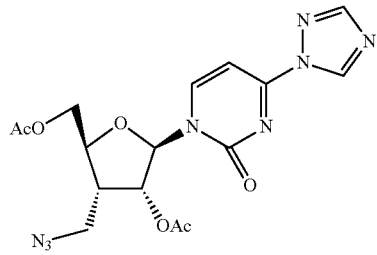 [SMILES: CC(=O)OC[C@H]1O[C@@H](n2ccc(-n3cncn3)nc2=O)[C@H](OC(C)=O)[C@@H]1CN=[N+]=[N-]]

Compound 52 was synthesized from compound 51 (0.95 mmol) as described for compound 28 (in this case the equivalent of dichloromethane was 10 mL/mmol) and obtained as a green solid in 49% yield. MS (ESI) m/z=419.2 (MH$^+$).

Preparation of Compound 218

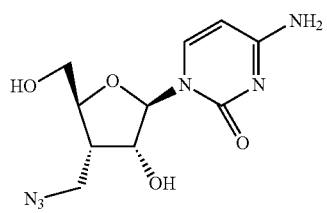 [SMILES: [N-]=[N+]=NC[C@H]1[C@@H](O)[C@H](n2ccc(N)nc2=O)O[C@@H]1CO]

Compound 218 was synthesized from compound 52 (0.47 mmol) as described for compound 29 and obtained as a white solid in 72% yield. $^1$H NMR (DMSO-$d_6$, 400 MHz) δ (ppm) 2.19-2.27 (m, 1H), 3.30-3.34 (m, 1H), 3.54-3.59 (m, 2H), 3.78 (dd, J=12.51 Hz and 2.27 Hz, 1H), 3.90 (td, J=9.93 Hz and 2.55 Hz, 1H), 4.08 (d, J=4.99 Hz, 1H), 5.15 (brs, 1H), 5.62 (s, 1H), 5.66 (d, J=7.46 Hz, 1H), 5.90 (brs, 1H), 7 (brs, 1H), 7.10 (brs, 1H), 8.02 (d, J=7.43 Hz, 1H); MS (ESI) m/z=283.2 (MH$^+$).

217

Preparation of Compound 219

Scheme 8

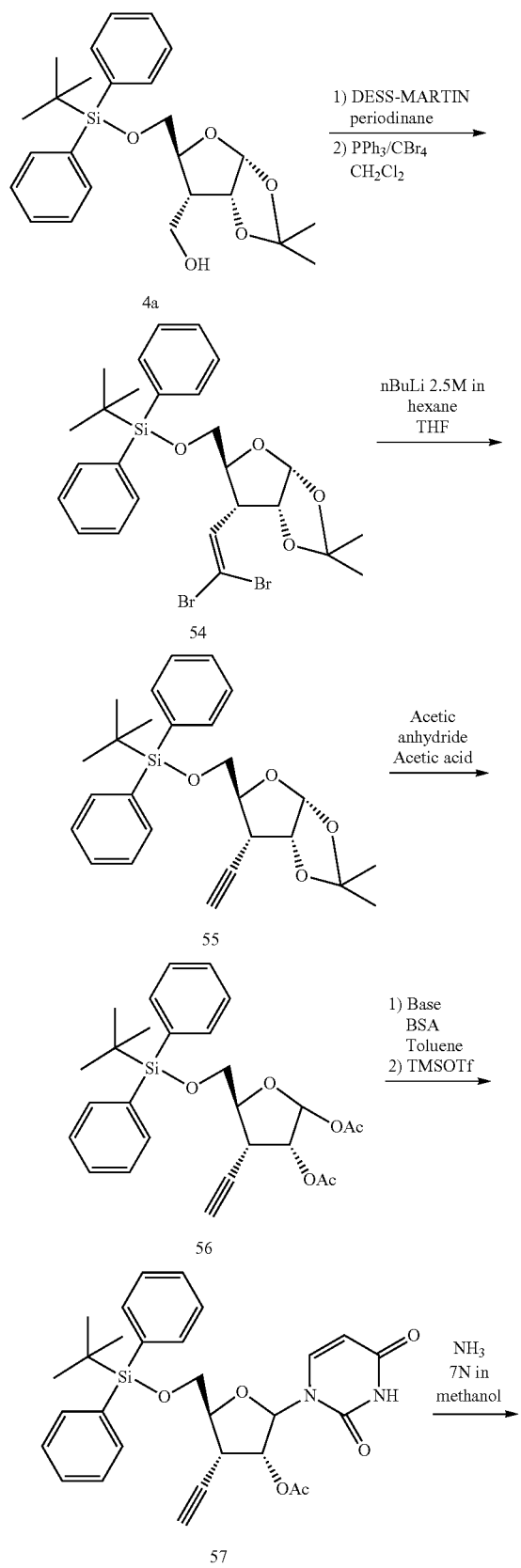

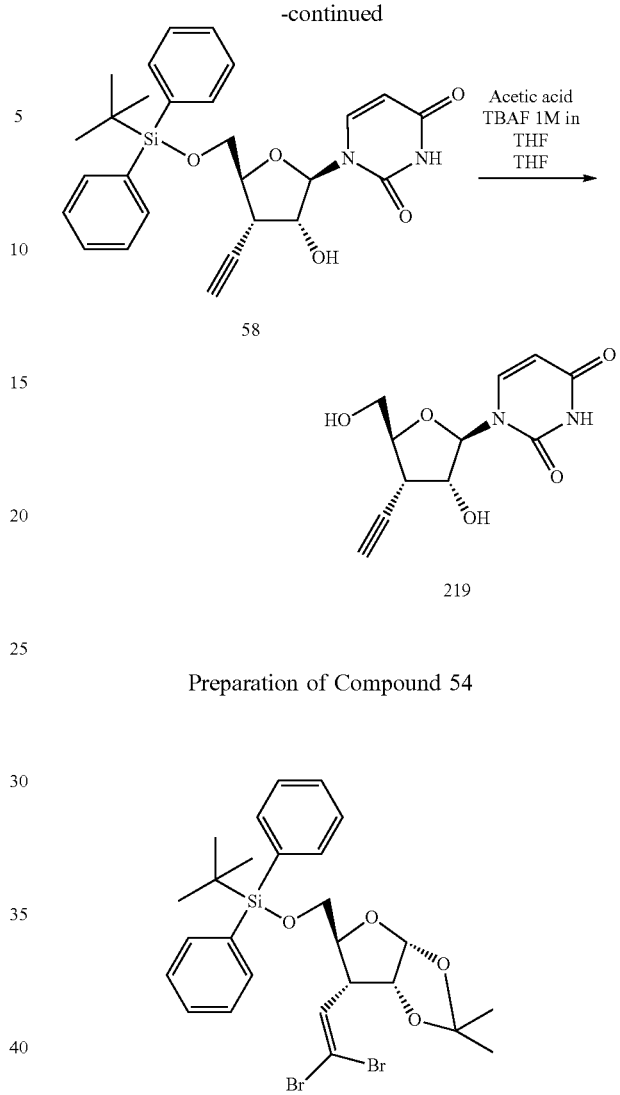

Preparation of Compound 54

To an ice-cooled solution of compound 4a (6.10 mmol) in anhydrous dichloromethane (5 mL/mmol) was added Dess-Martin periodinane (7.32 mmol) portionwise. The reaction mixture was stirred at room temperature during 2 hours. The reaction mixture was quenched with a mixture of saturated solution of NaHCO$_3$ (140 mL) and sodium thiosulfate pentahydrate (11 g). The reaction mixture was vigorously stirred during 5 minutes and layers were separated through a phase separator and the organic layer was evaporated to dryness to give crude mixture. To an ice-cooled solution of carbon tetrabromide (6.10 mmol) in anhydrous dichloromethane (5 mL/mmol) under nitrogen stream was added triphenylphosphine (12 mmol) portionwise. The reaction mixture was stirred at 0° C. during 30 minutes, then cooled down to −78° C. A solution of precedent crude mixture in anhydrous dichloromethane (5 mL/mmol) was added dropwise at −78° C. and the resultant reaction mixture was stirred at this temperature during 2 hours. Then, the mixture was allowed to warm up slowly to room temperature and stirred overnight. The reaction mixture was washed with a saturated solution of NaHCO$_3$ and brine, dried and concentrated under reduced pressure. The crude residue was purified by chromatography on silica gel column (eluent: petroleum ether/diethyl ether) to give the expected compound as a colorless viscous oil in 31% yield. ¹H NMR (CDCl₃, 400 MHz) δ (ppm) 1.06 (s, 9H), 1.34 (s, 3H), 1.53 (s, 3H), 3.15 (td, J=9.61 Hz and 4.64 Hz, 1H), 3.70 (dd, J=11.50 Hz and 3.38 Hz, 1H), 3.86 (dd, J=11.50 Hz and 3.40 Hz, 1H), 4.06 (td, J=9.88 Hz and 3.36 Hz, 1H), 4.72-4.74 (m, 1H), 5.86 (d, J=3.55 Hz, 1H), 6.48 (d, J=9.37 Hz, 1H), 7.37-7.46 (m, 6H), 7.66-7.73 (m, 4H). MS (ESI) m/z=619.2 (MNa⁺).

Preparation of Compound 55

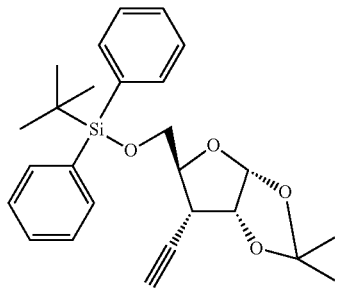 [SMILES: C#C[C@H]1[C@H]2OC(C)(C)O[C@H]2O[C@@H]1CO[Si](c1ccccc1)(c1ccccc1)C(C)(C)C]

A solution of n-BuLi (2.5 mmol/mL) in hexane (15.03 mmol) was added dropwise at −78° C. to a stirred solution of compound 54 (3 mmol) in anhydrous tetrahydrofuran (10 mL/mmol) under nitrogen. After stirring at −78° C. during 30 minutes, the reaction mixture was quenched with a saturated solution of NH₄Cl and diluted with ethyl acetate. The organic layer was washed with water and brine, dried over Na₂SO₄ and concentrated under reduced pressure. The crude residue was purified by chromatography on silica gel column (eluent: petroleum ether/diethyl ether) to give the expected compound as a yellowish oil in 74% yield. ¹H NMR (CDCl₃, 400 MHz) δ (ppm) 1.05 (s, 9H), 1.38 (s, 3H), 1.56 (s, 3H), 2.2 (d, J=2.50 Hz, 1H), 3.13-3.17 (m, 1H), 3.84 (dd, J=11.75 Hz and 2.90 Hz, 1H), 4 (dd, J=11.75 Hz and 2.09 Hz, 1H), 4.16 (td, J=10.05 Hz and 2.49 Hz, 1H), 4.75-4.78 (m, 1H), 5.86 (d, J=3.61 Hz, 1H), 7.35-7.45 (m, 6H), 7.68-7.71 (m, 4H).

Preparation of Compound 56

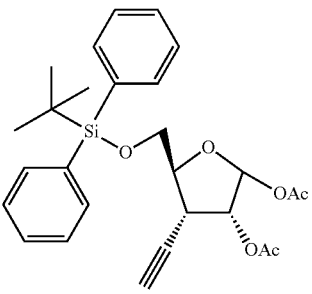 [SMILES: C#C[C@@H]1[C@@H](CO[Si](c2ccccc2)(c2ccccc2)C(C)(C)C)OC(OC(C)=O)[C@@H]1OC(C)=O]

Compound 56 was synthesized from compound 55 (2.22 mmol) as described for compound 24 (in this case, compound will be used for the next step without purification) as a yellow gum in 53% yield. MS (ESI) m/z=503.3 (MH⁺).

Preparation of Compound 57

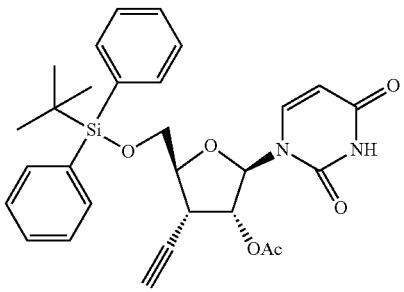 [SMILES: C#C[C@H]1[C@@H](OC(C)=O)[C@H](n2ccc(=O)[nH]c2=O)O[C@@H]1CO[Si](c1ccccc1)(c1ccccc1)C(C)(C)C]

A solution of compound 56 (1.17 mmol), uracil (2.34 mmol) and N,O-bis-(trimethylsilyl)-acetamide (4.1 mmol) in anhydrous acetonitrile (15 mL/mmol) was heated at reflux under nitrogen during 1 hour. The reaction mixture was cooled down to 0° C. then trimethylsilyl trifluoromethanesulfonate (2.93 mmol) was slowly added. The reaction mixture was refluxed under nitrogen for 1 hour. The reaction mixture was poured onto a saturated solution of NaHCO₃ and extracted with ethyl acetate. The organic layer was further washed with saturated solution of NaHCO₃ and brine, dried and concentrated under reduced pressure. The crude residue was purified by chromatography on silica gel column (eluent: CH₂Cl₂/CH₃CH₂OH) to give the expected compound as a white foam in 91%. ¹H NMR (CDCl₃, 400 MHz) δ (ppm) 1.10 (s, 9H), 2.17 (d, J=2.47 Hz, 1H), 2.18 (s, 3H), 3.50-3.54 (m, 1H), 3.89 (dd, J=12.07 Hz and 1.97 Hz, 1H), 4 (dd, J=12.09 Hz and 1.65 Hz, 1H), 4.16 (td, J=9.91 Hz and 1.82 Hz, 1H), 5.37 (dd, J=8.19 Hz and 2.30 Hz, 1H), 5.53 (dd, J=5.61 Hz and 1.22 Hz, 1H), 5.99 (d, J=1.38 Hz, 1H), 7.37-7.49 (m, 6H), 7.63-7.69 (m, 4H), 7.84 (d, J=8.20 Hz, 1H), 8.22 (brs, 1H); MS (ESI) m/z=533.3 (MH⁺).

Preparation of Compound 58

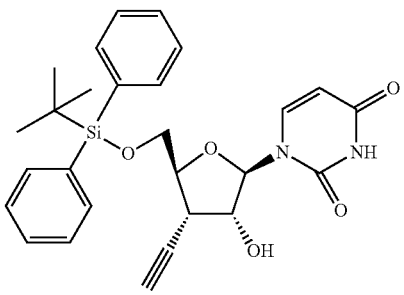 [SMILES: C#C[C@H]1[C@@H](O)[C@H](n2ccc(=O)[nH]c2=O)O[C@@H]1CO[Si](c1ccccc1)(c1ccccc1)C(C)(C)C]

A solution of compound 57 (1.06 mmol) in ammonia solution 7N in methanol (53 mmol) was stirred at room temperature during 4 hours and concentrated under reduced pressure. The crude residue was purified by chromatography on silica gel column (eluent: CH₂Cl₂/CH₃CH₂OH) to give the expected compound as a white foam in 94% yield. ¹H NMR (CDCl₃, 400 MHz) δ (ppm) 1.10 (s, 9H), 2.27 (d, J=2.43 Hz, 1H), 3.29-3.33 (m, 1H), 3.88 (d, J=2.06 Hz, 1H), 3.92 (dd, J=12.21 Hz and 1.66 Hz, 1H), 4.23 (dd, J=12.18 Hz and 1.38 Hz, 1H), 4.35-4.42 (m, 2H), 5.35 (dd, J=8.14 Hz and 2.02 Hz, 1H), 5.86 (s, 1H), 7.38-7.49 (m, 6H), 7.65-7.70 (m, 4H), 8.07 (d, J=8.15 Hz, 1H), 9.21 (brs, 1H); MS (ESI) m/z=491.4 (MH⁺).

Preparation of Compound 219

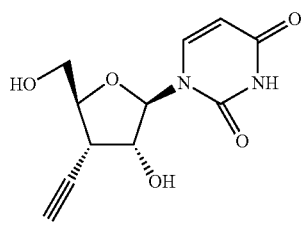 [SMILES: C#C[C@H]1[C@@H](O)[C@H](n2ccc(=O)[nH]c2=O)O[C@@H]1CO]

To a solution of compound 58 (1 mmol) and acetic acid (4 mmol) in anhydrous tetrahydrofuran (10 m L/mmol) was added tetra-n-butylammonium fluoride 1M in THF (2 mmol). The reaction mixture was stirred at room temperature overnight and concentrated under reduced pressure. The crude mixture was cleaned up through a SXC-2 cartridge with methanol to scavenge the TBAF. This fraction was evaporated and the resulting crude was purified by chromatography on silica gel column (eluent: CH$_2$Cl$_2$/CH$_3$CH$_2$OH) to give, after drying at 40° C. under high vacuum during 2 days, the expected compound as a white foam in 93% yield. ¹H NMR (DMSO-d$_6$, 400 MHz) δ (ppm) 2.96-3.0 (m, 1H), 3.03 (d, J=2.39 Hz, 1H), 3.54-3.59 (m, 1H), 3.78-3.84 (m, 1H), 4.07 (td, J=9.95 Hz and 2.37 Hz, 1H), 4.22-4.24 (m, 1H), 5.25-5.28 (m, 1H), 5.54 (d, J=8.09 Hz, 1H), 5.64 (d, J=1.14 Hz, 1H), 6 (d, J=5.48 Hz, 1H), 7.97 (d, J=8.09 Hz, 1H), 11.28 (brs, 1H); MS (ESI) m/z=253.1 (MH⁺).

Preparation of Compound 220

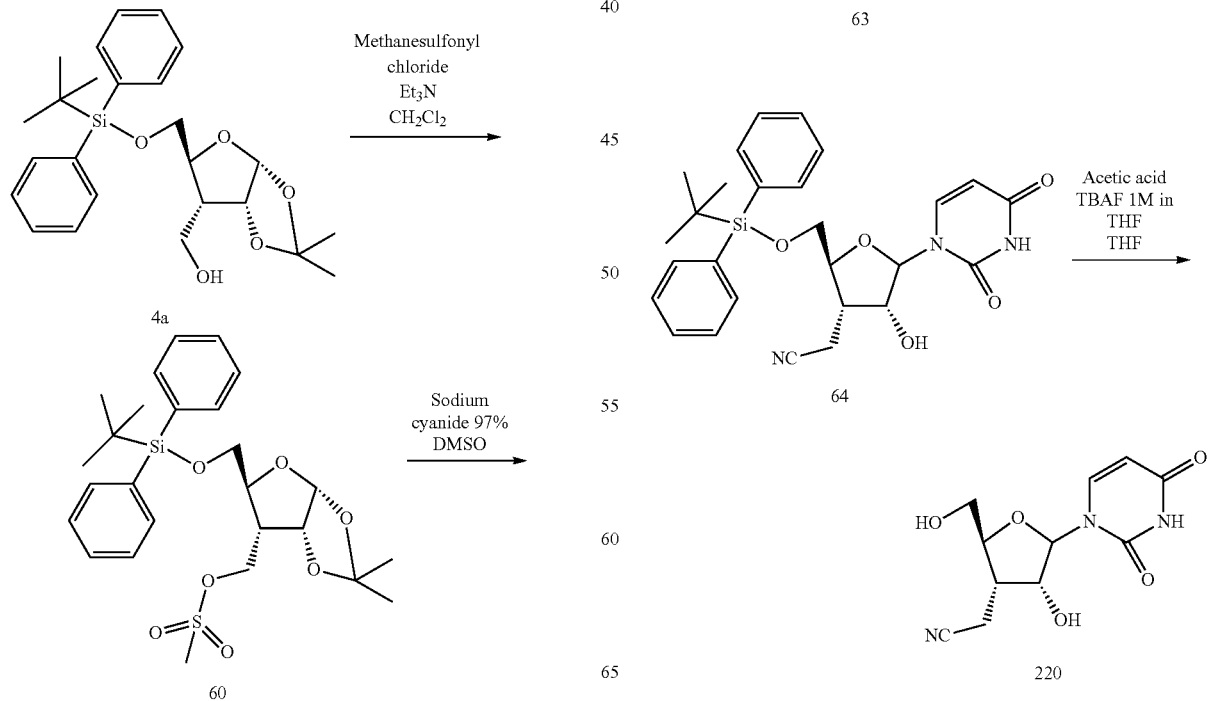

Preparation of Compound 60

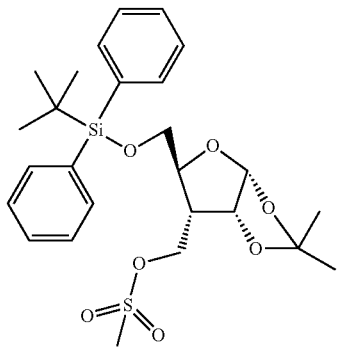

To a solution of compound 4a (3.05 mmol) and triethylamine (6.10 mmol) in anhydrous dichloromethane (5 mL/mmol) was added dropwise methanesulfonyl chloride (4.58 mmol). The reaction mixture was stirred at room temperature during 1 hour, then washed with 1N HCl, a saturated solution of NaHCO$_3$ and brine. The organic layer was dried over Na$_2$SO$_4$, filtered and concentrated under reduced pressure to give the expected compound as a yellow viscous oil in quantitative yield. $^1$H NMR (CDCl$_3$, 400 MHz) δ (ppm) 1.06 (s, 9H), 1.34 (s, 3H), 1.50 (s, 3H), 2.61-2.69 (m, 1H), 2.97 (s, 3H), 3.75 (dd, J=11.22 Hz and 3.45 Hz, 1H), 3.85 (dd, J=11.25 Hz and 4.16 Hz, 1H), 3.95 (td, J=9.80 Hz and 3.79 Hz, 1H), 4.34-4.45 (m, 2H), 4.75-4.77 (m, 1H), 5.86 (d, J=3.62 Hz, 1H), 7.37-7.46 (m, 6H), 7.65-7.68 (m, 4H); MS (ESI) m/z=543.1 (MNa$^+$).

Preparation of Compound 61

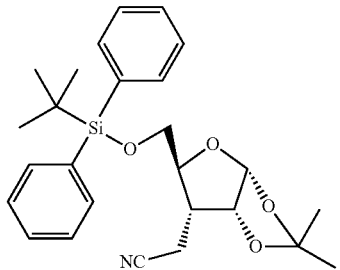

To a stirred solution of compound 60 (3.20 mmol) in dimethylsulfoxide (4 mL/mmol) was added sodium cyanide 97% (9.59 mmol). The reaction mixture was stirred at 70° C. during 3 hours, then cooled partitioned between diethyl ether and water. The aqueous layer was extracted with diethyl ether. Combined organic layers were washed with water and brine, dried and concentrated under reduced pressure. The crude residue was purified by chromatography on silica gel column (eluent: petroleum ether/diethyl ether) to give the expected compound as a white solid in 77% yield. $^1$H NMR (CDCl$_3$, 400 MHz) δ (ppm) 1.06 (s, 9H), 1.35 (s, 3H), 1.50 (s, 3H), 2.40-2.48 (m, 2H), 2.54-2.61 (m, 1H), 3.77-3.82 (m, 1H), 3.84-3.88 (m, 2H), 4.73-4.75 (m, 1H), 5.84 (d, J=3.65 Hz, 1H), 7.37-7.47 (m, 6H), 7.64-7.68 (m, 4H).

Preparation of Compound 62

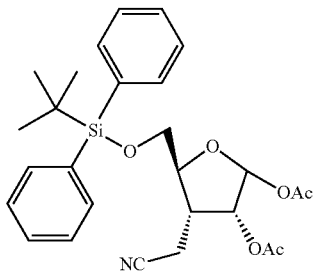 [SMILES: CC(=O)OC1O[C@H](CO[Si](c2ccccc2)(c2ccccc2)C(C)(C)C)[C@@H](CC#N)[C@H]1OC(C)=O]

Compound 62 was synthesized from compound 61 (4.81 mmol) as described for compound 56 and obtained as a colorless gum in 77% yield. MS (ESI) m/z=518.2 (MNa$^+$).

Preparation of Compound 63

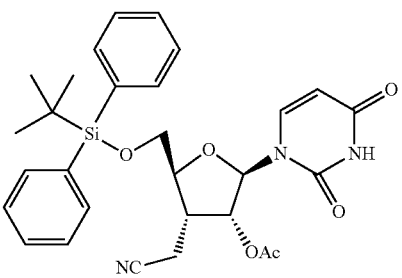 [SMILES: CC(=O)O[C@@H]1[C@H](CC#N)[C@@H](CO[Si](c2ccccc2)(c2ccccc2)C(C)(C)C)O[C@H]1n1ccc(=O)[nH]c1=O]

Compound 63 was synthesized from compound 62 (3.68 mmol) as described for compound 57 and obtained as a white foam in 71% yield. $^1$H NMR (DMSO-d$_6$, 400 MHz) δ (ppm) 1 (s, 9H), 2.10 (s, 3H), 2.66-2.78 (m, 2H), 2.93-3 (m, 1H), 3.85 (dd, J=11.74 Hz and 4.05 Hz, 1H), 3.99 (dd, J=11.77 Hz and 2.61 Hz, 1H), 4.03-4.07 (m, 1H), 5.33 (d, J=8.03 Hz, 1H), 5.44 (dd, J=6.80 Hz and 2.52 Hz, 1H), 5.78 (d, J=2.55 Hz, 1H), 7.38-7.49 (m, 6H), 7.62-7.68 (m, 5H), 11.39 (brs, 1H); MS (ESI) m/z=548.3 (MH$^+$).

Preparation of Compound 64

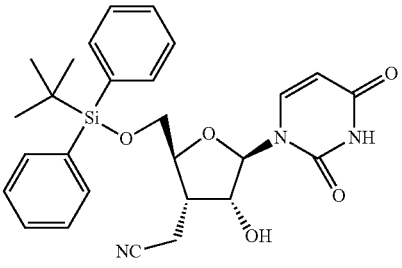 [SMILES: CC(C)(C)[Si](OC[C@H]1O[C@@H](n2ccc(=O)[nH]c2=O)[C@H](O)[C@@H]1CC#N)(c1ccccc1)c1ccccc1]

A solution of compound 63 (2.43 mmol) and potassium carbonate (12.1 mmol) in anhydrous methanol (10 mL/mmol) was stirred at room temperature during 1.5 hours. The reaction mixture was partitioned between ethyl acetate and 1N HCl. The organic layer was washed with a saturated solution of NaHCO$_3$ and brine, dried and concentrated under reduced pressure. The crude residue was purified by chromatography on silica gel column (eluent: CH$_2$Cl$_2$/CH$_3$CH$_2$OH) to give the expected compound as a white solid in 85% yield. $^1$H NMR (CDCl$_3$, 400 MHz) δ (ppm) 1.11 (s, 9H), 1.96-2 (m, 1H), 2.53-2.64 (m, 2H), 3.73 (dd, J=12.55 Hz and 1.73 Hz, 1H), 4.08-4.11 (m, 1H), 4.27 (dd, J=12.56 Hz and 1.74 Hz, 1H), 4.42-4.44 (m, 1H), 5.32 (d, J=3.16 Hz, 1H), 5.41 (dd, J=8.06 Hz, 1H), 5.8 (s, 1H), 7.41-7.51 (m, 6H), 7.64-7.70 (m, 4H), 8.16 (d, J=8.08 Hz, 1H), 10.27 (brs, 1H); MS (ESI) m/z=506.3 (MH+).

Preparation of Compound 220

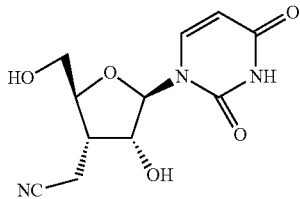 [SMILES: N#CC[C@H]1[C@@H](O)[C@H](n2ccc(=O)[nH]c2=O)O[C@@H]1CO]

Compound 220 was synthesized from compound 64 (0.742 mmol) as described for compound 219 as a white solid in 71% yield (in this case a lyophilisation was necessary to eliminate methanol). $^1$H NMR (DMSO-d$_6$, 400 MHz) δ (ppm) 2.38-2.45 (m, 1H), 2.59 (d, J=7.17 Hz, 2H), 3.57-3.62 (m, 1H), 3.74-3.80 (m, 1H), 3.89 (td, J=9.41 Hz and 2.66 Hz, 1H), 4.17-4.21 (m, 1H), 5.17-5.20 (m, 1H), 5.57 (d, J=8.11 Hz, 1H), 5.64 (d, J=1.60 Hz, 1H), 6.08 (d, J=4.82 Hz, 1H), 8.01 (d, J=8.11 Hz, 1H), 11.29 (brs, 1H); MS (ESI) m/z=268.2 (MH+).

Preparation of Compounds 104a, 104b, 105b, 116b and 123a

Scheme 10

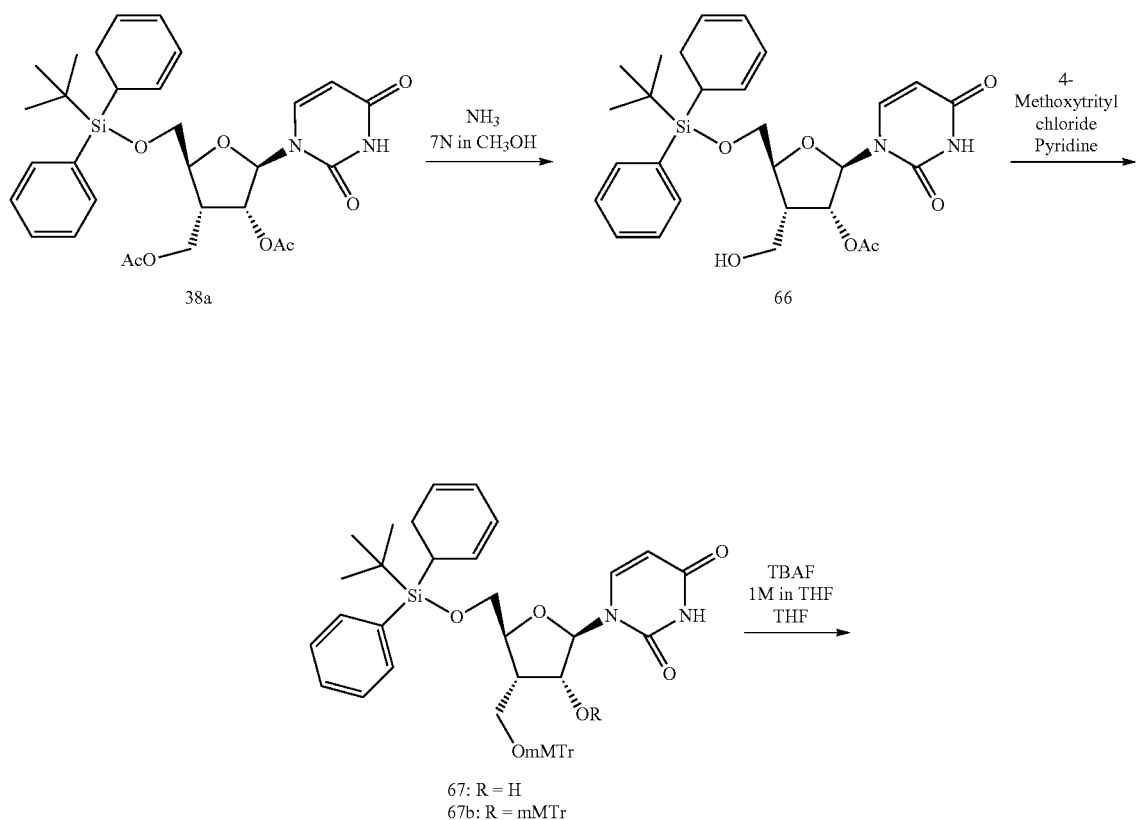

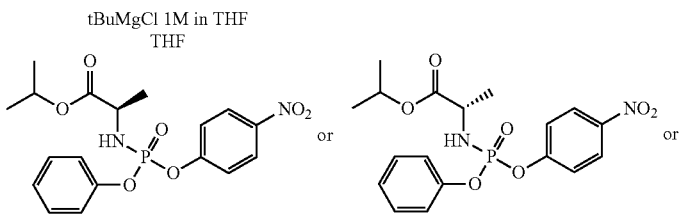

-continued
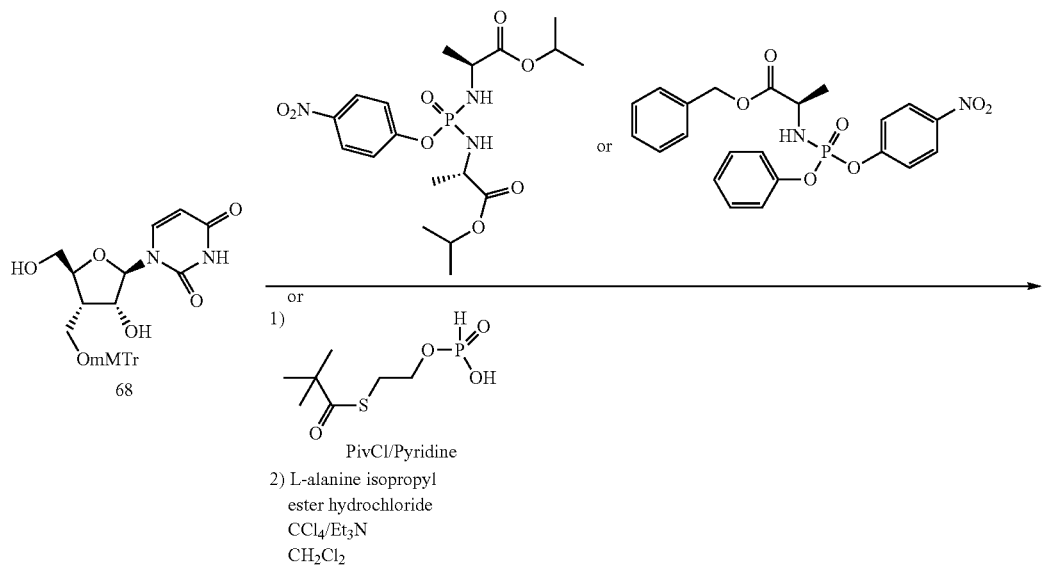
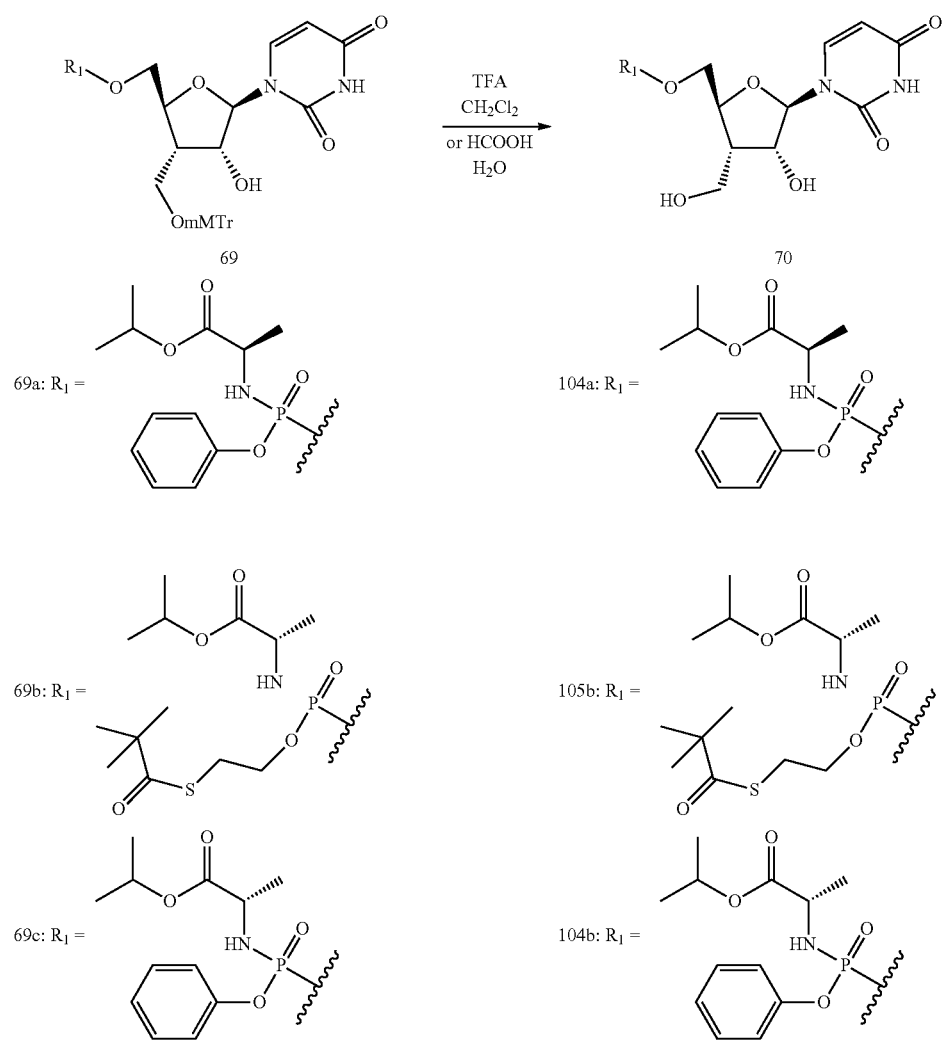

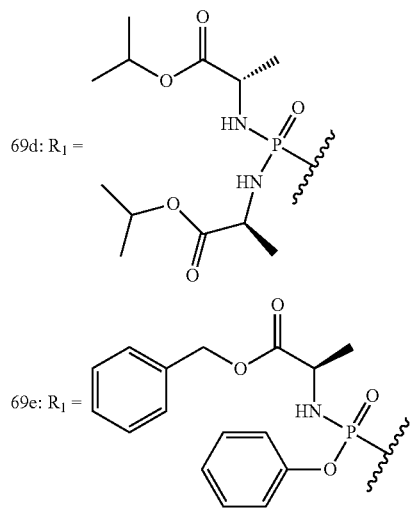

69d: R₁ =

69e: R₁ =

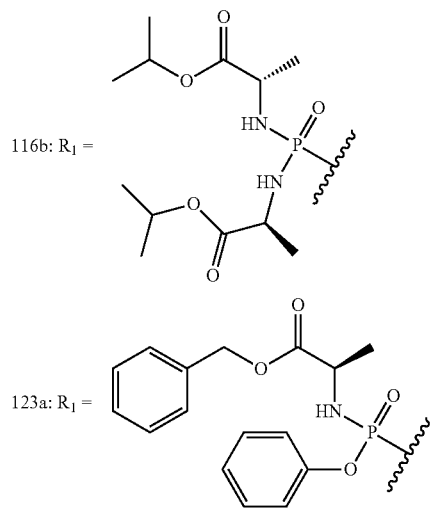

116b: R₁ =

123a: R₁ =

Preparation of Compound 66

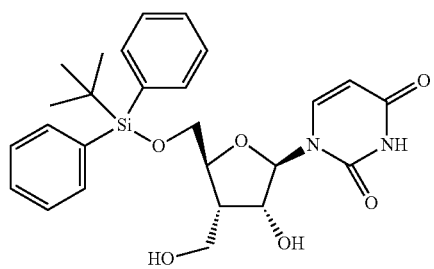 [SMILES: CC(C)(C)[Si](OC[C@H]1O[C@@H](n2ccc(=O)[nH]c2=O)[C@H](O)[C@@H]1CO)(c1ccccc1)c1ccccc1]

Compound 66 was synthesized from compound 38a (2.6 mmol) as described for compound 58 (reaction time=2 days) and obtained as a white foam in quantitative yield. MS (ESI) m/z=497.3 (MH⁺).

Preparation of Compound 67

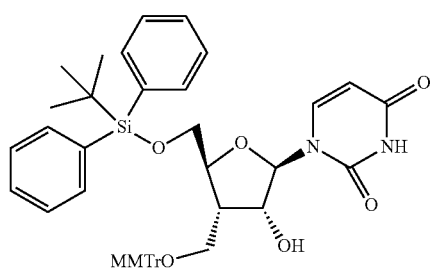

To a solution of compound 66 (2.72 mmol) in anhydrous pyridine (11 mL/mmol) was added under nitrogen 4-methoxytrityl chloride (3.3 mmol). The reaction mixture was stirred at 23° C. overnight and at 40° C. during 24 hours. The mixture was diluted in ethyl acetate, washed with water and the organic layer was dried over Na₂SO₄, filtered and concentrated under reduced pressure. The crude residue was purified by chromatography on silica gel column (eluent: CH₂Cl₂/CH₃OH 0 to 10%) to give the expected compound as a white foam in 73% yield. MS (ESI) m/z=767.8 (MH⁻).

Preparation of Compound 67b

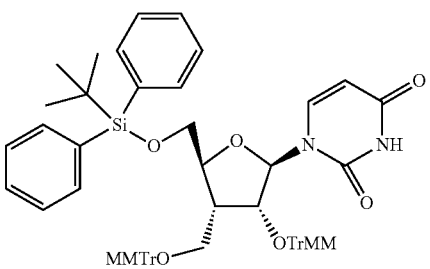

Compound 67b was synthesized according to Scheme 10.

Preparation of Compound 68

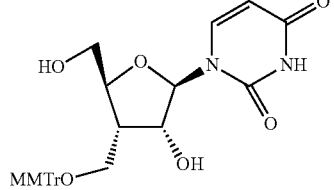

Compound 68 was synthesized from compound 67 (2 mmol) as described for compound 22 (reaction time=2 days) and obtained as a white foam in 96% yield. MS (ESI) m/z=529.4 (MH⁻).

Preparation of Compound 69a

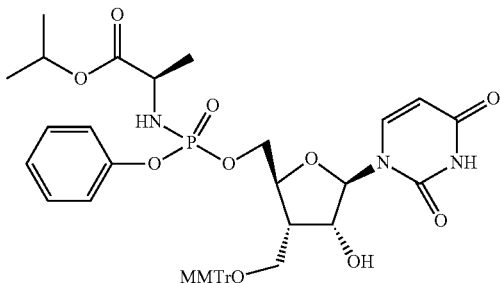

To a stirred solution of compound 68 (0.933 mmol) in anhydrous tetrahydrofuran (20 mL/mmol) was added tert-butylmagnesium chloride 1.0M in THF (2.80 mmol). The reaction mixture was stirred at room temperature during 10 minutes. Isopropyl (2R)-2-[[(4-nitrophenoxy)-phenoxyphosphoryl]amino]propanoate (1.03 mmol) was dissolved in anhydrous tetrahydrofuran (5 mL/mmol) and added to the reaction mixture. After stirring at room temperature during 20 hours, the mixture was diluted with ethyl acetate and washed with water and brine. The organic layer was dried over Na$_2$SO$_4$, filtered and concentrated under reduced pressure. The crude residue was purified by chromatography on silica gel column (eluent: CH$_2$Cl$_2$/CH$_3$OH 0 to 10%) to give the expected compound as a white solid in 41% yield. MS (ESI) m/z=798.6 (MH$^-$).

Preparation of Compound 69b

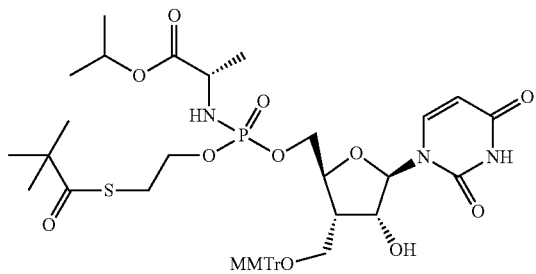

To a solution of compound 68 (0.933 mmol) and 2-(2,2-dimethylpropanoylsulfanyl) ethoxyphosphinic acid (1.40 mmol) in anhydrous pyridine (12 mL/mmol) was slowly added trimethylacetyl chloride (1.866 mmol) at 0° C. The reaction mixture was stirred during 1 hour at 0° C. and 2 hours at room temperature. The reaction mixture was quenched with NH$_4$Cl 1M (100 mL) and extracted with ethyl acetate. The organic layer was dried over Na$_2$SO$_4$ and concentrated under reduced pressure. The crude mixture was diluted in anhydrous dichloromethane (10 mL/mmol). Carbon tetrachloride (5 mL/mmol) was added followed by addition of triethylamine (5.597 mmol) and H-Ala-Oipr.HCl (2.799 mmol) at room temperature. The reaction mixture was stirred overnight at room temperature. The mixture was directly purified by chromatography on silica gel column (eluent: CH$_2$Cl$_2$/CH$_3$OH 0 to 10%) to give the expected compound as a white solid in 47% yield. MS (ESI) m/z=866.7 (MH$^-$).

Preparation of Compound 69c

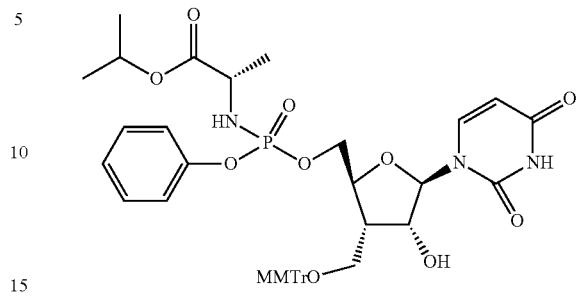

Compound 69c was synthesized from compound 68 (0.723 mmol) as described for compound 69a and obtained as a white solid in 39% yield. MS (ESI) m/z=798.7 (MH$^-$).

Preparation of Compound 69d

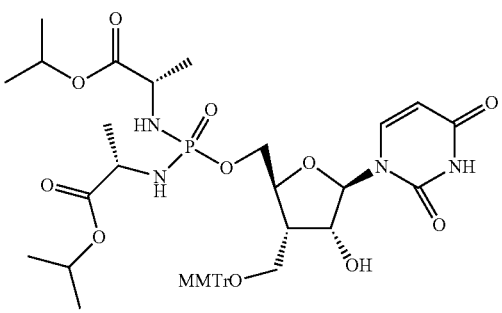

Compound 69d was synthesized according to Scheme 10.

Preparation of Compound 104a (Two Diastereomers)

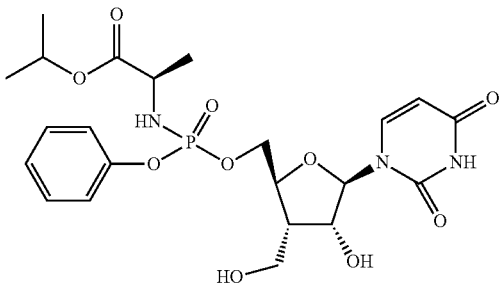 [SMILES: CC(C)OC(=O)[C@@H](C)NP(=O)(OC[C@H]1O[C@@H](n2ccc(=O)[nH]c2=O)[C@H](O)[C@@H]1CO)Oc1ccccc1]

To a solution of compound 69a (0.384 mmol) in anhydrous dichloromethane (50 mL/mmol) at 0° C. was added trifluoroacetic acid (3.86 mmol) and the mixture was stirred at 0-5° C. during 2 hours. The mixture was purified directly by chromatography on silica gel column (eluent: CH$_2$Cl$_2$/ CH$_3$OH 0 to 10%) and by prepMS to give a mixture of diastereoisomers (104a) as a white solid in 65% yield. $^1$H NMR (DMSO-d$_6$, 400 MHz) δ (ppm) 1.12-1.14 (m, 6H), 1.17-1.21 (m, 3H), 2.11-2.21 (m, 1H), 3.47-3.55 (m, 1H), 3.63-3.70 (m, 1H), 3.71-3.82 (m, 1H), 4.11-4.24 (m, 3H), 4.28-4.38 (m, 1H), 4.57-4.61 (m, 1H), 4.80-4.88 (m, 1H), 5.42 (d, J=8.07 Hz, 0.4H), 5.51 (d, J=8.07 Hz, 0.6H), 5.61 (d, J=5.04 Hz, 0.6H), 5.63 (d, J=5.06 Hz, 0.4H), 5.66 (d, J=2.49 Hz, 1H), 5.94-6.06 (m, 1H), 7.14-7.23 (m, 3H), 7.33-7.38 (m, 2H), 7.63 (d, J=8.06 Hz, 0.6H), 7.67 (d, J=8.08 Hz, 0.4H), 11.31 (brs, 1H); $^{31}$P NMR (DMSO-d$_6$, 162 MHz) δ (ppm) 3.49 (s, 0.6P), 3.84 (s, 0.4P); MS (ESI) m/z=528.3 (MH$^+$).

The mixture of diastereomers of compound 104a was purified by chiral separation to give the 2 pure diastereoisomers.

Compound 104a (diastereoisomer 1): white solid; $^1$H NMR (DMSO-d$_6$, 400 MHz) δ (ppm) 1.13 (d, J=6.25 Hz, 3H), 1.14 (d, J=6.25 Hz, 3H), 1.18 (d, J=7.13 Hz, 3H), 2.15-2.22 (m, 1H), 3.49-3.55 (m, 1H), 3.64-3.70 (m, 1H), 3.72-3.81 (m, 1H), 4.13-4.24 (m, 3H), 4.33-4.38 (m, 1H), 4.59-4.61 (m, 1H), 4.83 (septuplet, J=6.25 Hz, 1H), 5.42 (d, J=8.08 Hz, 1H), 5.63 (d, J=5.08 Hz, 1H), 5.66 (d, J=2.48 Hz, 1H), 5.94-5.99 (m, 1H), 7.15-7.18 (m, 3H), 7.34-7.38 (m, 2H), 7.67 (d, J=8.07 Hz, 1H), 11.24 (brs, 1H); $^{31}$P NMR (DMSO-d$_6$, 162 MHz) δ (ppm) 3.84 (s, 1P); MS (ESI) m/z=528.16 (MH$^+$).

Compound 104a (diastereoisomer 2): white solid; $^1$H NMR (DMSO-d$_6$, 400 MHz) δ (ppm) 1.13 (d, J=6.24 Hz, 3H), 1.14 (d, J=6.24 Hz, 3H), 1.20 (d, J=7.10 Hz, 3H), 2.11-2.18 (m, 1H), 3.47-3.53 (m, 1H), 3.63-3.68 (m, 1H), 3.71-3.82 (m, 1H), 4.11-4.19 (m, 3H), 4.28-4.34 (m, 1H), 4.57-4.59 (m, 1H), 4.83 (septuplet, J=6.26 Hz, 1H), 5.42 (d, J=8.09 Hz, 1H), 5.63 (d, J=5.10 Hz, 1H), 5.66 (d, J=2.50 Hz, 1H), 5.94-5.99 (m, 1H), 7.15-7.18 (m, 3H), 7.34-7.38 (m, 2H), 7.67 (d, J=8.10 Hz, 1H), 11.27 (brs, 1H); $^{31}$P NMR (DMSO-d$_6$, 162 MHz) δ (ppm) 3.49 (s, 1P); MS (ESI) m/z=528.16 (MH$^+$).

Preparation of Compound 105b (Two Diastereomers)

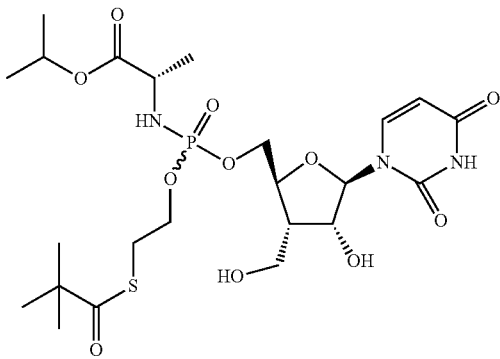 [SMILES: CC(C)OC(=O)[C@H](C)NP(=O)(OCCSC(=O)C(C)(C)C)OC[C@H]1O[C@@H](n2ccc(=O)[nH]c2=O)[C@H](O)[C@@H]1CO]

Compounds 105b (diastereoisomer 1) and 105b (diastereoisomer 2) were synthesized from compound 69b (0.439 mmol) as described for compound 104a. The 2 diastereoisomers were separated by PrepMS and each diastereoisomer was purified again by chromatography on silica gel column (eluent: CH$_2$Cl$_2$/CH$_3$OH 0 to 20%).

Compound 105b (diastereoisomer 1): white solid; 12%; $^1$H NMR (DMSO-d$_6$, 400 MHz) δ (ppm) 1.17-1.20 (m, 15H), 1.24 (d, J=7.08 Hz, 3H), 2.13-2.20 (m, 1H), 3.06 (t, J=6.55 Hz, 2H), 3.47-3.52 (m, 1H), 3.60-3.70 (m, 2H), 3.87-3.95 (m, 2H), 4.01-4.06 (m, 1H), 4.13-4.18 (m, 1H), 4.19-4.25 (m, 2H), 4.57 (t, J=4.90 Hz, 1H), 4.88 (septuplet, J=6.25 Hz, 1H), 5.57 (d, J=8.03 Hz, 1H), 5.60-5.66 (m, 3H), 7.72 (d, J=8.05 Hz, 1H), 11.30 (brs, 1H); $^{31}$P NMR (DMSO-d$_6$, 162 MHz) δ (ppm) 7.93 (s, 1P); MS (ESI) m/z=596.4 (MH$^+$).

Compound 105b (diastereoisomer 2): white solid; 13%; $^1$H NMR (DMSO-d$_6$, 400 MHz) δ (ppm) 1.16-1.18 (m, 15H), 1.24 (d, J=7.10 Hz, 3H), 2.10-2.17 (m, 1H), 3.09 (t, J=6.48 Hz, 2H), 3.46-3.52 (m, 1H), 3.62-3.76 (m, 2H), 3.89-4.03 (m, 3H), 4.11-4.16 (m, 1H), 4.18-4.24 (m, 2H), 4.56 (t, J=4.91 Hz, 1H), 4.87 (septuplet, J=6.26 Hz, 1H), 5.51-5.57 (m, 1H), 5.57 (d, J=8.07 Hz, 1H), 5.61-5.65 (m, 2H), 7.69 (d, J=8.09 Hz, 1H), 11.30 (brs, 1H); $^{31}$P NMR (DMSO-d$_6$, 162 MHz) δ (ppm) 8.22 (s, 1P); MS (ESI) m/z=596.4 (MH$^+$).

Preparation of Compound 104b (Two Diastereomers)

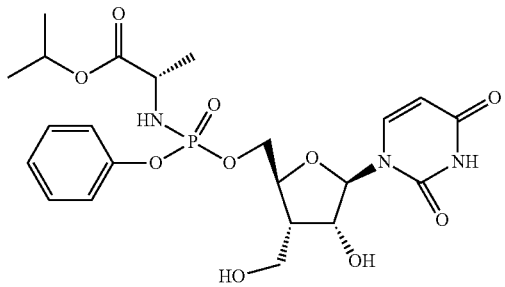 [SMILES: CC(C)OC(=O)[C@H](C)NP(=O)(OC[C@H]1O[C@@H](n2ccc(=O)[nH]c2=O)[C@H](O)[C@@H]1CO)Oc1ccccc1]

Compound 104b (mixture of diastereoisomers) was synthesized from compound 69c (0.284 mmol) as described for compound 105b as a white solid in 52% yield. $^1$H NMR (DMSO-d$_6$, 400 MHz) δ (ppm) 1.13-1.15 (m, 6H), 1.18-1.22 (m, 3H), 2.13-2.20 (m, 1H), 3.48-3.55 (m, 1H), 3.63-3.69 (m, 1H), 3.73-3.84 (m, 1H), 4.09-4.22 (m, 3H), 4.32-4.39 (m, 1H), 4.57-4.61 (m, 1H), 4.81-4.88 (m, 1H), 5.40 (d, J=8.06 Hz, 0.64H), 5.50 (d, J=8.08 Hz, 0.36H), 5.62-5.68 (m, 2H), 5.95-6.05 (m, 1H), 7.14-7.22 (m, 3H), 7.33-7.38 (m, 2H), 7.65 (d, J=8.11 Hz, 0.64H), 7.68 (d, J=8.11 Hz, 0.36H), 11.30 (brs, 1H); $^{31}$P NMR (DMSO-d$_6$, 162 MHz) δ (ppm) 3.70 (s, 0.36P), 3.82 (s, 0.64P); MS (ESI) m/z=528.3 (MH$^+$).

The mixture of diastereomers of compound 104b was purified by prepMS and each diastereoisomer was purified again by chromatography on silica gel column (eluent: CH$_2$Cl$_2$/CH$_3$OH 0 to 20%) to give the 2 pure diastereoisomers.

Compound 104b (diastereoisomer 1): white solid; $^1$H NMR (DMSO-d$_6$, 400 MHz) δ (ppm) 1.13 (d, J=6.22 Hz, 3H), 1.14 (d, J=6.22 Hz, 3H), 1.19 (d, J=7.10 Hz, 3H), 2.14-2.20 (m, 1H), 3.49-3.54 (m, 1H), 3.64-3.69 (m, 1H), 3.71-3.80 (m, 1H), 4.14-4.22 (m, 3H), 4.33-4.40 (m, 1H), 4.59-4.61 (m, 1H), 4.83 (septuplet, J=6.25 Hz, 1H), 5.50 (d, J=8.09 Hz, 1H), 5.63 (d, J=4.95 Hz, 1H), 5.67 (d, J=2.45 Hz, 1H), 5.99-6.05 (m, 1H), 7.14-7.19 (m, 3H), 7.33-7.38 (m, 2H), 7.68 (d, J=8.09 Hz, 1H), 11.31 (brs, 1H); $^{31}$P NMR (DMSO-d$_6$, 162 MHz) δ (ppm) 3.70 (s, 1P); MS (ESI) m/z=528.4 (MH$^+$).

Compound 104b (diastereoisomer 2): white solid; $^1$H NMR (DMSO-d$_6$, 400 MHz) δ (ppm) 1.14 (d, J=6.23 Hz, 6H), 1.21 (d, J=7.10 Hz, 3H), 2.13-2.19 (m, 1H), 3.48-3.53 (m, 1H), 3.63-3.68 (m, 1H), 3.74-3.84 (m, 1H), 4.08-4.22 (m, 3H), 4.32-4.37 (m, 1H), 4.57-4.60 (m, 1H), 4.85 (septuplet, J=6.24 Hz, 1H), 5.44 (d, J=8.09 Hz, 1H), 5.63 (brs, 1H), 5.65 (d, J=2.64 Hz, 1H), 5.95-6 (m, 1H), 7.15-7.22 (m, 3H), 7.34-7.39 (m, 2H), 7.65 (d, J=8.09 Hz, 1H), 11.30 (brs, 1H); $^{31}$P NMR (DMSO-d$_6$, 162 MHz) δ (ppm) 3.82 (s, 1P); MS (ESI) m/z=528.4 (MH$^+$).

Preparation of Compound 116b

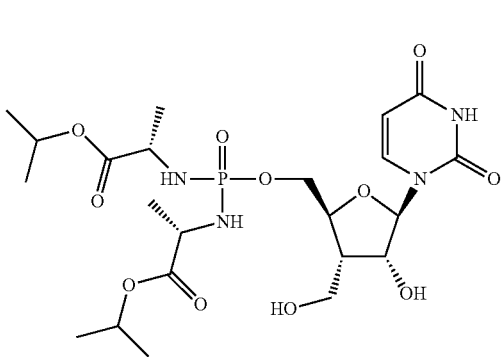 [SMILES: CC(C)OC(=O)[C@H](C)NP(=O)(N[C@@H](C)C(=O)OC(C)C)OC[C@H]1O[C@@H](n2ccc(=O)[nH]c2=O)[C@H](O)[C@@H]1CO]

Compound 116b was synthesized according to Scheme 10.

MS (ESI) m/z=565.2 (MH$^+$). $^1$H NMR (400 MHz, DMSO) δ (ppm) 11.33 (brs, 1H), 7.80 (d, J=8.13 Hz, 1H), 5.67 (d, J=2.26 Hz, 1H), 5.65 (d, J=5.02 Hz, 1H), 5.63 (d, J=8.22 Hz, 1H), 4.91-4.81 (m, 4H), 4.6 (t, J=5 Hz, 1H), 4.23-4.20 (m, 1H), 4.18-4.11 (m, 2H), 3.99-3.94 (m, 1H), 3.79-3.64 (m, 3H), 3.54-3.48 (m, 1H), 2.24-2.17 (m, 1H), 1.25 (d, J=7.09 Hz, 3H), 1.24 (d, J=7.09 Hz, 3H), 1.20-1.17 (m, 12H). $^{31}$P NMR (162 MHz, DMSO) δ (ppm) 12.98 (s, 1P).

Compound 123a

Compound 123a (diastereoisomer 1): white solid; $^1$H NMR (CDCl$_3$, 400 MHz) δ (ppm) 10.53 (brs, 1H), 7.88 (d, J=8.15 Hz, 1H), 7.36-7.27 (m, 7H), 7.19-7.12 (m, 3H), 5.67 (s, 1H), 5.53 (d, J=8.49 Hz, 1H), 5.13-5.06 (m, 2H), 4.75-4.70 (m, 1H), 4.52-4.47 (m, 1H), 4.41-4.35 (m, 3H), 4.15-4.05 (m, 1H), 3.92-3.83 (m, 2H), 2.45-2.38 (m, 1H), 1.33 (d, J=7.13 Hz, 3H); $^{31}$P NMR (DMSO-d$_6$, 162 MHz) δ (ppm) 3.95 (s, 1P); MS (ESI) m/z=575.9 (MH$^+$).

Compound 123a (diastereoisomer 2): white solid; $^1$H NMR (DMSO-d$_6$, 400 MHz) δ (ppm) 10.31 (brs, 1H), 7.78 (d, J=8.10 Hz, 1H), 7.36-7.25 (m, 7H), 7.18-7.11 (m, 3H), 5.70 (brs, 1H), 5.65-5.63 (m, 1H), 5.15-5.09 (m, 2H), 4.44-4.38 (m, 4H), 4.33-4.27 (m, 1H), 4.04-3.94 (m, 1H), 3.86-3.84 (m, 2H), 2.34-2.28 (m, 1H), 1.34 (d, J=7.09 Hz, 3H); $^{31}$P NMR (DMSO-d$_6$, 162 MHz) δ (ppm) 3.01 (s, 1P); MS (ESI) m/z=575.9 (MH$^+$).

Preparation of Compound 122a

Scheme 10bis:

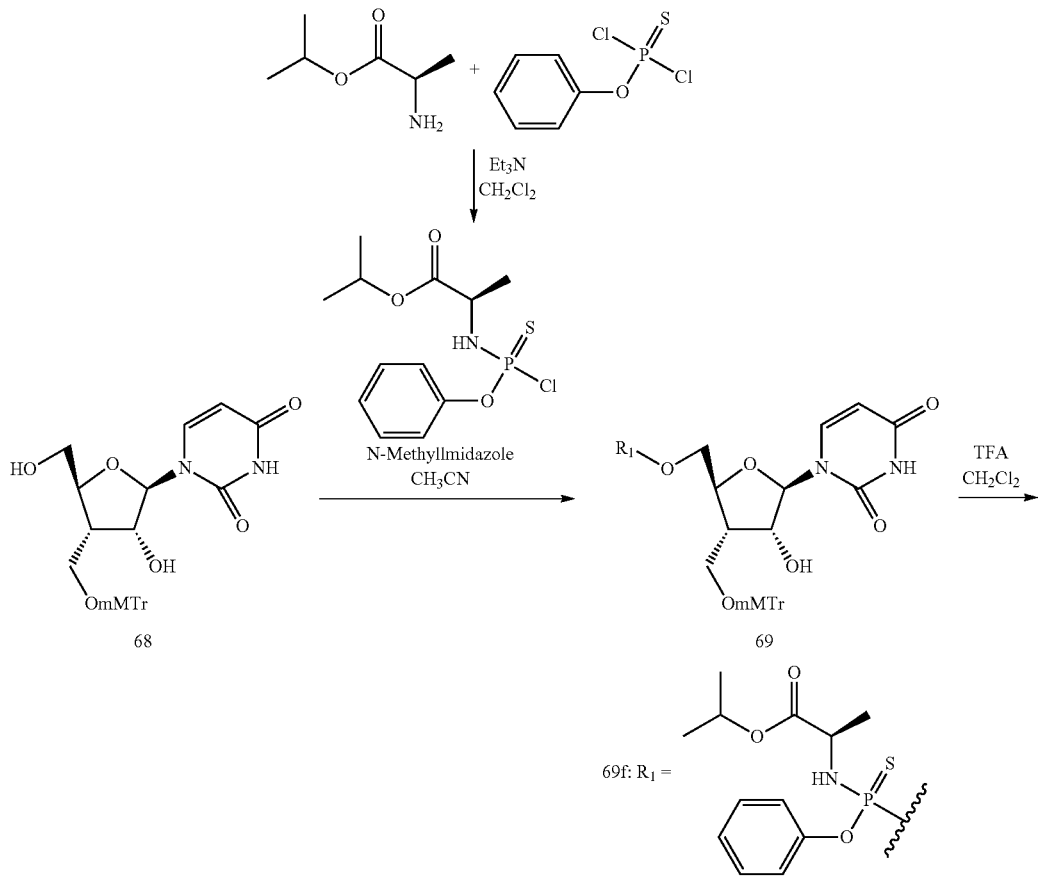

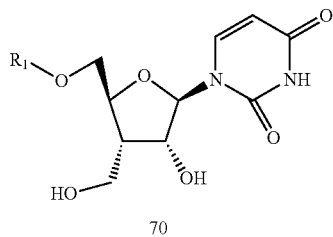

70

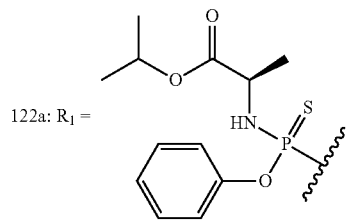

122a: R₁ =

Compound 122a

Preparation of Compounds 221, 321, and 325

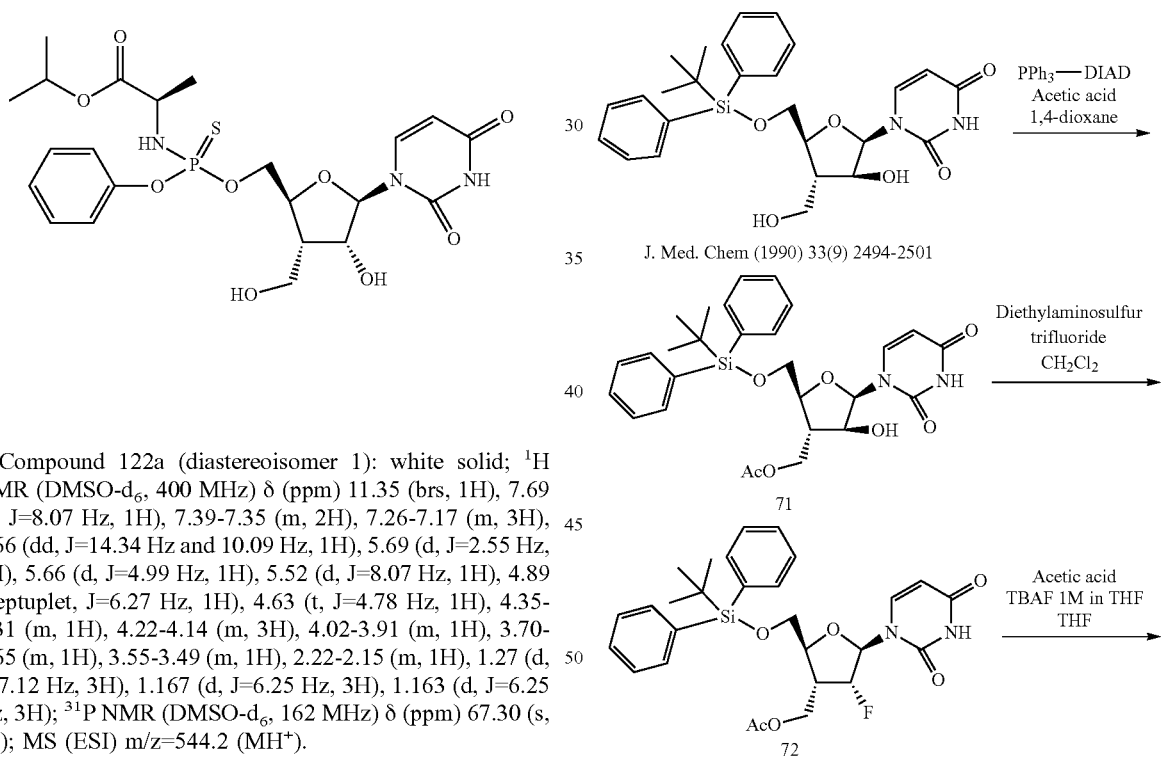

Compound 122a (diastereoisomer 1): white solid; ¹H NMR (DMSO-d₆, 400 MHz) δ (ppm) 11.35 (brs, 1H), 7.69 (d, J=8.07 Hz, 1H), 7.39-7.35 (m, 2H), 7.26-7.17 (m, 3H), 6.66 (dd, J=14.34 Hz and 10.09 Hz, 1H), 5.69 (d, J=2.55 Hz, 1H), 5.66 (d, J=4.99 Hz, 1H), 5.52 (d, J=8.07 Hz, 1H), 4.89 (heptuplet, J=6.27 Hz, 1H), 4.63 (t, J=4.78 Hz, 1H), 4.35-4.31 (m, 1H), 4.22-4.14 (m, 3H), 4.02-3.91 (m, 1H), 3.70-3.65 (m, 1H), 3.55-3.49 (m, 1H), 2.22-2.15 (m, 1H), 1.27 (d, J=7.12 Hz, 3H), 1.167 (d, J=6.25 Hz, 3H), 1.163 (d, J=6.25 Hz, 3H); ³¹P NMR (DMSO-d₆, 162 MHz) δ (ppm) 67.30 (s, 1P); MS (ESI) m/z=544.2 (MH⁺).

Compound 122a (diastereoisomer 2): white solid; ¹H NMR (DMSO-d₆, 400 MHz) δ (ppm) 11.34 (brs, 1H), 7.72 (d, J=8.07 Hz, 1H), 7.40-7.36 (m, 2H), 7.21-7.18 (m, 3H), 6.61 (dd, J=12.48 Hz and 9.75 Hz, 1H), 5.69 (d, J=2.48 Hz, 1H), 5.67 (d, J=4.98 Hz, 1H), 5.45 (d, J=8.07 Hz, 1H), 4.87 (heptuplet, J=6.23 Hz, 1H), 4.65 (t, J=4.82 Hz, 1H), 4.41-4.37 (m, 1H), 4.27-4.13 (m, 3H), 3.99-3.89 (m, 1H), 3.72-3.67 (m, 1H), 3.57-3.52 (m, 1H), 2.26-2.19 (m, 1H), 1.24 (d, J=7.06 Hz, 3H), 1.17-1.14 (m, 6H); ³¹P NMR (DMSO-d₆, 162 MHz) δ (ppm) 68.11 (s, 1P); MS (ESI) m/z=544.2 (MH⁺).

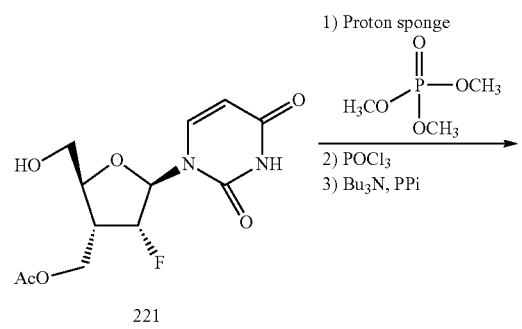

-continued

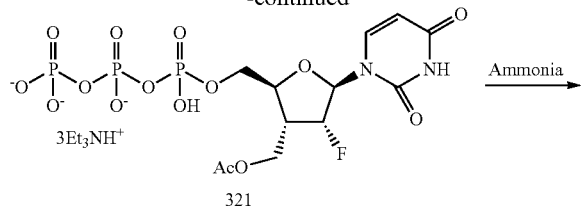

321

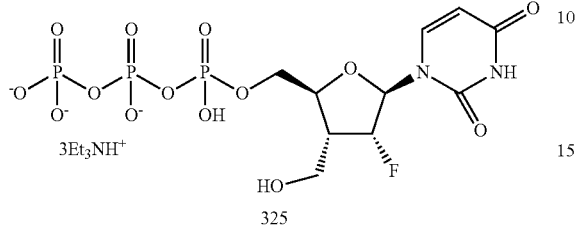

325

Preparation of Compound 71

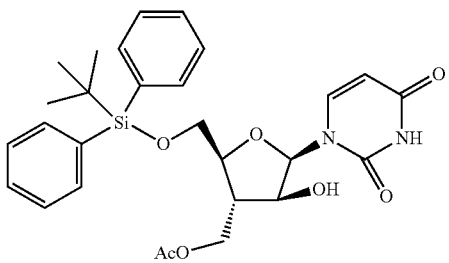 [SMILES: CC(=O)OC[C@H]1[C@H](O)[C@H](n2ccc(=O)[nH]c2=O)O[C@@H]1CO[Si](c1ccccc1)(c1ccccc1)C(C)(C)C]

To a solution of 1-[(2R,3S,4S,5S)-5-[[tert-butyl(diphenyl)silyl]oxymethyl]-3-hydroxy-4-(hydroxymethyl)tetrahydrofuran-2-yl]pyrimidine-2,4-dione (JMC (1990) 33(9) 2494-2501) (1.007 mmol) in 1,4-dioxane (50 mL/mmol) was added triphenylphosphine (3.021 mmol) and acetic acid (10.07 mmol). The reaction mixture was heated at 60° C. and a solution of diisopropyl azodicarboxylate (3.021 mmol) in 1,4-dioxane (10 mL/mmol) was added dropwise. The reaction mixture was stirred at 60° C. during 1 hour. After cooling to room temperature and concentration under reduced pressure, the residue was purified by chromatography on silica gel column (eluent: $CH_2Cl_2/CH_3OH$ 0 to 5%) to give the expected compound as a white solid in 96% yield. $^1H$ NMR (DMSO-$d_6$, 400 MHz) δ (ppm) 1.02 (s, 9H), 1.93 (s, 3H), 3.81-3.88 (m, 2H), 3.93-3.98 (m, 1H), 4.03-4.07 (m, 1H), 4.20-4.26 (m, 2H), 5.12 (d, J=8.08 Hz, 1H), 5.68 (d, J=4.84 Hz, 1H), 6 (d, J=5.89 Hz, 1H), 7.40-7.49 (m, 6H), 7.59-7.66 (m, 5H), 11.25 (brs, 1H); MS (ESI) m/z=539 (MH$^+$).

Preparation of Compound 72

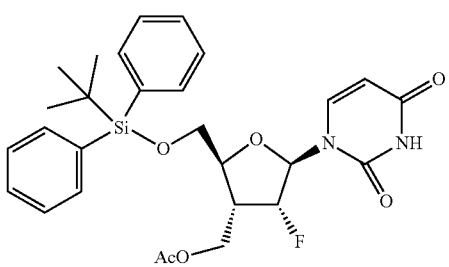 [SMILES: CC(=O)OC[C@H]1[C@@H](F)[C@H](n2ccc(=O)[nH]c2=O)O[C@@H]1CO[Si](c1ccccc1)(c1ccccc1)C(C)(C)C]

Compound 72 was synthesized from compound 71 (0.886 mmol) as described for compound 12 (conditions for the reaction: 2 hours at 0° C. followed by 2.5 hours at 20° C.) and obtained as a white foam in 43% yield. MS (ESI) m/z=563.2 (MNa$^+$).

Preparation of Compound 221

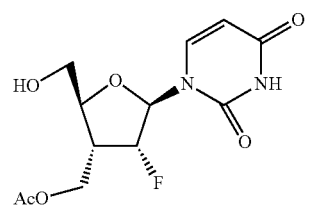 [SMILES: CC(=O)OC[C@H]1[C@@H](F)[C@H](n2ccc(=O)[nH]c2=O)O[C@@H]1CO]

Compound 73 was synthesized from compound 72 (0.44 mmol) as described for compound 212 (only one purification by chromatography on silica gel column (eluent: $CH_2Cl_2/CH_3OH$ 0 to 5%)) as a foam in 68% yield. $^1H$ NMR (DMSO-$d_6$, 400 MHz) δ (ppm) 2.02 (s, 3H), 2.57-2.73 (m, 1H), 3.58-3.63 (m, 1H), 3.81-3.86 (m, 1H), 4.05-4.20 (m, 3H), 5.28 (t, J=5.13 Hz, 1H), 5.31 (dd, J=52.02 Hz and 4.21 Hz, 1H), 5.58 (dd, J=8.08 Hz and 2.14 Hz, 1H), 5.86 (d, J=18.49 Hz, 1H), 8.02 (d, J=8.08 Hz, 1H), 11.36 (brs, 1H); $^{19}F$ NMR (DMSO-$d_6$, 376.5 MHz) δ (ppm) −195.23 (s, 1F); MS (ESI) m/z=303 (MH$^+$).

Preparation of Compound 321

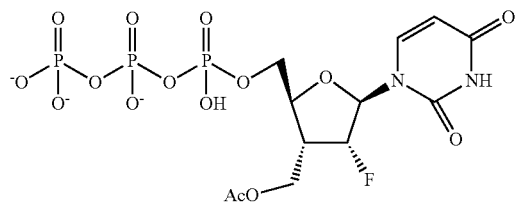

Compound 321 was synthesized from compound 221 according to general method A.

Preparation of Compound 325

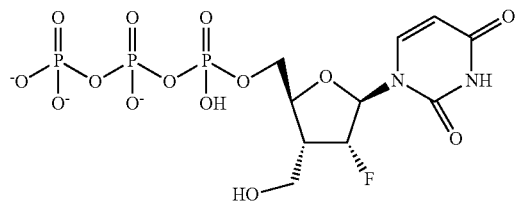

Compound 325 was synthesized from compound 321 according to general method B.

MS (ESI) m/z=499 (MH$^-$).

Preparation of Triphosphate Compounds

Scheme 12

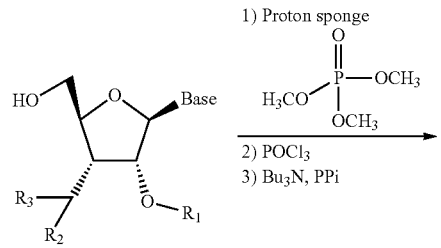

1) Proton sponge, (MeO)$_3$P=O
2) POCl$_3$
3) Bu$_3$N, PPi

202: Base = U, R$_1$ = H, R$_2$ = H and R$_3$ = —F
201: Base = U, R$_1$ = H, R$_2$ = F and R$_3$ = —F
212: Base = U, R$_1$ = Ac, R$_2$ = H and R$_3$ = —OAc
204: Base = C, R$_1$ = H, R$_2$ = H and R$_3$ = —F
211: Base = U, R$_1$ = H, R$_2$ = —CH$_3$ and R$_3$ = —OH
216: Base = U, R$_1$ = H, R$_2$ = H and R$_3$ = —N$_3$
217: Base = G, R$_1$ = H, R$_2$ = H and R$_3$ = —N$_3$
213: Base = C, R$_1$ = Ac, R$_2$ = H and R$_3$ = —OAc
220: Base = U, R$_1$ = H, R$_2$ = H and R$_3$ = —CN
230: Base = A, R$_1$ = Ac, R$_2$ = H and R$_3$ = —OAc
231: Base = G, R$_1$ = Ac, R$_2$ = H and R$_3$ = —OAc
225: Base = A, R$_1$ = H, R$_2$ = H and R$_3$ = —F
226: Base = G, R$_1$ = H, R$_2$ = H and R$_3$ = —F
240: Base = 2,6-diaminopurine, R$_1$ = Ac, R$_2$ = H and R$_3$ = —OAc
241: Base = 8-azaG, R$_1$ = Ac, R$_2$ = H and R$_3$ = —OAc
242: Base = 5-Me—U, R$_1$ = Ac, R$_2$ = H and R$_3$ = —OAc

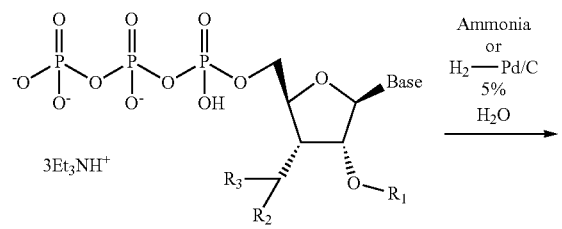

Ammonia or H$_2$—Pd/C 5% H$_2$O

302: Base = U, R$_1$ = H, R$_2$ = H and R$_3$ = —F
301: Base = U, R$_1$ = H, R$_2$ = F and R$_3$ = —F
312: Base = U, R$_1$ = Ac, R$_2$ = H and R$_3$ = —OAc
304: Base = C, R$_1$ = H, R$_2$ = H and R$_3$ = —F
311: Base = U, R$_1$ = H, R$_2$ = —CH$_3$ and R$_3$ = —OH
316: Base = U, R$_1$ = H, R$_2$ = H and R$_3$ = —N$_3$
317: Base = G, R$_1$ = H, R$_2$ = H and R$_3$ = —N$_3$
313: Base = C, R$_1$ = Ac, R$_2$ = H and R$_3$ = —OAc
320: Base = U, R$_1$ = H, R$_2$ = H and R$_3$ = —CN
228: Base = A, R$_1$ = Ac, R$_2$ = H and R$_3$ = —OAc
329: Base = G, R$_1$ = Ac, R$_2$ = H and R$_3$ = —OAc
326: Base = A, R$_1$ = H, R$_2$ = H and R$_3$ = —F
327: Base = G, R$_1$ = H, R$_2$ = H and R$_3$ = —F
340: Base = 2,6-diaminopurine, R$_1$ = Ac, R$_2$ = H and R$_3$ = —OAc
341: Base = 8-azaG, R$_1$ = Ac, R$_2$ = H and R$_3$ = —OAc
342: Base = 5-Me—U, R$_1$ = Ac, R$_2$ = H and R$_3$ = —OAc

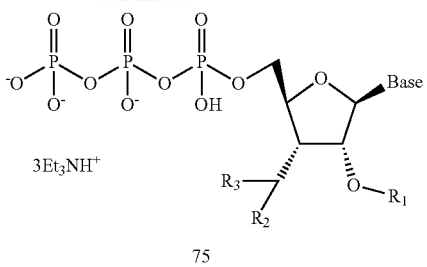

305: Base = U, R$_1$ = H, R$_2$ = H and R$_3$ = OH
306: Base = C, R$_1$ = H, R$_2$ = H and R$_3$ = OH
322: Base = G, R$_1$ = H, R$_2$ = H and R$_3$ = NH$_2$
323: Base = U, R$_1$ = H, R$_2$ = H and R$_3$ = NH$_2$
307: Base = A, R$_1$ = H, R$_2$ = H and R$_3$ = OH
308: Base = G, R$_1$ = H, R$_2$ = H and R$_3$ = OH
330: Base = 2,6-diaminopurine, R$_1$ = H, R$_2$ = H and R$_3$ = —OH
331: Base = 8-azaG, R$_1$ = H, R$_2$ = H and R$_3$ = —OH
332: Base = 5-Me—U, R$_1$ = Ac, R$_2$ = H and R$_3$ = —OH General Method A.

The following procedure was used to obtain compounds 301, 302, 304, 311-313, 316, 320, and 326-329.

The appropriate nucleoside (100 mg) was dried under vacuum overnight. Trimethylphosphate (1.9 ml) and proton sponge (100 mg) were added to the flask and the reaction mixture was stirred under nitrogen cooled by an ice/water bath. Distilled phosphorus oxychloride (45 µl) was added and the reaction mixture was stirred during 4 hours with cooling. Tributylamine (0.32 ml) and tributylamine pyrophosphate (4.0 ml of a 0.5 M solution in DMF) were added and the reaction was allowed to stir for an additional 45 min with cooling. The reaction was quenched with triethylammonium bicarbonate (0.5 M, 20 ml) and the solvents were concentrated under reduced pressure. The crude mixture was dissolved in 10 ml of water and purified using a Sephadex DEAE A-25 column with a linear gradient of 0-1M NaCl buffered with 20 mM Tris-HCl (pH 7.0) (triphosphates eluted at ~0.4 M NaCl) and desalted on a C18 column to give the expected compound, or with a linear gradient of 0-1 M triethylammonium (pH 7.5) to afford after evaporation a residue solid which was dissolved in water and the concentration was adjusted to 10 mM with water.

Compound 302

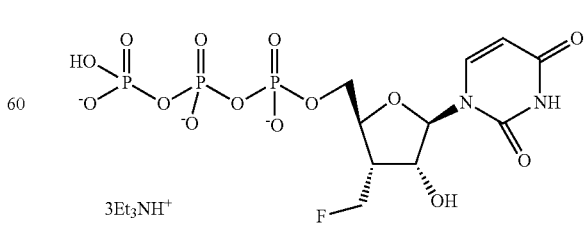

White solid; MS (ESI) m/z=499.0 (MH$^-$).

Compound 301
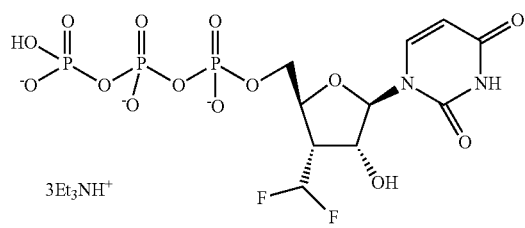
White solid; MS (ESI) m/z=517.0 (MH⁻).
Compound 312
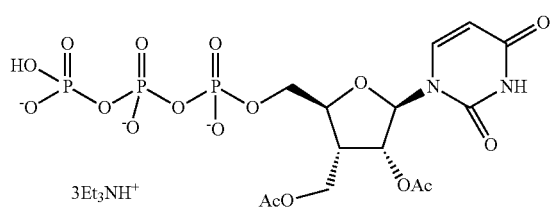
Not isolated.
Compound 304
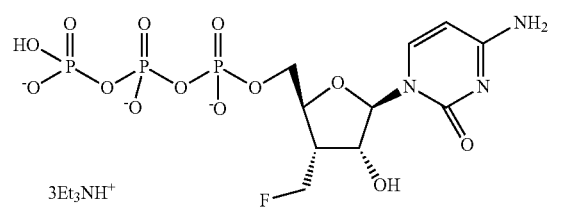
Powder; MS (ESI) m/z=498.0 (MH⁻).
Compound 311
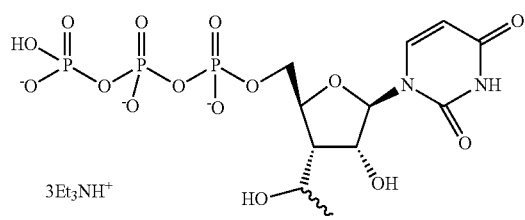
Solid; MS (ESI) m/z=511.0 (MH⁻).
Compound 316
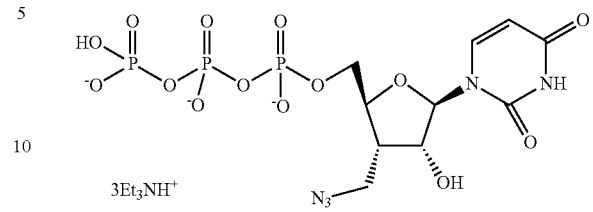
White solid; MS (ESI) m/z=522.0 (MH⁻).
Compound 317
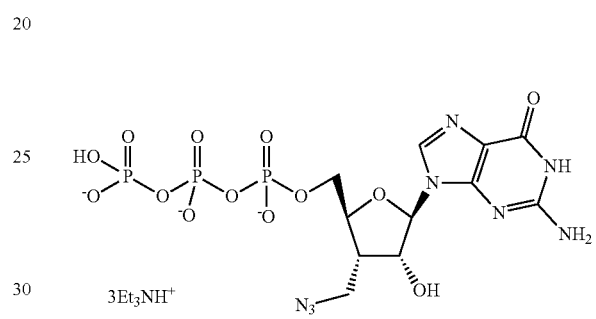
Not isolated.
Compound 320
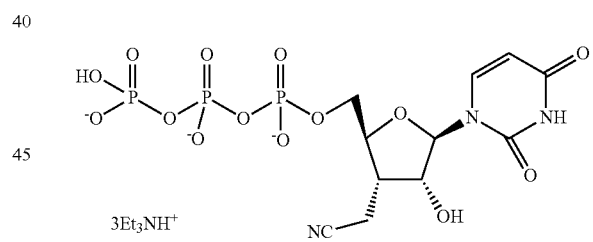
Powder; MS (ESI) m/z=506.0 (MH⁻).
Compound 326
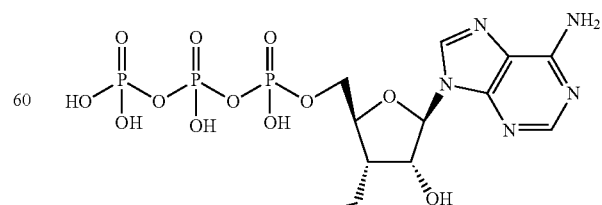
MS (ESI) m/z=522 (MH⁻).

Compound 327

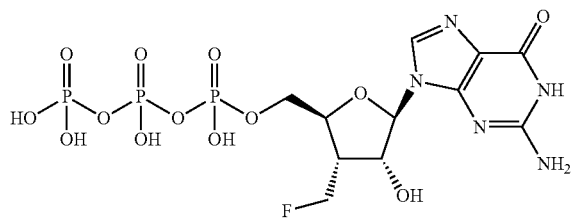

MS (ESI) m/z=538 (MH⁻).

General Method B.

The following procedure was used to obtain compounds 305-308 and 325.

The purified acetyl protected triphosphate (10-100 mg) was dissolved in concentrated aqueous ammonia and the reaction solution was left in refrigerator (4° C.) overnight. The product was purified using a Sephadex DEAE A-25 column with a linear gradient of 0-1M triethylammonium bicarbonate. The product containing fractions were pooled, concentrated and freeze-dried to give the desired compound.

Compound 305

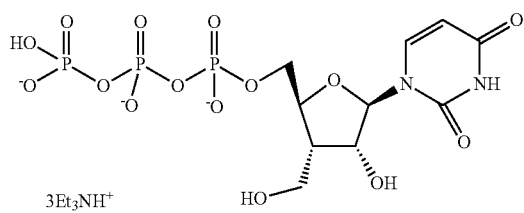

White solid; MS (ESI) m/z=497.0 (MH⁻).

Compound 306

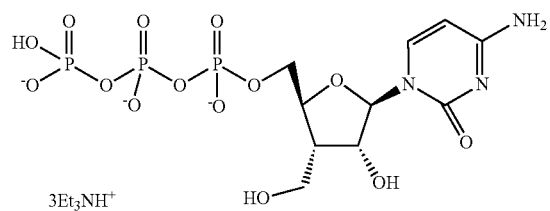

White solid; MS (ESI) m/z=496.0 (MH⁻).

Compound 307

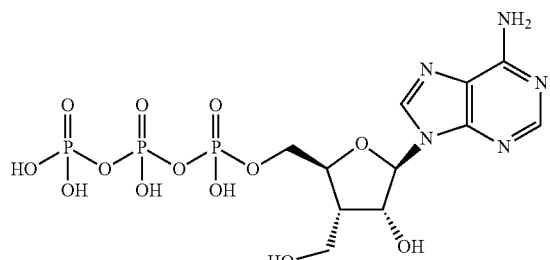

MS (ESI) m/z=520 (MH⁻).

Compound 308

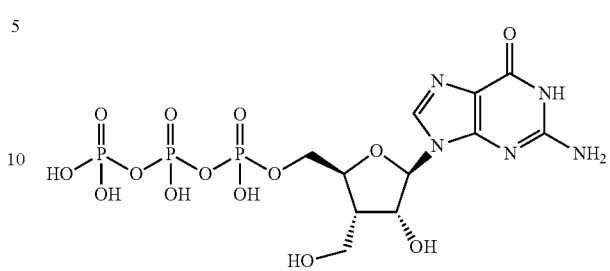

MS (ESI) m/z=536.0 (MH⁻).

General Method C.

The following procedure was used to obtain compounds 322 and 323.

The purified azido triphosphate (10-100 mg) was dissolved in water (10 ml). Pd/C (5%, 10 mg) was added and the reaction mixture was stirred under hydrogen atmosphere during 30 minutes. The product was purified using a Sephadex DEAE A-25 column with a linear gradient of 0-1M triethylammonium bicarbonate. The product containing fractions were pooled and concentrated and freeze-dried to give the desired compound.

Compound 322

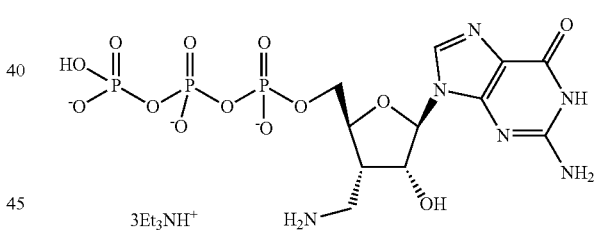

White solid; MS (ESI) m/z=535.0 (MH⁻).

Compound 323

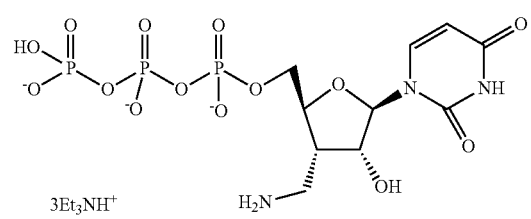

White solid; MS (ESI) m/z=496.0 (MH⁻).

247

Compound 340

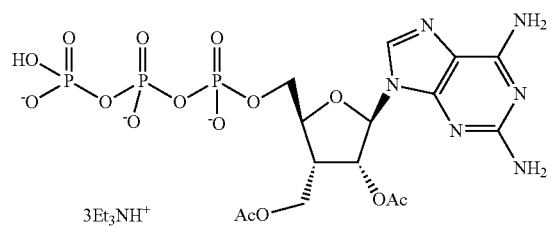

3Et$_3$NH$^+$    AcO    OAc

Not isolated.

Compound 330

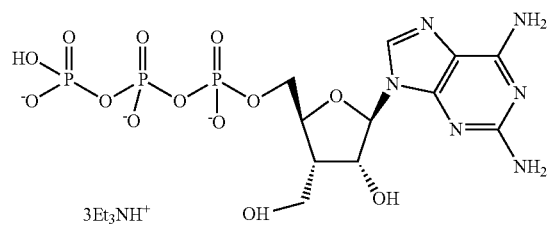

3Et$_3$NH$^+$    OH    OH

MS (ESI) m/z=535 (MH$^-$).

Compound 341

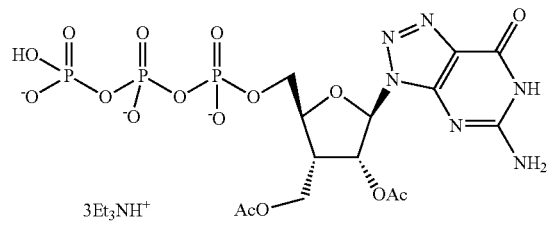

3Et$_3$NH$^+$    AcO    OAc

Not isolated.

Compound 331

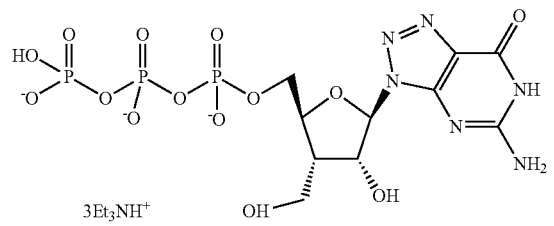

3Et$_3$NH$^+$    OH    OH

MS (ESI) m/z=537 (MH$^-$).

248

Compound 342

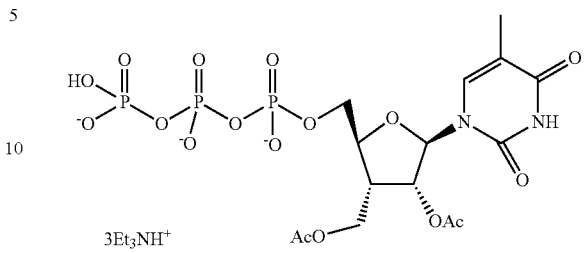

3Et$_3$NH$^+$    AcO    OAc

Not isolated.

Compound 332

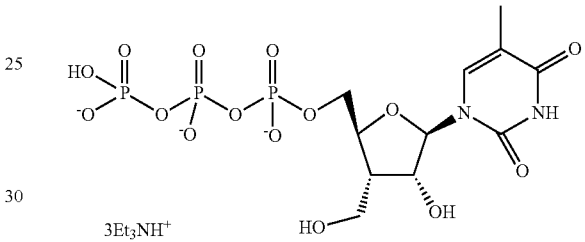

3Et$_3$NH$^+$    HO    OH

MS (ESI) m/z=511 (MH$^-$).

Scheme 12 bis

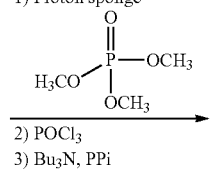

1) Proton sponge $$\underset{\underset{OCH_3}{OCH_3}}{\overset{O}{\underset{\|}{H_3CO-P-OCH_3}}}$$

2) POCl$_3$
3) Bu$_3$N, PPi

243: Base = 2,6-diaminopurine,
R$_2$ = H and R$_3$ = ——OAc
244: Base = U, R$_2$ = H and R$_3$ =
——OAc
245: Base = G, R$_2$ = H and R$_3$ =
——OAc

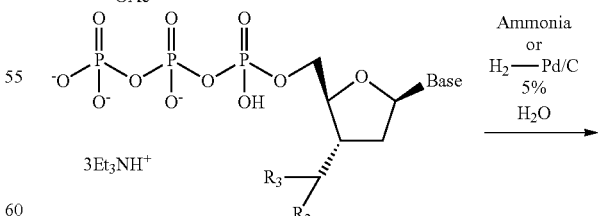

3Et$_3$NH$^+$

Ammonia
or
H$_2$——Pd/C
5%
H$_2$O
→

343: Base = 2,6-diaminopurine,
R$_2$ = H and R$_3$ = ——OAc
344: Base = U, R$_2$ = H and R$_3$ =
——OAc
345: Base = G, R$_2$ = H and R$_3$ =
——OAc

249
-continued

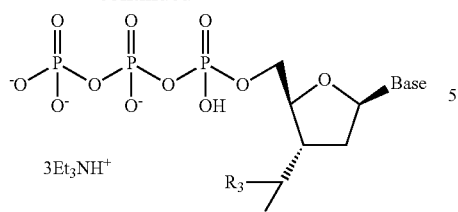

333: Base = 2,6-diaminopurine, R₂ = H and R₃ = ——OH
334: Base = U, R₂ = H and R₃ = ——OH
335: Base = G, R₂ = H and R₃ = ——OH Compound 343:

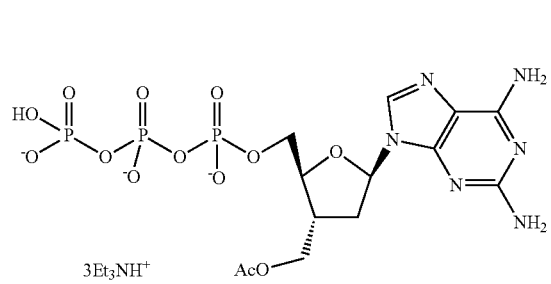

Not isolated.

Compound 333

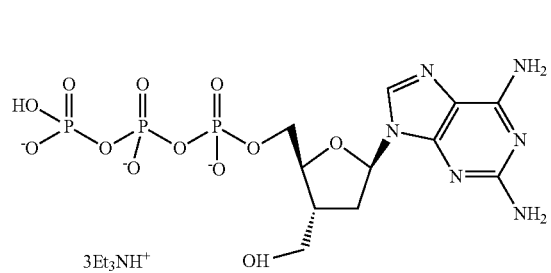

MS (ESI) m/z=519 (MH⁻).

Compound 344

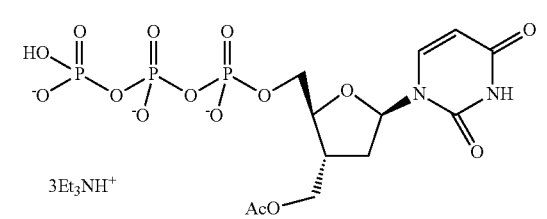

Not isolated.

250

Compound 334

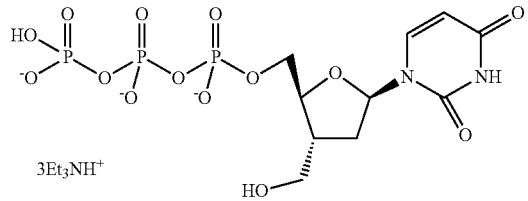

MS (ESI) m/z=481 (MH⁻).

Compound 345

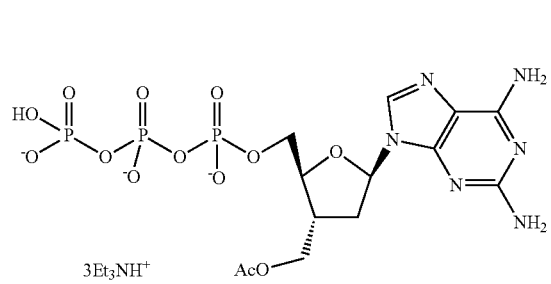

Not isolated.

Compound 335

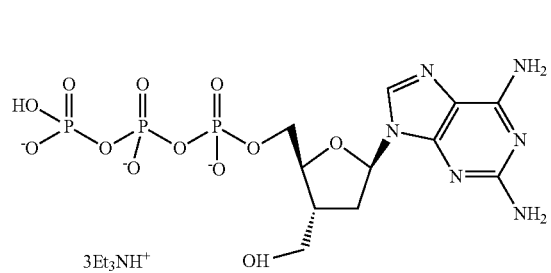

MS (ESI) m/z=520 (MH⁻).

Scheme 12 ter:

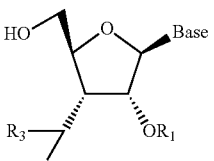

212: Base = U, R₁ = ——Ac
R₂ = H and R₃ = ——OAc 1) 2-Chloro4H-1,3,2-benzodioxaphosphorin-4-one, 0.5M in DMF DMF/Pyridine
2) PPi 1M
3) Bu₃N, Borane-dimethyl-sulfide 2M in THF
4) H₂O
5) NH₄OH

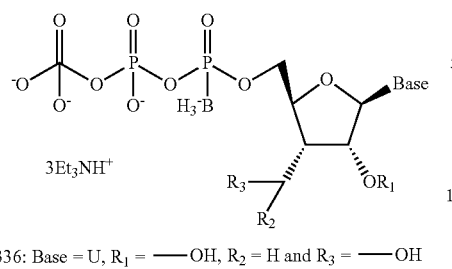

336: Base = U, R$_1$ = —OH, R$_2$ = H and R$_3$ = —OH

Compound 336

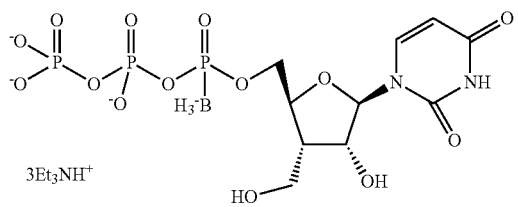

MS (ESI) m/z=495 (MH⁻).

The appropriate nucleoside was dissolved in anhydrous DMF and anhydrous pyridine (0.15 mL). A freshly prepared 0.5M solution of 2-chloro-4H-1,3,2-benzodioxaphosphorin-4-one in anhydrous DMF (0.55 mL) was added. After 10 min, a 1 M solution (2.5 ml) of tributylammonium pyrophosphate was added to the reaction mixture. After 30 min, tributylamine (1.0 mL) and a solution of 2M borane-dimethyl sulfide in THF were added (5 mL). The reaction mixture was stirred for 60 min, and water (2 mL) was added. After 30 min, the reaction was concentrated to dryness and the residue was treated with concentrated ammonium hydroxide (10 mL) at room temperature for 5 h. The reaction mixture was concentrated to dryness again and the residue was partitioned between water (20 mL) and diethyl ether (20 mL). The aqueous layer was purified using a Sephadex DEAE A-25 column with a linear gradient of 0-1 M triethylammonium (pH 7.5) to give the expected compound. The residue solid was dissolved in water and the concentration was adjusted to 10 mM with water (2.5 ml).

Preparation of Cyclic Phosphates and Cyclic Phosphonates

Scheme 13

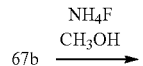

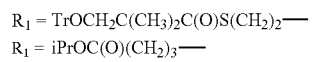

R$_1$ = TrOCH$_2$C(CH$_3$)$_2$C(O)S(CH$_2$)$_2$—
R$_1$ = iPrOC(O)(CH$_2$)$_3$—

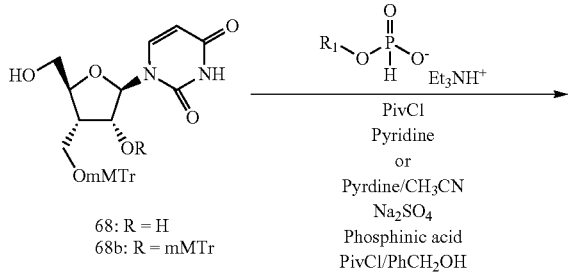

68: R = H
68b: R = mMTr

PivCl
Pyridine
or
Pyridine/CH$_3$CN
Na$_2$SO$_4$
Phosphinic acid
PivCl/PhCH$_2$OH

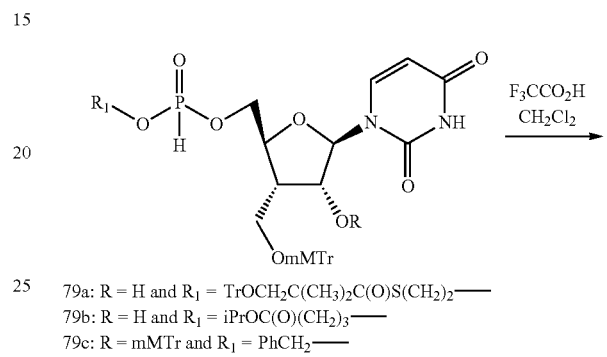

F$_3$CCO$_2$H
CH$_2$Cl$_2$

79a: R = H and R$_1$ = TrOCH$_2$C(CH$_3$)$_2$C(O)S(CH$_2$)$_2$—
79b: R = H and R$_1$ = iPrOC(O)(CH$_2$)$_3$—
79c: R = mMTr and R$_1$ = PhCH$_2$—

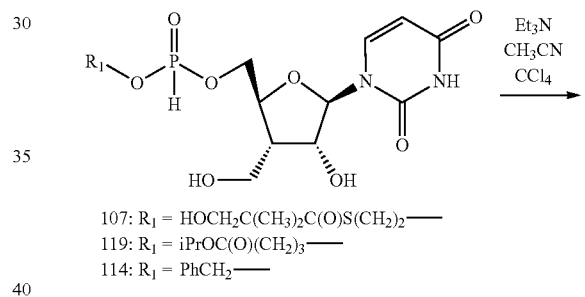

Et$_3$N
CH$_3$CN
CCl$_4$

107: R$_1$ = HOCH$_2$C(CH$_3$)$_2$C(O)S(CH$_2$)$_2$—
119: R$_1$ = iPrOC(O)(CH$_2$)$_3$—
114: R$_1$ = PhCH$_2$—

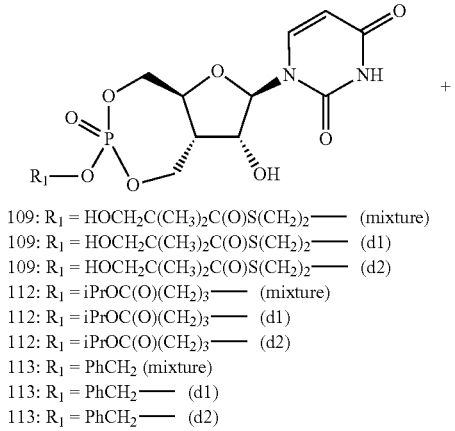

109: R$_1$ = HOCH$_2$C(CH$_3$)$_2$C(O)S(CH$_2$)$_2$— (mixture)
109: R$_1$ = HOCH$_2$C(CH$_3$)$_2$C(O)S(CH$_2$)$_2$— (d1)
109: R$_1$ = HOCH$_2$C(CH$_3$)$_2$C(O)S(CH$_2$)$_2$— (d2)
112: R$_1$ = iPrOC(O)(CH$_2$)$_3$— (mixture)
112: R$_1$ = iPrOC(O)(CH$_2$)$_3$— (d1)
112: R$_1$ = iPrOC(O)(CH$_2$)$_3$— (d2)
113: R$_1$ = PhCH$_2$ (mixture)
113: R$_1$ = PhCH$_2$— (d1)
113: R$_1$ = PhCH$_2$— (d2)

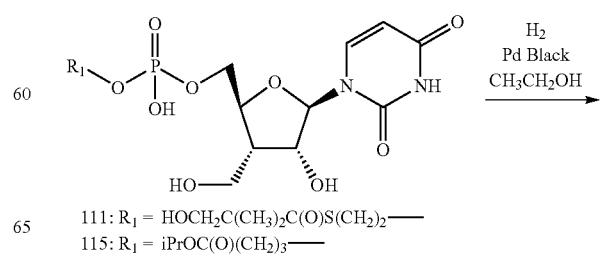

H$_2$
Pd Black
CH$_3$CH$_2$OH

111: R$_1$ = HOCH$_2$C(CH$_3$)$_2$C(O)S(CH$_2$)$_2$—
115: R$_1$ = iPrOC(O)(CH$_2$)$_3$—

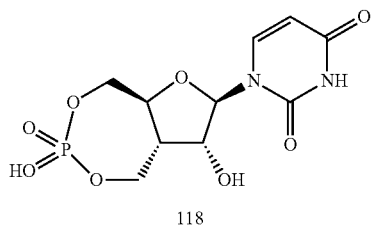

118

Compounds 107, 119, 114, 109, 112, 113, 111, 115 and 118 were prepared according to Scheme 13.

Compound 107

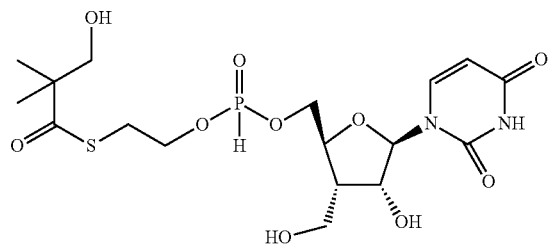 [SMILES: CC(C)(CO)C(=O)SCCO[PH](=O)OC[C@H]1O[C@@H](n2ccc(=O)[nH]c2=O)[C@H](O)[C@@H]1CO]

MS (ESI) m/z=505.2 (MNa⁺). ¹H NMR (400 MHz, DMSO) δ (ppm) 11.33 (s, 1H), 7.81 (d, J=6.85 Hz, 0.5H), 7.68-7.65 (m, 1H), 6.03 (d, J=7.05 Hz, 0.5H), 5.67 (d, J=2.44 Hz, 1H), 5.65-5.63 (m, 1H), 5.59 (dd, J=1.97 Hz and 8.07 Hz, 1H), 4.92 (t, J=5.53 Hz, 1H), 4.63-4.61 (m, 1H), 4.38-4.31 (m, 1H), 4.27-4.15 (m, 3H), 4.09-4.04 (m, 2H), 3.70-3.65 (m, 1H), 3.55-3.49 (m, 1H), 3.44 (d, J=5.48 Hz, 2H), 3.13-3.09 (m, 2H), 2.19-2.10 (m, 1H), 1.11 (s, 6H). ³¹P NMR (162 MHz, DMSO) δ (ppm) 9.69 (s, 0.45P), 9.27 (s, 0.55P).

Compound 114

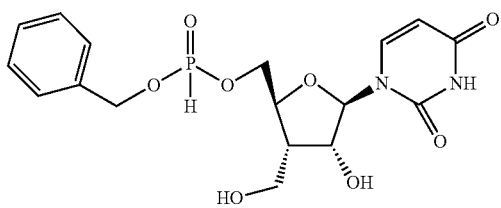 [SMILES: O=c1ccn([C@@H]2O[C@H](CO[PH](=O)OCc3ccccc3)[C@@H](CO)[C@H]2O)c(=O)[nH]1]

MS (ESI) m/z=413.2 (MH⁺). ¹H NMR (400 MHz, DMSO) δ (ppm) 11.33 (brs, 1H), 7.88 (d, J=7.82 Hz, 0.5H), 7.66 (dd, J=6.16 Hz and 8.09 Hz, 1H), 7.42-7.34 (m, 5H), 6.11 (d, J=8.20 Hz, 0.5H), 5.67 (d, J=2.39 Hz, 1H), 5.64 (brs, 1H), 5.52 (td, J=2.26 Hz and 8.45 Hz, 1H), 5.08 (d, J=9.10 Hz, 2H), 4.63 (brs, 1H), 4.38-4.31 (m, 1H), 4.26-4.16 (m, 3H), 3.67 (dd, J=5.61 Hz and 10.71 Hz, 1H), 3.51 (dd, J=7.31 Hz and 10.72 Hz, 1H), 2.19-2.11 (m, 1H). ³¹P NMR (162 MHz, DMSO) δ (ppm) 9.72 (s, 0.5P), 9.28 (s, 0.5P).

Compound 109

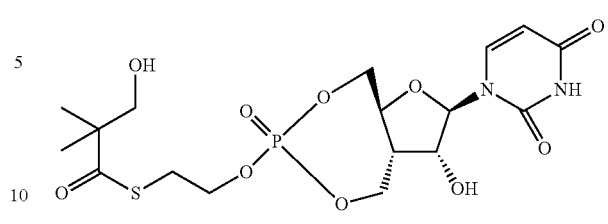

MS (ESI) m/z=503.2 (MNa⁺). ¹H NMR (400 MHz, DMSO) δ (ppm) 11.39-11.37 (m, 1H), 7.61-7.57 (m, 1H), 5.97-5.95 (m, 1H), 5.68-5.67 (m, 1H), 5.60 (td, J=2.11 Hz and 8.07 Hz, 1H), 4.96-4.89 (m, 1H), 4.47-4.24 (m, 4H), 4.19-4.0 (m, 4H), 3.44-3.43 (m, 2H), 3.14-3.09 (m, 2H), 2.68-2.52 (m, 1H), 1.13-1.12 (m, 6H). ³¹P NMR (162 MHz, DMSO) δ (ppm) -1.63 (s, 0.35P), -2.06 (s, 0.65P).

Diastereomer 1: MS (ESI) m/z=481.1 (MH⁺). ¹H NMR (400 MHz, DMSO) δ (ppm) 11.38 (brs, 1H), 7.57 (d, J=8.07 Hz, 1H), 5.95 (d, J=5.24 Hz, 1H), 5.67 (s, 1H), 5.59 (d, J=8.07 Hz, 1H), 4.93 (t, J=5.50 Hz, 1H), 4.46-4.27 (m, 4H), 4.15-4.03 (m, 4H), 3.43 (d, J=5.29 Hz, 2H), 3.12 (t, J=6.41 Hz, 2H), 2.58-2.51 (m, 1H), 1.11 (s, 6H). ³¹P NMR (162 MHz, DMSO) δ (ppm) -2.06 (s, 1P).

Diastereomer 2: MS (ESI) m/z=481.2 (MH⁺). ¹H NMR (400 MHz, DMSO) δ (ppm) 11.36 (brs, 1H), 7.58 (d, J=8.09 Hz, 1H), 5.97 (d, J=5.16 Hz, 1H), 5.66 (brs, 1H), 5.58 (d, J=8.04 Hz, 1H), 4.91 (t, J=5.45 Hz, 1H), 4.45-4.32 (m, 3H), 4.29-4.23 (m, 1H), 4.18-4.11 (m, 1H), 4.08-4.0 (m, 3H), 3.43 (d, J=5.47 Hz, 2H), 3.1 (t, J=6.41 Hz, 2H), 2.67-2.59 (m, 1H), 1.12 (s, 6H). ³¹P NMR (162 MHz, DMSO) δ (ppm) -1.63 (s, 1P).

Compound 112

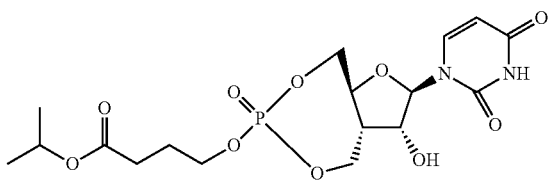

MS (ESI) m/z=449 (MH⁺). ¹H NMR (400 MHz, CDCl3) δ (ppm) 10.15 (s, 0.4H), 9.98 (s, 0.6H), 7.41 (d, J=8.10 Hz, 1H), 5.80-5.78 (m, 1H), 5.73 (s, 0.4H), 5.72 (s, 0.6H), 5.06-4.96 (m, 1H), 4.73 (td, J=4.06 Hz and 10.1 Hz, 1H), 4.62-4.52 (m, 1H), 4.50-4.42 (m, 2H), 4.40-4.25 (m, 1H), 4.22-4.15 (m, 2.4H), 4.04-3.96 (m, 0.6H), 2.74-2.66 (m, 0.4H), 2.43-2.39 (m, 2H), 2.35-2.28 (m, 0.6H), 2.05-1.98 (m, 2H), 1.24 (d, J=6.20 Hz, 6H). ³¹P NMR (162 MHz, CDCl3) δ (ppm) -0.34 (s, 0.40P), -1.00 (s, 0.60P).

Diastereomer 1: MS (ESI) m/z=449 (MH⁺). ¹H NMR (400 MHz, CDCl3) δ (ppm) 10.16 (brs, 1H), 7.42 (d, J=8.06 Hz, 1H), 5.80 (d, J=8.05 Hz, 1H), 5.73 (s, 1H), 5.05-4.95 (m, 2H), 4.72 (td, J=3.96 Hz and 10.02 Hz, 1H), 4.62-4.54 (m, 1H), 4.50-4.33 (m, 3H), 4.20-4.16 (m, 2H), 4 (q, J=10.50 Hz, 1H), 2.40 (t, J=7.06 Hz, 2H), 2.37-2.28 (m, 1H), 2.02 (quintuplet, J=6.67 Hz, 2H), 1.24 (d, J=6.25 Hz, 6H). ³¹P NMR (162 MHz, CDCl3) δ (ppm) -1.01 (s, 1P).

Diastereomer 2: MS (ESI) m/z=449 (MH⁺). ¹H NMR (400 MHz, CDCl3) δ (ppm) 10.27 (brs, 1H), 7.41 (d, J=7.68 Hz, 1H), 5.77 (d, J=7.71 Hz, 1H), 5.74 (s, 1H), 5.11 (brs, 1H), 5.04-4.98 (m, 1H), 4.62-4.43 (m, 4H), 4.35-4.17 (m, 4H), 2.73-2.66 (m, 1H), 2.41 (t, J=6.97 Hz, 2H), 2.01 (t, J=6.04 Hz, 2H), 1.24 (d, J=6.15 Hz, 6H). $^{31}$P NMR (162 MHz, CDCl3) δ (ppm) −0.34 (s, 1P).

Compound 113

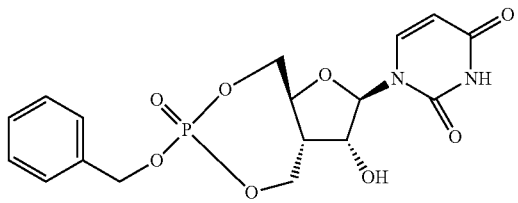

MS (ESI) m/z=411.2 (MH$^+$). $^1$H NMR (400 MHz, DMSO) δ (ppm) 11.39 (brs, 1H), 7.60 (d, J=8.02 Hz, 0.43H), 7.54 (d, J=8.07 Hz, 0.57H), 7.43-7.35 (m, 5H), 5.95 (brs, 1H), 5.67-5.66 (m, 1H), 5.61-5.57 (m, 1H), 5.11-5.07 (m, 2H), 4.45-4.00 (m, 7H). $^{31}$P NMR (162 MHz, DMSO) δ (ppm) −1.18 (s, 0.43P), −1.54 (s, 0.57P).

Diastereomer 1: MS (ESI) m/z=411.1 (MH$^+$). $^1$H NMR (400 MHz, DMSO) δ (ppm) 11.38 (brs, 1H), 7.54 (d, J=8.07 Hz, 1H), 7.43-7.34 (m, 5H), 5.95 (d, J=5.22 Hz, 1H), 5.66 (brs, 1H), 5.58 (d, J=8.03 Hz, 1H), 5.10 (d, J=8.08 Hz, 2H), 4.45-4.29 (m, 4H), 4.17-4.03 (m, 2H), 2.58-2.50 (m, 1H). $^{31}$P NMR (162 MHz, DMSO) δ (ppm) −1.54 (s, 1P).

Diastereomer 2: MS (ESI) m/z=411.1 (MH$^+$). $^1$H NMR (400 MHz, DMSO) δ (ppm) 11.37 (brs, 1H), 7.60 (d, J=8.08 Hz, 1H), 7.43-7.34 (m, 5H), 5.96 (d, J=4.77 Hz, 1H), 5.67 (s, 1H), 5.59 (d, J=8.05 Hz, 1H), 5.11-5.07 (m, 2H), 4.46-4.09 (m, 5H), 4.04 (q, J=10.80 Hz, 1H), 2.69-2.61 (m, 1H). $^{31}$P NMR (162 MHz, DMSO) δ (ppm) −1.18 (s, 1P).

Compound 111

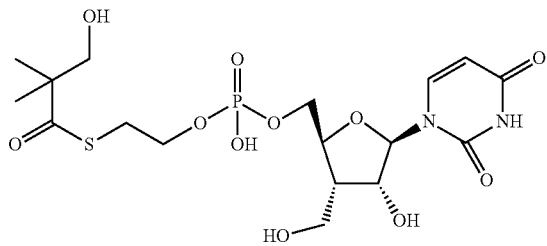 [SMILES: CC(C)(CO)C(=O)SCCOP(=O)(O)OC[C@H]1O[C@@H](n2ccc(=O)[nH]c2=O)[C@H](O)[C@@H]1CO]

MS (ESI) m/z=499 (MH$^+$). $^1$H NMR (400 MHz, MeOD) δ (ppm) 8.15 (d, J=8.06 Hz, 1H), 5.79 (d, J=8.06 Hz, 1H), 5.79 (d, J=1.96 Hz, 1H), 4.37 (dd, J=1.96 Hz and 5.54 Hz, 1H), 4.30-4.24 (m, 2H), 4.08-4.03 (m, 1H), 3.97-3.90 (m, 2H), 3.86 (dd, J=6.72 Hz and 11.19 Hz, 1H), 3.75 (dd, J=6.06 Hz and 11.14 Hz, 1H), 3.57 (s, 2H), 3.15-3.11 (m, 2H), 2.49-2.42 (m, 1H), 1.193 (s, 3H), 1.190 (s, 3H). $^{31}$P NMR (162 MHz, MeOD) δ (ppm) −0.03 (s, 1P).

Compound 115

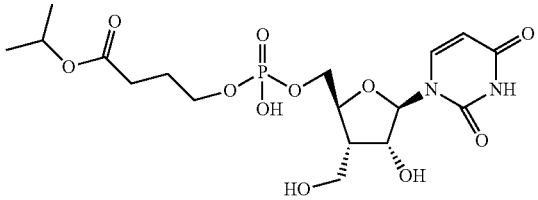 [SMILES: CC(C)OC(=O)CCCOP(=O)(O)OC[C@H]1O[C@@H](n2ccc(=O)[nH]c2=O)[C@H](O)[C@@H]1CO]

MS (ESI) m/z=467 (MH$^+$). $^1$H NMR (400 MHz, DMSO) δ (ppm) 11.24 (brs, 1H), 8.12 (brs, 1H), 5.66-5.63 (m, 2H), 5.52 (brs, 1H), 5.26 (brs, 1H), 4.87 (heptuplet, J=6.22 Hz, 1H), 4.16-4.14 (m, 1H), 4.09-3.98 (m, 2H), 3.95-3.88 (m, 1H), 3.69-3.65 (m, 3H), 3.49-3.45 (m, 1H), 2.93 (brs, 1H), 2.33-2.27 (m, 3H), 1.76-1.69 (m, 2H), 1.16 (d, J=6.24 Hz, 6H). $^{31}$P NMR (162 MHz, DMSO) δ (ppm) −1.52 (s, 1P).

Compound 118

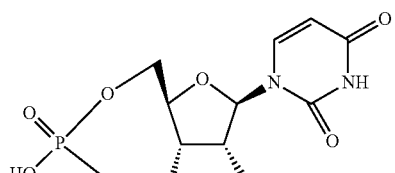

MS (ESI) m/z=343.1 (MNa$^+$). $^1$H NMR (400 MHz, DMSO) δ (ppm) 11.36 (brs, 1H), 7.56 (d, J=8.07 Hz, 1H), 5.89 (brs, 1H), 5.65 (brs, 1H), 5.60 (dd, J=2.18 Hz and 8.06 Hz, 1H), 4.34-4.12 (m, 5H), 4.01-3.92 (m, 1H), 2.63-2.53 (m, 1H), 1.23 (brs, 1H). $^{31}$P NMR (162 MHz, DMSO) δ (ppm) −1.30 (s, 1P).

Scheme 14

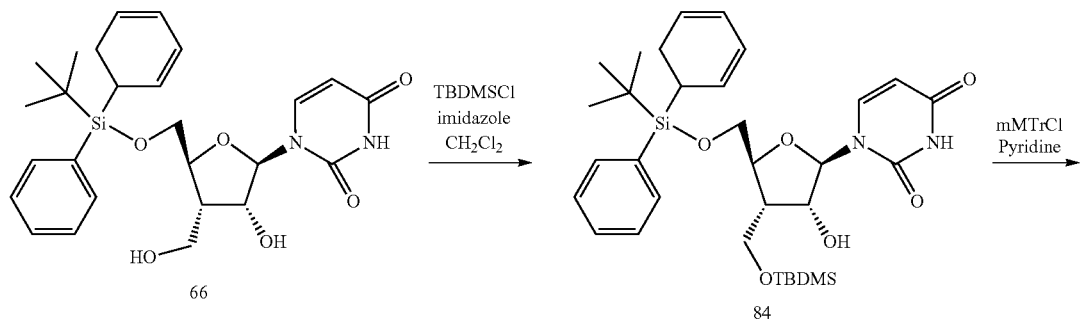

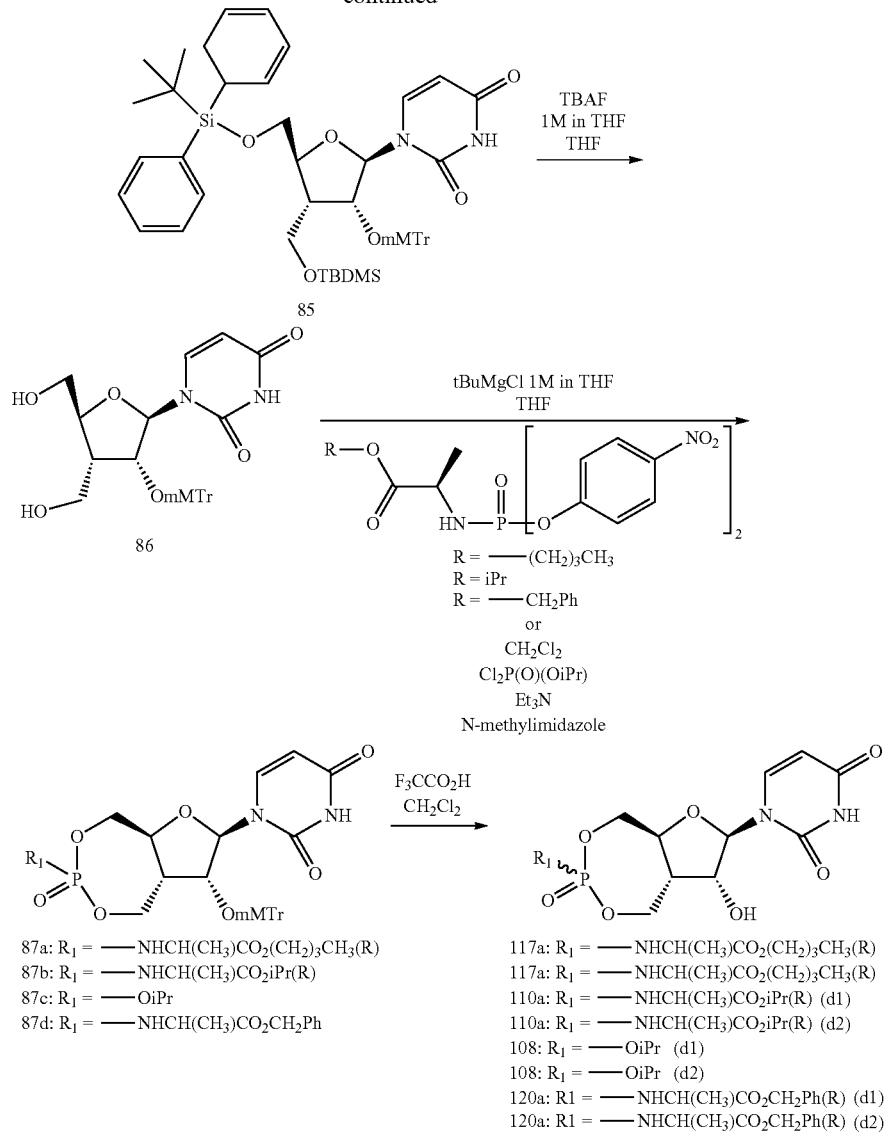
Compounds 117a, 110a, 108, and 120a were prepared according to Scheme 14.
Compound 117a
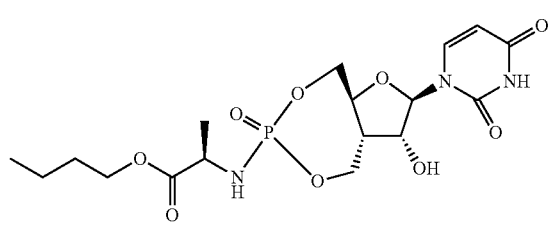
Diastereomer 1: MS (ESI) m/z=448 (MH+). $^1$H NMR (400 MHz, MeOD) δ (ppm) 7.56 (d, J=8.11 Hz, 1H), 5.71 (s, 1H), 5.69 (d, J=8.10 Hz, 1H), 4.52-4.26 (m, 5H), 4.19-4.09 (m, 3H), 3.96-3.88 (m, 1H), 2.51-2.44 (m, 1H), 1.68-1.61 (m, 2H), 1.46-1.38 (m, 5H), 0.96 (t, J=7.34 Hz, 3H). $^{31}$P NMR (162 MHz, MeOD) δ (ppm) 9.76 (s, 1P).
Diastereomer 2: MS (ESI) m/z=448.2 (MH+). $^1$H NMR (400 MHz, MeOD) δ (ppm) 7.58 (d, J=8.10 Hz, 1H), 5.73 (s, 1H), 5.70 (d, J=8.10 Hz, 1H), 4.46-4.36 (m, 4H), 4.23-4.12 (m, 4H), 3.92-3.85 (m, 1H), 2.63-2.56 (m, 1H), 1.68-1.61 (m, 2H), 1.47-1.36 (m, 5H), 0.96 (t, J=7.34 Hz, 3H). $^{31}$P NMR (162 MHz, MeOD) δ (ppm) 10.08 (s, 1P).
Compound 110a
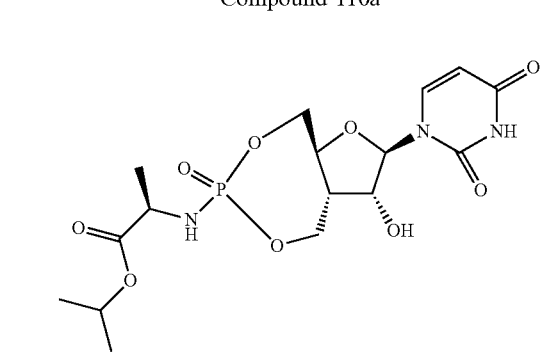
Diastereomer 1: MS (ESI) m/z=434.2 (MH+). $^1$H NMR (400 MHz, DMSO) δ (ppm) 11.38 (brs, 1H), 7.50 (d, J=8.11

Hz, 1H), 5.89 (brs, 1H), 5.66-5.60 (m, 3H), 4.89 (heptuplet, J=6.22 Hz, 1H), 4.36-4.17 (m, 4H), 4.08-4.0 (m, 2H), 3.79-3.69 (m, 1H), 2.48-2.39 (m, 1H), 1.25 (d, J=7.19 Hz, 3H), 1.21-1.18 (m, 6H). $^{31}$P NMR (162 MHz, DMSO) δ (ppm) 8.57 (s, 1P).

Diastereomer 2: MS (ESI) m/z=434.2 (MH$^+$). $^1$H NMR (400 MHz, DMSO) δ (ppm) 11.36 (brs, 1H), 7.56 (d, J=8.10 Hz, 1H), 5.92 (brs, 1H), 5.68-5.63 (m, 2H), 5.59 (d, J=8.08 Hz, 1H), 4.89 (heptuplet, J=6.21 Hz, 1H), 4.35 (d, J=5.32 Hz, 1H), 4.31-4.16 (m, 3H), 4.12-3.95 (m, 2H), 3.75-3.65 (m, 1H), 2.56-2.52 (m, 1H), 1.23 (d, J=7.13 Hz, 3H), 1.20-1.17 (m, 6H). $^{31}$P NMR (162 MHz, DMSO) δ (ppm) 8.69 (s, 1P).

Compound 108

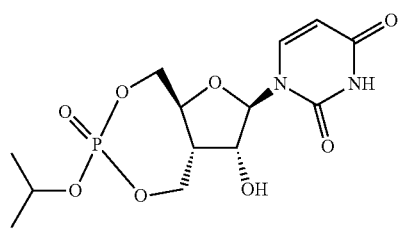

Diastereomer 1: MS (ESI) m/z=361.3 (MH$^-$). $^1$H NMR (400 MHz, DMSO) δ (ppm) 11.36 (brs, 1H), 7.58 (d, J=8.04 Hz, 1H), 5.95 (brs, 1H), 5.66 (brs, 1H), 5.59 (d, J=8.07 Hz, 1H), 4.63-4.55 (m, 1H), 4.44-4.29 (m, 4H), 4.13-4.0 (m, 2H), 2.56-2.52 (m, 1H), 1.28 (d, J=6.17 Hz, 3H), 1.27 (d, J=6.17 Hz, 3H). $^{31}$P NMR (162 MHz, DMSO) δ (ppm) −2.24 (s, 1P).

Diastereomer 2: MS (ESI) m/z=363.2 (MH$^+$). $^1$H NMR (400 MHz, DMSO) δ (ppm) 11.37 (brs, 1H), 7.58 (d, J=8.08 Hz, 1H), 5.98 (brs, 1H), 5.66 (brs, 1H), 5.59 (d, J=8.08 Hz, 1H), 4.64-4.53 (m, 1H), 4.42-4.30 (m, 3H), 4.27-4.21 (m, 1H), 4.16-4.09 (m, 1H), 4.05-3.97 (m, 1H), 2.68-2.59 (m, 1H), 1.26 (d, J=6.16 Hz, 6H). $^{31}$P NMR (162 MHz, DMSO) δ (ppm) −1.94 (s, 1P).

Compound 120a

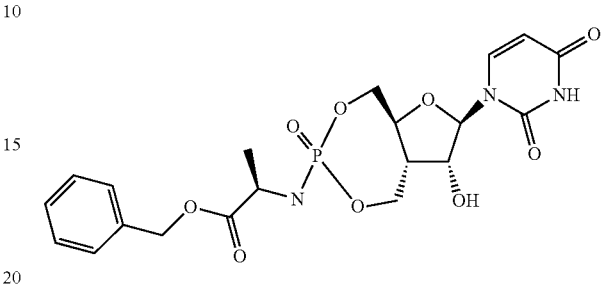

Diastereomer 1: White powder; MS (ESI) m/z=482.0 (MH$^+$); $^1$H NMR (CD$_3$OD, 400 MHz) δ (ppm) 7.55 (d, J=8.16 Hz, 1H), 7.42-7.31 (m, 5H), 5.71 (d, J=8.16 Hz, 1H), 5.71 (s, 1H), 5.20 (s, 2H), 4.51-4.24 (m, 5H), 4.18-4.10 (m, 1H), 4.03-3.95 (m, 1H), 2.47-2.40 (m, 1H), 1.41 (d, J=7.17 Hz, 3H); $^{31}$P NMR (CD$_3$OD, 162 MHz) δ (ppm) 9.65 (s, 1P).

Diastereomer 2: White powder. MS (ESI) m/z=482.2 (MH$^+$). $^1$H NMR (CD$_3$OD, 400 MHz) δ (ppm) 7.58 (d, J=8.12 Hz, 1H), 7.42-7.32 (m, 5H), 5.74 (s, 1H), 5.72 (d, J=8.12 Hz, 1H), 5.19 (s, 2H), 4.45 (d, J=5.23 Hz, 1H), 4.42-4.37 (m, 2H), 4.35-4.31 (m, 1H), 4.22-4.14 (m, 2H), 4.00-3.92 (m, 1H), 2.63-2.56 (m, 1H), 1.40 (d, J=7.23 Hz, 3H). $^{31}$P NMR (CD$_3$OD, 162 MHz) δ (ppm) 10.06 (s, 1P).

Preparation of Compound 106b

Scheme 15

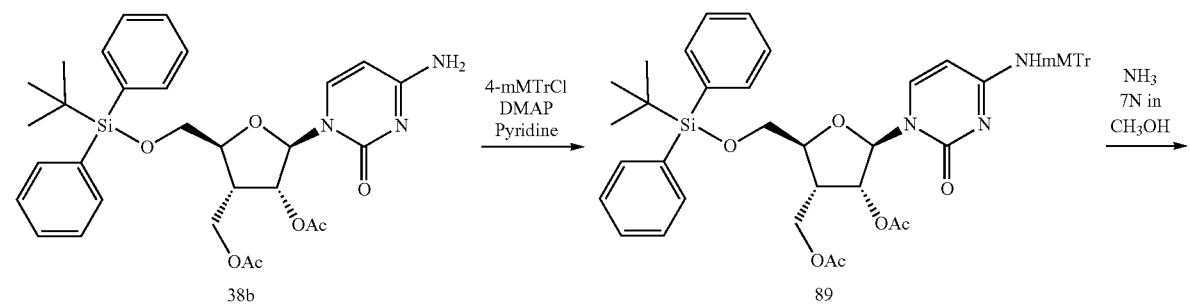

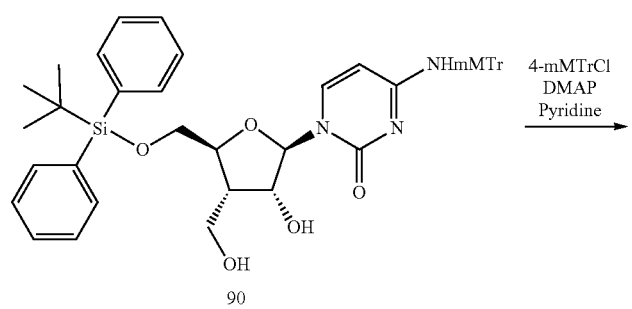

-continued
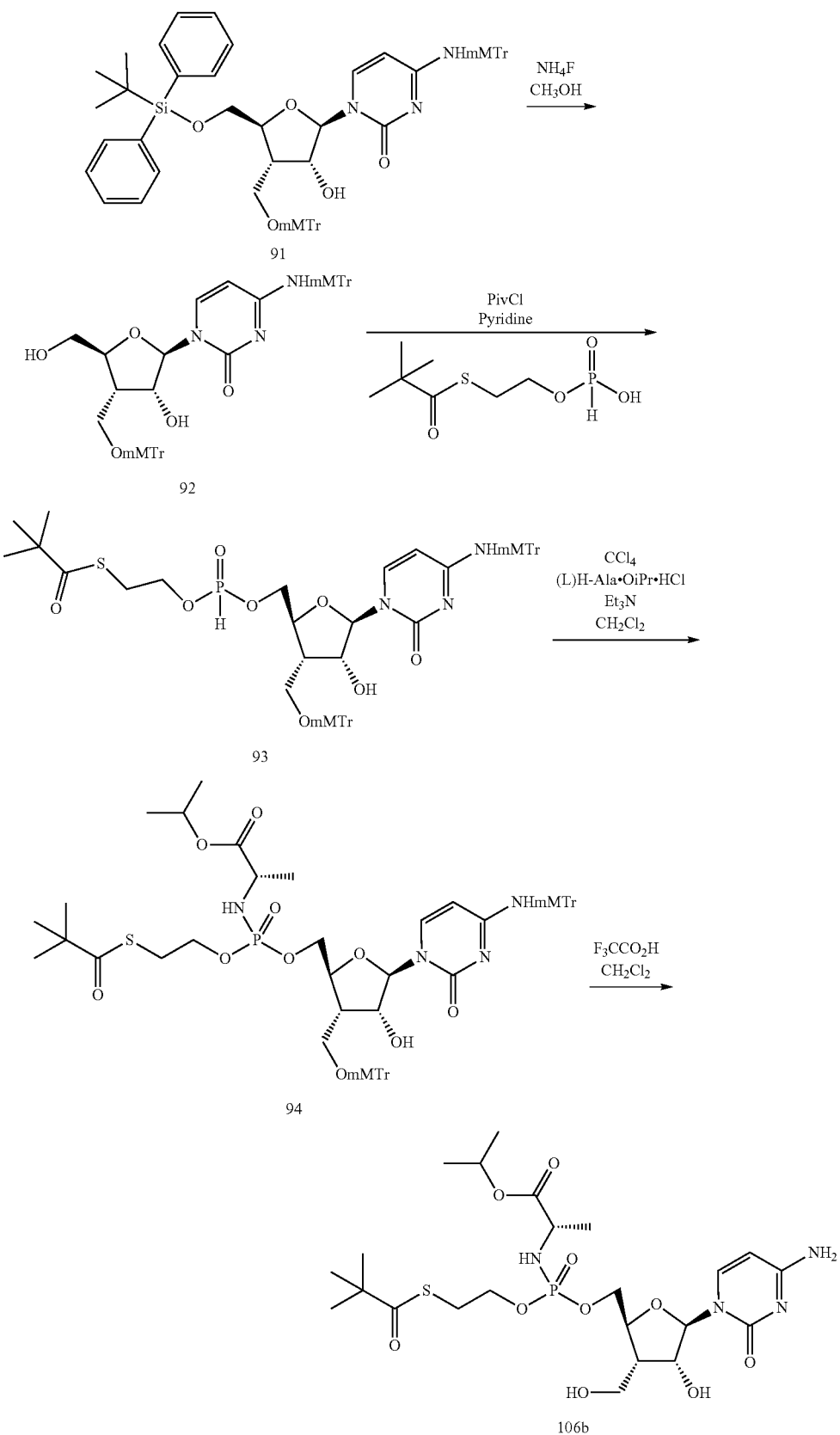

Compound 106b was prepared according to Scheme 15. MS (ESI) m/z=595.3 (MH+). $^1$H NMR (400 MHz, DMSO) δ (ppm) 7.71-7.67 (m, 1H), 7.15 (brs, 1H), 7.03 (brs, 1H), 5.70 (d, J=7.39 Hz, 0.52H), 5.69 (d, J=7.39 Hz, 0.48H), 5.66-5.53 (m, 3H), 4.92-4.85 (m, 1H), 4.53-4.49 (m, 1H), 4.29-4.22 (m, 1H), 4.16-3.89 (m, 5H), 3.77-3.63 (m, 2H), 3.50-3.44 (m, 1H), 3.12-3.05 (m, 2H), 2.09-2.00 (m, 1H), 1.26 (d, J=7.04 Hz, 3H), 1.20-1.17 (m, 15H). $^{31}$P NMR (162 MHz, DMSO) δ (ppm) 8.11 (s, 0.52P), 7.88 (s, 0.48P).
Preparation of Mono-, Di- and Tri-Phosphates
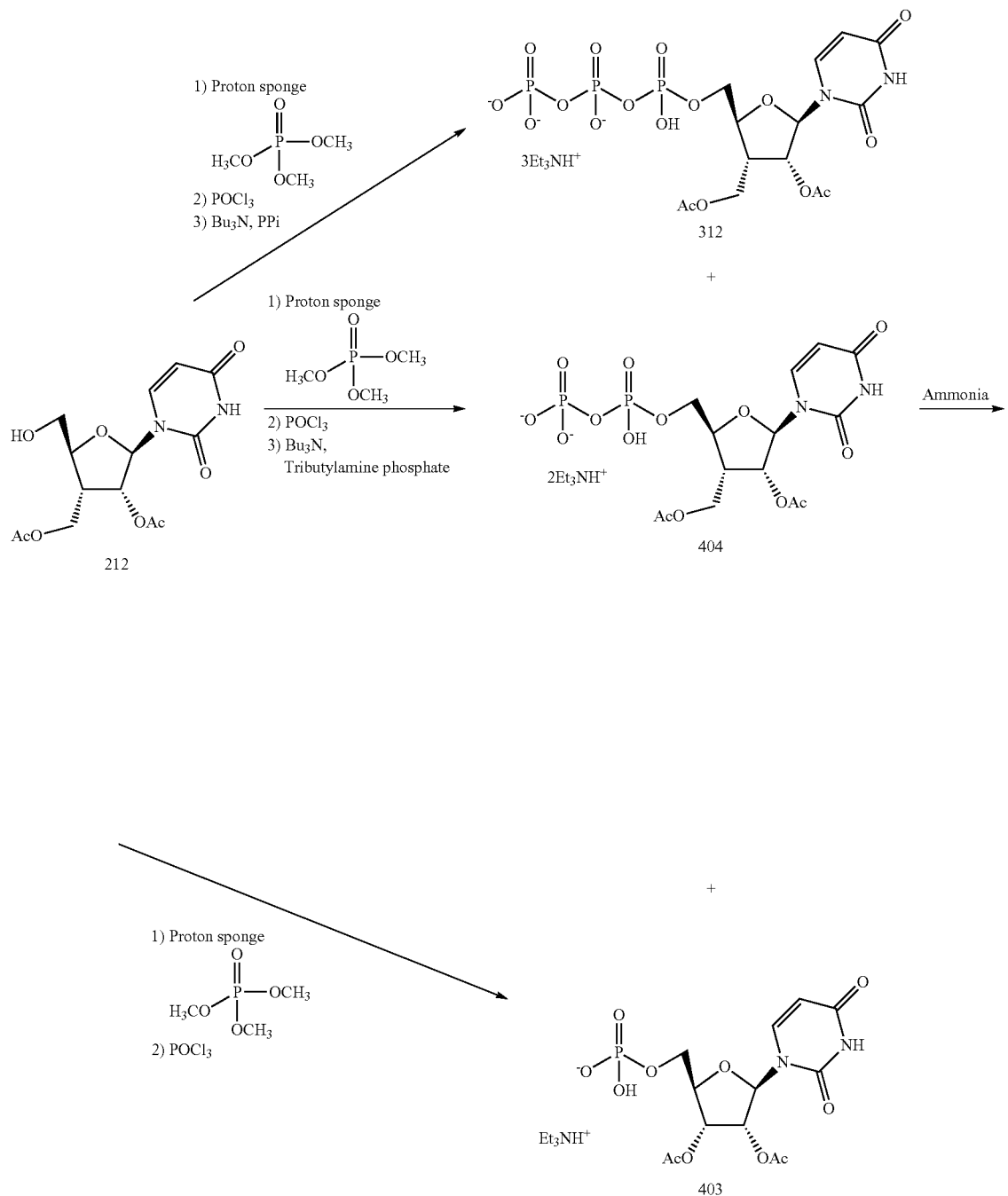

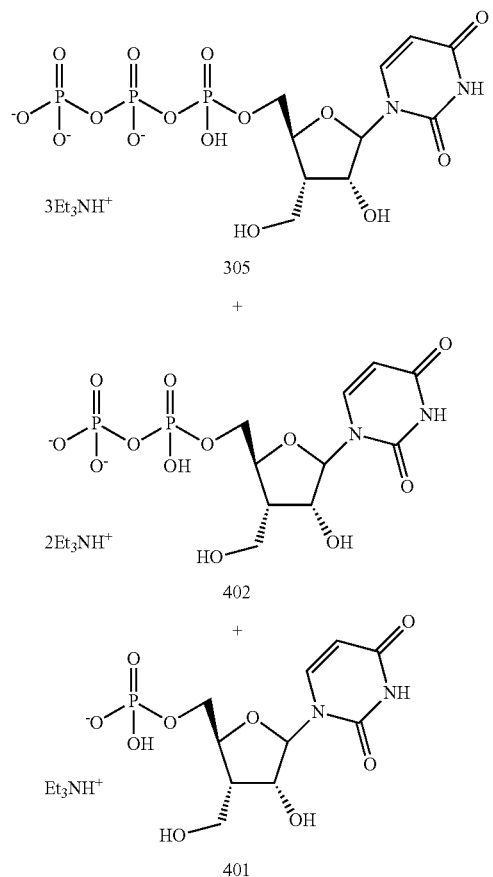

305

+

402

+

401

The following procedure was used to obtain compound 404.

The appropriate nucleoside (100 mg) was dried under vacuum overnight. Trimethylphosphate (1.9 mL) and proton sponge (100 mg) were added to the flask and the reaction mixture was stirred under nitrogen cooled by an ice/water bath. Distilled phosphorus oxychloride (45 µL) was added and the reaction mixture was stirred for 4 hours with cooling. Tributylamine (0.32 mL) and tributylamine phosphate (4.0 mL of a 0.5 M solution in DMF) were added and the reaction was allowed to stir for an additional 45 min with cooling. The reaction was quenched with triethylammonium bicarbonate (0.5 M, 20 mL) and the solvents were concentrated under reduced pressure. The crude mixture was dissolved in 10 mL of water and purified using a Sephadex DEAE A-25 column with a linear gradient of 0-1M NaCl buffered with 20 mM Tris-HCl (pH 7.0) (diphosphates eluted at ~0.2 M NaCl) and desalted on a C18 column to give the expected compound.

The following procedure was used to obtain compound 403.

The appropriate nucleoside (100 mg) was dried under vacuum overnight. Trimethylphosphate (1.9 mL) and proton sponge (100 mg) were added to the flask and the reaction mixture was stirred under nitrogen cooled by an ice/water bath. Distilled phosphorus oxychloride (45 µL) was added and the reaction mixture was stirred for 4 hours with cooling.

The reaction was quenched with triethylammonium bicarbonate (0.5 M, 20 mL) and the reaction mixture was concentrated under reduced pressure. The crude mixture was dissolved in 10 mL of water and purified using a Sephadex DEAE A-25 column with a linear gradient of 0-1M NaCl buffered with 20 mM Tris-HCl (pH 7.0) (monophosphates eluted at ~0.1 M NaCl) and desalted on a C18 column to give the expected compound.

Compounds 402 and 401 were prepared according to Scheme 16 and according to general method B.

Compound 402

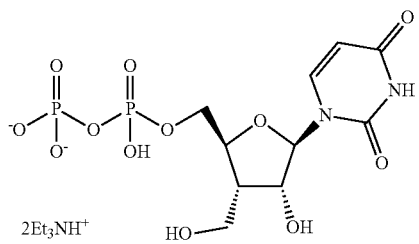

MS (ESI) m/z=417 (MH$^-$).

Compound 401

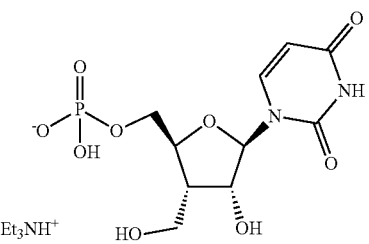

MS (ESI) m/z=337 (MH$^-$).

Scheme 17:
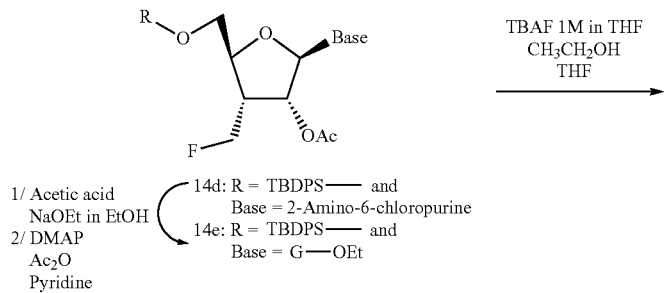
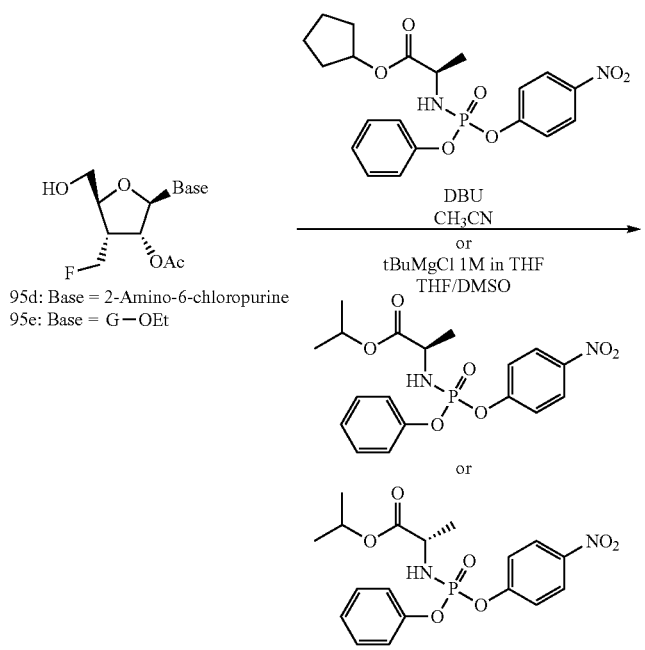
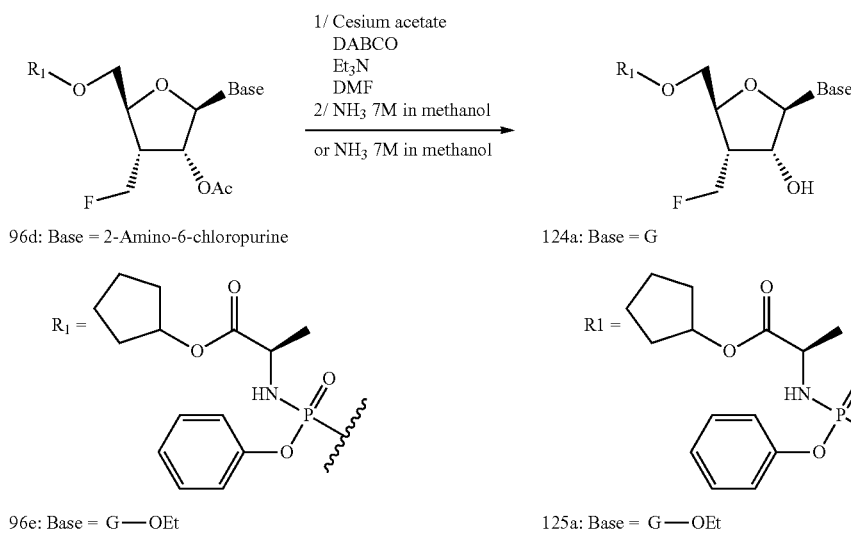

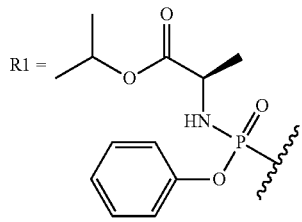

96f: Base = G—OEt

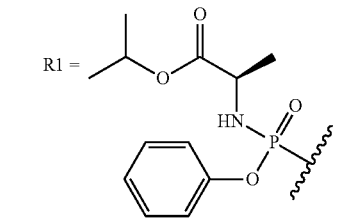

125b: Base = G—OEt

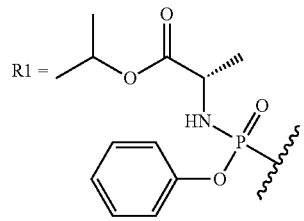

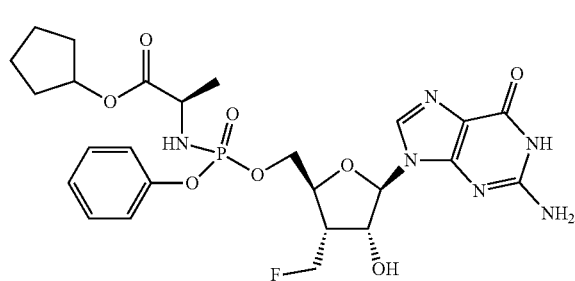 [SMILES: C[C@@H](NP(=O)(OC[C@H]1O[C@@H](n2cnc3c(=O)[nH]c(N)nc32)[C@H](O)[C@@H]1CF)Oc1ccccc1)C(=O)OC1CCCC1]

Compound 124a

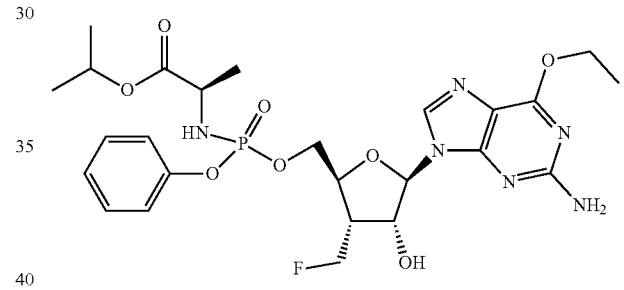

Compound 125a

Compound 124a (diastereoisomer 1): white solid; $^1$H NMR (DMSO-d$_6$, 400 MHz) δ (ppm) 10.72 (brs, 1H), 7.86 (s, 1H), 7.37-7.33 (m, 2H), 7.18-7.15 (m, 3H), 6.54 (brs, 2H), 5.99 (dd, J=12.96 Hz and 10.07 Hz, 1H), 5.96-5-95 (m, 1H), 5.72 (d, J=3.26 Hz, 1H), 5.01-4.97 (m, 1H), 4.79-4.69 (m, 1H), 4.67-4.57 (m, 2H), 4.31-4.24 (m, 2H), 4.17-4.11 (m, 1H), 3.78-3.67 (m, 1H), 2.89-2.78 (m, 1H), 1.79-1.71 (m, 2H), 1.60-1.46 (m, 6H), 1.13 (d, J=7.14 Hz, 3H); $^{19}$F NMR (DMSO-d$_6$, 376 MHz) δ (ppm) −225.21 (s, 1F); $^{31}$P NMR (DMSO-d$_6$, 162 MHz) δ (ppm) 3.81 (s, 1P); MS (ESI) m/z=595.4 (MH$^+$).

Compound 124a (diastereoisomer 2): white solid; $^1$H NMR (DMSO-d$_6$, 400 MHz) δ (ppm) 10.69 (brs, 1H), 7.81 (s, 1H), 7.36-7.32 (m, 2H), 7.21-7.14 (m, 3H), 6.52 (brs, 2H), 6.04 (dd, J=13.22 Hz and 10.05 Hz, 1H), 5.96-5-95 (m, 1H), 5.71 (d, J=3.17 Hz, 1H), 5.04-4.99 (m, 1H), 4.77-4.55 (m, 3H), 4.29-4.20 (m, 2H), 4.16-4.11 (m, 1H), 3.78-3.68 (m, 1H), 2.81-2.71 (m, 1H), 1.80-1.71 (m, 2H), 1.60-1.47 (m, 6H), 1.17 (d, J=7.21 Hz, 3H); $^{19}$F NMR (DMSO-d$_6$, 376 MHz) δ (ppm) −225.42 (s, 1F); $^{31}$P NMR (DMSO-d$_6$, 162 MHz) δ (ppm) 3.61 (s, 1P); MS (ESI) m/z=595.4 (MH$^+$).

Compound 125a (diastereoisomer 1): white solid; $^1$H NMR (DMSO-d$_6$, 400 MHz) δ (ppm) 7.98 (s, 1H), 7.35-7.31 (m, 2H), 7.21-7.14 (m, 3H), 6.45 (brs, 2H), 6.02 (dd, J=13.12 Hz and 10.09 Hz, 1H), 5.96 (brs, 1H), 5.81 (d, J=2.97 Hz, 1H), 4.84 (heptuplet, J=6.20 Hz, 1H), 4.79-4.68 (m, 1H), 4.67-4.56 (m, 2H), 4.46 (q, J=7.10 Hz, 2H), 4.31-4.23 (m, 2H), 4.18-4.12 (m, 1H), 3.80-3.69 (m, 1H), 2.87-2.75 (m, 1H), 1.36 (t, J=7.10 Hz, 3H), 1.19 (d, J=7.10 Hz, 3H), 1.13 (d, J=6.54 Hz, 3H), 1.11 (d, J=6.54 Hz, 3H); $^{19}$F NMR (DMSO-d$_6$, 376 MHz) δ (ppm) −225.32 (s, 1F); $^{31}$P NMR (DMSO-d$_6$, 162 MHz) δ (ppm) 3.59 (s, 1P); MS (ESI) m/z=597.2 (MH$^+$).

Compound 125a (diastereoisomer 2): white solid; $^1$H NMR (DMSO-d$_6$, 400 MHz) δ (ppm) 8.03 (s, 1H), 7.37-7.33 (m, 2H), 7.18-7.15 (m, 3H), 6.46 (brs, 2H), 5.99-5.93 (m, 2H), 5.82 (d, J=3.03 Hz, 1H), 4.82 (heptuplet, J=6.21 Hz, 1H), 4.79-4.58 (m, 3H), 4.46 (q, J=7.12 Hz, 2H), 4.34-4.27 (m, 2H), 4.19-4.13 (m, 1H), 3.78-3.68 (m, 1H), 2.94-2.82 (m, 1H), 1.36 (t, J=7.12 Hz, 3H), 1.14-1.10 (m, 9H); $^{19}$F NMR (DMSO-d$_6$, 376 MHz) δ (ppm) −225.16 (s, 1F); $^{31}$P NMR (DMSO-d$_6$, 162 MHz) δ (ppm) 3.82 (s, 1P); MS (ESI) m/z=597.2 (MH$^+$).

Scheme 18:
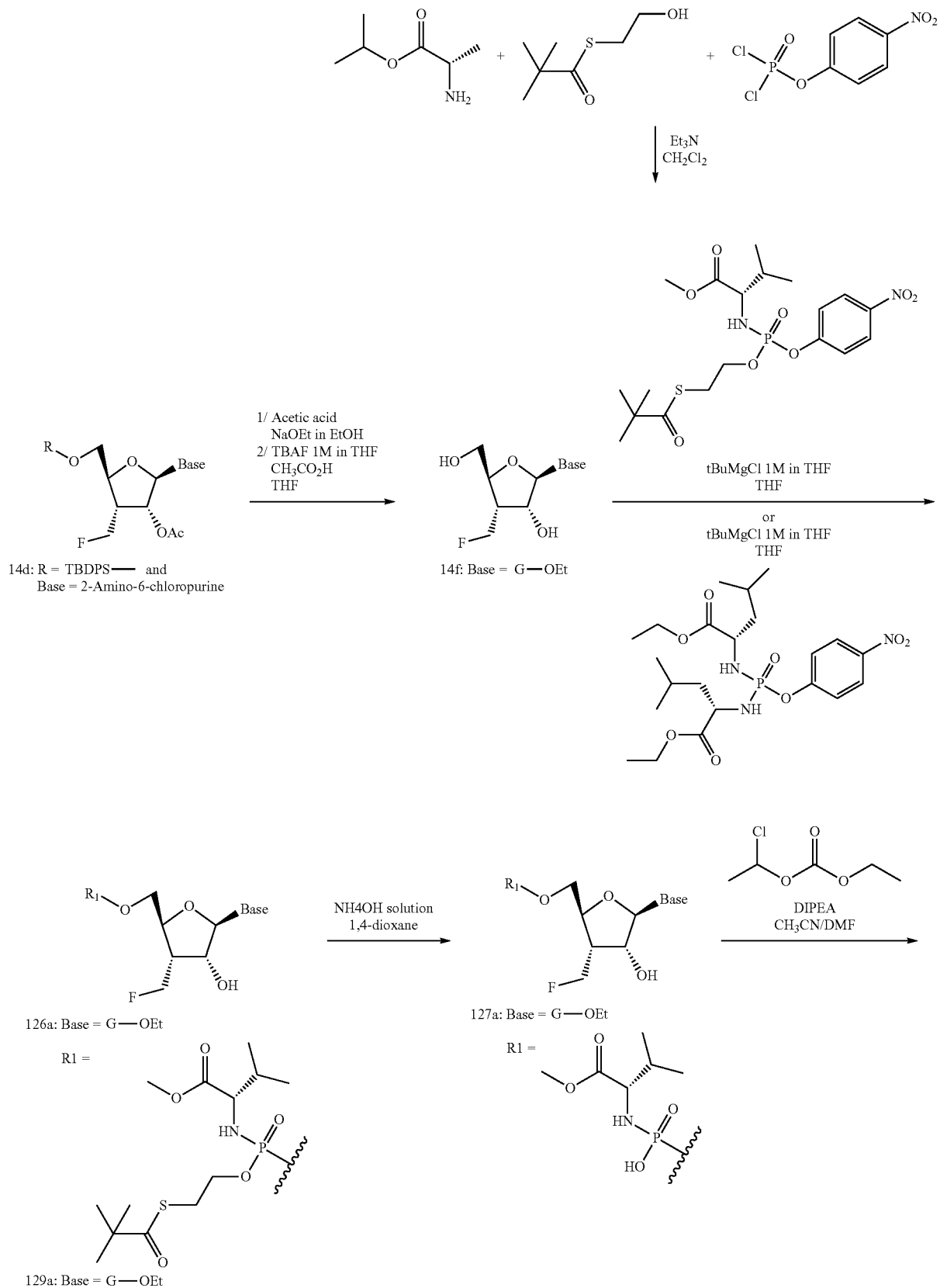

-continued

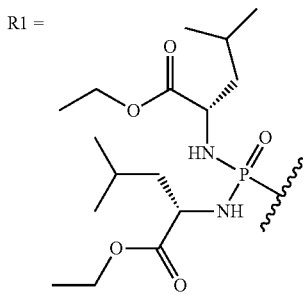

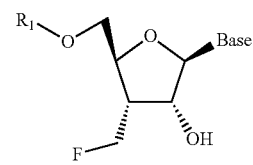

128a: Base = G—OEt

R1 =

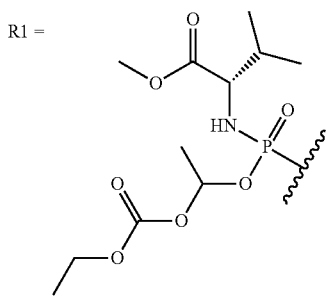

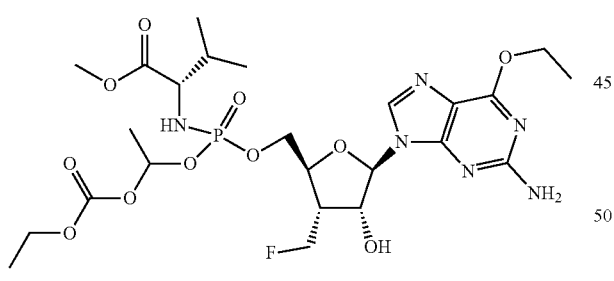

Compound 128a

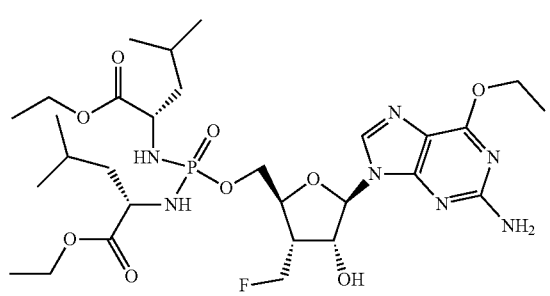 [SMILES: CCOC(=O)[C@H](CC(C)C)NP(=O)(N[C@@H](CC(C)C)C(=O)OCC)OC[C@H]1O[C@@H](n2cnc3c(OCC)nc(N)nc32)[C@H](O)[C@@H]1CF]

Compound 129a

Compound 128a (Mixture of 4 dias): white solid; $^1$H NMR (DMSO-d$_6$, 400 MHz) δ (ppm) 8.07-8.03 (m, 1H), 6.42-6.41 (m, 2H), 6.26-6.14 (m, 1H), 6.04-5.98 (m, 1H), 5.37-5.31 (m, 1H), 5.20-5.11 (m, 1H), 4.81-4.61 (m, 2H), 4.45 (q, J=6.95 Hz, 2H), 4.18-3.95 (m, 3H), 3.70-3.48 (m, 6H), 3.12-3.01 (m, 1H), 1.94-1.78 (m, 1H), 1.40-1.34 (m, 6H), 1.25-1.14 (m, 4H), 0.81-0.74 (m, 6H); $^{19}$F NMR (DMSO-d$_6$, 376 MHz) δ (ppm) −225.80 (s, 0.15F), −225.86 (s, 0.35F), −225.98 (s, 0.35F), −226.00 (s, 0.15F); $^{31}$P NMR (DMSO-d$_6$, 162 MHz) δ (ppm) 5.90 (s, 0.15P), 5.36 (s, 0.55P), 5.18 (s, 0.3P); MS (ESI) m/z=637.2 (MH$^+$).

Compound 129a: white solid; $^1$H NMR (DMSO-d$_6$, 400 MHz) δ (ppm) 8.02 (s, 1H), 6.46 (brs, 2H), 5.95 (d, J=5.07 Hz, 1H), 5.78 (d, J=3.45 Hz, 1H), 4.78-4.56 (m, 5H), 4.45 (q, J=6.89 Hz, 2H), 4.24-4.20 (m, 1H), 4.12-3.99 (m, 5H), 3.95-3.89 (m, 1H), 3.70-3.60 (m, 2H), 2.85-2.73 (m, 1H), 1.72-1.59 (m, 2H), 1.41-1.33 (m, 7H), 1.15 (dt, J=7.11 Hz and 3.48 Hz, 6H), 0.85-0.79 (m, 12H); $^{19}$F NMR (DMSO-d$_6$, 376 MHz) δ (ppm) −224.96 (s, 1F); $^{31}$P NMR (DMSO-d$_6$, 162 MHz) δ (ppm) 13.03 (s, 1P); MS (ESI) m/z=690.4 (MH$^+$).

275

Scheme 19:

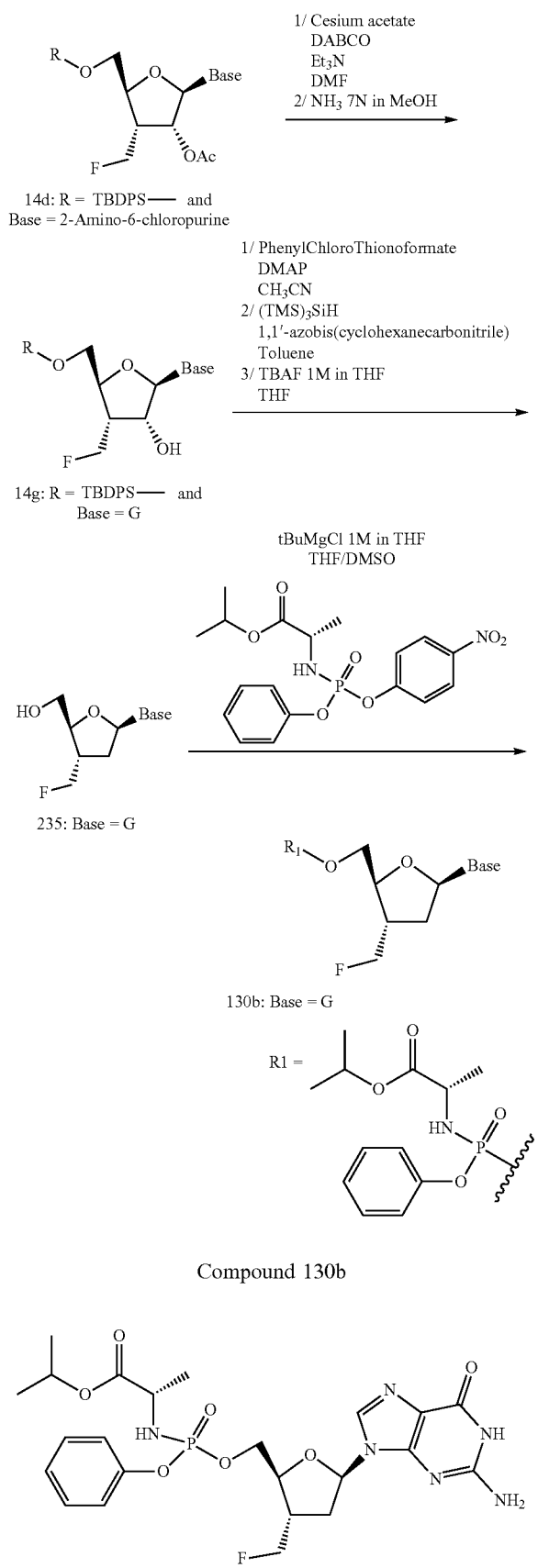

Compound 130b

276

Compound 130b (diastereoisomer 1): white solid; $^1$H NMR (DMSO-$d_6$, 400 MHz) δ (ppm) 10.65 (s, 1H), 7.86 (s, 1H), 7.36-7.32 (m, 2H), 7.18-7.14 (m, 3H), 6.50 (brs, 2H), 6.06 (dd, J=7.08 Hz and 4.56 Hz, 1H), 5.97 (dd, J=12.78 Hz and 9.93 Hz, 1H), 4.83 (heptuplet, J=6.23 Hz, 1H), 4.65-4.61 (m, 1H), 4.53-4.49 (m, 1H), 4.27-4.22 (m, 1H), 4.19-4.12 (m, 2H), 3.77-3.67 (m, 1H), 2.95-2.84 (m, 1H), 2.48-2.45 (m, 1H), 2.35 (dt, J=13.67 Hz and 7.65 Hz, 1H), 1.175 (d, J=6.97 Hz, 3H), 1.14 (d, J=6.21 Hz, 3H), 1.135 (d, J=6.21 Hz, 3H); $^{19}$F NMR (DMSO-$d_6$, 376 MHz) δ (ppm) −222.74 (s, 1F); $^{31}$P NMR (DMSO-$d_6$, 162 MHz) δ (ppm) 3.80 (s, 1P); MS (ESI) m/z=553.4 (MH$^+$).

Compound 130b (diastereoisomer 2): white solid; $^1$H NMR (DMSO-$d_6$, 400 MHz) δ (ppm) 10.62 (s, 1H), 7.88 (s, 1H), 7.37-7.33 (m, 2H), 7.20-7.15 (m, 3H), 6.48 (brs, 2H), 6.05 (dd, J=7.00 Hz and 4.55 Hz, 1H), 6.00 (dd, J=12.90 Hz and 10.08 Hz, 1H), 4.83 (heptuplet, J=6.27 Hz, 1H), 4.61-4.60 (m, 1H), 4.50-4.48 (m, 1H), 4.27-4.21 (m, 1H), 4.12-4.06 (m, 2H), 3.83-3.73 (m, 1H), 2.96-2.85 (m, 1H), 2.48-2.46 (m, 1H), 2.39-2.31 (m, 1H), 1.20 (d, J=6.97 Hz, 3H), 1.135 (d, J=6.28 Hz, 3H), 1.125 (d, J=6.28 Hz, 3H); $^{19}$F NMR (DMSO-$d_6$, 376 MHz) δ (ppm) −222.69 (s, 1F); $^{31}$P NMR (DMSO-$d_6$, 162 MHz) δ (ppm) 3.78 (s, 1P); MS (ESI) m/z=553.4 (MH$^+$).

Example 2

HCV Polymerase Enzyme Assay

Test compounds in the form of nucleoside triphosphates were examined for inhibitory activity against purified HCV polymerase in a standard assay. Bacterial expression constructs encoding the approximately 65 kDa HCV genotype 1b NS5B protein were used to generate recombinant HCV polymerases (with a deletion of the 21 carboxy terminal amino acids). Both the wild-type genotype 1b protein and protein containing the S282T mutation were expressed and purified for use in the enzymatic activity assay.

The enzymatic activity assay measured the inhibitory effect of increasing concentrations of test compound on the incorporation of α-[$^{33}$P]-labeled nucleotide into trichloroacetic acid-precipitable material. Recombinant polymerase and synthetic RNA template were combined in reaction buffer containing ribonucleoside triphosphates, α-[$^{33}$P]-labeled nucleotide and eight concentrations of test compound in three-fold dilutions. Reactions were incubated for two hours at 30° C.

Reactions were terminated by the addition of ice-cold trichloroacetic acid and sodium pyrophosphate to promote precipitation of newly-synthesized ribonucleic acid. Precipitable material from the reactions was collected by filtration onto 96-well filter plates, washed extensively with water, and quantified by liquid scintillation.

The inhibitory activity of test compounds was determined by fitting results to dose-response curves using XLfit software.

Results are provided in Table 1.

TABLE 1

| HCV Polymerase Enzyme Activity | | |
|---|---|---|
| Compound | Wild-Type IC$_{50}$ (µM) | S282T IC$_{50}$ (µM) |
| Compound 301 | ++ | |
| Compound 302 | ++++ | ++++ |

TABLE 1-continued

HCV Polymerase Enzyme Activity

| Compound | Wild-Type $IC_{50}$ (μM) | S282T $IC_{50}$ (μM) |
|---|---|---|
| Compound 305 | ++++ | ++++ |
| Compound 307 | +++ | |
| Compound 308 | ++++ | ++++ |
| Compound 325 | ++ | |
| Compound 326 | ++ | |
| Compound 327 | ++++ | ++++ |
| Compound 330 | +++ | ++++ |
| Compound 331 | + | |
| Compound 332 | +++ | |
| Compound 334 | + | |
| Compound 335 | + | |
| Compound 401 | + | |
| Compound 402 | ++ | |

$IC_{50}$ is provided as follows: ++++ ≤250 nM < +++ ≤1μM < ++ ≤10 μM < +

Example 3

HCV Replicon Assay

Huh-7-derived cell line (Zluc) that harbors an HCV genotype 1b replicon and a luciferase reporter gene was grown in Dulbecco's Modified Eagle Medium (DMEM) supplemented with 10% fetal bovine serum, 2 mM GlutaMAX, 1% MEM nonessential amino acids, 100 IU/mL penicillin, 100 μg/mL streptomycin, and 0.5 mg/mL Geneticin® (G418). For dose response testing the cells were seeded in 96-well plates at 7.5×10³ cells per well in a volume of 50 μL, and incubated at 37° C./5% $CO_2$. Drug solutions were made up freshly in Huh-7 media as 2× stocks. Ten additional 5-fold dilutions were prepared from these stocks in DMEM without G418. At least three hours after Zluc cells were seeded, drug treatment was initiated by adding 50 μL of drug dilutions to the plates in duplicate. Final concentrations of drug ranged from 100 μM to 0.0000512 μM. Cells were then incubated at 37° C./5% $CO_2$. Alternatively, compounds were tested at two concentrations (1 μM and 10 μM). In all cases, Huh-7 (which do not harbors the HCV replicon) served as negative control. After 72 hours of incubation, the inhibition of HCV replication was measured by quantification of photons emitted after mono-oxygenation of 5'-fluoroluciferin to oxyfluoroluciferin by firefly luciferase. For this, media was removed from the plates via gentle tapping. Fifty microliters of ONE-glo luciferase assay reagent was added to each well. The plates were shaken gently for 3 min at room temperature and luminescence was measured on a Victor³ V 1420 multilabel counter (Perkin Elmer) with a 1 second read time using a 700 nm cut-off filter. The $EC_{50}$ values were calculated from dose response curves from the resulting best-fit equations determined by Microsoft Excel and XLfit 4.1 software. When screening at two fixed concentrations, the results were expressed as % inhibition at 1 μM and 10 μM.

For cytotoxicity evaluation, Zluc cells were treated with compound as described herein, and cell viability was monitored using the CellTiter-Blue Cell Viability Assay (Promega) by adding 20 μL of the assay solution to each well. The plates were then incubated at 37° C./5% $CO_2$ for at least 3 hours. Fluorescence was detected in plates using excitation and emission wavelengths of 560 and 590 nm, respectively, in a Victor³ V 1420 multilabel counter (Perkin Elmer) and $CC_{50}$ values were determined using Microsoft Excel and XLfit 4.1 software.

Compounds presented in Table 2 below were assayed according to the replicon assay described herein.

TABLE 2

HCV Replicon Activity

| Compound Reference | HCV Replicon $EC_{50}$ | $CC_{50}$ | Compound Reference | HCV Replicon $EC_{50}$ | $CC_{50}$ |
|---|---|---|---|---|---|
| Compound 101 | + | + | Compound 106b (Mixture of diastereomers) | + | + |
| Compound 107 (Mixture of diastereomers) | + | + | Compound 108 (Diastereomer 1) | + | + |
| Compound 109 (Mixture of diastereomers) | + | + | Compound 108 (Diastereomer 2) | + | + |
| Compound 110a (Diastereomer 1) | + | + | Compound 110a (Diastereomer 2) | + | + |
| Compound 112 (Mixture of diastereomers) | + | + | Compound 113 (Mixture of diastereomers) | + | + |
| Compound 114 (Mixture of diastereomers) | + | + | Compound 112 (Diastereomer 1) | + | + |
| Compound 109 (Diastereomer 1) | + | + | Compound 112 (Diastereomer 2) | + | + |
| Compound 109 (Diastereomer 2) | + | + | Compound 113 (Diastereomer 1) | + | + |
| Compound 115 | + | + | Compound 113 (Diastereomer 2) | + | + |
| Compound 116 | + | + | Compound 118 | + | + |
| Compound 201 | + | + | Compound 203 | + | + |
| Compound 202 | + | + | Compound 205 | + | + |
| Compound 204 | + | + | Compound 207 | + | + |
| Compound 206 | + | + | Compound 209 | + | + |
| Compound 208 | + | + | Compound 212 | + | + |
| Compound 211 (Single Isomer) | + | + | Compound 225 | + | + |
| Compound 213 | + | + | Compound 227 | + | + |
| Compound 120a (Diastereomer 1) | + | + | Compound 120a (Diastereomer 2) | + | + |
| Compound 226 | + | + | | | |
| Compound 122a Diastereomer 1 | + | + | Compound 122a Diastereomer 2 | + | + |
| Compound 123a Diastereomer 1 | + | + | Compound 123a Diastereomer 2 | + | + |
| Compound 124a Diastereomer 1 | + | + | Compound 124a Diastereomer 2 | + | + |
| Compound 125a Diastereomer 1 | + | + | Compound 125a Diastereomer 2 | + | + |
| Compound 128a Mixture of diastereomers | + | + | Compound 129a | + | + |

$EC_{50}$ is provided as follows: ++++ ≤250 nM < +++ ≤1 μM < ++ ≤10 μM < +
$CC_{50}$ is provided as follows: ++ ≤50 μM < +

Example 4

Pharmacokinetics of Liver Triphosphate Following a Single Oral Dose in CD-1 Mice Abbreviations Ms=Mouse; TP=triphosphate.

A single oral dose of Compound 1 at 10 mg/kg in PEG 200 (dose volume 5 mL/kg) was administered to nine CD-1 male mice. Five untreated animals were used for the collection of control liver. Liver samples were collected from three animals per time point at 4, 12 and 24 hours post dose. Liver specimens were collected from all animals immediately after the incision. Freezing forceps stored in liquid nitrogen were used to freeze the liver before excision.

Liver samples were analyzed for the active species nucleoside triphosphate by LC-MS/MS. The triphosphate levels were assayed by homogenizing (on ice) a known weight of mouse liver with 4× volume of 0.95 M trichloroacetic acid (TCA). Internal standard solution was added to the homogenate followed by neutralization with 20% ammonium hydroxide solution and addition of 500 µL 1% formic acid. The tissue samples were extracted by weak anion exchange solid phase extraction (SPE). Post extraction, the eluates were evaporated under nitrogen, followed by reconstitution before injection onto the LC-MS/MS system. The samples were chromatographed on a Luna NH$_2$ column using a gradient system of ammonium acetate (1 mM to 20 mM and pH 8.0 to pH 10.0) in water and acetonitrile (70:30). The analyte was detected and quantified by tandem mass spectrometry in positive ion mode on an API4000 equipped with a Turbo Ionspray® interface.

Results are provided in Table 3 below.

TABLE 3

Mouse Liver Pharmacokinetic Parameters

| Compound | Ms Liver TP $C_{max}$ (pmol/g at 1 µmol/kg)[1] | Ms Liver TP AUC (pmol · hr/g at 1 µmol/kg)[2] |
|---|---|---|
| Compound 125a Dia 1 | +++ | +++ |
| Compound 125a Dia 2 | +++ | +++ |
| Compound 125b Dia 1 | ++ | ++ |
| Compound 125b Dia 2 | ++ | ++ |

[1]Single point concentration provided as follows: + ≤15 < ++ ≤50 < +++ ≤100 < ++++
[2]Integrated concentration provided as follows: + ≤150 < ++ ≤500 <+++ ≤1500 < ++++

While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A compound according to Formula I:

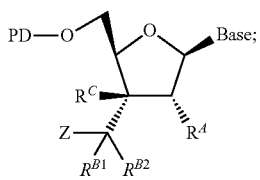

(I)

or a pharmaceutically acceptable salt, solvate, or tautomeric form thereof, wherein:
R$^A$ is hydroxyl, bromo, chloro, iodo, azido, —NH$_2$, or alkylcarbonyloxy;
R$^{B1}$ is hydrogen, C$_2$-C$_6$alkenyl, C$_2$-C$_6$alkynyl, fluoro, azido, —NH$_2$, CN, or benzyloxycarbonyloxy;
R$^{B2}$ is hydrogen or methyl;
R$^C$ is hydrogen, alkyl, alkenyl, alkynyl, or azido;
Base is a nucleobase;

PD is

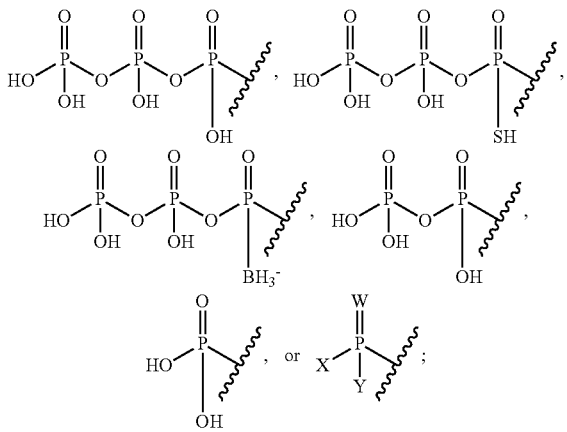

W is S or O;
each of X and Y is independently hydrogen, —OR$^1$, —SR$^1$, —NR$^1$R$^2$, or an N-linked or O-linked amino acid residue, or derivative thereof;
Z is methyl, azido, amino, cyano, hydroxyl, alkylcarbonyloxy, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$—, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene;
each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl;
each R$^2$ is independently hydrogen, alkyl, cycloalkyl, aryl, or arylalkyl;
with the proviso that when: PD is

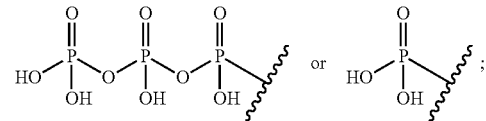

R$^A$ is hydroxyl; R$^{B1}$ is hydrogen; R$^{B2}$ is hydrogen; R$^C$ is hydrogen; and Z is fluoro; then Base is other than guanine; and
with the proviso that when: PD is

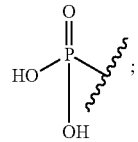 [SMILES: *P(=O)(O)O]

R$^A$ is hydroxyl; R$^{B1}$ is hydrogen; R$^{B2}$ is hydrogen; R$^C$ is hydrogen; and Z is azido or —NH$_2$; then Base is other than thymine.

2. The compound of claim 1 according to Formula I, wherein
the nucleobase is purine, pyrimidine, adenine, N$^6$-alkylpurines, N$^6$-acylpurines, N$^6$-benzylpurine, N$^6$-halopurine, N⁶-vinylpurine, N⁶-acetylenic purine, N⁶-acyl purine, N⁶-hydroxyalkyl purine, N⁶-alkylaminopurine, N⁶-alkylthio purine, N²-alkylpurines, N²-alkyl-6-thiopurines, thymine, cytosine, 5-fluorocytosine, 5-methyl cytosine, 6-azapyrimidine, including 6-azacytosine, 2- and/or 4-mercaptopyrmidine, uracil, benzyloxymethyluracil,
5-halouracil, 5-fluorouracil, C⁵-alkylpyrimidines, C⁵-benzylpyrimidines, C⁵-halopyrimidines, C⁵-vinylpyrimidine, C⁵-acetylenic pyrimidine, C⁵-acyl pyrimidine, C⁵-hydroxyalkyl purine, C⁵-amidopyrimidine, C⁵-cyanopyrimidine, C⁵-iodopyrimidine, C⁶-iodo-pyrimidine, C⁵—Br-vinyl pyrimidine, C⁶—Br-vinyl pyrimidine, C⁵-nitropyrimidine, C⁵-amino-pyrimidine, N²-alkylpurines, N²-alkyl-6-thiopurines, 5-azacytosine, 5-azauracil, triazolopyridine, imidazolopyridine, pyrrolopyrimidine, triazolopyrimidine, pyrazolopyrimidine, 8-azaguanine, guanine, hypoxanthine, 7-deazaguanine, 7-deazaadenine, 2-aminopurine, 6-aminopurine, 2,6-diaminopurine, 6-chloropurine, 7-fluoro-7-deazaguanine, 7-fluoro-7-deazaadenine, 2-amino-6-chloropurine, 6-methoxypurine, 6-ethoxypurine, 2-amino-6-hydroxypurine, 2-amino-6-methoxypurine, 2-amino-6-ethoxypurine, 2-amino-6-(n-propoxy)-purine, 2-amino-6-isopropoxypurine, 6-alkylthio-2-aminopurine, 4-azido-2-hydroxy-pyrimidine, or pyrrolotriazine; where acyl is —C(O)R and R is alkyl, aryl, alkylaryl, or arylalkyl;

$R^A$ is hydroxyl, bromo, chloro, iodo, azido, —NH₂, or alkyl-carbonyl-oxy;

$R^{B1}$ is hydrogen, $C_2$-$C_6$alkenyl, $C_2$-$C_6$alkynyl, fluoro, azido, —NH₂, CN, or benzyloxycarbonyloxy;

$R^{B2}$ is hydrogen or methyl;

$R^C$ is hydrogen, alkyl, alkenyl, alkynyl, or azido;

PD is

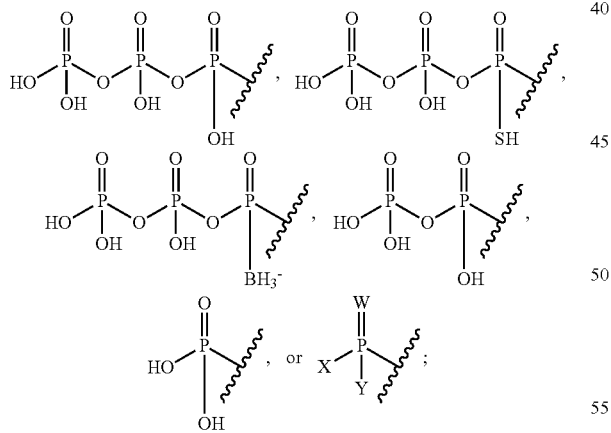

W is S or O;

each of X and Y is independently hydrogen, —OR¹, —SR¹, —NR¹R², or an N-linked or O-linked amino acid residue, or derivative thereof;

Z is methyl, azido, amino, cyano, hydroxyl, alkylcarbonyloxy, or fluoro; or, in the alternative, Y and Z, together with the atoms to which they are attached, combine to form a seven-membered heterocyclic ring wherein Y and Z together represent a single divalent —O—, and X is —OR¹, —SR¹, —NR¹R², or an N-linked or O-linked amino acid residue, or derivative thereof; or Z, $R^{B1}$ and $R^{B2}$ combine to form $C_{2-6}$ alkenylene or $C_{2-6}$ alkynylene;

each R¹ is independently hydrogen, alkyl, aryl, arylalkyl, cycloalkyl, heterocyclo-alkyl, alkoxy-carbonyl-alkyl, alkoxycarbonyloxyalkyl, or alkyl-carbonyl-thio-alkyl;

each R² is independently hydrogen, alkyl, cycloalkyl, aryl, or aryl-alkyl;

each alkyl is independently straight or branched $C_{1-10}$ alkyl, unsubstituted or substituted with one or more groups independently selected from halogen, fluoro, chloro, bromo, iodo, hydroxyl, carbonyl, $C_{3-15}$ cycloalkyl, phenyl $C_{1-10}$ alkyl, biphenyl $C_{1-10}$ alkyl, naphthyl $C_{1-10}$ alkyl, sulfanyl, amino, $C_{1-10}$ alkylamino, phenyl-amino, biphenyl-amino, naphthyl-amino, $C_{1-10}$ alkoxy, alkoxycarbonyl, alkoxycarbonyloxy, alkylcarbonylthio, phenyloxy, biphenyloxy, naphthyloxy, nitro, cyano, sulfonic acid, sulfate, phosphonic acid, phosphate, or phosphonate;

each cycloalkyl is independently a $C_{3-15}$ cycloalkyl, unsubstituted or substituted with one or more groups independently selected from halogen, fluoro, chloro, bromo, iodo, hydroxyl, carbonyl, sulfanyl, amino, $C_{1-10}$ alkylamino, phenyl-amino, biphenyl-amino, naphthylamino, $C_{1-10}$ alkoxy, phenyloxy, biphenyloxy, naphthyloxy, nitro, cyano, sulfonic acid, sulfate, phosphonic acid, phosphate, and phosphonate;

each aryl is independently phenyl, biphenyl, or naphthyl, unsubstituted or substituted by one or more groups independently selected from halogen, fluoro, chloro, bromo, iodo, $C_{1-10}$ alkyl, halo $C_{1-10}$ alkyl, hydroxyl, amino, $C_{1-10}$ alkyl-amino, phenyl-amino, biphenyl-amino, naphthyl-amino, $C_{1-10}$ alkoxy, phenyloxy, biphenyloxy, naphthyloxy, nitro, cyano, sulfonic acid, sulfate, phosphonic acid, phosphate, or phosphonate;

each arylalkyl is independently aryl $C_{1-10}$ alkyl; wherein aryl is defined above;

each heteroaryl is independently each heteroaryl is independently furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, triazolyl, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, thienopyridyl, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, or xanthenyl; and is unsubstituted or substituted by one or more groups independently selected from halogen, fluoro, chloro, bromo, iodo, $C_{1-10}$ alkyl, halo $C_{1-10}$ alkyl, hydroxyl, amino, $C_{1-10}$ alkyl-amino, phenyl-amino, biphenyl-amino, naphthyl-amino, alkoxy, phenyloxy, biphenyloxy, naphthyloxy, nitro, cyano, sulfonic acid, sulfate, phosphonic acid, phosphate, or phosphonate;

each alkenyl and alkenylene is independently straight or branched alkenyl and alkenylene, respectively, each having 2 to 11 carbon atoms, and is unsubstituted or substituted by one or more groups independently selected from halogen, fluoro, chloro, bromo, iodo, hydroxyl, carbonyl, sulfanyl, amino, alkylamino, arylamino, alkoxy, aryloxy, nitro, cyano, sulfonic acid, sulfate, phosphonic acid, phosphate, or phosphonate, each alkynyl and alkynylene is independently straight or branched alkynyl and alkynylene, respectively, each having 2 to 11 carbon atoms, and is unsubstituted or substituted by one or more groups independently selected from halogen, fluoro, chloro, bromo, iodo, hydroxyl, carbonyl, sulfanyl, amino, $C_{1-10}$ alkyl-amino, phenyl-amino, biphenyl-amino, naphthyl-amino, $C_{1-10}$ alkoxy, phenyloxy, biphenyloxy, naphthyloxy, nitro, cyano, sulfonic acid, sulfate, phosphonic acid, phosphate, or phosphonate;

each heteroaryl-alkyl is independently heteroaryl $C_{1-10}$ alkyl; wherein heteroaryl is defined above;

each alkoxy is independently —OR' wherein R' is alkyl or cycloalkyl, and wherein alkyl is $C_{1-10}$ alkyl and cycloalkyl is $C_{3-15}$ cycloalkyl;

each amino is independently —NR$^{1'}$R$^{2'}$ or —NR$^{1'}$—, wherein R$^{1'}$ and R$^{2'}$ are independently hydrogen, alkyl, or cycloalkyl.

3. The compound of claim 1 wherein
R$^A$ is hydroxyl, bromo, chloro, iodo, or alkylcarbonyloxy;
R$^{B1}$ is fluoro;
R$^{B2}$ is hydrogen or methyl;
R$^C$ is hydrogen, azido, or methyl;
Base is a nucleobase;
PD is

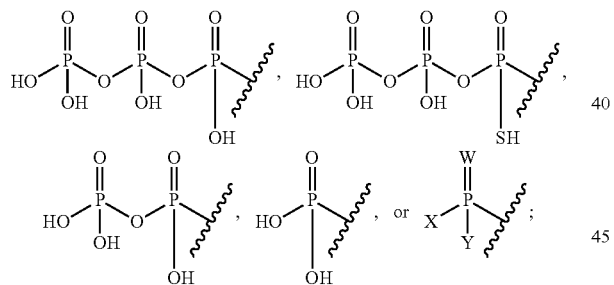

W is S or O;
each of X and Y is independently hydrogen, —OR$^1$, —SR$^1$, —NR$^1$R$^2$, or an N-linked or O-linked amino acid residue, or derivative thereof;
Z is methyl, azido, amino, cyano, hydroxyl, alkylcarbonyloxy, or fluoro; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form $C_{2-6}$ alkynylene;
each R$^1$ is independently hydrogen, alkyl, aryl, arylalkyl, cycloalkyl, heterocycloalkyl, alkoxylcarbonylalkyl, or alkylcarbonylthioalkyl; and
each R$^2$ is independently hydrogen, alkyl, cycloalkyl, aryl, or arylalkyl;

with the proviso that when: PD is

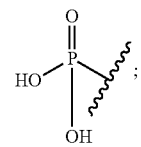

R$^A$ is hydroxyl; R$^{B1}$ is hydrogen; R$^{B2}$ is hydrogen; R$^C$ is hydrogen; and Z is azido or —NH$_2$; then Base is other than thymine.

4. The compound of claim 1 where PD is

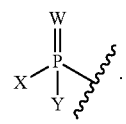

5. The compound of claim 1 according to Formula:

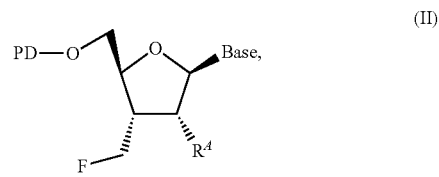

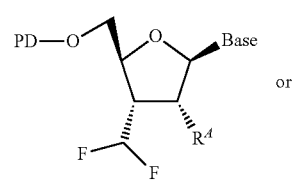

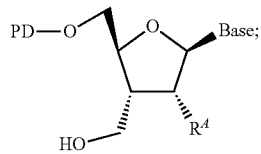

or a pharmaceutically acceptable salt, solvate, or tautomeric form thereof.

6. The compound of claim 1 according to Formula V:

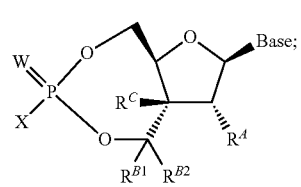

or a pharmaceutically acceptable salt, solvate, or tautomeric form thereof, wherein X is —OR$^1$, —SR$^1$, —NR$^1$R$^2$, or an N-linked or O-linked amino acid residue, or derivative thereof.

7. The compound of claim 1 according to Formula VI:

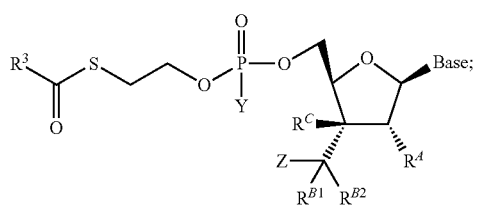
(VI)

or a pharmaceutically acceptable salt, solvate, or tautomeric form thereof, wherein $R^3$ is unsubstituted alkyl, alkoxyl, or hydroxylalkyl.

8. The compound of claim 1 according to any of Formulas VII or XLII:

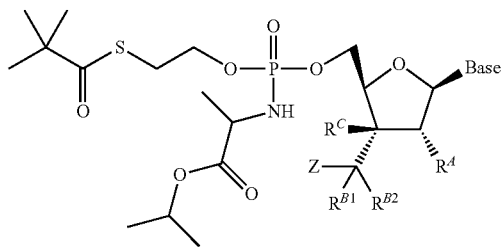
(VII)

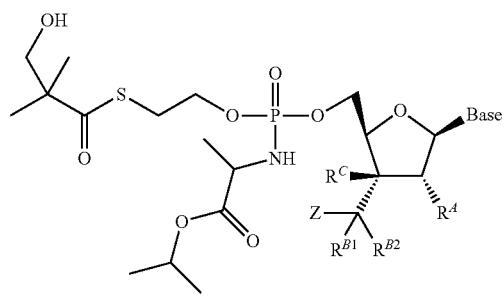
(XLII)

or a pharmaceutically acceptable salt, solvate, or tautomeric form thereof.

9. The compound of claim 1 according to Formula VIII:

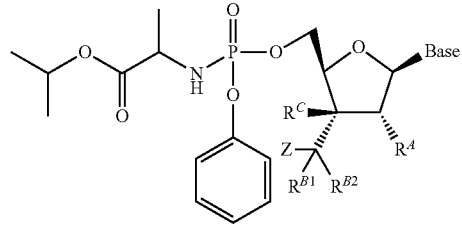
(VIII)

or a pharmaceutically acceptable salt, solvate, or tautomeric form thereof.

10. The compound of any of claim 9, wherein each Base is independently:

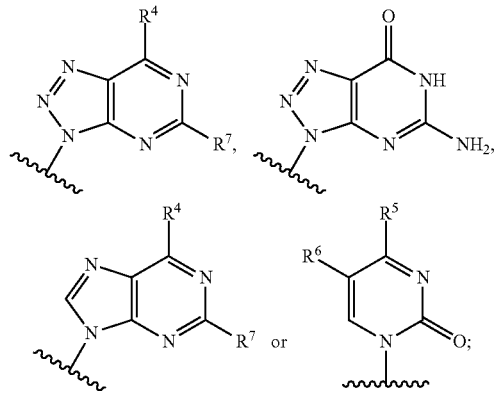

or a tautomeric form thereof, wherein:

$R^4$ is hydrogen, hydroxyl, alkylthio, alkoxyl, halo, amino, or aminoalkyl;

$R^5$ is hydrogen, hydroxyl, amino, or alkoxyl;

$R^6$ is hydrogen, halogen, or alkyl; and $R^7$ is hydrogen, hydroxyl, or amino.

11. The compound of claim 10, wherein Base is

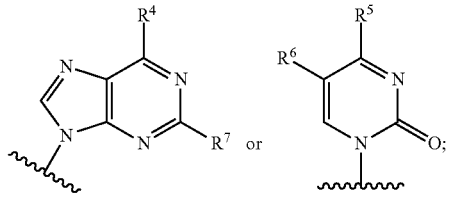

or a tautomeric form thereof, wherein: $R^4$ is hydrogen, hydroxyl, alkoxyl, amino, or aminoalkyl; $R^5$ is hydrogen, hydroxyl, amino, or alkoxyl; $R^6$ is hydrogen, halogen, or alkyl; and $R^7$ is hydrogen, hydroxyl, or amino.

12. The compound of claim 1 according to any of Formulas IX-XII:

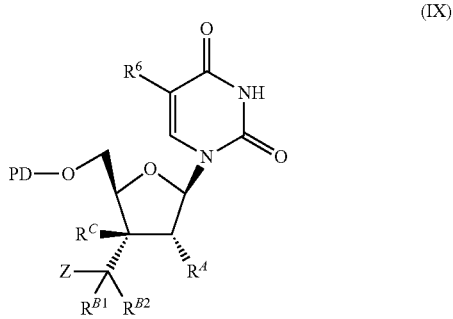
(IX)

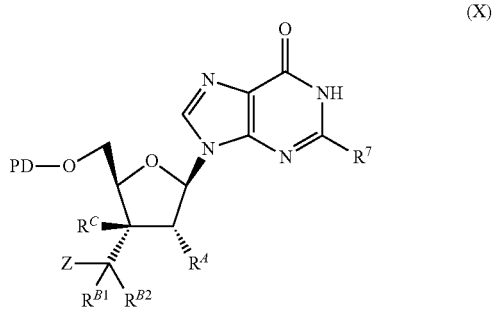
(X)

or a pharmaceutically acceptable salt, solvate, or tautomeric form thereof.
13. The compound of claim 1 according to any of Formulas XIII-XVIII:
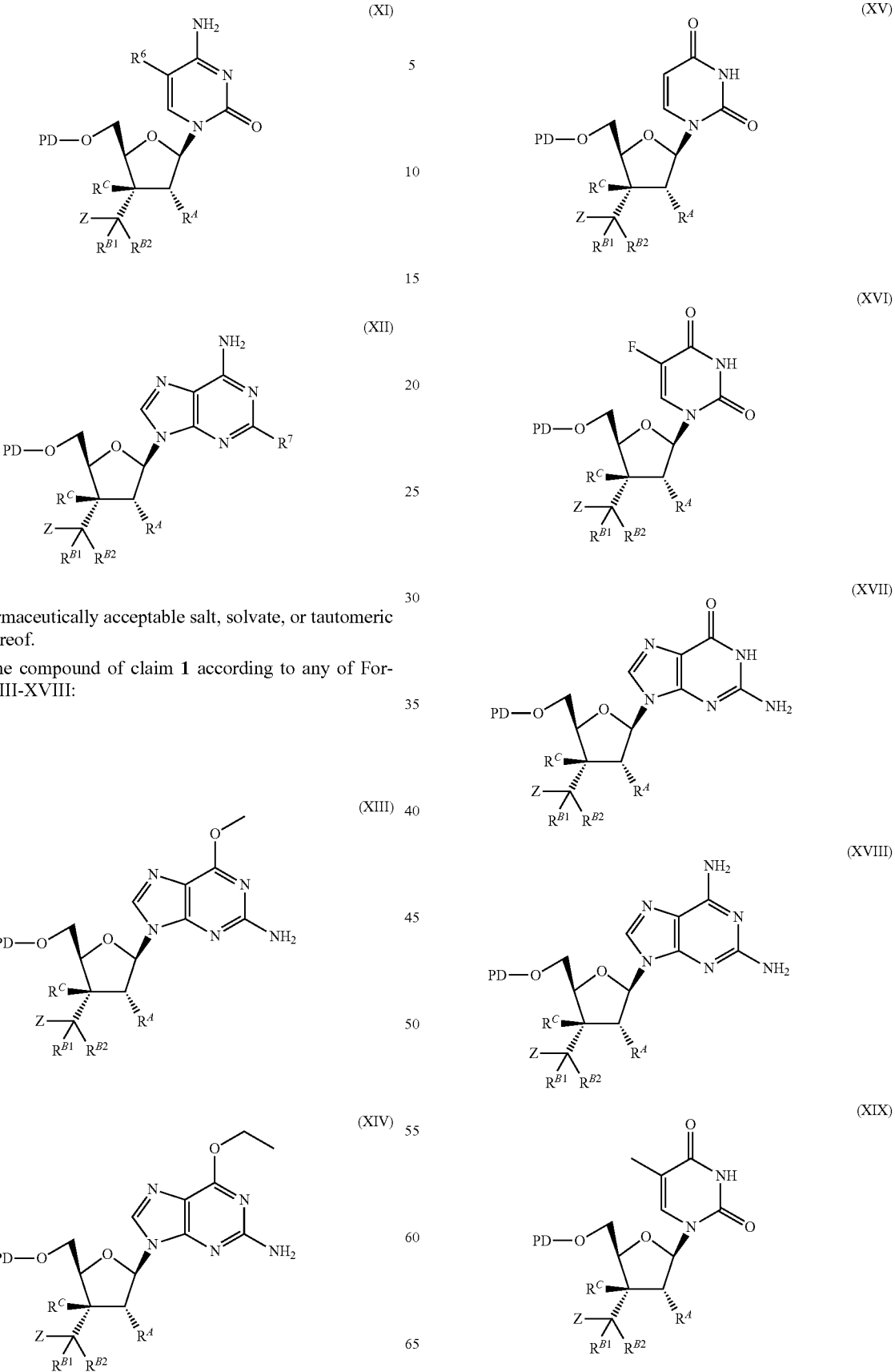

-continued (XX)
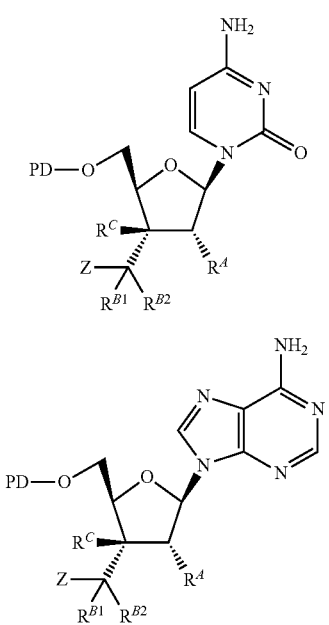

(XXI)

or a pharmaceutically acceptable salt, solvate, or tautomeric form thereof.

14. The compound of claim 1 according to Formula XLIII or XLIV:

(XLIII)
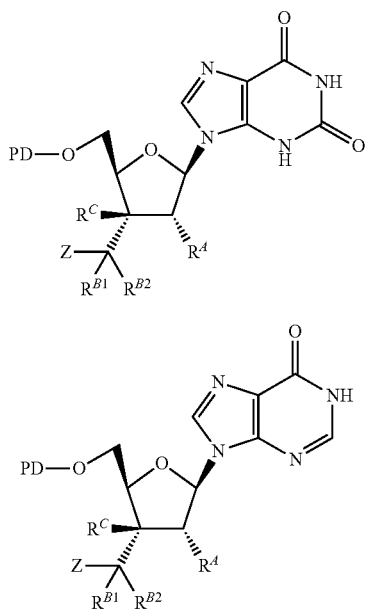

(XLIV)

or a pharmaceutically acceptable salt, solvate, or tautomeric form thereof.

15. The compound of claim 1 where $R^C$ is hydrogen.

16. The compound of claim 1 where X is N-linked amino acid residue or derivative thereof and Y is —$OR^1$.

17. The compound of claim 16 where X is —$NR^X$-G1($S_{C1}$)—C(O)-$Q^1$, where $Q^1$ is alkoxy, cycloalkyloxy, or aralkyloxy; G1 is $C_1$ alkylene; $R^X$ is hydrogen; and $S_{C1}$ is alkyl or arylalkyl; and Y is —$OR^1$.

18. The compound of claim 1, wherein $R^A$ is acetyloxy or hydroxyl.

19. The compound of claim 1 according to any of Formulas 101-122:

(101)
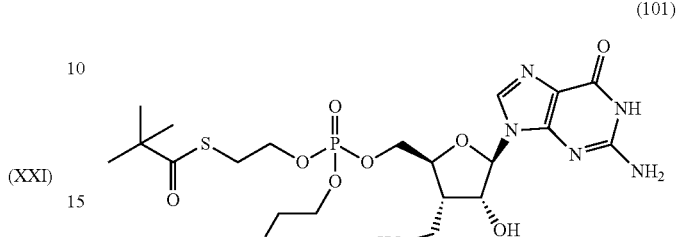

(102)
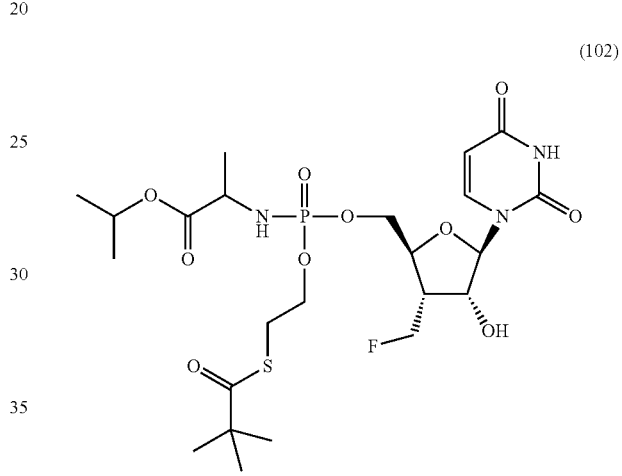

(103)
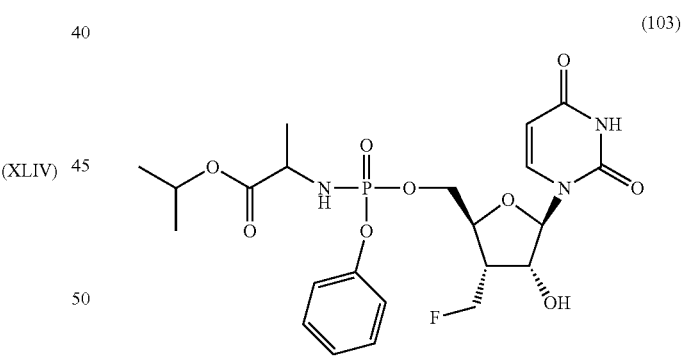

(104)
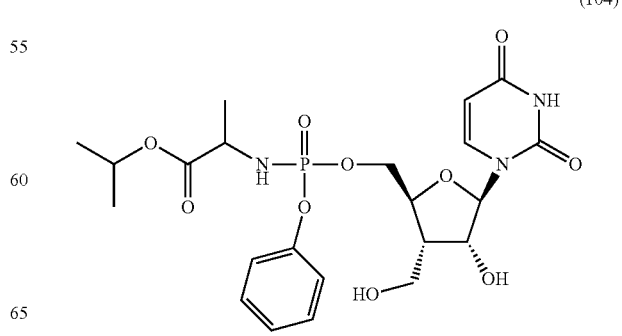

(105) 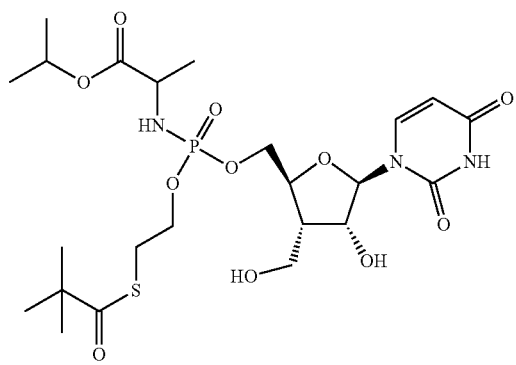
(110) 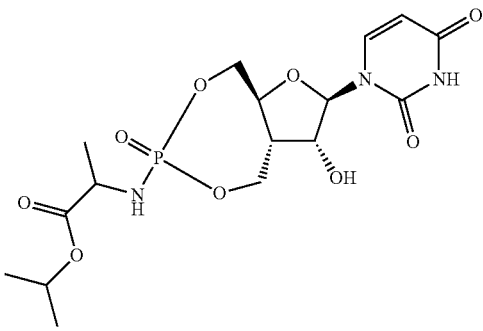
(106) 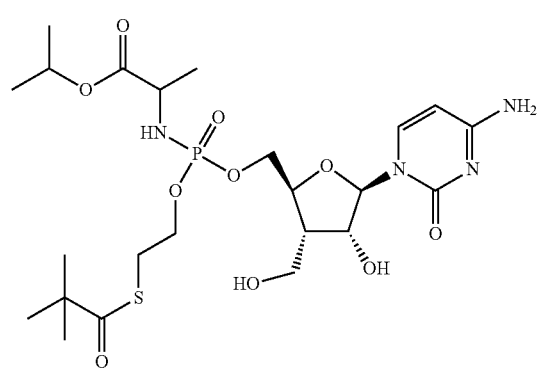
(111) 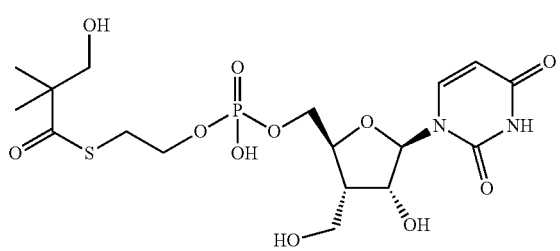
(107) 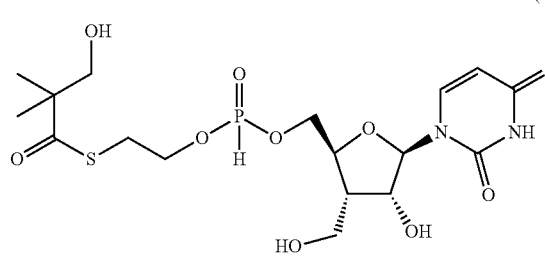
(112) 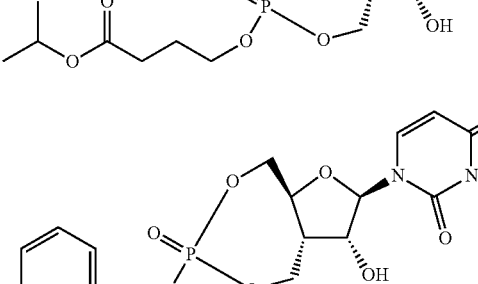
(108) 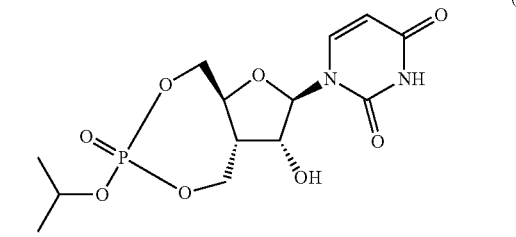
(113) 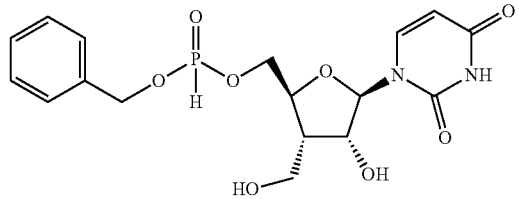
(109) 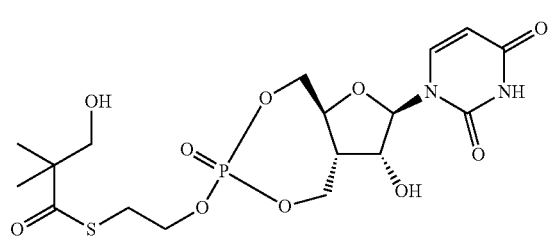
(114) 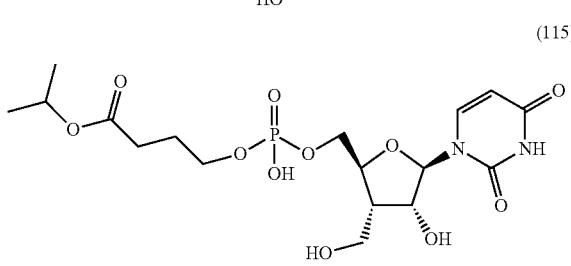

(116)
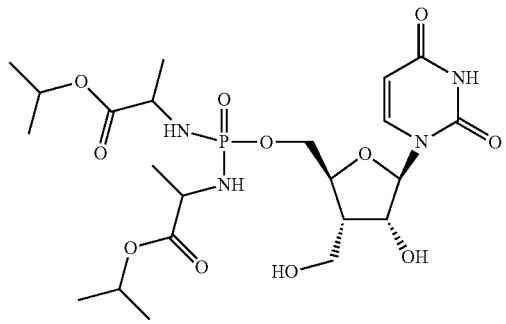
(117)
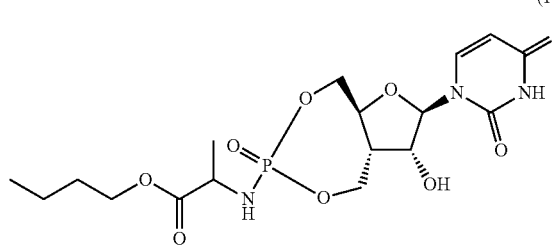
(118)
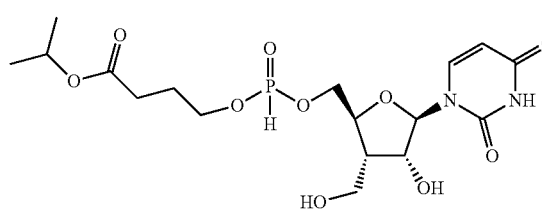
(119)
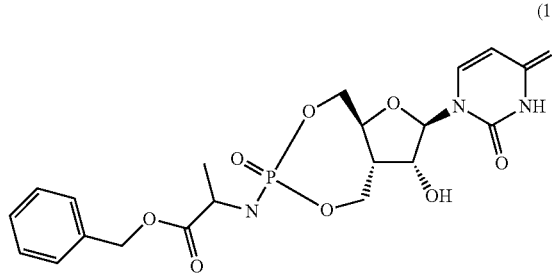
(120)
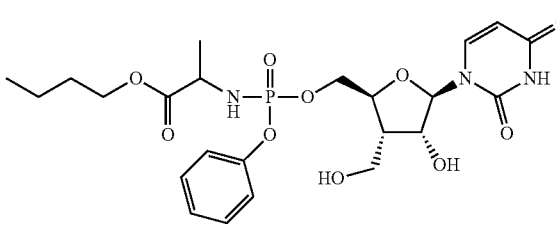
(121)
(122)
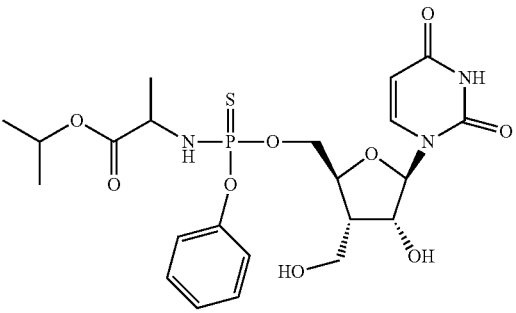
or a pharmaceutically acceptable salt, solvate, or tautomeric form thereof.
20. The compound of claim 1 according to any of Formulas 301-329:
(301)
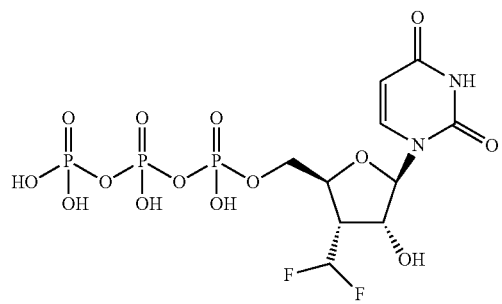
(302)
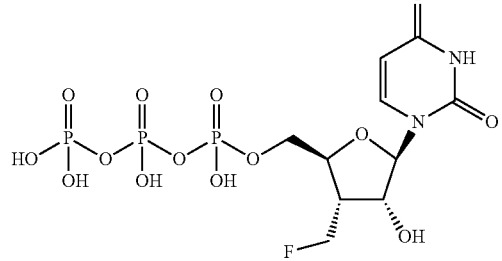
(303)
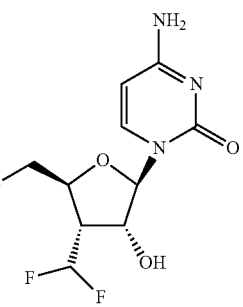

(304) 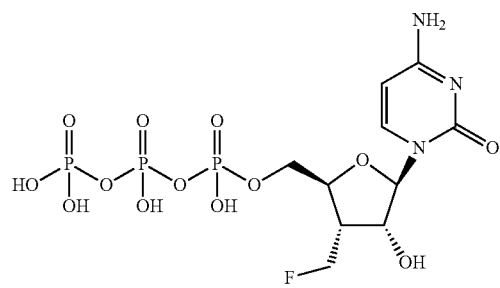
(309) 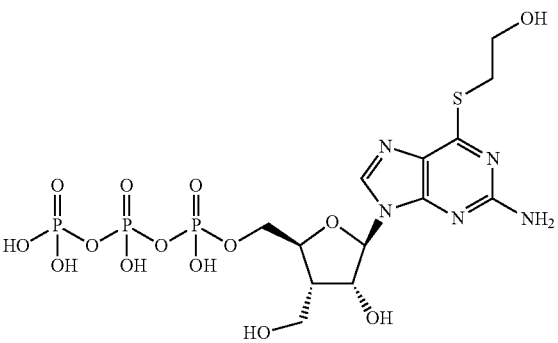
(305) 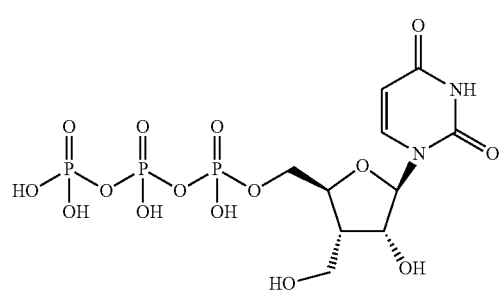
(310) 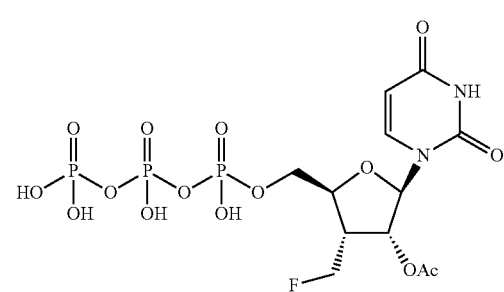
(306) 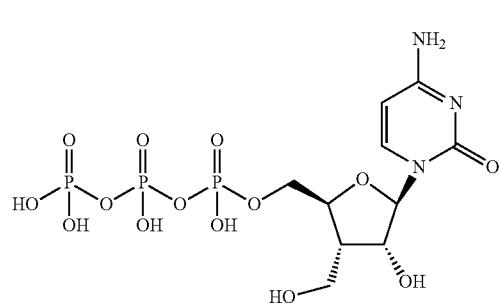
(311) 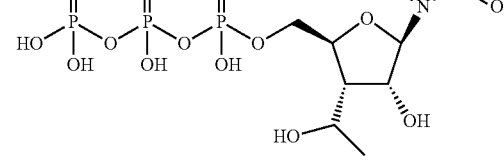
(307) 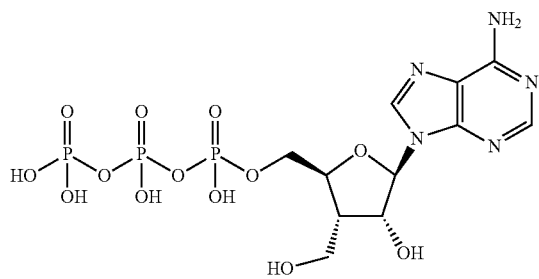
(312)
(308) 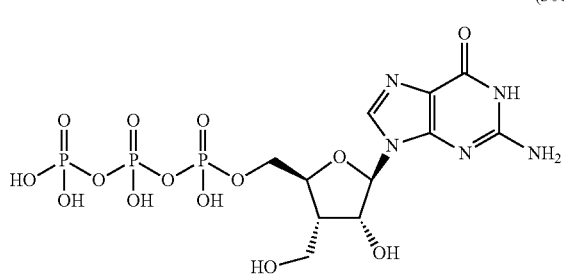
(313) 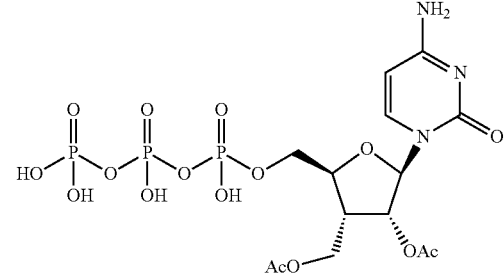

(314)
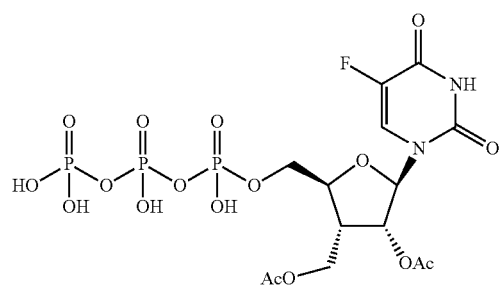
(315)
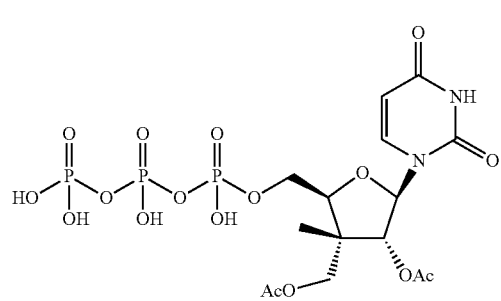
(316)
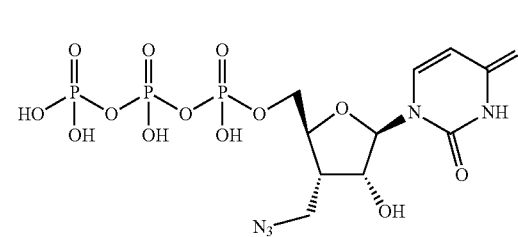
(317)
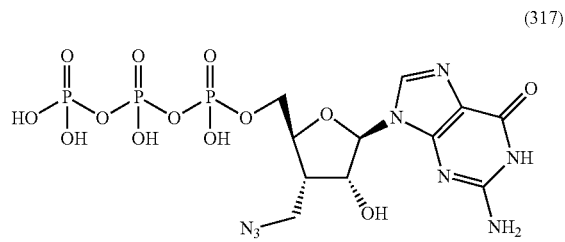
(318)
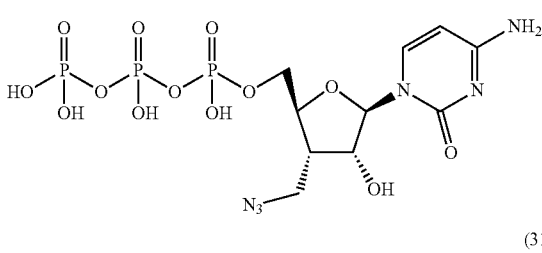
(319)
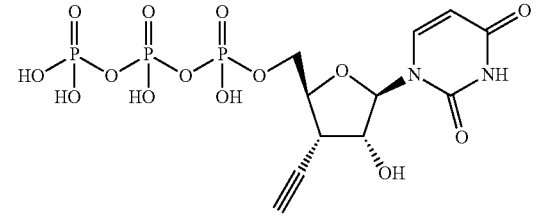
(320)
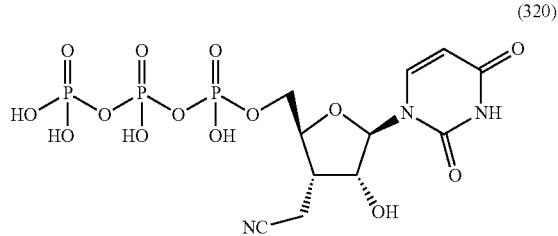
(322)
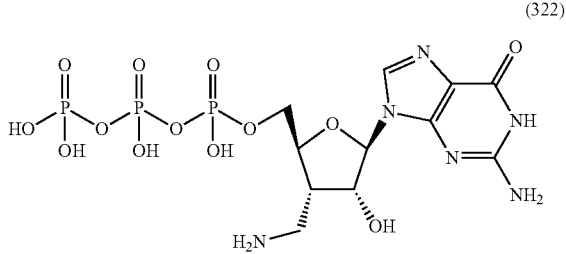
(323)
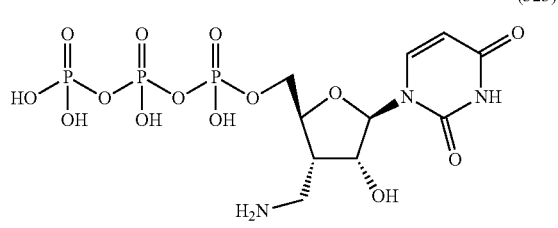
(326)
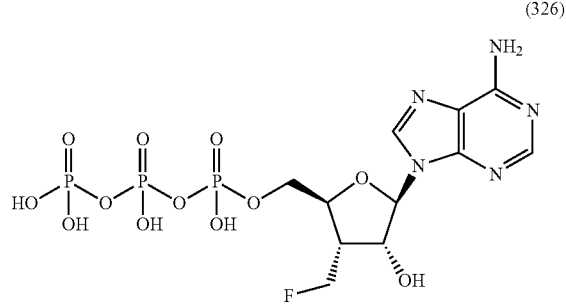
(327)
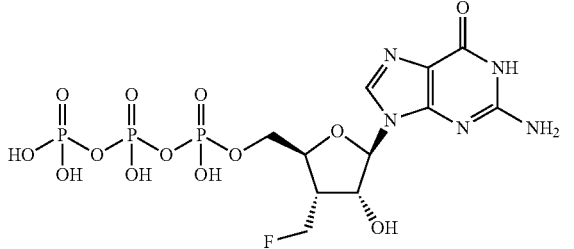
(328)
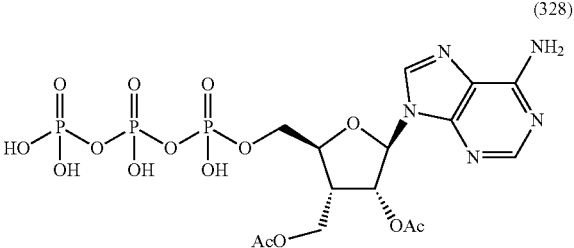

-continued (329)

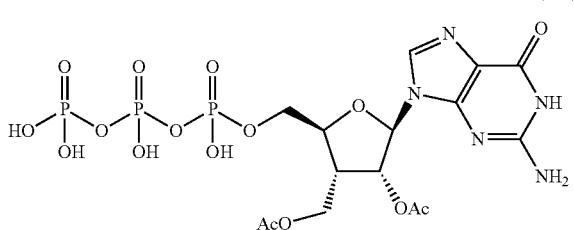

or a pharmaceutically acceptable salt, solvate, or tautomeric form thereof.

21. The compound of claim 1 according to any of Formulas 340, 330, 341, 331, 342, 332, 336, 123a to 125bii, 128a, 129a, 131a to 140, 142 to 164, 167 to 169, 172 to 186, 188, 190 to 190b, 191 to 193, 234 to 238, 240, 241, 242, 247, 249, 251 to 255, and 401-404, or a pharmaceutically acceptable salt thereof.

22. A compound according to Formula 1001:

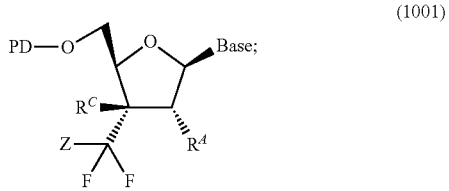

(1001)

or a pharmaceutically acceptable salt thereof, wherein:
$R^A$ is hydroxyl, bromo, chloro, iodo, azido, —NH$_2$, or alkylcarbonyloxy;
$R^C$ is hydrogen, azido, or methyl;
Base is a nucleobase;
PD is hydrogen, alkylcarbonyl,

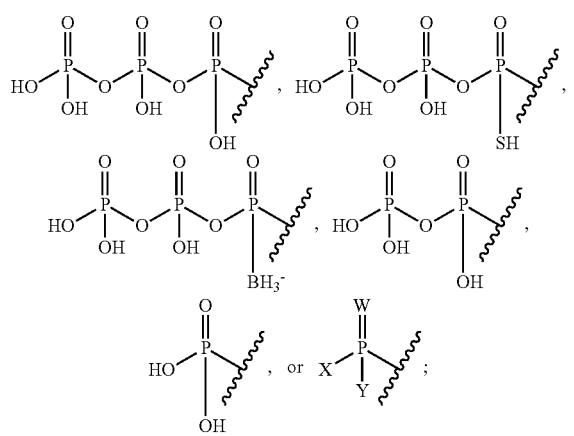

W is S or O;
each of X and Y is independently hydrogen, —OR$^1$, —SR$^1$, —NR$^1$R$^2$, or an N-linked or O-linked amino acid residue, or derivative thereof;
Z is methyl, azido, amino, cyano, hydroxyl, or alkylcarbonyloxy; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene;
each R$^1$ is independently hydrogen, alkyl, aryl, arylalkyl, cycloalkyl, heterocycloalkyl, alkoxycarbonylalkyl, alkoxycarbonyloxyalkyl, or alkylcarbonylthioalkyl; and
each R$^2$ is independently hydrogen, alkyl, cycloalkyl, aryl, or arylalkyl; and
provided that when R$^A$ is OH, R$^C$ is H and Z is fluoro, then PD is not hydrogen.

23. The compound of claim 22 where
R$^A$ is hydroxyl, bromo, chloro, iodo, or alkylcarbonyloxy;
R$^C$ is hydrogen, azido, or methyl;
Base is a nucleobase;
PD is hydrogen,

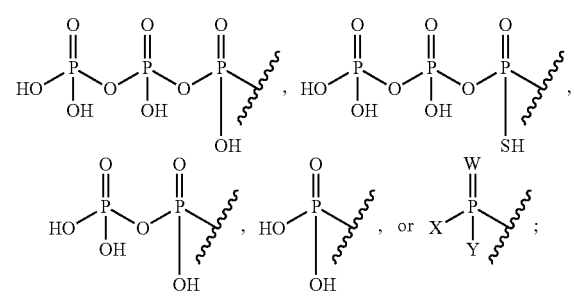

W is S or O;
each of X and Y is independently hydrogen, —OR$^1$, —SR$^1$, —NR$^1$R$^2$, or an N-linked or O-linked amino acid residue, or derivative thereof;
Z is methyl, azido, amino, cyano, hydroxyl, alkylcarbonyloxy; or, in the alternative, Y and Z, together with the atoms to which they are attached, combine to form a seven-membered heterocyclic ring wherein Y and Z together represent a single divalent —O—, and X is —OR$^1$, —SR$^1$, —NR$^1$R$^2$, or an N-linked or O-linked amino acid residue, or derivative thereof; or Z, R$^{B1}$ and R$^{B2}$ combine to form C$_{2-6}$ alkynylene;
each R$^1$ is independently hydrogen, alkyl, aryl, arylalkyl, cycloalkyl, heterocycloalkyl, alkoxycarbonylalkyl, or alkylcarbonylthioalkyl; and
each R$^2$ is independently hydrogen, alkyl, cycloalkyl, aryl, or arylalkyl.

24. The compound of claim 22 where PD is

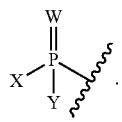

25. A pharmaceutical composition comprising the compound of claim 1 or a pharmaceutically acceptable salt, solvate, or tautomeric form thereof and a pharmaceutically acceptable excipient, carrier, or diluent.

26. A method for the treatment of a human host infected with a virus, comprising administering to the host an effective amount of a compound of claim 1 or a pharmaceutically acceptable salt, solvate, or tautomeric form thereof.

27. The method of claim 26, wherein the virus is a hepatitis C virus.

28. The method of any of claim 27, further comprising administering a second anti-viral agent in combination or alternation with the compound or the composition, wherein the second anti-viral agent is an interferon, a nucleotide analogue, a polymerase inhibitor, an NS3 protease inhibitor, an NS5A inhibitor, an entry inhibitor, a non-nucleoside polymerase inhibitor, a cyclosporine immune inhibitor, an NS4A antagonist, an NS4B-RNA binding inhibitor, a locked nucleic acid mRNA inhibitor, a cyclophilin inhibitor, or a combination thereof.

29. The method of claim 28, wherein the compound is of Formula I:

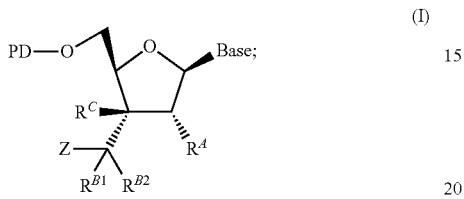

(I)

or a pharmaceutically acceptable salt thereof, wherein:
  $R^A$ is hydroxyl, bromo, chloro, iodo, azido, —NH$_2$, or alkylcarbonyloxy;
  $R^{B1}$ is hydrogen, C$_2$-C$_6$alkenyl, C$_2$-C$_6$alkynyl, fluoro, azido, —NH$_2$, CN, or benzyloxycarbonyloxy;
  $R^{B2}$ is hydrogen or methyl;
  $R^C$ is hydrogen, azido, or methyl;
  Base is a nucleobase;
  PD is alkylcarbonyl,

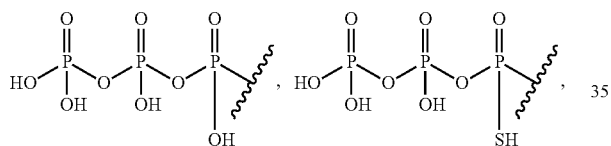

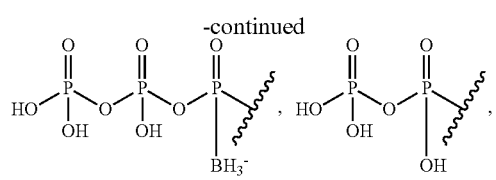

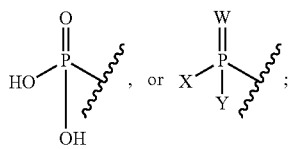

W is S or O;
each of X and Y is independently hydrogen, —OR$^1$, —SR$^1$, —NR$^1$R$^2$, or an N-linked or O-linked amino acid residue, or derivative thereof;
Z is methyl, azido, amino, cyano, hydroxyl, alkylcarbonyloxy, or fluoro; or, in the alternative, Y and Z, together with the atoms to which they are attached, combine to form a seven-membered heterocyclic ring wherein Y and Z together represent a single divalent —O—, and X is —OR$^1$,
—SR$^1$, —NR$^1$R$^2$, or an N-linked or O-linked amino acid residue, or derivative thereof; or Z, R$^{B1}$ and R$^{B2}$ combine to form C$_{2-6}$ alkenylene or C$_{2-6}$ alkynylene;
each R$^1$ is independently hydrogen, alkyl, aryl, arylalkyl, cycloalkyl, heterocycloalkyl, alkoxylcarbonylalkyl, alkoxycarbonyloxyalkyl, or alkylcarbonylthioalkyl; and
each R$^2$ is independently hydrogen, alkyl, cycloalkyl, aryl, or arylalkyl.

* * * * *